US008722638B2

(12) United States Patent
Ingber et al.

(10) Patent No.: US 8,722,638 B2

(45) Date of Patent: May 13, 2014

(54) METHODS FOR THE MODULATION OF ANGIOGENESIS

(75) Inventors: Donald E. Ingber, Boston, MA (US); Akiko Mammoto, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 12/999,746

(22) PCT Filed: Jun. 19, 2009

(86) PCT No.: PCT/US2009/047935

§ 371 (c)(1), (2), (4) Date: Dec. 17, 2010

(87) PCT Pub. No.: WO2009/155504

PCT Pub. Date: Dec. 23, 2009

(65) Prior Publication Data

US 2011/0135632 A1 Jun. 9, 2011

Related U.S. Application Data

(60) Provisional application No. 61/074,164, filed on Jun. 20, 2008, provisional application No. 61/147,850, filed on Jan. 28, 2009.

(51) Int. Cl.

| | |
|---|---|
| ***C12N 15/11*** | (2006.01) |
| ***A61K 48/00*** | (2006.01) |
| *C07H 21/02* | (2006.01) |
| *C07H 21/04* | (2006.01) |

(52) U.S. Cl.

USPC ....... 514/44 A; 514/44 R; 536/23.1; 536/24.5

(58) Field of Classification Search

None

See application file for complete search history.

(56) References Cited

U.S. PATENT DOCUMENTS

| | | | | |
|---|---|---|---|---|
| 5,270,163 | A | 12/1993 | Gold et al. | |
| 5,475,096 | A | 12/1995 | Gold et al. | |
| 6,060,248 | A | 5/2000 | Lane et al. | |
| 2003/0053989 | A1 | 3/2003 | Kovesdi | |
| 2005/0222065 | A1* | 10/2005 | Khachigian | 514/44 |
| 2006/0204478 | A1 | 9/2006 | Harats et al. | |
| 2007/0154482 | A1* | 7/2007 | Sukhatme et al. | 424/146.1 |
| 2008/0199430 | A1 | 8/2008 | Shai | |

OTHER PUBLICATIONS

Minami et al., 2004, The Journal of Biological Chemistry, vol. 279, pp. 20626-20635.*

Desai et al., Evidence of angiogeneic vessels in Alzheimer's disease, 2009, Journal of Neural Transmission, vol. 116, pp. 587-597.*

H. Roger Lijnen, Angiogenesis and obesity, 2008, Cardiovascular Research, vol. 78, pp. 286-293.*

Mammoto et al., A mechanosensitive transcriptional mechanism that controls angiogenesis, 2009, Nature, vol. 457, pp. 1103-1108. "Methods" pages is also attached.*

Mammoto et al., The Rho inhibitor p190RhoGAP controls VEGFR2 transcription and angiogenesis in vitro through antagonism between GATA2 and TFII-I, 2008, The FASEB Journal, vol. 22, Abstract No. 471.9.*

Han et al., Transcriptional up-regulation of endothelial cell matrix metalloproteinase-2 in response to extracellular cues involves GATA-2, 2003, The Journal of Biological Chemistry, vol. 278, pp. 47785-47791.*

Holinstat, M., et al., Suppression of RhoA activity by focal adhesion kinase-induced activation of p190RhoGAP: role in regulation of endothelial permeability, J Biol. Chem., 2006, vol. 281(4):2296-2305.

Jackson, T.A., et al., Vascular endothelial growth factor receptor-2: counter-regulation by the transcription factors, TFII-I and TFII-IRD1, J Biol. Chem., 2005, vol. 280(33):29856-29863.

Akhtar et al., J. Clin. Invest., 117(12):3623-3632 (2007). "Nonviral delivery of synthetic siRNAs in vivo."

Arthur et al., Current Biology, 10:719-722 (2000). "Integrin engagement suppresses RhoA activity via a c-Src-dependent mechanism."

Arthur et al., Molecular Biology of the Cell, 12:2711-2720 (2001). "RhoA Inactivation by p190RhoGAP Regulates Cell Spreading and Migration by Promoting Membrane Protrusion and Polarity."

Bartolome et al., Cancer Res, 68:8221-8230 (2008). "Activated Gα13 Impairs Cell Invasiveness through p190RhoGAP-Mediated Inhibition of RhoA Activity."

Campochiaro et al., Oncogene, 22:6537-6548 (2003). "Ocular neovascularization: a valuable model system."

Francke, Human Molecular Genetics, 8(10):1947-1954 (1999). "Williams-Beuren syndrome: genes and mechanisms."

(Continued)

*Primary Examiner* — Dana Shin

(74) *Attorney, Agent, or Firm* — David S. Resnick; Susanna C. Benn; Nixon Peabody LLP

(57) ABSTRACT

The present invention relates to methods and compositions for promoting or inhibiting capillary endothelial (CE) cell migration, promoting or inhibiting the formation of CE networks and promoting or inhibiting angiogenesis. Some embodiments relate to methods and compositions for treating angiogenesis-related disorders characterized by loss or decreased angiogenesis. One aspect relates to the use of at least one pro-angiogenic agent selected from at least one of an p190RhoGAP inhibitor, a TFII-I inhibitor or a GATA-2 activator for promoting the formation of CE networks and angiogenesis, and methods for treating angiogenesis-related disorders characterized by loss or decreased angiogenesis. Another aspect of the invention related to use of at least one anti-angiogenic agent selected from at least one of an p190RhoGAP activator, a TFII-I activator or a GATA-2 inhibitor for inhibiting the formation of CE networks and inhibiting angiogenesis, and methods for treating angiogenesis-related disorders characterized by uncontrolled or elevated angiogenesis.

8 Claims, 16 Drawing Sheets

(56) References Cited

OTHER PUBLICATIONS

Jiang et al., Molecular Cell, 17:23-35 (2005). "An FF Domain-Dependent Protein Interaction Mediates a Signaling Pathway for Growth Factor-Induced Gene Expression."
Mammoto et al., J. Biol. Chem., 279:26323-26330 (2004). "Role of RhoA, mDia, and ROCK in Cell Shape dependent Control of the Skp2-p27 kip1 Pathway and the G1/S Transition."
Mammoto et al., Journal of Cell Science, 120:456-467 (2007). Filamin links cell shape and cytoskeletal structure to Rho regulation by controlling accumulation of p190RhoGAP in lipid rafts.
Mammoto et al., J. Biol. Chem., 282:23910-23918 (2007). "Angiopoietin-1 Requires p190 RhoGAP to Protect against Vascular Leakage in Vivo."
Martin et al., Methods, 28:267-275 (2002). "Gene delivery to the eye using adeno-associated viral vectors."
Minami et al., J. Biol. Chem., 276:5395-5402 (2001). "Transforming Growth Factor-betal-mediated Inhibition of the flk-1/KDR Gene is Mediated by a 5'-Untranslated Region Palindromic Gata Site."
Minami et al., J. Biol. Chem., 279:20626-20635 (2004). "Interaction between Hex and GATA Transcription Factors in Vascular Endothelial Cells Inhibits flk-1/KDR-mediated Vascular Endothelial Growth Factor Signaling."
Montezuma et al., Semin. Opthamol., 24(2):52-61 Abstract only (2009). "Review of the ocular angiogenesis animal models."
Robinson et al., Journal of Cell Science, 114:853-865 (2001). "The splice variants of vascular endothelial growth factor (VEGF) and their receptors."
Roy, Biochim Biophys Acta., 1769(11-12):613-621 Author Manuscript (2007). "Signal-Induced Functions of the Transcription Factor TFII-I."
Roy, Gene, 274:1-13 (2001). "Biochemistry and biology of the inducible multifunctional transcription factor TFII-I."
Sheibani et al., Molecular Biology of the Cell, 9:701-713 (1998). "Down-Regulation of Platelet Endothelial Cell Adhesion Molecular-1 Results in Thrombospondin-1 Expression and Concerted Regulation of Endothelial Cell Phenotype."
Su et al., PNAS, 101(33):12212-12217 (2004). "A vascular cell-restricted RhoGAP, p73RhoGAP, is a key regulator of angiogenesis."
Veeramani et al., International Journal of PharmTech Research, 2(4):2379-2387 (2010). "An Essential Review on Current Techniques Used in Angiogenesis Assays."
Wolf, Genes Dev., 17:476-487 (2003). "p190RhoGAP can act to inhibit PDGF-induced gliomas in mice: a putative tumor suppressor encoded on human Chromosome 19q13.3."
Wu et al., J. Biol. Chem., 274:3207-3214 (1999). "The Human KDR/flk-1 Gene Contains a Functional Initiator Element That is Bound and Transactivated by TFII-I."
Zhang et al., PNAS, 105(6):2076-2081 (2008). "Gain-of-function mutation of GATA-2 in acute myeloid transformation of chronic myeloid leukemia."

* cited by examiner

SEQUENCE LISTING

<160> NUMBER OF SEQ ID NOS: 60

<210> SEQ ID NO 1
<211> LENGTH: 835
<212> TYPE: PRT
<213> ORGANISM: Homo sapiens

<400> SEQUENCE: 1

Met Asp Ala Thr Ser His Ile Asp Asn Met Glu Asn Glu Arg Ile Pro
1 5 10 15

Phe Asp Leu Met Asp Thr Val Pro Ala Glu Ala Leu Tyr Glu Ala His
20 25 30

Leu Glu Lys Leu Arg Asn Glu Arg Lys Arg Val Glu Met Arg Arg Ala
35 40 45

Phe Lys Glu Asn Leu Glu Thr Ser Pro Phe Ile Thr Pro Gly Lys Pro
50 55 60

Trp Glu Glu Ala Arg Ser Phe Ile Met Asn Glu Asp Phe Tyr Gln Trp
65 70 75 80

Leu Glu Glu Ser Val Tyr Thr Asp Ile Tyr Gly Lys His Gln Lys Gln
85 90 95

Ile Ile Asp Lys Ala Lys Glu Glu Phe Gln Glu Leu Leu Leu Glu Tyr
100 105 110

Ser Glu Leu Phe Tyr Glu Leu Glu Leu Asp Ala Lys Pro Ser Lys Glu
115 120 125

Lys Met Gly Val Ile Gln Asp Val Leu Gly Glu Glu Gln Arg Phe Lys
130 135 140

Ala Ile Tyr Lys Ser Ser Lys Gln Ser Val Asp Ala Leu Ile Leu Lys
145 150 155 160

His Ile His Phe Val Tyr His Pro Thr Lys Glu Thr Cys Pro Ser Cys
165 170 175

Pro Ala Cys Val Asp Ala Lys Ile Glu His Leu Ile Ser Ser Arg Phe
180 185 190

Ile Arg Pro Ser Asp Arg Asn Gln Lys Asn Ser Leu Ser Asp Pro Asn
195 200 205

Ile Asp Arg Ile Asn Leu Val Ile Leu Gly Lys Asp Ala Leu Pro Glu
210 215 220

Ser Trp Pro Met Glu Ile Arg Ala Leu Cys Thr Asn Asp Asp Lys Tyr
225 230 235 240

Val Ile Asp Gly Lys Met Tyr Glu Leu Ser Leu Arg Pro Ile Glu Gly
245 250 255

Asn Val Arg Leu Pro Val Asn Ser Phe Gln Thr Pro Thr Phe Gln Pro
260 265 270

His Gly Cys Leu Cys Leu Tyr Asn Ser Lys Glu Ser Leu Ser Tyr Val
275 280 285

Val Glu Ser Ile Glu Lys Ser Arg Glu Ser Thr Leu Gly Arg Arg Asp
290 295 300

Asn His Leu Val His Leu Pro Leu Thr Leu Ile Leu Val Asn Lys Arg
305 310 315 320

-continued

```
Gly Asp Thr Ser Gly Glu Thr Leu His Ser Leu Ile Gln Gln Gly Gln
                325                 330                 335

Gln Ile Ala Ser Lys Leu Gln Cys Val Phe Leu Asp Pro Ala Ser Ala
            340                 345                 350

Gly Ile Gly Tyr Gly Arg Asn Ile Asn Glu Lys Gln Ile Ser Gln Val
        355                 360                 365

Leu Lys Gly Leu Leu Asp Ser Lys Arg Asn Leu Asn Leu Val Ser Ser
    370                 375                 380

Thr Ala Ser Ile Lys Asp Leu Ala Asp Val Asp Leu Arg Ile Val Met
385                 390                 395                 400

Cys Leu Met Cys Gly Asp Pro Phe Ser Ala Asp Asp Ile Leu Phe Pro
                405                 410                 415

Val Leu Gln Ser Gln Thr Cys Lys Ser Ser His Cys Gly Ser Asn Asn
            420                 425                 430

Ser Val Leu Leu Glu Leu Pro Ile Gly Leu His Lys Lys Arg Ile Glu
        435                 440                 445

Leu Ser Val Leu Ser Tyr His Ser Ser Phe Ser Ile Arg Lys Ser Arg
    450                 455                 460

Leu Val His Gly Tyr Ile Val Phe Tyr Ser Ala Lys Arg Lys Ala Ser
465                 470                 475                 480

Leu Ala Met Leu Arg Ala Phe Leu Cys Glu Val Gln Asp Ile Ile Pro
                485                 490                 495

Ile Gln Leu Val Ala Leu Thr Asp Gly Ala Val Asp Val Leu Asp Asn
            500                 505                 510

Asp Leu Ser Arg Glu Gln Leu Thr Glu Gly Glu Glu Ile Ala Gln Glu
        515                 520                 525

Ile Asp Gly Arg Phe Thr Ser Ile Pro Cys Ser Gln Pro Gln His Lys
    530                 535                 540

Leu Glu Ile Phe His Pro Phe Phe Lys Asp Val Val Glu Lys Lys Asn
545                 550                 555                 560

Ile Ile Glu Ala Thr His Met Tyr Asp Asn Ala Ala Glu Ala Cys Ser
                565                 570                 575

Thr Thr Glu Glu Val Phe Asn Ser Pro Arg Ala Gly Ser Pro Leu Cys
            580                 585                 590

Asn Ser Asn Leu Gln Asp Ser Glu Glu Asp Ile Glu Pro Ser Tyr Ser
        595                 600                 605

Leu Phe Arg Glu Asp Thr Ser Leu Pro Ser Leu Ser Lys Asp His Ser
    610                 615                 620

Lys Leu Ser Met Glu Leu Glu Gly Asn Asp Gly Leu Ser Phe Ile Met
625                 630                 635                 640

Ser Asn Phe Glu Ser Lys Leu Asn Asn Lys Val Pro Pro Pro Val Lys
                645                 650                 655

Pro Lys Pro Pro Val His Phe Glu Ile Thr Lys Gly Asp Leu Ser Tyr
            660                 665                 670

Leu Asp Gln Gly His Arg Asp Gly Gln Arg Lys Ser Val Ser Ser Ser
        675                 680                 685

Pro Trp Leu Pro Gln Asp Gly Phe Asp Pro Ser Asp Tyr Ala Glu Pro
    690                 695                 700

Met Asp Ala Val Val Lys Pro Arg Asn Glu Glu Glu Asn Ile Tyr Ser
705                 710                 715                 720

Val Pro His Asp Ser Thr Gln Gly Lys Ile Ile Thr Ile Arg Asn Ile
                725                 730                 735

Asn Lys Ala Gln Ser Asn Gly Ser Gly Asn Gly Ser Asp Ser Glu Met
            740                 745                 750
```

```
Asp Thr Ser Ser Leu Glu Arg Gly Arg Lys Val Ser Ile Val Ser Lys
        755                 760                 765

Pro Val Leu Tyr Arg Thr Arg Cys Thr Arg Leu Gly Gly Leu Leu Val
    770                 775                 780

Thr Gly Pro Ala Ser Ala Trp Gly Val Met Met Ser Trp Gly Pro Ser
785                 790                 795                 800

Gly Arg Lys Arg Arg Ile Arg His Pro Arg Val Ile Lys Gly Thr Met
                805                 810                 815

Leu Ser Phe His Thr Lys Gln Thr Lys Thr Arg Gly Gly Gly Ile Phe
            820                 825                 830

Phe Ala Ala
        835


<210> SEQ ID NO 2
<211> LENGTH: 8904
<212> TYPE: DNA
<213> ORGANISM: Homo sapiens

<400> SEQUENCE: 2

atgatgatgg caagaaagca agatgtccga attcccacct acaacatcag tgtggtggga     60

ttatctggga ccgagaagga aaagggccag tgtgggattg gaaagtcttg tttgtgcaac    120

cgcttcgtgc gcccgagtgc tgacgagttt cacttggacc atacctccgt cctcagcacc    180

agtgactttg gagggcgagt ggtcaataat gaccactttc tctactgggg agaagttagc    240

cgctccctgg aggattgtgt ggaatgtaag atgcacattg tggagcagac tgaatttatt    300

gatgatcaga cttttcaacc tcatcgaagc acggccctgc agccctatat caagagagct    360

gctgcgacca agcttgcatc agctgaaaaa ctcatgtact tttgcactga ccagctgggg    420

ctggagcagg actttgagca gaaacaaatg ccagacggaa agctgctggt tgatggtttt    480

cttcttggta ttgatgttag caggggcatg aataggaact ttgatgacca gctcaagttt    540

gtctccaatc tctacaatca gcttgcaaaa acaaaaaagc ccatagtggt ggtcctgact    600

aagtgtgacg aaggtgttga gcggtacatt agagatgcac atacttttgc cttaagcaaa    660

aagaacctcc aggttgtgga gacctcagcg agatccaatg taaacgtgga cttggctttc    720

agcaccttag tgcaactcat tgataaaagt cggggaaaga caaaaatcat tccttattt     780

gaagctctca agcagcagag tcagcagata gctacagcaa aagacaagta tgagtggctg    840

gtgagtcgca ttgtgaaaaa ccacaatgag aactggctga gtgtcagccg aaagatgcag    900

gcctctccag aataccagga ctatgtctac ctggaaggga ctcagaaagc caagaagctg    960

tttctacagc acatccaccg cctcaagcat gagcatatcg agcgtaggag aaagctgtac   1020

ctggcagccc tgccattagc ttttgaagct cttataccta atctagatga aatagaccac   1080

ctaagctgca taaaagccaa aaagctctta gaaaccaagc cagaattctt gaagtggttt   1140

gttgtgcttg aagagacccc atgggatgcc accagtcaca ttgacaacat ggaaaacgaa   1200

cggattccct ttgatttaat ggataccgtc cctgcagagc agctatacga ggcccactta   1260

gagaagctga ggaacgaaag gaaaagagtt gagatgcgaa gggcgtttaa agaaaacctg   1320

gagacttctc ctttcataac tcccggaaag ccttgggaag aggcccgtag ttttattatg   1380

aatgaggatt tctaccagtg gctggaggaa tctgtataca tggatattta tggcaaacac   1440

caaaagcaaa ttatagataa agcaaaggaa gaatttcagg agttgctttt ggaatattca   1500

gaattgtttt atgaactgga gctggatgct aagcccagca aggagaagat gggtgttatt   1560

caggatgttc tgggagagga acagcgattt aaagcattac aaaagctcca agcagagcgt   1620
```

gatgccctta ttctgaaaca cattcatttt gtgtaccacc caacaaagga gacatgcccc 1680
agctgcccag cttgtgtgga cgctaagatt gagcacttga ttagttctcg gtttatccgg 1740
ccgtctgacc ggaatcagaa aaattcactc tctgacccta acattgatag aatcaacttg 1800
gttatattgg gcaaagacgg ccttgcccga gagttggcca atgagattcg agctctttgt 1860
acaaatgatg acaagtatgt gatagatggt aaaatgtatg agctttccct gaggccaata 1920
gaggggaatg tcaggcttcc tgtgaactct ttccagacgc caacatttca gccccacggc 1980
tgtctctgcc tttacaattc aaaggaatcg ctatcctatg tagtggaaag tatagagaag 2040
agtagagagt ccacgctggg ccggcgggat aatcatttag tccatctccc ccttacatta 2100
attttggtta acaagagagg agacaccagt ggagagactc tgcatagctt aatacagcaa 2160
ggtcaacaaa ttgctagcaa acttcagtgt gtctttctcg accctgcttc tgctggcatt 2220
ggttacggac gcaacattaa tgaaaagcaa atcagtcaag ttttgaaggg actcctggac 2280
tctaagcgta acttaaacct ggtcagttct actgctagca tcaaagattt ggctgatgtt 2340
gatctgcgaa ttgttatgtg tctgatgtgt ggagatcctt ttagtgcaga tgacatactt 2400
tttcctgtcc ttcagtccca aacctgtaaa tcttcccatt gtggaagcaa caactctgtt 2460
ttacttgaac taccaatcgg actgcacaag aagcggattg aactgtctgt tctttcatac 2520
cattcctcct ttagcatcag aaagagccgg ttggttcatg ggtacattgt tttttattca 2580
gccaaacgta aggcctcttt ggctatgtta cgtgcctttc tttgtgaagt gcaggatatt 2640
atccctattc agcttgtagc actcactgat ggcgctgtag atgtcctgga caatgactta 2700
agtagggaac agctaactga gggggaggag attgctcaag aaattgacgg aaggttcaca 2760
agcatcccct gtagccaacc ccagcataaa cttgagatct ttcacccatt ttttaaagat 2820
gtggtggaaa aaaagaacat aatcgaggct actcatatgt acgataatgc tgccgaggcc 2880
tgtagcacca ccgaagaggt gtttaactcc ccccgggcag gatcaccgct ctgcaactca 2940
aacctgcagg attcagaaga agatatcgag ccatcttaca gcctgtttcg agaagacaca 3000
tcactgcctt ctctgtccaa agaccattct aagctctcta tggaactgga gggaaatgat 3060
gggctgtctt tcattatgag caattttgag agtaaactga acaacaaagt acctccgcca 3120
gtcaaaccaa agcctcctgt ccattttgaa attacaaagg gggatctatc ttatttagac 3180
caaggccata gggatggaca gaggaagtct gtgtcttcta gcccctggct gcctcaggat 3240
gggtttgatc cttctgacta tgctgaaccc atggatgctg tggtgaagcc aaggaatgaa 3300
gaagaaaaca tatactccgt gccccatgac agcacccaag gcaaaatcat caccattcgg 3360
aatatcaaca aagcccagtc caacggcagc gggaatggtt ctgacagtga aatggacacc 3420
agctctctag agcgagggcg caaggtttcc atcgtgagca agccagtgct gtacaggacg 3480
agatgcaccc ggctggggcg gtttgctagt taccggacca gcttcagcgt ggggagtgat 3540
gatgagctgg ggcccatccg gaagaaagag gaggatcagg catcccaggg ttataaaggg 3600
gacaatgctg tcattccata cgaaacagac gaagacccgc ggaggaggaa tattcttcgc 3660
agcctaagga ggaacactaa gaaaccaaag cccaaacccc ggccatccat cacaaaggca 3720
acctgggaga gtaactattt tggggtgccc ttaacaactg tcgtgactcc agagaagccg 3780
atccccattt ttattgaaag atgtattgag tacattgaag ccacaggact gagcacggaa 3840
ggcatctacc gggtcagcgg gaacaagtct gagatggaga gtctgcagag acagtttgat 3900
caagaccaca acctggacct ggcagagaaa gactttacgg tgaataccgt ggctggtgcc 3960
atgaagagct tttctcaga actgcctgac cccctggtcc cgtataacat gcagatcgac 4020

-continued

```
ttggtggaag cacacaaaat caacgaccgg gagcagaagt tgcatgccct taaggaggta   4080
ttaaagaaat ttccaaagga aaaccacgaa gtcttcaagt atgtcatctc tcacctaaac   4140
aaggtcagcc acaacaacaa ggtgaatctc atgaccagcg agaacctctc catctgcttc   4200
tggcccacct tgatgagacc tgatttcagc actatggacg ccctcacagc cacgcgcacc   4260
taccagacaa tcattgaact ctttatccag cagtgcccct tcttcttcta caatcggccc   4320
atcaccgagc cccccggcgc caggcccagc tccccctctg ccgtggcttc caccgtcccc   4380
ttcctcactt ccacgcctgt cacaagtcag ccgtcgcccc cacagtcgcc tccacccacc   4440
ccccagtccc caatgcagcc actgcttccc tcccagcttc aagccgaaca cacgctgtga   4500
gccaccaaga cctggggcga caggagaacc ggtcctctct ctgacggggt ggcatttggc   4560
cttgaacaaa accaagtcca ctggggacag aggcaggggc aagtggctct ccccattacc   4620
ttctcaagac ctcagtggga gcaccagcca atggtaccat cggctgggct gccaggtacc   4680
ctgggcctgg cgctgcagac ctgagctggc ttggacccat ttgaggactg aactaggcag   4740
gcaatggctc cagtgccctc cctctgttcc ctggaccacc accccacgta gctgctcaca   4800
ccagcctccg ggtgcctccc tctgcttgta cagagcccat ggtcgggaca gtgccctggc   4860
ctttgccggg gaggaggatg ctctgagatt cagggtgggg ctggcaaccc ctgaagagaa   4920
cacttcctgt tggtctgtct cttcccacct tccatctgca cacaccccca aggtaagggt   4980
acagcccggc tggcggcctc cttgggaacg tgtaggccac ggctctgcca ccactaggta   5040
cctgctgagg gcgctggctc tgcagatcag aacaacggag gatagctttg tgcctggacc   5100
cagagagtgt gggactcccc gcttcatccc caccgtccca ctccacagcc ttcccgaaac   5160
attccctggc aaacaaagga acactaggag aaaaaatgga aaaacccttc cagtaattaa   5220
aaaggaagaa accacagaaa gaaaactaca gacctcaaga ttccactctg tgcccgcctc   5280
tgccgggagg gagggaggca cacaggtgga gctgaccctc gtctttgtgg cagcaaaacc   5340
aggatgcctg gagctgtggc ctgagggcct gctggggtcc cactcaccca cttaggtcta   5400
gtcgctagat cccccgtttt cccaagaaga gggttcgagc ccttggtggg gacagctggg   5460
gagatggcag tgcaggctgg aacctgggct gccccagaac acagtccatt acgatagaaa   5520
cactaattga gcatgtgcgt ggggtggggg tgtgtgtgca catgtgagtg tgagtgtgtg   5580
tgggcgcttg gtgggggggtt ggggacagct ggaaggtgcc aggtgcactt ggggttgggg   5640
ttggtgtgtt gggtgttgaa gtggaatcgt ttcatcccag ccatggaggc caccagcagg   5700
agtgttcatg gggatgtggg cgaggtgggg cactttgaag gaatggcggt ctgctggtgc   5760
cctcgaaggg gcatccttcc tggtcttcgc tgacccagag gcgctgtgcc tgcatatcat   5820
ccaccaccac cctagcccag ccttcccact gccccaggaa aagctcttct cctggccacc   5880
tctgcccccc agcacctcaa acttgcatgg ctgggctgtg gcctctgcgg ccaggaagcc   5940
tgacactagg caccccccag gcgagagcta gtggggtgca gagggcccca tgccagacag   6000
cccttggggc tcgttgcact ttaagaaata ggatctgtgg tgtattccag ggggcctgat   6060
ggacaccttt cccgggcgtc tgcagctgcc ctgcccgtgc ccgcctgcag tggttggaga   6120
cgggagtggc ccttcggctc ccgagctccc tctggggacg gctggctcac tgtctccagt   6180
tctcaatggc caacgaaggt gcttggaaac acctaacctt gcaagtttta ccgccttttg   6240
aggaacacaa atcggagaac aaacccaggg ttcaggcgtg ttttctgtga atgttggatg   6300
atgaattttt gtctcttctg gtggagctgt gcctggccct gtaggcccag ggttggctgg   6360
aaggtgacat ctgtgtttcg ttttagctga ggttggcaga aacgttccca aactccccca   6420
```

```
gccctggacc ccagcagatg aggaaacggc cccatttact gaccccgccc ccttttcgag   6480
gttatgctca cctggtcagc tcctcacgta attgggggtg gagggaaagc atggtggtgc   6540
cctgggccgt ccctgtgtga acgcaggcaa aagcagccca gtccccctca ctgcttgagc   6600
taacactgcc acctcttttg tgtgagcaca aaagccacgt cccaagccac ctggcccgat   6660
tccacagatg tatgtgcggc cagtgacttc cccaggagtg tggagggggt ggtgaggagg   6720
agcacctggg ctctctaccc ctctcctcac agaagtacct gaaactaggt ctggggcact   6780
cccaatgcag cgccttgtca gccaaggtgg gcaggcaggg actgtggcag cttatgtcca   6840
aagggagccc ccatgcacag gaagccacag ggttcctctt gtttcccccg ctaacttcag   6900
cctctcatct gctgctccgg gctgagggac tagaggacat ctcggtcgtt tgaggggcat   6960
ggccagtcgt ggcaggccgg ccttcagcgt ccggtcaggg aagcgtgcag cccaaatggg   7020
cacttgcatg ggagccacag aggagcgtcc ctggggattg ttgggaccat gctgccccca   7080
ctcccgcttt tgttggggct ctaagttctg gaaggtgtgt gcacagaggg tgctcatggg   7140
actcgcatgc agctctcagc actgggtggg agggcgttgg cttgtccaga atggggacgt   7200
ggggcagcca cccctgccca gcgagagcgc agacaccgtg tgaggggaca gcagcccttg   7260
gtgcaaagcc agagactgat cctggctctg acggctgaag agggaagacc caaggctggg   7320
tggcgtggct cgtgaatcca cttagaattc ttggcttgtg tcgcatactg ggtgtcacgg   7380
cacacattta ctctgcattg tccccgtctt tcccatcgcc tagcgtttgg ggaggaacag   7440
ggagagagct tcggggcgtc tgtctccgtg ctctcctgcc tccaccgcct tggttttgct   7500
tcctgctgga ggcagggcac ctgctgcgac ccagattctt ctgcaggatg tgtctgtctt   7560
tgtcacggtg gacagagggt gacatcatag gagcagctcg ctggccagaa ggggatgggg   7620
gcatccctgt gcctcactca gctcctgctg ctcttaggga aaggaggcct gggtcaagcc   7680
agcatcccct tggtaaagac ccccgcaggc caccaggcat tctggacacg cacacacaca   7740
cacacacaca cacacacaca caaaacttca cagcaggcca gctgcagtga cttgtcatca   7800
agagtcacct cagctgcgcc cccctcccat cctttcctat gagaagccac tgctttgggg   7860
gcgccggcta gaaaaagtag ggtgcggtgg ccaggagggc ccctgccgcg cgggggggctg   7920
ggtctggttg agtcgctgct ttcccgaggg cagcgcaggg atccggggaa gctgcggcag   7980
ggagcgggcg ccggcttcgt ggctctgagg tgtaacgggg gtgggctccc tccctcggag   8040
gacatcgtct gtgtccaggt cagaaagtgg cccaggaagg gggcagtttc tgtcgcgggt   8100
ccggtggggg cgcggccgcg gtgcggtcgg tgcagcgtgg ccaatgcgcg gcgcgcgcgg   8160
gggacagagc aggaggcggt ctgtcacctc ggccactgct gacctgggct ggcctccccc   8220
agccctcccg tggcggagcc ggcagcgatg ctacaggcct aagttattgt ttgcataaaa   8280
agaatcatgt tccctgtgta catttaagaa aaaaacaaaa aaacggaaat gtcagaattg   8340
tatggaaata aaacttgttt gaaaatttgg aatagtgctg ctgccagctt atttttctgg   8400
tacttgtatt ttcacatgtt aaatgatctt tatatatgtt gaattaacaa atattttgag   8460
tttctgagaa aaaacaaaac atattaatgg tattgaaatg tgttagtagt ctggctgtgt   8520
gcccaaaatt ctgtttcgca gcaaaagtga agacctgtat gtaaagaaag tataacaatt   8580
atttctttgt attttagggg ctttaaccgg aacatcgtct agctggtgtt aggaatgttt   8640
gcttaatttc cagacttttt tttaaaaaca catcgtgggt tttttgaggc tccaacctga   8700
ttagtgcatg gtcagccctc aatgaaggct gaggcatctc tgactgaggt gtttttgttt   8760
ggttttgttt tttaaaatca tgtatttgct acaaagtatt gtacttgtct caatgggaat   8820
```

ggtgtaaaaa acaaaaggcc ttatgtgatc tgtatcatag ttaataaatg aatcttgtaa 8880
aaaaccaaaa aaaaaaaaaa aaaa 8904

<210> SEQ ID NO 3
<211> LENGTH: 3233
<212> TYPE: DNA
<213> ORGANISM: Homo sapiens

<400> SEQUENCE: 3
cttgaagtgg tttgttgtgc ttgaagagac cccatggatg ccaccagtca cattgacaac 60
atggaaaacg aacggattcc ctttgattta atggataccg tccctgcaga ggcactatac 120
gaggcccact tagagaagct gaggaacgaa aggaaaagag ttgagatgcg aagggcgttt 180
aaagaaaacc tggagacttc tcctttcata actcccggaa agccttggga agaggcccgt 240
agttttatta tgaatgagga tttctaccag tggctggagg aatctgtata cacggatatt 300
tatggcaaac accaaaagca aattatagat aaagcaaagg aagaatttca ggagttgctt 360
ttggaatatt cagaattgtt ttatgaactg gagctggatg ctaagcccag caaggagaag 420
atgggtgtta ttcaggatgt tctgggagag gaacagcgat ttaaagccat ttacaaaagc 480
tccaagcaga gcgttgatgc ccttattctg aaacacattc attttgtgta ccacccaaca 540
aaggagacat gccccagctg cccagcttgt gtggacgcta agattgagca cttgattagt 600
tctcggttta tccggccgtc tgaccggaat cagaaaaatt cactctctga ccctaacatt 660
gatagaatca acttggttat attgggcaaa gacgccttgc ccgagagttg gccaatggag 720
attagagctc tttgtacaaa tgatgacaag tatgtgatag atggtaaaat gtatgagctt 780
tccctgaggc caatagaggg gaatgtcagg cttcctgtga actctttcca gacgccaaca 840
tttcagcccc acggctgtct ctgcctttac aattcaaagg aatcgctatc ctatgtagtg 900
gaaagtatag agaagagtag agagtccacg ctgggccggc gggataatca tttagtccat 960 ctcccccctta cattaatttt ggttaacaag agaggagaca ccagtggaga gactctgcat 1020
agcttaatac agcaaggtca acaaattgct agcaaacttc agtgtgtctt tctcgaccct 1080
gcttctgctg gcattggtta cggacgcaac attaatgaaa agcaaatcag tcaagttttg 1140
aagggactcc tggactctaa gcgtaactta aacctggtca gttctactgc tagcatcaaa 1200
gatttggctg atgttgatct gcgaattgtt atgtgtctga tgtgtggaga tccttttagt 1260
gcagatgata tactttttcc tgtccttcag tcccaaacct gtaaatcttc ccattgtgga 1320
agcaacaact ctgttttact tgaactacca atcggactgc acaagaagcg gattgaactg 1380
tctgttcttt cataccattc ctcctttagc atcagaaaga gccggttggt tcatgggtac 1440
attgtttttt attcagccaa acgtaaggcc tctttggcta tgttacgtgc ctttctttgt 1500
gaagtgcagg atattatccc tattcagctt gtagcactca ctgatggcgc tgtagatgtc 1560
ctggacaatg acttaagtag ggaacagcta actgaggggg aggagattgc tcaagaaatt 1620
gacggaaggt tcacaagcat cccctgtagc caaccccagc ataaacttga gatctttcac 1680
ccatttttta aagatgtggt ggaaaaaaag aacataatcg aggctactca tatgtacgat 1740
aatgctgccg aggcctgtag caccaccgaa gaggtgttta actcccccg ggcaggatca 1800 ccgctctgca actcaaacct gcaggattca gaagaagata tcgagccatc ttacagcctg 1860
tttcgagaag acacatcact gccttctctg tccaaagacc attctaagct ctctatggaa 1920
ctggagggaa atgatgggct gtctttcatt atgagcaatt ttgagagtaa actgaacaac 1980
aaagtacctc cgccagtcaa accaaagcct cctgtccatt ttgaaattac aaagggggat 2040

-continued ctatcttatt tagaccaagg ccatagggat ggacagagga agtctgtgtc ttctagcccc 2100
tggctgcctc aggatgggtt tgatccttct gactatgctg aacccatgga tgctgtggtg 2160
aagccaagga atgaagaaga aaacatatac tccgtgcccc atgacagcac ccaaggcaaa 2220
atcatcacca ttcggaatat caacaaagcc cagtccaacg gcagcgggaa tggttctgac 2280
agtgaaatgg acaccagctc tctagagcga gggcgcaagg tttccatcgt gagcaagcca 2340
gtgctgtaca ggacgagatg cacccggctg ggcggtttgc tagttaccgg accagcttca 2400
gcgtggggag tgatgatgag ctggggccca tccggaagaa agaggaggat caggcatccc 2460
agggttataa aggggacaat gctgtcattc catacgaaac agacgaagac ccgcggagga 2520
ggaatattct tcgcagccta aggaggaaca ctaagaaacc aaagcccaaa ccccggccat 2580
ccatcacaaa ggccaacctg ggagagtaac tattttgggg tgcccttaac aactgtcgtg 2640
actccagaga agccgatccc catttttatt gaaagatgta ttgagtacat tgaagccaca 2700
ggactgagca cggaaggcat ctaccgggtc agcgggaaca agtctgagat ggagagtctg 2760
cagagacagt ttgatcaaga ccacaacctg gacctggcag agaaagactt tacggtgaat 2820
accgtggctg gtgccatgaa gagctttttc tcagaactgc ctgacccccct ggtccgtata 2880 acatgcagat cgacttggtg gaagcacaca aaatcaacga ccgggagcag aagttgcatg 2940
cccttaagga ggtattaaag aaatttccaa aggaaaacca cgaagtcttc aagtatgtca 3000
tctctcacct aaacaaggtc agccacaaca acaaggtgaa tctcatgacc agcgagaacc 3060
tctccatctg cttctggccc accttgatga gacctgattt cagcactatg gacgccctca 3120
cagccacgcg cacctaccag acaatcattg aactctttat ccagcagtgc cccttcttct 3180
tctacaatcg gcccatcacc gagcccccgg cgccaggccc agctcccgga att 3233

<210> SEQ ID NO 4
<211> LENGTH: 998
<212> TYPE: PRT
<213> ORGANISM: Homo sapiens

<400> SEQUENCE: 4

Met Ala Gln Val Ala Met Ser Thr Leu Pro Val Glu Asp Glu Glu Ser
1 5 10 15

Ser Glu Ser Arg Met Val Val Thr Phe Leu Met Ser Ala Leu Glu Ser
20 25 30

Met Cys Lys Glu Leu Ala Lys Ser Lys Ala Glu Val Ala Cys Ile Ala
35 40 45

Val Tyr Glu Thr Asp Val Phe Val Val Gly Thr Glu Arg Gly Arg Ala
50 55 60

Phe Val Asn Thr Arg Lys Asp Phe Gln Lys Asp Phe Val Lys Tyr Cys
65 70 75 80

Val Glu Glu Glu Glu Lys Ala Ala Glu Met His Lys Met Lys Ser Thr
85 90 95

Thr Gln Ala Asn Arg Met Ser Val Asp Ala Val Glu Ile Glu Thr Leu
100 105 110

Arg Lys Thr Val Glu Asp Tyr Phe Cys Phe Cys Tyr Gly Lys Ala Leu
115 120 125

Gly Lys Ser Thr Val Val Pro Val Pro Tyr Glu Lys Met Leu Arg Asp
130 135 140

Gln Ser Ala Val Val Val Gln Gly Leu Pro Glu Gly Val Ala Phe Lys
145 150 155 160

His Pro Glu Asn Tyr Asp Leu Ala Thr Leu Lys Trp Ile Leu Glu Asn

-continued

```
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Ala Gly
                245                 250                 255

Pro Ser Glu Thr Asp Asp Val Asp Glu Lys Gln Pro Leu Ser Lys Pro
            260                 265                 270

Leu Gln Gly Ser His His Ser Ser Glu Gly Asn Glu Gly Thr Glu Met
        275                 280                 285

Glu Val Pro Ala Glu Asp Ser Thr Gln His Val Pro Ser Glu Thr Ser
    290                 295                 300

Glu Asp Pro Glu Val Glu Val Thr Ile Glu Asp Asp Asp Tyr Ser Pro
305                 310                 315                 320

Pro Ser Lys Arg Pro Lys Ala Asn Glu Leu Pro Gln Pro Pro Val Pro
                325                 330                 335

Glu Pro Ala Asn Ala Gly Lys Arg Lys Val Arg Glu Phe Asn Phe Glu
            340                 345                 350

Lys Trp Asn Ala Arg Ile Thr Asp Leu Arg Lys Gln Val Glu Glu Leu
        355                 360                 365

Phe Glu Arg Lys Tyr Ala Gln Ala Ile Lys Ala Lys Gly Pro Val Thr
    370                 375                 380

Ile Pro Tyr Pro Leu Phe Gln Ser His Val Glu Asp Leu Tyr Val Glu
385                 390                 395                 400

Gly Leu Pro Glu Gly Ile Pro Phe Arg Arg Pro Ser Thr Tyr Gly Ile
                405                 410                 415

Pro Arg Leu Glu Arg Ile Leu Leu Ala Lys Glu Arg Ile Arg Phe Val
            420                 425                 430

Ile Lys Lys His Glu Leu Leu Asn Ser Thr Arg Glu Asp Leu Gln Leu
        435                 440                 445

Asp Lys Pro Ala Ser Gly Val Lys Glu Glu Trp Tyr Ala Arg Ile Thr
    450                 455                 460

Lys Leu Arg Lys Met Val Asp Gln Leu Phe Cys Lys Lys Phe Ala Glu
465                 470                 475                 480

Ala Leu Gly Ser Thr Glu Ala Lys Ala Val Pro Tyr Gln Lys Phe Glu
                485                 490                 495

Ala His Pro Asn Asp Leu Tyr Val Glu Gly Leu Pro Glu Asn Ile Pro
            500                 505                 510

Phe Arg Ser Pro Ser Trp Tyr Gly Ile Pro Arg Leu Glu Lys Ile Ile
        515                 520                 525

Gln Val Gly Asn Arg Ile Lys Phe Val Ile Lys Arg Pro Glu Leu Leu
    530                 535                 540

Thr His Ser Thr Thr Glu Val Thr Gln Pro Arg Thr Asn Thr Pro Val
545                 550                 555                 560

Lys Glu Asp Trp Asn Val Arg Ile Thr Lys Leu Arg Lys Gln Val Glu
                565                 570                 575

Glu Ile Phe Asn Leu Lys Phe Ala Gln Ala Leu Gly Leu Thr Glu Ala
            580                 585                 590
```

```
Val Lys Val Pro Tyr Pro Val Phe Glu Ser Asn Pro Glu Phe Leu Tyr
        595                 600                 605

Val Glu Gly Leu Pro Glu Gly Ile Pro Phe Arg Ser Pro Thr Trp Phe
    610                 615                 620

Gly Ile Pro Arg Leu Glu Arg Ile Val Arg Gly Ser Asn Lys Ile Lys
625                 630                 635                 640

Phe Val Val Lys Lys Pro Glu Leu Val Ile Ser Tyr Leu Pro Pro Gly
                645                 650                 655

Met Ala Ser Lys Ile Asn Thr Lys Ala Leu Gln Ser Pro Lys Arg Pro
            660                 665                 670

Arg Ser Pro Gly Ser Asn Ser Lys Val Pro Glu Ile Glu Val Thr Val
        675                 680                 685

Glu Gly Pro Asn Asn Asn Asn Pro Gln Thr Ser Ala Val Arg Thr Pro
    690                 695                 700

Thr Gln Thr Asn Gly Ser Asn Val Pro Phe Lys Pro Arg Gly Arg Glu
705                 710                 715                 720

Phe Ser Phe Glu Ala Trp Asn Ala Lys Ile Thr Asp Leu Lys Gln Lys
                725                 730                 735

Val Glu Asn Leu Phe Asn Glu Lys Cys Gly Glu Ala Leu Gly Leu Lys
            740                 745                 750

Gln Ala Val Lys Val Pro Phe Ala Leu Phe Glu Ser Phe Pro Glu Asp
        755                 760                 765

Phe Tyr Val Glu Gly Leu Pro Glu Gly Val Pro Phe Arg Arg Pro Ser
    770                 775                 780

Thr Phe Gly Ile Pro Arg Leu Glu Lys Ile Leu Arg Asn Lys Ala Lys
785                 790                 795                 800

Ile Lys Phe Ile Ile Lys Lys Pro Glu Met Phe Glu Thr Ala Ile Lys
                805                 810                 815

Glu Ser Thr Ser Ser Lys Ser Pro Pro Arg Lys Ile Asn Ser Ser Pro
            820                 825                 830

Asn Val Asn Thr Thr Ala Ser Gly Val Glu Asp Leu Asn Ile Ile Gln
        835                 840                 845

Val Thr Ile Pro Asp Asp Asp Asn Glu Arg Leu Ser Lys Val Glu Lys
    850                 855                 860

Ala Arg Gln Leu Arg Glu Gln Val Asn Asp Leu Phe Ser Arg Lys Phe
865                 870                 875                 880

Gly Glu Ala Ile Gly Met Gly Phe Pro Val Lys Val Pro Tyr Arg Lys
                885                 890                 895

Ile Thr Ile Asn Pro Gly Cys Val Val Val Asp Gly Met Pro Pro Gly
            900                 905                 910

Val Ser Phe Lys Ala Pro Ser Tyr Leu Glu Ile Ser Ser Met Arg Arg
        915                 920                 925

Ile Leu Asp Ser Ala Glu Phe Ile Lys Phe Thr Val Ile Arg Pro Phe
    930                 935                 940

Pro Gly Leu Val Ile Asn Asn Gln Leu Val Asp Gln Ser Glu Ser Glu
945                 950                 955                 960

Gly Pro Val Ile Gln Glu Ser Ala Glu Pro Ser Gln Leu Glu Val Pro
                965                 970                 975

Ala Thr Glu Glu Ile Lys Glu Thr Asp Gly Ser Ser Gln Ile Lys Gln
            980                 985                 990

Glu Pro Asp Pro Thr Trp
        995
```

<210> SEQ ID NO 5

<211> LENGTH: 3328
<212> TYPE: DNA
<213> ORGANISM: Homo sapiens

<400> SEQUENCE: 5
gggatcatgg cccaagttgc aatgtccacc ctccccgttg aagatgagga gtcctcggag 60
agcaggatgg tggtgacatt cctcatgtca gctctcgagt ccatgtgtaa agaactggcc 120
aagtccaaag ccgaagtggc ctgcattgca gtgtatgaaa cagacgtgtt tgtcgtcgga 180
actgaaagag gacgtgcttt tgtcaatacc agaaaggatt ttcaaaaaga ttttgtaaaa 240
tattgtgttg aagaagaaga aaaagctgca gagatgcata aaatgaaatc tacaacccag 300
gcaaatcgga tgagtgtaga tgctgtagaa attgaaacac tcagaaaaac agttgaggac 360
tatttctgct tttgctatgg gaaagcttta ggcaaatcca cagtggtacc tgtaccatat 420
gagaagatgc tgagagacca gtcggctgtg gtagtgcagg ggcttccgga aggtgttgcc 480
tttaaacacc ccgagaacta tgatcttgca accctgaaat ggattgggga gaacaaagga 540
gggatttcat tcatcattaa gagacctttt ttagagccaa agaagcatgt aggtggtcgt 600
gtgatggtaa cagatgctga caggtcaata ctatctccag gtggaagttg tggccccatc 660
aaagtgaaaa ctgaacccac agaagattct ggcatttccc tggaaatggc agctgtgaca 720
gtaaaggaag aatcagaaga tcctgattat tatcaatata acattcaagg aagccaccat 780
tcttcagagg gcaatgaagg cacagaaatg gaagtaccag cagaagatga tgattattct 840
ccaccgtcta agagaccaaa ggccaatgag ctaccgcagc caccagtccc ggaacccgcc 900
aatgctggga agcggaaagt gagggagttc aacttcgaga aatggaatgc tcgcatcact 960
gatctacgta aacaagttga agaattgttt gaaaggaaat atgctcaagc cataaaagcc 1020
aaaggtccgg tgacgatccc gtaccctctt ttccagtctc atgttgaaga tctttatgta 1080
gaaggacttc ctgaaggaat tccttttaga aggccatcta cttacggaat tcctcgcctg 1140
gagaggatat tacttgcaaa ggaaaggatt cgttttgtga ttaagaaaca tgagcttctg 1200
aattcaacac gtgaagattt acagcttgat aagccagctt caggagtaaa ggaagaatgg 1260
tatgccagaa tcactaaatt aagaaagatg gtggatcagc ttttctgcaa aaaatttgcg 1320
gaagccttgg ggagcactga agccaaggct gtaccgtacc aaaaatttga ggcacacccg 1380
aatgatctgt acgtggaagg actgccagaa aacattcctt tccgaagtcc ctcatggtat 1440
ggaatcccaa ggctggaaaa aatcattcaa gtgggcaatc gaattaaatt tgttattaaa 1500
agaccagaac ttctgactca cagtaccact gaagttactc agccaagaac gaatacacca 1560
gtcaaagaag attggaatgt cagaattacc aagctacgga agcaagtgga agagattttt 1620
aatttgaaat ttgctcaagc tcttggactc accgaggcag taaaagtacc atatcctgtg 1680
tttgaatcaa acccggagtt cttgtatgtg gaaggcttgc cagaggggat tcccttccga 1740
agccctacct ggtttggaat tccacgactt gaaaggatcg tccacgggag taataaaatc 1800
aagttcgttg ttaaaaaacc tgaactagtt atttcctact tgcctcctgg gatggctagt 1860
aaaataaaca ctaaagcttt gcagtccccc aaaagaccac gaagtcctgg gagtaattca 1920
aaggttcctg aaattgaggt caccgtggaa ggccctaata acaacaatcc tcaaacctca 1980
gctgttcgaa ccccgaccca gactaacggt tctaacgttc ccttcaagcc acgagggaga 2040
gagttttcct ttgaggcctg gaatgccaaa atcacggacc taaaacagaa agttgaaaat 2100
ctcttcaatg agaaatgtgg ggaagctctt ggccttaaac aagctgtgaa ggtgccgttc 2160
gcgttatttg agtctttccc ggaagacttt tatgtggaag gcttacctga gggtgtgcca 2220

-continued

```
ttccgaagac catcgacttt tggcattccg aggctggaga agatactcag aaacaaagcc   2280

aaaattaagt tcatcattaa aaagcccgaa atgtttgaga cggcgattaa ggagagcacc   2340

tcctctaaga gccctcccag aaaaataaat tcatcaccca atgttaatac tactgcatca   2400

ggtgttgaag accttaacat cattcaggtg acaattccag atgatgataa tgaaagactc   2460

tcgaaagttg aaaaagctag acagctaaga gaacaagtga atgacctctt tagtcggaaa   2520

tttggtgaag ctattggtat gggttttcct gtgaaagttc cctacaggaa aatcacaatt   2580

aaccctggct gtgtggtggt tgatggcatg cccccggggg tgtccttcaa agcccccagc   2640

tacctggaaa tcagctccat gagaaggatc ttagactctg ccgagtttat caaattcacg   2700

gtcattagac catttccagg acttgtgatt aataaccagc tggttgatca gagtgagtca   2760

aaaggccccg tgatacaaga atcagctgaa ccaagccagt tggaagttcc agccacagaa   2820

gaaataaaag agactgatgg aagctctcag atcaagcaag aaccagaccc cacgtggtag   2880

acctcttccc tcctaggctt aaagtatcag tggttgagaa gagcttttcg gacctgttac   2940

taccccaagc tgtgtaatat acttgtataa cagaaatacc ttctatacaa accttttttt   3000

ctacttttag atagaaatgt ctactttttc agcagttctg tgaattaaag agcagagtga   3060

ctgtgggtct ggaatggctg gtgtacttgg gaatgtacta tcaggatttt acagcaatgc   3120

tgggaaatga cagggaaaat gacaggaatg aatctcacca gatttttat gtactcagca    3180

gagccttgag ttacggtgtt tattttccaa tcaagtgaag atatctccta cttctcctac   3240

tggaacatct cagcttctgc agtgaagaaa aattcctgtg atagttcagt tctttagttt   3300

ttctatttga aaaaaaaaaa aaaaaaaa                                      3328
```

<210> SEQ ID NO 6
<211> LENGTH: 4529
<212> TYPE: DNA
<213> ORGANISM: Homo sapiens

<400> SEQUENCE: 6

```
aggaggagga gggtgagaga gaagctggga gagcagagaa aaggggccac cggtcgcccc     60

cccgcttccc cgcacgcgct ctccagccgc ggccgcccgc ctgccgcggt caccccggcc    120

tctgcctctg tcccccagtg atcggatcaa ggcgctgagc gaggccctgc ctgcggggcg    180

gccatgcggc ggtgacagga gcgcgaccga cacgcacggg cccctcgccc cctctcgcct    240

cccgtccgct cgccagctcc cctcagccga ggctgctccg cggcggccgc agcccgcgcg    300

cggcccacac tcgcctcccc tcggcacccc cggccccgga gctgcctgga ggcggccgca    360

ctcggggatc atggcccaag ttgcaatgtc caccctcccc gttgaagatg aggagtcctc    420

ggagagcagg atggtggtga cattcctcat gtcagctctc gagtccatgt gtaaagaact    480

ggccaagtcc aaagccgaag tggcctgcat tgcagtgtat gaaacagacg tgtttgtcgt    540

cggaactgaa agaggacgtg cttttgtcaa taccagaaag gattttcaaa aagattttgt    600

aaaatattgt gttgaagaag aagaaaaagc tgcagagatg cataaaatga aatctacaac    660

ccaggcaaat cggatgagtg tagatgctgt agaaattgaa acactcagaa aaacagttga    720

ggactatttc tgcttttgct atgggaaagc tttaggcaaa tccacagtgg tacctgtacc    780

atatgagaag atgctgcgag accagtcggc tgtggtagtg caggggcttc cggaaggtgt    840

tgcctttaaa caccccgaga actatgatct tgcaaccctg aaatggattt tggagaacaa    900

agcagggatt tcattcatca ttaagagacc ttttttagag ccaaagaagc atgtaggtgg    960

tcgtgtgatg gtaacagatg ctgacaggtc aatactatct ccaggtggaa gttgtggccc   1020
```

-continued

```
catcaaagtg aaaactgaac ccacagaaga ttctggcatt tccctggaaa tggcagctgt   1080
gacagtaaag gaagaatcag aagatcctga ttattatcaa tataacattc aagcaggccc   1140
ttctgaaact gatgatgttg atgaaaaaca gcccctatcg aagcctttgc aaggaagcca   1200
ccattcttca gagggcaatg aaggcacaga aatggaagta ccagcagaag attctactca   1260
acatgtccct tcagaaacaa gtgaggaccc tgaagttgag gtgactattg aagatgatga   1320
ttattctcca ccgtctaaga gaccaaaggc caatgagcta ccgcagccac cagtcccgga   1380
acccgccaat gctgggaagc ggaaagtgag ggagttcaac ttcgagaaat ggaatgctcg   1440
catcactgat ctacgtaaac aagttgaaga attgtttgaa aggaaatatg ctcaagccat   1500
aaaagccaaa ggtccggtga cgatcccgta ccctcttttc cagtctcatg ttgaagatct   1560
ttatgtagaa ggacttcctg aaggaattcc ttttagaagg ccatctactt acggaattcc   1620
tcgcctggag aggatattac ttgcaaagga aaggattcgt tttgtgatta agaaacatga   1680
gcttctgaat tcaacacgtg aagatttaca gcttgataag ccagcttcag gagtaaagga   1740
agaatggtat gccagaatca ctaaattaag aaagatggtg gatcagcttt tctgcaaaaa   1800
atttgcggaa gccttgggga gcactgaagc caaggctgta ccgtaccaaa aatttgaggc   1860
acacccgaat gatctgtacg tggaaggact gccagaaaac attcctttcc gaagtccctc   1920
atggtatgga atcccaaggc tggaaaaaat cattcaagtg ggcaatcgaa ttaaatttgt   1980
tattaaaaga ccagaacttc tgactcacag taccactgaa gttactcagc caagaacgaa   2040
tacaccagtc aaagaagatt ggaatgtcag aattaccaag ctacggaagc aagtggaaga   2100
gatttttaat ttgaaatttg ctcaagctct tggactcacc gaggcagtaa aagtaccata   2160
tcctgtgttt gaatcaaacc cggagttctt gtatgtggaa ggcttgccag aggggattcc   2220
cttccgaagc cctacctggt ttggaattcc acgacttgaa aggatcgtcc gcgggagtaa   2280
taaaatcaag ttcgttgtta aaaaacctga actagttatt tcctacttgc ctcctgggat   2340
ggctagtaaa ataaacacta aagctttgca gtcccccaaa agaccacgaa gtcctgggag   2400
taattcaaag gttcctgaaa ttgaggtcac cgtggaaggc cctaataaca acaatcctca   2460
aacctcagct gttcgaaccc cgacccagac taacggttct aacgttccct tcaagccacg   2520
agggagagag ttttcctttg aggcctggaa tgccaaaatc acggacctaa aacagaaagt   2580
tgaaaatctc ttcaatgaga aatgtgggga agctcttggc cttaaacaag ctgtgaaggt   2640
gccgttcgcg ttatttgagt ctttcccgga agacttttat gtggaaggct tacctgaggg   2700
tgtgccattc cgaagaccat cgacttttgg cattccgagg ctggagaaga tactcagaaa   2760
caaagccaaa attaagttca tcattaaaaa gcccgaaatg tttgagacgg cgattaagga   2820
gagcacctcc tctaagagcc ctcccagaaa aataaattca tcacccaatg ttaatactac   2880
tgcatcaggt gttgaagacc ttaacatcat tcaggtgaca attccagatg atgataatga   2940
aagactctcg aaagttgaaa aagctagaca gctaagagaa caagtgaatg acctctttag   3000
tcggaaattt ggtgaagcta ttggtatggg ttttcctgtg aaagttccct acaggaaaat   3060
cacaattaac cctggctgtg tggtggttga tggcatgccc ccgggggtgt ccttcaaagc   3120
ccccagctac ctggaaatca gctccatgag aaggatctta gactctgccg agtttatcaa   3180
attcacggtc attagaccat ttccaggact tgtgattaat aaccagctgg ttgatcagag   3240
tgagtcagaa ggccccgtga tacaagaatc agctgaacca agccagttgg aagttccagc   3300
cacagaagaa ataaaagaga ctgatggaag ctctcagatc aagcaagaac cagaccccac   3360
gtggtagacc tcttccctcc taggcttaaa gtatcagtgg ttgagaagag cttttcggac   3420
```

ctgttactac cccaagctgt gtaatatact tgtataacag aaataccttc tatacaaacc 3480
tttttttcta cttttagata gaaatgtcta ctttttcagc agttctgtga attaaagagc 3540
agagtgactg tgggtctgga atggctggtg tacttgggaa tgtactatca ggattttaca 3600
gcaatgctgg gaaatgacag ggaaaatgac aggaatgaat ctcaccagat tttttatgta 3660
ctcagcagag ccttgagtta cggtgtttat tttccaatca agtgaagata tctcctactt 3720
ctcctactgg aacatctcag cttctgcagt gaagaaaaat tcctgtgata gttcagttct 3780
ttagtttttc tatttgaaaa aaaaaaatca tttaaatgat cctttgttca cggctctcct 3840
taatgactga gtgaacagtt cctatctgta tatttgacta aaccttttcc taagctatct 3900
ctcatggttc ctatgttttt ttatcataat taaaagcaaa accatctgga tcacctaaca 3960
gtcagaggtc agtatctcag cgtgtgaatt atagaggaaa tacagagaga acctcttcca 4020
cttttacttt tcgtccaaat aaaatgcatg gtgtaccaga agttgaagat cgggttgagg 4080
attggggcta gctcgatgac actaaggccc caacatcgcg ggacctgctg tggcgcggat 4140
tcttaggaac gctgttctag ccggccccct ctccaggggt cgccgtggcc ggcattattt 4200
cctagttctt cttgtaaccc tgaggtgcca gcgcggggag tgaggagggg tcagggggct 4260
aaggatgcaa cctctgacgt tctgcgcctt cctaggagag tcttacatgt gttgagattt 4320
cacaagcaat gcgagttgta aaataccagc tctacaagaa gctaggctct gtgacggcat 4380
agttttcagt agctttatca caatattcac aatggagaat tatatgacat ggtagcagaa 4440
ataggccctt ttatgtgttg cttctatttt acctcaaatt gtagatatag ggtaatcaat 4500
aaaatccatc catgcctttc acacactaa 4529

<210> SEQ ID NO 7
<211> LENGTH: 480
<212> TYPE: PRT
<213> ORGANISM: Homo sapiens

<400> SEQUENCE: 7

Met Glu Val Ala Pro Glu Gln Pro Arg Trp Met Ala His Pro Ala Val
1 5 10 15

Leu Asn Ala Gln His Pro Asp Ser His His Pro Gly Leu Ala His Asn
20 25 30

Tyr Met Glu Pro Ala Gln Leu Leu Pro Pro Asp Glu Val Asp Val Phe
35 40 45

Phe Asn His Leu Asp Ser Gln Gly Asn Pro Tyr Tyr Ala Asn Pro Ala
50 55 60

His Ala Arg Ala Arg Val Ser Tyr Ser Pro Ala His Ala Arg Leu Thr
65 70 75 80

Gly Gly Gln Met Cys Arg Pro His Leu Leu His Ser Pro Gly Leu Pro
85 90 95

Trp Leu Asp Gly Gly Lys Ala Ala Leu Ser Ala Ala Ala Ala His His
100 105 110

His Asn Pro Trp Thr Val Ser Pro Phe Ser Lys Thr Pro Leu His Pro
115 120 125

Ser Ala Ala Gly Gly Pro Gly Gly Pro Leu Ser Val Tyr Pro Gly Ala
130 135 140

Gly Gly Gly Ser Gly Gly Gly Ser Gly Ser Ser Val Ala Ser Leu Thr
145 150 155 160

Pro Thr Ala Ala His Ser Gly Ser His Leu Phe Gly Phe Pro Pro Thr
165 170 175

Pro Pro Lys Glu Val Ser Pro Asp Pro Ser Thr Thr Gly Ala Ala Ser

-continued

```
            180                 185                 190

Pro Ala Ser Ser Ser Ala Gly Gly Ser Ala Ala Arg Gly Glu Asp Lys
        195                 200                 205

Asp Gly Val Lys Tyr Gln Val Ser Leu Thr Glu Ser Met Lys Met Glu
    210                 215                 220

Ser Gly Ser Pro Leu Arg Pro Gly Leu Ala Thr Met Gly Thr Gln Pro
225                 230                 235                 240

Ala Thr His His Pro Ile Pro Thr Tyr Pro Ser Tyr Val Pro Ala Ala
                245                 250                 255

Ala His Asp Tyr Ser Ser Gly Leu Phe His Pro Gly Gly Phe Leu Gly
            260                 265                 270

Gly Pro Ala Ser Ser Phe Thr Pro Lys Gln Arg Ser Lys Ala Arg Ser
        275                 280                 285

Cys Ser Glu Gly Arg Glu Cys Val Asn Cys Gly Ala Thr Ala Thr Pro
    290                 295                 300

Leu Trp Arg Arg Asp Gly Thr Gly His Tyr Leu Cys Asn Ala Cys Gly
305                 310                 315                 320

Leu Tyr His Lys Met Asn Gly Gln Asn Arg Pro Leu Ile Lys Pro Lys
                325                 330                 335

Arg Arg Leu Ser Ala Ala Arg Arg Ala Gly Thr Cys Cys Ala Asn Cys
            340                 345                 350

Gln Thr Thr Thr Thr Thr Leu Trp Arg Arg Asn Ala Asn Gly Asp Pro
        355                 360                 365

Val Cys Asn Ala Cys Gly Leu Tyr Tyr Lys Leu His Asn Val Asn Arg
    370                 375                 380

Pro Leu Thr Met Lys Lys Glu Gly Ile Gln Thr Arg Asn Arg Lys Met
385                 390                 395                 400

Ser Asn Lys Ser Lys Lys Ser Lys Lys Gly Ala Glu Cys Phe Glu Glu
                405                 410                 415

Leu Ser Lys Cys Met Gln Glu Lys Ser Ser Pro Phe Ser Ala Ala Ala
            420                 425                 430

Leu Ala Gly His Met Ala Pro Val Gly His Leu Pro Pro Phe Ser His
        435                 440                 445

Ser Gly His Ile Leu Pro Thr Pro Thr Pro Ile His Pro Ser Ser Ser
    450                 455                 460

Leu Ser Phe Gly His Pro His Pro Ser Ser Met Val Thr Ala Met Gly
465                 470                 475                 480


<210> SEQ ID NO 8
<211> LENGTH: 3383
<212> TYPE: DNA
<213> ORGANISM: Homo sapiens

<400> SEQUENCE: 8

gtgagcgcca ggaaggtagc gaggccagcg tcgccccggg actcgctgct caagtctgtc      60

tattgcctgc cgccacatcc atcctagcag ggccccgtcg cccaccaggc ggacaaaagc     120

ggtccgctga acaccatgcg gccgctcggc gtgccgccca ggctctgctg gtgagcgccg     180

ccaccccgcg cccaggtccc gcgagcccgc ctgccgcgca cctcgccctg ctcccagctc     240

tactccaggc cccgtccgcc cgggggcgcc gcccaccgcg cctcgctcgg gccgttgccg     300

tctgcaccca gaccctgagc cgccgccgcc ggccatggag gtggcgcccg agcagccgcg     360

ctggatggcg cacccggccg tgctgaatgc gcagcacccc gactcacacc acccgggcct     420

ggcgcacaac tacatggaac ccgcgcagct gctgcctcca gacgaggtgg acgtcttctt     480
```

-continued

```
caatcacctc gactcgcagg gcaacccta ctatgccaac cccgctcacg cgcgggcgcg    540
cgtctcctac agccccgcgc acgcccgcct gaccggaggc cagatgtgcc gcccacactt    600
gttgcacagc ccgggtttgc cctggctgga cgggggcaaa gcagccctct ctgccgctgc    660
ggcccaccac cacaacccct ggaccgtgag cccccttctcc aagacgccac tgcacccctc    720
agctgctgga ggccctggag gcccactctc tgtgtaccca ggggctgggg gtgggagcgg    780
gggaggcagc gggagctcag tggcctccct cacccctaca gcagcccact ctggctccca    840
ccttttcggc ttcccaccca cgccacccaa agaagtgtct cctgacccta gcaccacggg    900
ggctgcgtct ccagcctcat cttccgcggg gggtagtgca gcccgaggag aggacaagga    960
cggcgtcaag taccaggtgt cactgacgga gagcatgaag atggaaagtg gcagtcccct   1020
gcgcccaggc ctagctacta tgggcaccca gcctgctaca caccacccca tccccaccta   1080
cccctcctat gtgccggcgg ctgcccacga ctacagcagc ggactcttcc accccggagg   1140
cttcctgggg ggaccggcct ccagcttcac ccctaagcag cgcagcaagg ctcgttcctg   1200
ttcagaaggc cgggagtgtg tcaactgtgg ggccacagcc acccctctct ggcggcggga   1260
cggcaccggc cactacctgt gcaatgcctg tggcctctac cacaagatga atgggcagaa   1320
ccgaccactc atcaagccca agcgaagact gtcggccgcc agaagagccg gcacctgttg   1380
tgcaaattgt cagacgacaa ccaccacctt atggcgccga aacgccaacg gggaccctgt   1440
ctgcaacgcc tgtggcctct actacaagct gcacaatgtt aacaggccac tgaccatgaa   1500
gaaggaaggg atccagactc ggaaccggaa gatgtccaac aagtccaaga agagcaagaa   1560
aggggcggag tgcttcgagg agctgtcaaa gtgcatgcag gagaagtcat ccccccttcag   1620
tgcagctgcc ctggctggac acatggcacc tgtgggccac ctcccgccct tcagccactc   1680
cggacacatc ctgcccactc cgacgcccat ccacccctcc tccagcctct ccttcggcca   1740
cccccacccg tccagcatgg tgaccgccat gggctaggga acagatggac gtcgaggacc   1800
gggcactccc gggatgggtg gaccaaaccc ttagcagccc agcatttccc gaaggccgac   1860
accactcctg ccagcccggc tcggcccagc acccccctctc ctggagggcg cccagcagcc   1920
tgccagcagt tactgtgaat gttccccacc gctgagaggc tgcctccgca cctgaccgct   1980
gcccaggtgg ggtttcctgc atggacagtt gtttggagaa caacaaggac aactttatgt   2040
agagaaaagg aggggacggg acagacgaag gcaaccattt ttagaaggaa aaaggattag   2100
gcaaaaataa tttattttgc tcttgtttct aacaaggact tggagacttg gtggtctgag   2160
ctgtcccaag tcctccggtt cttcctcggg attggcgggt ccacttgcca gggctctggg   2220
ggcagatttg tggggacctc agcctgcacc ctcttctcct ctggcttccc tctctgaaat   2280
agccgaactc caggctgggc tgagccaaag ccagagtggc cacggcccag ggagggtgag   2340
ctggtgcctg ctttgacggg ccaggccctg gagggcagag acaatcacgg gcggtcctgc   2400
acagattccc aggccagggc tgggtcacag gaaggaaaca acattttctt gaaaggggaa   2460
acgtctccca gatcgctccc ttggctttga ggccgaagct gctgtgactg tgtcccctta   2520
ctgagcgcaa gccacagcct gtcttgtcag gtggaccctg taaatacatc ctttttctgc   2580
taacccttca accccctcgc ctcctactct gagacaaaag aaaaaatatt aaaaaaatgc   2640
ataggcttaa ctcgctgatg agttaattgt tttattttta aactcttttt gggtccagtt   2700
gattgtacgt agccacagga gccctgctat gaaaggaata aaacctacac acaaggttgg   2760
agctttgcaa ttctttttgg aaaagagctg ggatcccaca gccctagtat gaaagctggg   2820
ggtggggagg ggcctttgct gcccttggtt tctgggggct ggttggcatt tgctggcctg   2880
```

-continued gcagggggtg aaggcaggag ttgggggcag gtcaggacca ggacccaggg agaggctgtg 2940
tccctgctgg ggtctcaggt ccagctttac tgtggctgtc tggatccttc ccaaggtaca 3000
gctgtatata aacgtgtccc gagcttagat tctgtatgcg gtgacggcgg ggtgtggtgg 3060
cctgtgaggg gcccctggcc caggaggagg attgtgctga tgtagtgacc aagtgcaata 3120
tgggcgggca gtcgctgcag ggagcaccac ggccagaagt aacttatttt gtactagtgt 3180
ccgcataaga aaaagaatcg gcagtatttt ctgtttttat gttttatttg gcttgtttta 3240
ttttggatta gtgaactaag ttattgttaa ttatgtacaa catttatata ttgtctgtaa 3300
aaaatgtatg ctatcctctt attcctttaa agtgagtact gttaagaata ataaaatact 3360
ttttgtgaat gcccaaaaaa aaa 3383

<210> SEQ ID NO 9
<211> LENGTH: 13759
<212> TYPE: DNA
<213> ORGANISM: Homo sapiens

<400> SEQUENCE: 9
gagcgccagg aaggtagcga ggccagcgtc gccccgggac tcgctgctca agtctgtcta 60
ttgcctgccg ccacatccat cctagcaggg ccccgtcgcc caccaggcgg acaaaagcgg 120
tccgctgaac accatgcggc cgctcggcgt gccgcccagg ctctgctggt gagcgccgcc 180
accccgcgcc caggtcccgc gagcccgcct gccgcgcacc tcgccctgct cccagctcta 240
ctccaggccc cgtccgcccg ggggcgccgc ccaccgcgcc tcgctcggtg agtttcttcc 300
acttccacct tccctgggcc cggcccttcc cgcccccggc ccggcccgcc tggcacccga 360
atcgcttggt ccgtttgccc tgtggcccct acctttgggg ctcgccttgg ccctgccaga 420
gaccggaaac cctggttata gggactttaa ccagagggag tatttggtta cctgggcaca 480
gcaggcccgc ctcgggcctc ttgtcttccc atttctcgga gccacaggcc acgagaccct 540
ggcattccca gagcctcgca aagcaccccc gcctcccggc ccccgaactg gggcctttgt 600
ctcggccgcc cccaatcccc aggccaccgc ggcggatgcg tccgagccgg gccgccgagc 660
ggcggctgca cctgccggct ggtcccgtgc gccggctttt cgcggcttaa cccagctcgc 720
tcctgcttgc gcccccgcgc gctgcgcccc gcagcccttt atcctgtgtg actggggtgc 780
gtgtggggga gagcgccggg tctggaagtc tccccccgcc ccaagccgga gtcggaatcc 840
gtttagtggg atttcaataa gaatggggcc gccgcgggct tgaagatctg ccgccggtag 900
gcgtagacgg cgttctggat ctgtctgaaa acggggcatt taaaattatt ctgtggcggc 960
caggcttgaa ctccgcgttg ctccaaccac gaggggaaag gccccgcgtt cagggacccc 1020
gtgtgtggcg aacgctcctt taccggaaaa caaggaagga aattcgttgt tttggaaaaa 1080
gcctcctctc ccgaggtcgg gaacatctgg tggtgagctc caggtctacg caggcacccc 1140
gtgctaggat tcgtttatga gcaggcagga ttcgagaacc aggtagggcc cgtgcggcag 1200
ccgaggcgtc tggggagcgt ttcccagccg ggctgacaaa ttgcagacaa attgtgccta 1260
acgaaacgga tttaccagtt gtcaggccgc cggccccggc cgctccaaat aaaccgtggc 1320
tgttcgtgga ggagggagaa gcacggcccg attgtctccg ggtctcagca gggttccgcg 1380
gggagcctgc caggcttgaa ggtaggggtc agaagcgata tagaatctcg gaggcgcctg 1440
ggtccagggt gccgagacac ctaggacgtg ggggccacag actctacgat tcccaaagac 1500
acagaacagt aatgaggtgg gagagcctgc actgatgccg agggagggag ccttctgctt 1560
taaggggctg gaattgaacc tcaaggagca ggaggggccg ttatagcagt agtccccccc 1620

-continued

```
ttgggaaccc ccccggaggg atggctgctg gcctgagatc taatgccccg gctttaaggg   1680
aacttctgaa cccatctgct aaggcacccc acttcctccc cgtacccctc aaggtttatt   1740
gccagtgtgg ggctgggagg ccgctgggtt gcgaattaaa tttctctatg gaaggtagtc   1800
ccttagcaaa tgggtttcct tgacacccca cccccagccc cacaccgcgg gccaattagc   1860
tgcccataag gaaaaggcga gaagaattag gttacaaagg gagggcaaac ttatggtccc   1920
aaaggggccg cctcggatga gctaacttta aacaaagggc tcagaggggg ggggggggctg   1980
gacggccggg gagacctggg catctctgtg tccccacctg gcacccgcgg cttagtagag   2040
gcctgagaag cactctagaa ccgggcacca gatctgctac ctccccagct cccaggcaga   2100
agcacccagg tcaaatggtg gcgatcgccg ctgtgagttc tcgggccaaa agggtccttc   2160
gaaaattctg cttcctggct gaccttctcc agtcctcaga gaaatcttgt tcccaagtaa   2220
ggaaagtgac agcttcttaa tgtgatcaaa ggcagcgcca gcatttccaa ctatactccc   2280
gaacgaacaa agtactgaaa aagggaacgc gtccctctaa aggtgttttg ggaccccaa   2340
agttccagcc cataaattgg agtaaatctg ctctcaccag gcctggaaca gcgcctcaag   2400
accccagcag attctggggg ctgcgttgac cctccccggg agtttgtttg gggcccaagg   2460
tgggaggacc atgtcttcgg cctaatgggg aggggcccgg ttggtgtccc tcggtctgcc   2520
tggcacacac agacattgtc gagcgcgggt ccctctttat tggccagctg ggcgccctgc   2580
tacttggcgt cgcatttctc tctcccaggc gggttcgttt ccgccagaga atgcagcagt   2640
cccgcatcct acgcaggacc tgcaaccgag gtggaggctt cggtcaagcc ggctcctgcc   2700
tgcgttgtcg aggaaggcaa ccccaaggcc tgaaaggacc tggcagaact cctgtttcct   2760
ttttttcctc tacaccggat tgcgggcaag gaggctggtt cgggtctccc gaggcccctg   2820
ctcaagcact ccttaaccgt cctgctaagc ccctctgtgc ggcgattttc tgagctgccg   2880
agcggggtaa ttaaatcccc tccctcgctc cgctctgcgt caggcaggcg gcagcacagg   2940
gctgacgttt gggcagggga ctcagccagg ctggccacct ccactaccgc agtggccggg   3000
accctgccgc ggaggggtta gacgccgagc tcgctgcgct gaaactggga atacacacgg   3060
aacggggagg gggagggtaa tttttaccgc gccggtggga gaaaaaggcg aattacctgc   3120
tttcccgagg gacgcgcgta gccacttccc tgagagccgc ggcaccgatc gcggccgggc   3180
gggaagcttc cgctcggtcc tggcgttcac agcccagcgg ccagctgctg gtctgcctcc   3240
cgcgctgggt cccagggttc gcgctcgagc ggggcagctt tgccggacac gggggattat   3300
ccctggggac gcggtgtctt tcagagggtc ttgctagtct ccggagacgc caaataggct   3360
cgagctccgc ggcgatctca ttttacgagt tgatgaagaa tcgtaagcta aaggatggga   3420
aaagttgaga gacagacgga cggagagaca gtgggccccg gcgggaccgc acgcgttgag   3480
gggaacgcca accgggaggc acggagactg ctcacctgcc cggcctggcc gcggaggccc   3540
ggcgccaagg gcctcgcgct cggcctcccg ccccctgcgc ggcttcccgg gctggcgccg   3600
gcctccgctc ccgcagagtg gagttccgag cagaccgggc tccgcgcgct ccagcgtgga   3660
ggggagcggg aggcttagca ggcggctcgg gcaggcgggt cccccaaggg cacgagacgc   3720
gctggttccc agcccaatgg agctctgcgc cccccagccc cgcgctttac ctgcgctgag   3780
gcctcggaca gacaaacgga cgccagacgc ctaggcagga ggaggcctca gcctgagccc   3840
gcggcccctt ggcgctgccc tgaactggcc tgggaggggg tgacgggggc gcgcccgcgg   3900
agctgggccc agccgggcgc ccccggagcc gaggggaccg agggctttcc tccctcctcg   3960
gattattaaa aagttcattt cctggcgaat cgggtgacgt caggggctcg gcgtcgcggt   4020
```

-continued

```
ggcggggccg cccggccgga gaagccgcct ccagttaccc aattaccgac tgtcaatccc   4080
gccgcccctc ccccactctc ccgggggtgg ccgggacccc agccctcctc ctgcccccga   4140
cccacctggg ggccctctgg acatctaccc cgggagcctc gggcccaaca gggaagaggg   4200
ctggaggacg ctgttgagtc cccccagtac tcggcacctg tctaggtccc ccaaaatgcc   4260
tttgtcctgg acctccctcc tcggcccggg gctcccttcg agcctccgtc tccccagtct   4320
gtacaatggg agggaggaag acttgtgcgc ccggcccaca cgaaccatag agccgatctc   4380
cgggctagaa gtgagtgggg agcacttcca ggtgacttag aagacggaga cctcagacca   4440
ccgcctcccc ctcaccagag gccacctcgg ggaccccccc cggaggaaaa aaaatgccac   4500
ctcttgcccg gggcgtctc cctccagctg gcgccggcgc cagtccgggt ctccacggcc   4560
tcgccccagg caattgggcc cgttggcctg cgaaggccac gcccggggag gggtgccccc   4620
tccccctttc tggagccacc ggccgggcca cctccactgg gtcaagcaca gccctgagcg   4680
gccgcgtgtc cgaggcccag gtgccctcta gagccctgta gttcctgccc ctctctgccc   4740
ctctcggctc ctgctgttcc gccgctgtcg tccgaaccat cccaaccccc agtccaccca   4800
gacagcgccc gagctagggg agggaacggt ctgggtaggt aactgcgctc ggactgacca   4860
cgttcagcgg tgaaggagcg tggcggggtt agggtctcgg ggagaggcca tccagagggt   4920
gtgcggcccg ggctcctggg gagggggcag ttggtggtta gttactgcta gggaggccca   4980
gagcatcgag ggatcccgga gtgttcgcaa gaggggctgc aggggtcggg ccttggggtg   5040
agggtccctt agtggtgggg cgcgttggca gcaggggccg ccaggagcgc gcagggaggg   5100
ggcccgccgg ctgagggggg ccggcccgcg ggtcagtccc ggagtccagc ggttcgggaa   5160
ttgcggacgc agccaatggg aggcggaggc tgggaggcgc gcggcgttga ttggctggct   5220
tgggcttctt aggcgtgcgc ggcccccgct tcatgtctgt gcaggagtcg gcagctggcg   5280
ccagggcggc cggaggatgc cgaggggccg gagccgggag ggcccgaggc cgaggcgcac   5340
tctaccccca gctcctaccc tgtaagcccc gccagcctcc ggacgtgctg tccctgggcc   5400
cgtcgccctc ggggctcccg ccggaactcc ttcactctca gaggccgagt ccctcccctc   5460
cccacggctg cgtgtgtaag tttggggttt gagagccggc tgggggcctg gggcgctcct   5520
agctttgagg ggactctggg gggacttagg gcggggggcc aggctgcggg cgactgcttt   5580
ggtgtgcttt gttgagaggt cctgattgtg ccgcttagta ctgcgctcag gggggctgcgt  5640
gtgcatgttt tcggggttga gatcagtatg tgtatctggc gccaagtgtg ggtgtgtgcg   5700
tgtcgctggg atcaagtgcc acactgggtg cccgggcgcc tgtctccaac ttttgagtct   5760
gtgttcatgt gtttgtctac cgggcggggg ggctcagtgt gagtgtctga ctgaagtgct   5820
gctctgtgcg tttgttgggg tcactggtgt cgggacccgt ccccgggcgt gaccccatgt   5880
gcacgggtgt gtgattctgg agccgcgggt caccacgtga gtgtgcgtgg ctgaaccccc   5940
tcccccgcct tcctttcgtt ttgagccttg ggctttcctc ccacccggga ctggtgctct   6000
ttctcgccgg atctgggctg gggctccgtg gcgtgcggga cacctcgtgg tgggactttg   6060
gggggtgtca ggcgctggcg gcacgcctca ctccccctc ctcgcgcagg gccgttgccg    6120
tctgcaccca gaccctgagc cgccgccgcc ggccatggag gtggcgcccg agcagccgcg   6180
ctggatggcg cacccggccg tgctgaatgc gcagcacccc gactcacacc acccgggcct   6240
ggcgcacaac tacatggaac ccgcgcagct gctgcctcca gacgaggtgg acgtcttctt   6300
caatcacctc gactcgcagg gcaaccccta ctatgccaac cccgctcacg cgcgggcgcg   6360
cgtctcctac agccccgcgc acggtgagca ctgggcccgt ggtgatgaga acccaggcgc   6420
```

-continued

```
cgcgcgccag gcgagggagg ggaggagggc ccgtctgctt gcttcccgga tgtaggatcc   6480
gcaggaatcg agctgctgaa aaattggggc gggagaggtg ggagcagcgg ccgattgggg   6540
agggtctggg acccacaggg tttctgccca cttccagctg gcctgtgagg gttccctgta   6600
gggtctgtcc ggtggggttc cttctatgcc acttgtcctt cagcttggac tgacattcct   6660
gattattacc ggtggggtat tatgtttctg gctttctttg gggaggggat gactgctggt   6720
tctgggagtc gtgatctcaa tgtctgtcag gggcgtccct agctctgcct accctgatct   6780
ttctgcccac cctgatcctc tctctctttg cccgcagccc gcctgaccgg aggccagatg   6840
tgccgcccac acttgttgca cagcccgggt ttgccctggc tggacggggg caaagcagcc   6900
ctctctgccg ctgcggccca ccaccacaac ccctggaccg tgagcccctt ctccaagacg   6960
ccactgcacc cctcagctgc tggaggccct ggaggcccac tctctgtgta cccaggggct   7020
gggggtggga gcgggggagg cagcgggagc tcagtggcct ccctcacccc tacagcagcc   7080
cactctggct cccacctttt cggcttccca cccacgccac ccaaagaagt gtctcctgac   7140
cctagcacca cgggggctgc gtctccagcc tcatcttccg cggggggtag tgcagcccga   7200
ggagaggaca aggacggcgt caagtaccag gtgtcactga cggagagcat gaagatggaa   7260
agtggcagtc ccctgcgccc aggcctagct actatgggca cccagcctgc tacacaccac   7320
cccatcccca cctacccctc ctatgtgccg gcggctgccc acgactacag cagcggactc   7380
ttccaccccg gaggcttcct gggggaccg gcctccagct tcacccctaa gcagcgcagc   7440
aaggctcgtt cctgttcagg taaaggcagg tgctggggac ttcgtggaag aggggagcat   7500
ttgcgttttt gtggtgggga gctgtgactt gggagaggtg gcagtgttgg tttcccagat   7560
ctggggatgg gtgatgtctc gctctaatag cccccagcag atgtttgaga cccccgggtc   7620
agggagagga gactctaaaa cttttgccat tttcttaagt gcttccagtg tacccccaaa   7680
gttcagttcc ttgccccagg gttggtcact gcctgaccag aacatagaac aggaattccc   7740
cctttccctc cctgaatctt aagtgaaaat tcaagccacc tcaggactta gtatgtgaag   7800
cgagggaagt gactctgtat gtgcatgtgt ttgggagcgt gtgtgcatgt gtatacgtgt   7860
gtctgtgtgc atgttgtgtg tgcatgtttc aggcactccg gaggttccag accattaagg   7920
aatctgggtc tctaactcaa tcagtctgat cttgggattt cgatggctcc ctgatctcct   7980
cgggagattt tccccagagc aaaattccca ggacctgctc ctgctccctg ccctcgccag   8040
gcccttccct ctccctccct gagggctgga gtgaggggat gaagctgcag tgcccccgcc   8100
ccttttcccg cagctggctg ggccaaaact gggtttgtcc aagaatctgg ccacagagca   8160
taaacccaga aactcgtggc tagtgtggag ttcttgctgt ccatgtctct ttcccgaatc   8220
cctttgagcc acagaggggg aaggttttta aaacagttac tcctgagtgc aggaaccacc   8280
ttctcttgcc aggctgtact cctcatttag tttaaactaa atcaagaata acttcctggg   8340
gaacacgatg ccagccagtg atcctgctca acttggtccc cagccccagc ccccgctggc   8400
cccagcaccc gctgagcccc ggctcagggt cctagttctg ctcagacccg tcagcttgcc   8460
ttttcttggt cctttctcct gtttgttttg cattttattt gaattccaga tggtctttta   8520
attgaaaaaa aaaatacaaa caaaaaaaac ccaggccact tatctaaaaa agaaagagct   8580
tattatttat tttattttaa agaacaacaa cttcgatcca ttatttccag gactcagaaa   8640
aattctagag ctttggtgga agaggagaaa agttggggag aaagagggaa atgcttctgg   8700
acttagagca gaaagacggg gtggggcaga cacagttggg tagaaaggag agggacaaaa   8760
gaggagaggg ggagagacgc gccagagcgg gaaggagaga gcctcctggg cccagccagg   8820
```

-continued

```
ttgagctggg tgactcctgc caccacccta ccctcggcaa agtttgcagt aaataccctc   8880
ctggttgctc cagaacgcct ggggccctgg gcccctcctc ccctcctcct tcgtttccat   8940
ccctcctggt gaggattgga agcaggggat ttggctttaa acgactctgg acctgtgccc   9000
cctcccatgt gggagaccct ctcgtccctc ttcctgccca ggctgttgca gccaggccca   9060
ggccaaccgt gtgcctgaga ggcaccggca ctgctcggct ggctgctttc ctgccctgga   9120
ctccctcccg agaacttgcc ggttaagcag gcccccgtgt ctctccctgt tcccctgcag   9180
aaggccggga gtgtgtcaac tgtggggcca cagccacccc tctctggcgg cgggacggca   9240
ccggccacta cctgtgcaat gcctgtggcc tctaccacaa gatgaatggg cagaaccgac   9300
cactcatcaa gcccaagcga agactggtag gagcgggcac aggtggctgg gagggggctg   9360
ctgggcagga gctggcggtt aattacaggg gaaaaaaact ccttcaaatg cagacgcttt   9420
gccgcttgaa atcctctttt atcatgaaaa gcactgggat gtcagttggg gtcgtctctc   9480
tttctggcca gattctttcg ggccagattt cctcctcggg tatagggagc ccaccgggca   9540
cccttgcgcc accccactct gctccgggat ccccgaagtt gagtgtccac gggccggact   9600
cctgtcctct ggcctctgct tagctctttt ttaaaaatag ggccatgaag tacttttcct   9660
tgtggctcag ccctccccga cagccccgct cacaagctcc tcgtgcttat ttaaataaaa   9720
cacaaactca caccggccac taaaaaaacc tgccctttat tatttttcca tggagtcacc   9780
tatactgtgt attttcattt gagtgatttt aaaaaaatgc cctttcggat ctcctgccgg   9840
agtttcctat ccggacatct gcagcctgaa gataaggaaa cttcgtgtat ctgtttccgg   9900
actctgcgag tttttagagt ctcctcagct cagtcctgcc tctcgctggg ctgttttgaa   9960
atttctaata ccctccactc tgcaaataat gcgtaaaatg ctaagaataa taaatatatt  10020
ttttcagggc gaagtgattt atgaggctta aatcgttccc tgctttgggg gccttttttt  10080
cccctggagc gagggcgggg tgaggcccgg gtgggggtag aggtggagga cgcggcgttg  10140
gcccctgagt cagaattcca gcttcaggct gcttactcac ccctccctgc ccccgcggct  10200
gcagtccctc tgtcccttct gtgaccaggc ttgggcctgg ggctgttcca ggctctgcag  10260
gcctcagccc ccagcccccc acactcacca cctggtgcac tcccgcctgc agttctctgg  10320
gaagtgttgg gggacccccct ctgtcactgt ggggctggcg ttggtggaac cgggagaggg  10380
gatctgtttt cttgggtaaa gcctccctct agcttctctc tgcaaggacc aggcgctcat  10440
ttccagaccc tacctctgcc aggcatttcc tgagggacta ggactcagag gggctgcggg  10500
gtggttaaag ctctaagggt tggggtatgg ggggctggat gggggggatc agcactcaca  10560
tcagctggag agatggaaaa gttctgtgtc tgcactgccc actgtggtag cccctggcca  10620
catgtgaata ttgatcactt gaaatgtggc tcgtgcaatt gagggaactg ggtttttaat  10680
tttgttaatt tgtagttaga tcttatttaa atggctgcct gtggccagct gctacagtgt  10740
tggacggtgc agctctgcac tctgtaaacc tgcgctggcc tcagcgacac tgactcaccc  10800
aggattatgg attttgagcg gagtcgtgct agaggagaca cagaatcggc cccagatcca  10860
ggggctcgag ggggaccaag ccggctcagc ctcaggatgc ctgtgctact agagagccct  10920
tctcagggcc tcagtttccc catttatgga gttagagcgc agggtagttg gggggaggtag  10980
ctaattctcc tctgtagctc ttgcaatccc gttgattcta acatcaggct tctgagagtt  11040
ctttattcca aagttctgtg agtcttgact tatttcgttc tcaaattcta aaattccatg  11100
gttctgagat gctttgattc ccatgtgaga tttagccctc cttgactgag ctggtgggga  11160
ctgggggtgg agcgagggtc agggaggggg gtcgaggtgg gcgtgggagt ccagcctgct  11220
```

-continued

```
gacgctgcct tgccctccca gtcggccgcc agaagagccg gcacctgttg tgcaaattgt  11280
cagacgacaa ccaccacctt atggcgccga aacgccaacg ggaccctgt ctgcaacgcc  11340
tgtggcctct actacaagct gcacaatgtg agtgcgcccc gccccggcca ccccgcccct  11400
cccaggggac ctctgcgctt tgtgctgcca ggcaagaggc cccagccaca atatccagct  11460
tggcttggct tgggaagctg ctgccctgag tgagcgccag aagggcttcc cgtaagaggg  11520
gtgccttgcc tctgctcagg aggtggagct ggctaggaca gggtctcgga ctagggaagt  11580
ggtttctctg cttaaaaagg gtcagggtgg gggggaggac ttcagttggc tgggcagtgc  11640
tggcatgcgg tgggcagagc cagggagggt gtgggtcagc cccatatgcc agaacccgcc  11700
cttcctggaa tggtagccat ctggtgatgg gactatgaag gtcgggcaca attcctggct  11760
tcctgggacc ctcagcttga cctgcctctg gtccacgctg tggcggggtg ggaggaatgt  11820
tgctggagga aggaactggc cctctgaaaa ctggtggttg cctctaggtt aacaggccac  11880
tgaccatgaa gaaggaaggg atccagactc ggaaccggaa gatgtccaac aagtccaaga  11940
agagcaagaa aggggcggag tgcttcgagg agctgtcaaa gtgcatgcag gagaagtcat  12000
ccccccttcag tgcagctgcc ctggctggac acatggcacc tgtgggccac ctcccgccct  12060
tcagccactc cggacacatc ctgcccactc cgacgcccat ccacccctcc tccagcctct  12120
ccttcggcca cccccacccg tccagcatgg tgaccgccat gggctaggga acagatggac  12180
gtcgaggacc gggcactccc gggatgggtg gaccaaaccc ttagcagccc agcatttccc  12240
gaaggccgac accactcctg ccagcccggc tcggcccagc accccctctc ctggagggcg  12300
cccagcagcc tgccagcagt tactgtgaat gttccccacc gctgagaggc tgcctccgca  12360
cctgaccgct gcccaggtgg ggtttcctgc atggacagtt gtttggagaa caacaaggac  12420
aactttatgt agagaaaagg aggggacggg acagacgaag gcaaccattt ttagaaggaa  12480
aaaggattag gcaaaaataa tttattttgc tcttgtttct aacaaggact tggagacttg  12540
gtggtctgag ctgtcccaag tcctccggtt cttcctcggg attggcgggt ccacttgcca  12600
gggctctggg ggcagatttg tggggacctc agcctgcacc ctcttctcct ctggcttccc  12660
tctctgaaat agccgaactc caggctgggc tgagccaaag ccagagtggc cacggcccag  12720
ggagggtgag ctggtgcctg ctttgacggg ccaggccctg gagggcagag acaatcacgg  12780
gcggtcctgc acagattccc aggccagggc tgggtcacag gaaggaaaca acattttctt  12840
gaaaggggaa acgtctccca gatcgctccc ttggctttga ggccgaagct gctgtgactg  12900
tgtcccctta ctgagcgcaa gccacagcct gtcttgtcag gtggaccctg taaatacatc  12960
ctttttctgc taacccttca acccccctcgc ctcctactct gagacaaaag aaaaaatatt  13020
aaaaaaatgc ataggcttaa ctcgctgatg agttaattgt tttattttta aactcttttt  13080
gggtccagtt gattgtacgt agccacagga gccctgctat gaaaggaata aaacctacac  13140
acaaggttgg agctttgcaa ttctttttgg aaaagagctg ggatcccaca gccctagtat  13200
gaaagctggg ggtggggagg ggcctttgct gcccttggtt tctgggggct ggttggcatt  13260
tgctggcctg gcagggggtg aaggcaggag ttgggggcag gtcaggacca ggacccaggg  13320
agaggctgtg tccctgctgg ggtctcaggt ccagctttac tgtggctgtc tggatccttc  13380
ccaaggtaca gctgtatata aacgtgtccc gagcttagat tctgtatgcg gtgacggcgg  13440
ggtgtggtgg cctgtgaggg gcccctggcc caggaggagg attgtgctga tgtagtgacc  13500
aagtgcaata tgggcgggca gtcgctgcag ggagcaccac ggccagaagt aacttatttt  13560
gtactagtgt ccgcataaga aaaagaatcg gcagtatttt ctgtttttat gtttatttg  13620
```

-continued gcttgtttta ttttggatta gtgaactaag ttattgttaa ttatgtacaa catttatata 13680
ttgtctgtaa aaaatgtatg ctatcctctt attcctttaa agtgagtact gttaagaata 13740
ataaaatact ttttgtgaa 13759

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 10
aguaucagug guugagaag 19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
gaaccggaag auguccaac 19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 12
ggauugugug gaauguaag 19

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 13
accgagagag gaaacacaau a 21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
gaaucggaag auguccagca a 21

<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 15
caaugaucuc uaugugga 18

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
caccactcaa acgctgacat gta 23

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ccaactgcca ataccagtgg a 21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
aaagaactgg ccaagtccaa agcc 24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
aagcacgtcc tctttcagtt ccga 24

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gtcactgacg gagagcatga 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gccttctgaa caggaacgag 20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
ctgtcatgct aatggtgtcc c 21

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
tgctgcttcc tggtcctaaa ata 23

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
ctcggctcac gcagaactt 19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
gctgcacaga tagcgtccc 19

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
gggcaacagc agcagcaacc aca 23

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
tcgctcggca tttcgcattt ttat 24

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
gaatggagag agaattgaaa aagtggagca 30

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
caatccaaat gcggcatctt caaac 25

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gccctgcctg tggtctcact ac 22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
caaagcattg cccattcgat 20

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
aaagagctgg ccaagtccaa ggct 24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
aagcacgccc tctttcggtt ccaa 24

<210> SEQ ID NO 34

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cacgccaccc aaagaagtgt 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ccgccttcca tcttcatgct 20

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gctctgctac cccgtagga 19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gttggaggaa agccacacac 20

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gcactggacc ctggctttac tgctgta 27

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gaacttgatc acttcatggg acttctgctc 30

<210> SEQ ID NO 40
<211> LENGTH: 19
<212> TYPE: DNA

-continued

<213> ORGANISM: Artificial Sequence
<220> FEATURE:
<223> OTHER INFORMATION: Description of Artificial Sequence: Synthetic primer

<400> SEQUENCE: 40
cagacgccac tgtcgcttt 19

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
tgtctttgga actttgtctg caa 23

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Arg Arg Lys Arg Arg Arg
1 5

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gtaaatgggc ttggggagct g 21

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
ggcggctgca ggggcgtct 19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
gtagtcgtgc caccagtag 19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
agacttggca tactcgctg 19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47
guagucgugc caccaguag 19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48
agacuuggca uacucgcug 19

<210> SEQ ID NO 49
<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
gatccccgta gtcgtgccac cagtagttca agagactact ggtggcacga ctactttttg 60
gaaa 64

<210> SEQ ID NO 50
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
gatccccaga cttggcatac tcgctgttca agagcagcga gtatgccaag tctttttgg 60 aaa 63

<210> SEQ ID NO 51
<211> LENGTH: 2936
<212> TYPE: DNA
<213> ORGANISM: Homo sapiens

<400> SEQUENCE: 51
ttttctaact tctgggactc tttgcgcaac tgctaggatt tctcaagtgc atgtggcaac 60
acagcccagc tccgggtgga aaccagcagg gctctggagg ggctcggaga ccaggggagc 120
tgtcaaggct gcggcgggga ccagagagga gcctggcggg ggtggctggg tggctggggg 180
aatcccccca acttcccatc gcaggcgcag ctctctcggc cgcctatttc ctccgaaacc 240

```
cgcgctgcgg agcagcccag tgcatagagt tcaacacttc cccttgttgt ggaaagtaaa    300
ggagcctcac taccaccttt ttttctttgc gttttcttac tgctggtcct gggagccttt    360
tccttcggag cagcagccct gtccggcatc tgtcttgagc tgccagcaag gaaagtccat    420
cagcttgata atggaggaga acaatgactc cacggagaac ccccaacaag gccaagggcg    480
gcagaatgcc atcaagtgtg ggtggctgag gaagcaagga ggctttgtca agacttggca    540
tactcgctgg tttgtgctca agggggatca gctctattat ttcaaagatg aagatgaaac    600
caagcccttg ggtactattt ttctgcctgg aaataaagtt tctgagcatc cctgcaatga    660
agagaaccca gggaagttcc tttttgaagt agttccagga ggcgatcgag atcggatgac    720
agcaaatcat gagagctacc tcctcatggc aagcacccag aatgatatgg aagactgggt    780
gaagtcaatc cgccgagtca tatggggacc tttcggagga ggcatttttg gacagaaact    840
ggaggatgct gttcgttatg agaagagata tgggaaccgt ctggctccga tgttggtgga    900
gcagtgcgtg gactttatcc gacaaagggg gctgaaagaa gagggtctct ttcgactgcc    960
aggccaggct aatcttgtta aggagctcca agatgccttt gactgtgggg agaagccatc   1020
atttgacagc aacacagatg tacacacggt ggcatcactt cttaagctgt acctccgaga   1080
acttccagaa ccagttattc cttatgcgaa gtatgaagat tttttgtcat gtgccaaact   1140
gctcagcaag gaagaggaag caggtgttaa ggaattagca aagcaggtga agagtttgcc   1200
agtggtaaat tacaacctcc tcaagtatat ttgcagattc ttggatgaag tacagtccta   1260
ctcgggagtt aacaaaatga gtgtgcagaa cttggcaacg gtctttggtc ctaatatcct   1320
gcgccccaaa gtggaagatc ctttgactat catggagggc actgtggtgg tccagcagtt   1380
gatgtcagtg atgattagca aacatgattg cctctttccc aaagatgcag aactacaaag   1440
caagccccaa gatggagtga gcaacaacaa cgaaattcag aagaaagcca ccatggggca   1500
gttacagaac aaggagaaca ataacaccaa ggacagccct agtagacagt gctcctggga   1560
caagtctgag tcaccccaga gaagcagcat gaacaatgga tcccccacag ctctatcagg   1620
cagcaaaacc aacagcccaa agaacagtgt tcacaagcta gatgtgtcta gaagcccccc   1680
tctcatggtc aaaaagaacc cagcctttaa taagggtagt gggatagtta ccaatgggtc   1740
cttcagcagc agtaatgcag aaggtcttga gaaaacccaa accacccccca atgggagcct   1800
acaggccaga aggagctctt cactgaaggt atctggtacc aaaatgggca cgcacagtgt   1860
acagaatgga acggtgcgca tgggcatttt gaacagcgac acactcggga accccacaaa   1920
tgttcgaaac atgagctggc tgccaaatgg ctatgtgacc ctgagggata acaagcagaa   1980
agaacaagct ggagagttag gccagcacaa cagactgtcc acctatgata atgtccatca   2040
acagttctcc atgatgaacc ttgatgacaa gcagagcatt gacagtgcta cctggtccac   2100
ttcctcctgt gaaatctccc tccctgagaa ctccaactcc tgtcgctctt ctaccaccac   2160
ctgcccagag caagactttt ttggggggaa ctttgaggac cctgttttgg atgggccccc   2220
gcaggacgac ctttcccacc ccagggacta tgaaagcaaa agtgaccaca ggagtgtggg   2280
aggtcgaagt agtcgtgcca ccagtagcag tgacaacagt gagacatttg tgggcaacag   2340
cagcagcaac cacagtgcac tgcacagttt agtttccagc ctgaaacagg aaatgaccaa   2400
acagaagata gagtatgagt ccaggataaa gagcttagaa cagcgaaact tgactttgga   2460
aacagaaatg atgagcctcc atgatgaact ggatcaggag aggaaaaagt tcacaatgat   2520
agaaataaaa atgcgaaatg ccgagcgagc aaaagaagat gccgagaaaa gaaatgacat   2580
gctacagaaa gaagtggagc agttttttttc cacgtttgga gaactgacag tggaacccag   2640
```

-continued

```
gagaaccgag agaggaaaca caatatggat tcagtgagcc tgctttcgcc tgctgtctct   2700

gatggctctg gcaaggactc cagggattct ggtgggatat gacttagaac caggtggctg   2760

gtcacctgga tgtacagaag tctaactggt gaaggaatat catttacaga cattaaacat   2820

ccatatctgc aatgtgtacc aaagttatat catgccccat aatgctactg tcaagtgtta   2880

caactggata tgtgtatata gagtagtttt tcaaaagtaa actaaaaatg agaagc        2936


<210> SEQ ID NO 52
<211> LENGTH: 748
<212> TYPE: PRT
<213> ORGANISM: Homo sapiens

<400> SEQUENCE: 52

Met Glu Glu Asn Asn Asp Ser Thr Glu Asn Pro Gln Gln Gly Gln Gly
1               5                   10                  15

Arg Gln Asn Ala Ile Lys Cys Gly Trp Leu Arg Lys Gln Gly Gly Phe
            20                  25                  30

Val Lys Thr Trp His Thr Arg Trp Phe Val Leu Lys Gly Asp Gln Leu
        35                  40                  45

Tyr Tyr Phe Lys Asp Glu Asp Glu Thr Lys Pro Leu Gly Thr Ile Phe
    50                  55                  60

Leu Pro Gly Asn Lys Val Ser Glu His Pro Cys Asn Glu Glu Asn Pro
65                  70                  75                  80

Gly Lys Phe Leu Phe Glu Val Val Pro Gly Gly Asp Arg Asp Arg Met
                85                  90                  95

Thr Ala Asn His Glu Ser Tyr Leu Leu Met Ala Ser Thr Gln Asn Asp
            100                 105                 110

Met Glu Asp Trp Val Lys Ser Ile Arg Arg Val Ile Trp Gly Pro Phe
        115                 120                 125

Gly Gly Gly Ile Phe Gly Gln Lys Leu Glu Asp Ala Val Arg Tyr Glu
    130                 135                 140

Lys Arg Tyr Gly Asn Arg Leu Ala Pro Met Leu Val Glu Gln Cys Val
145                 150                 155                 160

Asp Phe Ile Arg Gln Arg Gly Leu Lys Glu Glu Gly Leu Phe Arg Leu
                165                 170                 175

Pro Gly Gln Ala Asn Leu Val Lys Glu Leu Gln Asp Ala Phe Asp Cys
            180                 185                 190

Gly Glu Lys Pro Ser Phe Asp Ser Asn Thr Asp Val His Thr Val Ala
        195                 200                 205

Ser Leu Leu Lys Leu Tyr Leu Arg Glu Leu Pro Glu Pro Val Ile Pro
    210                 215                 220

Tyr Ala Lys Tyr Glu Asp Phe Leu Ser Cys Ala Lys Leu Leu Ser Lys
225                 230                 235                 240

Glu Glu Glu Ala Gly Val Lys Glu Leu Ala Lys Gln Val Lys Ser Leu
                245                 250                 255

Pro Val Val Asn Tyr Asn Leu Leu Lys Tyr Ile Cys Arg Phe Leu Asp
            260                 265                 270

Glu Val Gln Ser Tyr Ser Gly Val Asn Lys Met Ser Val Gln Asn Leu
        275                 280                 285

Ala Thr Val Phe Gly Pro Asn Ile Leu Arg Pro Lys Val Glu Asp Pro
    290                 295                 300

Leu Thr Ile Met Glu Gly Thr Val Val Val Gln Gln Leu Met Ser Val
305                 310                 315                 320

Met Ile Ser Lys His Asp Cys Leu Phe Pro Lys Asp Ala Glu Leu Gln
                325                 330                 335
```

```
Ser Lys Pro Gln Asp Gly Val Ser Asn Asn Asn Glu Ile Gln Lys Lys
            340                 345                 350

Ala Thr Met Gly Gln Leu Gln Asn Lys Glu Asn Asn Asn Thr Lys Asp
        355                 360                 365

Ser Pro Ser Arg Gln Cys Ser Trp Asp Lys Ser Glu Ser Pro Gln Arg
    370                 375                 380

Ser Ser Met Asn Asn Gly Ser Pro Thr Ala Leu Ser Gly Ser Lys Thr
385                 390                 395                 400

Asn Ser Pro Lys Asn Ser Val His Lys Leu Asp Val Ser Arg Ser Pro
                405                 410                 415

Pro Leu Met Val Lys Lys Asn Pro Ala Phe Asn Lys Gly Ser Gly Ile
            420                 425                 430

Val Thr Asn Gly Ser Phe Ser Ser Ser Asn Ala Glu Gly Leu Glu Lys
        435                 440                 445

Thr Gln Thr Thr Pro Asn Gly Ser Leu Gln Ala Arg Arg Ser Ser Ser
    450                 455                 460

Leu Lys Val Ser Gly Thr Lys Met Gly Thr His Ser Val Gln Asn Gly
465                 470                 475                 480

Thr Val Arg Met Gly Ile Leu Asn Ser Asp Thr Leu Gly Asn Pro Thr
                485                 490                 495

Asn Val Arg Asn Met Ser Trp Leu Pro Asn Gly Tyr Val Thr Leu Arg
            500                 505                 510

Asp Asn Lys Gln Lys Glu Gln Ala Gly Glu Leu Gly Gln His Asn Arg
        515                 520                 525

Leu Ser Thr Tyr Asp Asn Val His Gln Gln Phe Ser Met Met Asn Leu
    530                 535                 540

Asp Asp Lys Gln Ser Ile Asp Ser Ala Thr Trp Ser Thr Ser Ser Cys
545                 550                 555                 560

Glu Ile Ser Leu Pro Glu Asn Ser Asn Ser Cys Arg Ser Ser Thr Thr
                565                 570                 575

Thr Cys Pro Glu Gln Asp Phe Phe Gly Gly Asn Phe Glu Asp Pro Val
            580                 585                 590

Leu Asp Gly Pro Pro Gln Asp Asp Leu Ser His Pro Arg Asp Tyr Glu
        595                 600                 605

Ser Lys Ser Asp His Arg Ser Val Gly Gly Arg Ser Ser Arg Ala Thr
    610                 615                 620

Ser Ser Ser Asp Asn Ser Glu Thr Phe Val Gly Asn Ser Ser Ser Asn
625                 630                 635                 640

His Ser Ala Leu His Ser Leu Val Ser Ser Leu Lys Gln Glu Met Thr
                645                 650                 655

Lys Gln Lys Ile Glu Tyr Glu Ser Arg Ile Lys Ser Leu Glu Gln Arg
            660                 665                 670

Asn Leu Thr Leu Glu Thr Glu Met Met Ser Leu His Asp Glu Leu Asp
        675                 680                 685

Gln Glu Arg Lys Lys Phe Thr Met Ile Glu Ile Lys Met Arg Asn Ala
    690                 695                 700

Glu Arg Ala Lys Glu Asp Ala Glu Lys Arg Asn Asp Met Leu Gln Lys
705                 710                 715                 720

Glu Val Glu Gln Phe Phe Ser Thr Phe Gly Glu Leu Thr Val Glu Pro
                725                 730                 735

Arg Arg Thr Glu Arg Gly Asn Thr Ile Trp Ile Gln
            740                 745
```

<210> SEQ ID NO 53
<211> LENGTH: 4593
<212> TYPE: DNA
<213> ORGANISM: Homo sapiens

<400> SEQUENCE: 53
gggggagttt gaagacagaa aggaaagggg agaaacctgc agagagcatc aaaggatggg 60
gggtgctata aaagaagcag gggggtcctt tgaaagaaat ctatcatgca ctgaaatgct 120
ttctggagaa ggtgccgtta ttttcctccc ctcttgctca gatgaaagga gccagcaagg 180
acagtcctga aatattcctc aggggacttt ttgtcattgt tcctctttcc tcttgcacag 240
agctatttgc tgacctttcc agaggaatct cagtccagct gagaagacag ttcttaataa 300
aaacaaaaaa atgcaaaaac caattcctgc tgtttgaatg ggaatggtag cttgcttgct 360
gcagttcttt tcctgtgaca ttttggaatg tctgcagaaa cttaaaaaaa agaaaaaaaa 420
aaccttaaaa actccctgga ttaggcaaga gaaaaggaag tttttttttg ctaaacagga 480
gtaaatgaga ggtggtaact tatccctaag ccaggacctg gatgatcaaa accttcaaat 540
tctagggatc agcacttcaa aaataacaag taaacaagca tgaggagtgg ctgttgggtt 600
tcgctcagag gcaggtttta aaggaagcca aaaccgggtt cagaacttca ggcctgtacg 660
atgcctgaag accggaattc tggggggtgc ccggctggtg ccttagcctc aactcctttc 720
atccctaaaa ctacatacag aagaatcaaa cggtgtttta gttttcggaa aggcattttt 780
ggacagaaac tggaggatac tgttcgttat gagaagagat atgggaaccg tctggctccg 840
atgttggtgg agcagtgcgt ggactttatc cgacaaaggg ggctgaaaga agagggtctc 900
tttcgactgc caggccaggc taatcttgtt aaggagctcc aagatgcctt tgactgtggg 960
gagaagccat catttgacag caacacagat gtacacacgg tggcatcact tcttaagctg 1020
tacctccgag aacttccaga accagttatt ccttatgcga agtatgaaga tttttttgtca 1080
tgtgccaaac tgctcagcaa ggaagaggaa gcaggtgtta aggaattagc aaagcaggtg 1140
aagagtttgc cagtggtaaa ttacaacctc ctcaagtata tttgcagatt cttggatgaa 1200
gtacagtcct actcgggagt taacaaaatg agtgtgcaga acttggcaac ggtctttggt 1260
cctaatatcc tgcgccccaa agtggaagat cctttgacta tcatggaggg cactgtggtg 1320
gtccagcagt tgatgtcagt gatgattagc aaacatgatt gcctctttcc caaagatgca 1380
gaactacaaa gcaagcccca agatggagtg agcaacaaca atgaaattca gaagaaagcc 1440
accatggggc tgttacagaa caaggagaac aataacacca aggacagccc tagtaggcag 1500
tgctcctggg acaagtctga gtcaccccag agaagcagca tgaacaatgg atcccccaca 1560
gctctatcag gcagcaaaac caacagccca aagaacagtg ttcacaagct agatgtgtct 1620
agaagccccc ctctcatggt caaaaagaac ccagccttta ataagggtag tgggatagtt 1680
accaatgggt ccttcagcag cagtaatgca gaaggtcttg agaaaaccca aaccaccccc 1740
aatgggagcc tacaggccag aaggagctct tcactgaagg tatctggtac caaaatgggc 1800
acgcacagtg tacagaatgg aacggtgcgc atgggcattt tgaacagcga cacactcggg 1860
aaccccacaa atgttcgaaa catgagctgg ctgccaaatg gctatgtgac cctgagggat 1920
aacaagcaga aagaacaagc tggagagtta ggccagcaca acagactgtc cacctatgat 1980
aatgtccatc aacagttctc catgatgaac cttgatgaca agcagagcat tgacagtgct 2040
acctggtcca cttcctcctg tgaaatctcc ctccctgaga actccaactc ctgtcgctct 2100
tctaccacca cctgcccaga gcaagacttt tttgggggga actttgagga ccctgttttg 2160
gatgggcccc cgcaggacga cctttcccac cccagggact atgaaagcaa aagtgaccac 2220

-continued

```
aggagtgtgg gaggtcgaag tagtcgtgcc accagtagca gtgacaacag tgagacattt   2280
gtgggcaaca gcagcagcaa ccacagtgca ctgcacagtt tagtttccag cctgaaacag   2340
gaaatgacca aacagaagat agagtatgag tccaggataa agagcttaga acagcgaaac   2400
ttgactttgg aaacagaaat gatgagcctc catgatgaac tggatcagga gaggaaaaag   2460
ttcacaatga tagaaataaa aatgcgaaat gccgagcgag caaaagaaga tgccgagaaa   2520
agaaatgaca tgctacagaa agaaatggag cagttttttt ccacgtttgg agaactgaca   2580
gtggaaccca ggagaaccga gagaggaaac acaatatgga ttcagtgagc ctgctttcgc   2640
ctgctgtctc tgatggctct ggcaaggact ccagggattc tggtgggata tgacttagaa   2700
ccaggtggct ggtcacctgg atgtacagaa gtctaactgg tgaaggaata tcatttacag   2760
acattaaaca tccatatctg caatgtgtac caaagttata tcatgcccca taatgctact   2820
gtcaagtgtt acaactggat atgtgtatat agagtagttt ttcaaaagta aactaaaaat   2880
gagaagcata tttcaagaat tattttattg caagtcttgt atttaaatgt taaatcaata   2940
tgttgttgca atttagcttg ctttcaagct tcaccccttg cacttaacat aagctatttt   3000
tggcattgtg ttatcatcgg cttattttat agatcaatat ttttatttcc ctttttttgct   3060
gaggaaatga agataagcaa aaatataaat atatatataa atatatgagt tattaaaacc   3120
agaagaatac tttgtggctg tgctgtttgt gccaatagac tttgtcatga ccaaaaaagag   3180
aaatgtaaat agttttataa aatacagtcg aatcaccagg aacctttgag ctgcttttaa   3240
aattcttccc ctggcaccac tcagttttgc ttttgcgagg cgatttgaca taggaacttt   3300
gagactccat gagaaagtcc ctttctgagg cccactgtct accttgccag atcctcagtg   3360
cgtatcgcca atgcaggatg ctccttagaa aagaaaaaat ggtaaaggat ggcatttaac   3420
gattcaggct ttgaattact ctgtccctct ggaccgaatc tctttaactg ctggatagtt   3480
ttagaggaat tctcctgcta cttaggtact gggaaacaat gcttgctaaa ccatgcccac   3540
gtgagcacct gtctcccact caaacctctc ccatctccca acaactgcac tttagaatac   3600
cagcagtgaa atggtattac tgtttccctc tgagtgaaac tgctagagta tatgtcacgt   3660
agtgacattt ttttctcact caggctattg ccatctggga ttctctccct actacagctg   3720
gcaaagttgg tttgcagcaa gaagatagtg ggagggggcc aggctgcagg agaaggagaa   3780
aagtttagaa gaaacaaacc attttgcttc taattttgac agtatcactt tcctgttaaa   3840
acatacaata attttaaaag gtgaatgcct aaagttccaa ttttagcaaa tatgggaacc   3900
tcagcaatgc taattttcta gaaaaaccca gggctctttg gagctagagt tttgggagaa   3960
cagttcttca caataaggca atggttttga gaggccaggc aaataatctt tctcaccgta   4020
gaacaaaaag ttacaaaagg cataatcgga aatagagact acatacttga gtttatgggg   4080
tttgtgttgt ttgaaggttc aatgcttgca tgtgtttatt tattttcaag agggaaagtg   4140
gtctgtactg ctttcatcct tgccactgtc ttgcttttat tttttactct cccactgagc   4200
aagcgtctgt ggtcctatgg tatcaaccag tatctttata gcaataattt ctttaattcc   4260
cttttctctc tctttccaat tatttaacca gttacttcca cctggacata cgataggaaa   4320
ttcaaactca aaatatgaaa attgatctta ataactctcc cttcatatct tttcacctat   4380
ttccagtcct tatcatagtt gataaaaacc tcagactcat ccagaaagct atatgatgca   4440
ctagtaaaaa aaacaaagat atttaaactg cttgggttca aatggtatac aatttgccag   4500
ctgttactga accttctatg cataactttt tttttcctct gtgcaattgg aataataaaa   4560
atactactcc cataaaaaaa aaaaaaaaaa aac                                4593
```

<210> SEQ ID NO 54
<211> LENGTH: 655
<212> TYPE: PRT
<213> ORGANISM: Homo sapiens

<400> SEQUENCE: 54

```
Met Pro Glu Asp Arg Asn Ser Gly Gly Cys Pro Ala Gly Ala Leu Ala
1               5                   10                  15

Ser Thr Pro Phe Ile Pro Lys Thr Thr Tyr Arg Arg Ile Lys Arg Cys
            20                  25                  30

Phe Ser Phe Arg Lys Gly Ile Phe Gly Gln Lys Leu Glu Asp Thr Val
        35                  40                  45

Arg Tyr Glu Lys Arg Tyr Gly Asn Arg Leu Ala Pro Met Leu Val Glu
    50                  55                  60

Gln Cys Val Asp Phe Ile Arg Gln Arg Gly Leu Lys Glu Glu Gly Leu
65                  70                  75                  80

Phe Arg Leu Pro Gly Gln Ala Asn Leu Val Lys Glu Leu Gln Asp Ala
                85                  90                  95

Phe Asp Cys Gly Glu Lys Pro Ser Phe Asp Ser Asn Thr Asp Val His
            100                 105                 110

Thr Val Ala Ser Leu Leu Lys Leu Tyr Leu Arg Glu Leu Pro Glu Pro
        115                 120                 125

Val Ile Pro Tyr Ala Lys Tyr Glu Asp Phe Leu Ser Cys Ala Lys Leu
    130                 135                 140

Leu Ser Lys Glu Glu Glu Ala Gly Val Lys Glu Leu Ala Lys Gln Val
145                 150                 155                 160

Lys Ser Leu Pro Val Val Asn Tyr Asn Leu Leu Lys Tyr Ile Cys Arg
                165                 170                 175

Phe Leu Asp Glu Val Gln Ser Tyr Ser Gly Val Asn Lys Met Ser Val
            180                 185                 190

Gln Asn Leu Ala Thr Val Phe Gly Pro Asn Ile Leu Arg Pro Lys Val
        195                 200                 205

Glu Asp Pro Leu Thr Ile Met Glu Gly Thr Val Val Val Gln Gln Leu
    210                 215                 220

Met Ser Val Met Ile Ser Lys His Asp Cys Leu Phe Pro Lys Asp Ala
225                 230                 235                 240

Glu Leu Gln Ser Lys Pro Gln Asp Gly Val Ser Asn Asn Asn Glu Ile
                245                 250                 255

Gln Lys Lys Ala Thr Met Gly Leu Leu Gln Asn Lys Glu Asn Asn Asn
            260                 265                 270

Thr Lys Asp Ser Pro Ser Arg Gln Cys Ser Trp Asp Lys Ser Glu Ser
        275                 280                 285

Pro Gln Arg Ser Ser Met Asn Asn Gly Ser Pro Thr Ala Leu Ser Gly
    290                 295                 300

Ser Lys Thr Asn Ser Pro Lys Asn Ser Val His Lys Leu Asp Val Ser
305                 310                 315                 320

Arg Ser Pro Pro Leu Met Val Lys Lys Asn Pro Ala Phe Asn Lys Gly
                325                 330                 335

Ser Gly Ile Val Thr Asn Gly Ser Phe Ser Ser Ser Asn Ala Glu Gly
            340                 345                 350

Leu Glu Lys Thr Gln Thr Thr Pro Asn Gly Ser Leu Gln Ala Arg Arg
        355                 360                 365

Ser Ser Ser Leu Lys Val Ser Gly Thr Lys Met Gly Thr His Ser Val
    370                 375                 380
```

```
Gln Asn Gly Thr Val Arg Met Gly Ile Leu Asn Ser Asp Thr Leu Gly
385                 390                 395                 400

Asn Pro Thr Asn Val Arg Asn Met Ser Trp Leu Pro Asn Gly Tyr Val
                405                 410                 415

Thr Leu Arg Asp Asn Lys Gln Lys Glu Gln Ala Gly Glu Leu Gly Gln
            420                 425                 430

His Asn Arg Leu Ser Thr Tyr Asp Asn Val His Gln Gln Phe Ser Met
        435                 440                 445

Met Asn Leu Asp Asp Lys Gln Ser Ile Asp Ser Ala Thr Trp Ser Thr
    450                 455                 460

Ser Ser Cys Glu Ile Ser Leu Pro Glu Asn Ser Asn Ser Cys Arg Ser
465                 470                 475                 480

Ser Thr Thr Thr Cys Pro Glu Gln Asp Phe Phe Gly Gly Asn Phe Glu
                485                 490                 495

Asp Pro Val Leu Asp Gly Pro Pro Gln Asp Asp Leu Ser His Pro Arg
            500                 505                 510

Asp Tyr Glu Ser Lys Ser Asp His Arg Ser Val Gly Gly Arg Ser Ser
        515                 520                 525

Arg Ala Thr Ser Ser Ser Asp Asn Ser Glu Thr Phe Val Gly Asn Ser
    530                 535                 540

Ser Ser Asn His Ser Ala Leu His Ser Leu Val Ser Ser Leu Lys Gln
545                 550                 555                 560

Glu Met Thr Lys Gln Lys Ile Glu Tyr Glu Ser Arg Ile Lys Ser Leu
                565                 570                 575

Glu Gln Arg Asn Leu Thr Leu Glu Thr Glu Met Met Ser Leu His Asp
            580                 585                 590

Glu Leu Asp Gln Glu Arg Lys Lys Phe Thr Met Ile Glu Ile Lys Met
        595                 600                 605

Arg Asn Ala Glu Arg Ala Lys Glu Asp Ala Glu Lys Arg Asn Asp Met
    610                 615                 620

Leu Gln Lys Glu Met Glu Gln Phe Phe Ser Thr Phe Gly Glu Leu Thr
625                 630                 635                 640

Val Glu Pro Arg Arg Thr Glu Arg Gly Asn Thr Ile Trp Ile Gln
                645                 650                 655
```

<210> SEQ ID NO 55
<211> LENGTH: 2417
<212> TYPE: DNA
<213> ORGANISM: Homo sapiens

<400> SEQUENCE: 55

```
aaaacttaaa tatagctacc accgctttga aaggaatggt ttgtgtccaa acagcatttt      60

ccagacaagc tctgtacttt tttgccaaaa gaattaactt taaactgaag gcagtggaca     120

gttaaacaag agtcggcact gggaacagct gtgcgtagac cagaccagtg acttataagg     180

aggcgatcga gatcggatga cagcaaatca tgaaagctac ctcctcatgg caagcaccca     240

gaatgatatg gaagactggg tgaagtcaat ccgccgagtc atatggggac ctttcggagg     300

aggcattttt ggacagaaac tggaggatac tgttcgttat gagaagagat atgggaaccg     360

tctggctccg atgttggtgg agcagtgcgt ggactttatc cgacaaaggg ggctgaaaga     420

agagggtctc tttcgactgc caggccaggc taatcttgtt aaggagctcc aagatgcctt     480

tgactgtggg gagaagccat catttgacag caacacagat gtacacacgg tggcatcact     540

tcttaagctg tacctccgag aacttccaga accagttatt ccttatgcga agtatgaaga     600
```

```
tttttgtca tgtgccaaac tgctcagcaa ggaagaggaa gcaggtgtta aggaattagc    660

aaagcaggtg aagagtttgc cagtggtaaa ttacaacctc ctcaagtata tttgcagatt    720

cttggatgaa gtacagtcct actcgggagt taacaaaatg agtgtgcaga acttggcaac    780

ggtctttggt cctaatatcc tgcgccccaa agtggaagat cctttgacta tcatggaggg    840

cactgtggtg gtccagcagt tgatgtcagt gatgattagc aaacatgatt gcctctttcc    900

caaagatgca gaactacaaa gcaagcccca agatggagtg agcaacaaca atgaaattca    960

gaagaaagcc accatggggc agttacagaa caaggagaac aataacacca aggacagccc   1020

tagtaggcag tgctcctggg acaagtctga gtcaccccag agaagcagca tgaacaatgg   1080

atcccccaca gctctatcag gcagcaaaac caacagccca aagaacagtg ttcacaagct   1140

agatgtgtct agaagccccc ctctcatggt caaaaagaac ccagccttta ataagggtag   1200

tgggatagtt accaatgggt ccttcagcag cagtaatgca gaaggtcttg agaaaaccca   1260

aaccaccccc aatgggagcc tacaggccag aaggagctct tcactgaagg tatctggtac   1320

caaaatgggc acgcacagtg tacagaatgg aacggtgcgc atgggcattt tgaacagcga   1380

cacactcggg aaccccacaa atgttcgaaa catgagctgg ctgccaaatg gctatgtgac   1440

cctgagggat aacaagcaga aagaacaagc tggagagtta ggccagcaca acagactgtc   1500

cacctatgat aatgtccatc aacagttctc catgatgaac cttgatgaca agcagagcat   1560

tgacagtgct acctggtcca cttcctcctg tgaaatctcc ctccctgaga actccaactc   1620

ctgtcgctct tctaccacca cctgcccaga gcaagacttt tttgggggga actttgagga   1680

ccctgttttg gatgggcccc cgcaggacga cctttcccac cccagggact atgaaagcaa   1740

aagtgaccac aggagtgtgg gaggtcgaag tagtcgtgcc accagtagca gtgacaacag   1800

tgagacattt gtgggcaaca gcagcagcaa ccacagtgca ctgcacagtt tagtttccag   1860

cctgaaacag gaaatgacca aacagaagat agagtatgag tccaggataa agagcttaga   1920

acagcgaaac ttgactttgg aaacagaaat gatgagcctc catgatgaac tggatcagga   1980

gaggaaaaag ttcacaatga tagaaataaa aatgcgaaat gccgagcgag caaaagaaga   2040

tgccgagaaa agaaatgaca tgctacagaa agaagtggag cagttttttt ccacgtttgg   2100

agaactgaca gtggaaccca ggagaaccga gagaggaaac acaatatgga ttcagtgagc   2160

ctgctttcgc ctgctgtctc tgatggctct ggcaaggact ccagggattc tggtgggata   2220

tgacttagaa ccaggtggct ggtcacctgg atgtacagaa gtctaactgg tgaaggaata   2280

tcatttacag acattaaaca tccatatctg caatgtgtac caaagttata tcatgcccca   2340

taatgctact gtcaagtgtt acaactggat atgtgtatat agagtagttt ttcaaaagta   2400

aactaaaaat gagaagc                                                  2417
```

<210> SEQ ID NO 56
<211> LENGTH: 653
<212> TYPE: PRT
<213> ORGANISM: Homo sapiens

<400> SEQUENCE: 56

```
Met Thr Ala Asn His Glu Ser Tyr Leu Leu Met Ala Ser Thr Gln Asn
1               5                   10                  15

Asp Met Glu Asp Trp Val Lys Ser Ile Arg Arg Val Ile Trp Gly Pro
            20                  25                  30

Phe Gly Gly Gly Ile Phe Gly Gln Lys Leu Glu Asp Thr Val Arg Tyr
        35                  40                  45

Glu Lys Arg Tyr Gly Asn Arg Leu Ala Pro Met Leu Val Glu Gln Cys
```

```
    50                  55                  60

Val Asp Phe Ile Arg Gln Arg Gly Leu Lys Glu Glu Gly Leu Phe Arg
65                  70                  75                  80

Leu Pro Gly Gln Ala Asn Leu Val Lys Glu Leu Gln Asp Ala Phe Asp
                85                  90                  95

Cys Gly Glu Lys Pro Ser Phe Asp Ser Asn Thr Asp Val His Thr Val
            100                 105                 110

Ala Ser Leu Leu Lys Leu Tyr Leu Arg Glu Leu Pro Glu Pro Val Ile
        115                 120                 125

Pro Tyr Ala Lys Tyr Glu Asp Phe Leu Ser Cys Ala Lys Leu Leu Ser
    130                 135                 140

Lys Glu Glu Glu Ala Gly Val Lys Glu Leu Ala Lys Gln Val Lys Ser
145                 150                 155                 160

Leu Pro Val Val Asn Tyr Asn Leu Leu Lys Tyr Ile Cys Arg Phe Leu
                165                 170                 175

Asp Glu Val Gln Ser Tyr Ser Gly Val Asn Lys Met Ser Val Gln Asn
            180                 185                 190

Leu Ala Thr Val Phe Gly Pro Asn Ile Leu Arg Pro Lys Val Glu Asp
        195                 200                 205

Pro Leu Thr Ile Met Glu Gly Thr Val Val Val Gln Gln Leu Met Ser
    210                 215                 220

Val Met Ile Ser Lys His Asp Cys Leu Phe Pro Lys Asp Ala Glu Leu
225                 230                 235                 240

Gln Ser Lys Pro Gln Asp Gly Val Ser Asn Asn Asn Glu Ile Gln Lys
                245                 250                 255

Lys Ala Thr Met Gly Gln Leu Gln Asn Lys Glu Asn Asn Asn Thr Lys
            260                 265                 270

Asp Ser Pro Ser Arg Gln Cys Ser Trp Asp Lys Ser Glu Ser Pro Gln
        275                 280                 285

Arg Ser Ser Met Asn Asn Gly Ser Pro Thr Ala Leu Ser Gly Ser Lys
    290                 295                 300

Thr Asn Ser Pro Lys Asn Ser Val His Lys Leu Asp Val Ser Arg Ser
305                 310                 315                 320

Pro Pro Leu Met Val Lys Lys Asn Pro Ala Phe Asn Lys Gly Ser Gly
                325                 330                 335

Ile Val Thr Asn Gly Ser Phe Ser Ser Ser Asn Ala Glu Gly Leu Glu
            340                 345                 350

Lys Thr Gln Thr Thr Pro Asn Gly Ser Leu Gln Ala Arg Arg Ser Ser
        355                 360                 365

Ser Leu Lys Val Ser Gly Thr Lys Met Gly Thr His Ser Val Gln Asn
    370                 375                 380

Gly Thr Val Arg Met Gly Ile Leu Asn Ser Asp Thr Leu Gly Asn Pro
385                 390                 395                 400

Thr Asn Val Arg Asn Met Ser Trp Leu Pro Asn Gly Tyr Val Thr Leu
                405                 410                 415

Arg Asp Asn Lys Gln Lys Glu Gln Ala Gly Glu Leu Gly Gln His Asn
            420                 425                 430

Arg Leu Ser Thr Tyr Asp Asn Val His Gln Gln Phe Ser Met Met Asn
        435                 440                 445

Leu Asp Asp Lys Gln Ser Ile Asp Ser Ala Thr Trp Ser Thr Ser Ser
    450                 455                 460

Cys Glu Ile Ser Leu Pro Glu Asn Ser Asn Ser Cys Arg Ser Ser Thr
465                 470                 475                 480
```

-continued

```
Thr Thr Cys Pro Glu Gln Asp Phe Phe Gly Gly Asn Phe Glu Asp Pro
                485                 490                 495

Val Leu Asp Gly Pro Pro Gln Asp Asp Leu Ser His Pro Arg Asp Tyr
            500                 505                 510

Glu Ser Lys Ser Asp His Arg Ser Val Gly Gly Arg Ser Ser Arg Ala
        515                 520                 525

Thr Ser Ser Ser Asp Asn Ser Glu Thr Phe Val Gly Asn Ser Ser Ser
    530                 535                 540

Asn His Ser Ala Leu His Ser Leu Val Ser Ser Leu Lys Gln Glu Met
545                 550                 555                 560

Thr Lys Gln Lys Ile Glu Tyr Glu Ser Arg Ile Lys Ser Leu Glu Gln
                565                 570                 575

Arg Asn Leu Thr Leu Glu Thr Glu Met Met Ser Leu His Asp Glu Leu
            580                 585                 590

Asp Gln Glu Arg Lys Lys Phe Thr Met Ile Glu Ile Lys Met Arg Asn
        595                 600                 605

Ala Glu Arg Ala Lys Glu Asp Ala Glu Lys Arg Asn Asp Met Leu Gln
    610                 615                 620

Lys Glu Val Glu Gln Phe Phe Ser Thr Phe Gly Glu Leu Thr Val Glu
625                 630                 635                 640

Pro Arg Arg Thr Glu Arg Gly Asn Thr Ile Trp Ile Gln
                645                 650


<210> SEQ ID NO 57
<211> LENGTH: 1856
<212> TYPE: DNA
<213> ORGANISM: Homo sapiens

<400> SEQUENCE: 57

gcatttttgg acagaaactg gaggatactg ttcgttatga gaagagatat gggaaccgtc      60

tggctccgat gttggtggag cagtgcgtgg actttatccg acaaaggggg ctgaaagaag     120

agggtctctt tcgactgcca ggccaggcta atcttgttaa ggagctccaa gatgcctttg     180

actgtgggga gaagccatca tttgacagca acacagatgt acacacggtg gcatcacttc     240

ttaagctgta cctccgagaa cttccagaac cagttattcc ttatgcgaag tatgaagatt     300

ttttgtcatg tgccaaactg ctcagcaagg aagaggaagc aggtgttaag gaattagcaa     360

agcaggtgaa gagtttgcca gtggtaaatt acaacctcct caagtatatt tgcagattct     420

tggatgaagt acagtcctac tcgggagtta acaaaatgag tgtgcagaac ttggcaacgg     480

tctttggtcc taatatcctg cgccccaaag tggaagatcc tttgactatc atggagggca     540

ctgtggtggt ccagcagttg atgtcagtga tgattagcaa acatgattgc ctctttccca     600

aagatgcaga actacaaagc aagccccaag atggagtgag caacaacaat gaaattcaga     660

agaaagccac catggggcag ttacagaaca aggagaacaa taacaccaag gacagcccta     720

gtaggcagtg ctcctgggac aagtctgagt caccccagag aagcagcatg aacaatggat     780

cccccacagc tctatcaggc agcaaaacca acagcccaaa gaacagtgtt cacaagctag     840

atgtgtctag aagcccccct ctcatggtca aaaagaaccc agcctttaat aagggtagtg     900

ggatagttac caatgggtcc ttcagcagca gtaatgcaga aggtcttgag aaaacccaaa     960

ccacccccaa tgggagccta caggccagaa ggagctcttc actgaaggta tctggtacca    1020

aaatgggcac gcacagtgta cagaatggaa cggtgcgcat gggcattttg aacagcgaca    1080

cactcgggaa ccccacaaat gttcgaaaca tgagctggct gccaaatggc tatgtgaccc    1140

tgagggataa caagcagaaa gaacaagctg gagagttagg ccagcacaac agactgtcca    1200
```

```
cctatgataa tgtccatcaa cagttctcca tgatgaacct tgatgacaag cagagcattg   1260

acagtgctac ctggtccact tcctcctgtg aaatctccct ccctgagaac tccaactcct   1320

gtcgctcttc taccaccacc tgcccagagc aagacttttt tggggggaac tttgaggacc   1380

ctgttttgga tgggcccccg caggacgacc tttcccaccc cagggactat gaaagcaaaa   1440

gtgaccacag gagtgtggga ggtcgaagta gtcgtgccac cagtagcagt gacaacagtg   1500

agacatttgt gggcaacagc agcagcaacc acagtgcact gcacagttta gtttccagcc   1560

tgaaacagga aatgaccaaa cagaagatag agtatgagtc caggataaag agcttagaac   1620

agcgaaactt gactttggaa acagaaatga tgagcctcca tgatgaactg gatcaggaga   1680

ggaaaaagtt cacaatgata gaaataaaaa tgcgaaatgc cgagcgagca aaagaagatg   1740

ccgagaaaag aaatgacatg ctacagaaag aaatggagca gttttttcc acgtttggag    1800

aactgacagt ggaacccagg agaaccgaga gaggaaacac aatatggatt cagtga       1856


<210> SEQ ID NO 58
<211> LENGTH: 618
<212> TYPE: PRT
<213> ORGANISM: Homo sapiens

<400> SEQUENCE: 58

Gly Ile Phe Gly Gln Lys Leu Glu Asp Thr Val Arg Tyr Glu Lys Arg
1               5                   10                  15

Tyr Gly Asn Arg Leu Ala Pro Met Leu Val Glu Gln Cys Val Asp Phe
            20                  25                  30

Ile Arg Gln Arg Gly Leu Lys Glu Glu Gly Leu Phe Arg Leu Pro Gly
        35                  40                  45

Gln Ala Asn Leu Val Lys Glu Leu Gln Asp Ala Phe Asp Cys Gly Glu
    50                  55                  60

Lys Pro Ser Phe Asp Ser Asn Thr Asp Val His Thr Val Ala Ser Leu
65                  70                  75                  80

Leu Lys Leu Tyr Leu Arg Glu Leu Pro Glu Pro Val Ile Pro Tyr Ala
                85                  90                  95

Lys Tyr Glu Asp Phe Leu Ser Cys Ala Lys Leu Leu Ser Lys Glu Glu
            100                 105                 110

Glu Ala Gly Val Lys Glu Leu Ala Lys Gln Val Lys Ser Leu Pro Val
        115                 120                 125

Val Asn Tyr Asn Leu Leu Lys Tyr Ile Cys Arg Phe Leu Asp Glu Val
    130                 135                 140

Gln Ser Tyr Ser Gly Val Asn Lys Met Ser Val Gln Asn Leu Ala Thr
145                 150                 155                 160

Val Phe Gly Pro Asn Ile Leu Arg Pro Lys Val Glu Asp Pro Leu Thr
                165                 170                 175

Ile Met Glu Gly Thr Val Val Val Gln Gln Leu Met Ser Val Met Ile
            180                 185                 190

Ser Lys His Asp Cys Leu Phe Pro Lys Asp Ala Glu Leu Gln Ser Lys
        195                 200                 205

Pro Gln Asp Gly Val Ser Asn Asn Asn Glu Ile Gln Lys Lys Ala Thr
    210                 215                 220

Met Gly Gln Leu Gln Asn Lys Glu Asn Asn Asn Thr Lys Asp Ser Pro
225                 230                 235                 240

Ser Arg Gln Cys Ser Trp Asp Lys Ser Glu Ser Pro Gln Arg Ser Ser
                245                 250                 255

Met Asn Asn Gly Ser Pro Thr Ala Leu Ser Gly Ser Lys Thr Asn Ser
```

-continued

```
            260                 265                 270

Pro Lys Asn Ser Val His Lys Leu Asp Val Ser Arg Ser Pro Pro Leu
        275                 280                 285

Met Val Lys Lys Asn Pro Ala Phe Asn Lys Gly Ser Gly Ile Val Thr
    290                 295                 300

Asn Gly Ser Phe Ser Ser Ser Asn Ala Glu Gly Leu Glu Lys Thr Gln
305                 310                 315                 320

Thr Thr Pro Asn Gly Ser Leu Gln Ala Arg Arg Ser Ser Ser Leu Lys
                325                 330                 335

Val Ser Gly Thr Lys Met Gly Thr His Ser Val Gln Asn Gly Thr Val
            340                 345                 350

Arg Met Gly Ile Leu Asn Ser Asp Thr Leu Gly Asn Pro Thr Asn Val
        355                 360                 365

Arg Asn Met Ser Trp Leu Pro Asn Gly Tyr Val Thr Leu Arg Asp Asn
    370                 375                 380

Lys Gln Lys Glu Gln Ala Gly Glu Leu Gly Gln His Asn Arg Leu Ser
385                 390                 395                 400

Thr Tyr Asp Asn Val His Gln Gln Phe Ser Met Met Asn Leu Asp Asp
                405                 410                 415

Lys Gln Ser Ile Asp Ser Ala Thr Trp Ser Thr Ser Ser Cys Glu Ile
            420                 425                 430

Ser Leu Pro Glu Asn Ser Asn Ser Cys Arg Ser Ser Thr Thr Thr Cys
        435                 440                 445

Pro Glu Gln Asp Phe Phe Gly Gly Asn Phe Glu Asp Pro Val Leu Asp
    450                 455                 460

Gly Pro Pro Gln Asp Asp Leu Ser His Pro Arg Asp Tyr Glu Ser Lys
465                 470                 475                 480

Ser Asp His Arg Ser Val Gly Gly Arg Ser Ser Arg Ala Thr Ser Ser
                485                 490                 495

Ser Asp Asn Ser Glu Thr Phe Val Gly Asn Ser Ser Ser Asn His Ser
            500                 505                 510

Ala Leu His Ser Leu Val Ser Ser Leu Lys Gln Glu Met Thr Lys Gln
        515                 520                 525

Lys Ile Glu Tyr Glu Ser Arg Ile Lys Ser Leu Glu Gln Arg Asn Leu
    530                 535                 540

Thr Leu Glu Thr Glu Met Met Ser Leu His Asp Glu Leu Asp Gln Glu
545                 550                 555                 560

Arg Lys Lys Phe Thr Met Ile Glu Ile Lys Met Arg Asn Ala Glu Arg
                565                 570                 575

Ala Lys Glu Asp Ala Glu Lys Arg Asn Asp Met Leu Gln Lys Glu Met
            580                 585                 590

Glu Gln Phe Phe Ser Thr Phe Gly Glu Leu Thr Val Glu Pro Arg Arg
        595                 600                 605

Thr Glu Arg Gly Asn Thr Ile Trp Ile Gln
    610                 615
```

<210> SEQ ID NO 59
<211> LENGTH: 531
<212> TYPE: DNA
<213> ORGANISM: Homo sapiens

<400> SEQUENCE: 59

```
ccgtctggct ccgatgttgg tggagcagtg cgtggacttt atccgacaaa gggggctgaa      60

agaagagggt ctctttcgac tgccaggcca ggctaatctt gttaaggagc tccaagatgc     120
```

-continued

```
ctttgactgt ggggagaagc catcatttga cagcaacaca gatgtacaca cggtggcatc    180

acttcttaag ctgtacctcc gagaacttcc agaaccagtt attccttatg cgaagtatga    240

agattttttg tcatgtgcca aactgctcag caaggaagag gaagcaggtg ttaaggaatt    300

agcaaagcag gtgaagagtt tgccagtggt aaattacaac ctcctcaagt atatttgcag    360

attcttggat gaagtacagt cctactcggg agttaacaaa atgagtgtgc agaacttggc    420

aacggtcttt ggtcctaata tcctgcgccc caaagtggaa gatcctttga ctatcatgga    480

gggcactgtg gtggtccagc agttgatgtc agtgatgatt agcaaacatg a             531


<210> SEQ ID NO 60
<211> LENGTH: 177
<212> TYPE: PRT
<213> ORGANISM: Homo sapiens

<400> SEQUENCE: 60

Arg Leu Ala Pro Met Leu Val Glu Gln Cys Val Asp Phe Ile Arg Gln
1               5                   10                  15

Arg Gly Leu Lys Glu Glu Gly Leu Phe Arg Leu Pro Gly Gln Ala Asn
            20                  25                  30

Leu Val Lys Glu Leu Gln Asp Ala Phe Asp Cys Gly Glu Lys Pro Ser
        35                  40                  45

Phe Asp Ser Asn Thr Asp Val His Thr Val Ala Ser Leu Leu Lys Leu
    50                  55                  60

Tyr Leu Arg Glu Leu Pro Glu Pro Val Ile Pro Tyr Ala Lys Tyr Glu
65                  70                  75                  80

Asp Phe Leu Ser Cys Ala Lys Leu Leu Ser Lys Glu Glu Glu Ala Gly
                85                  90                  95

Val Lys Glu Leu Ala Lys Gln Val Lys Ser Leu Pro Val Val Asn Tyr
            100                 105                 110

Asn Leu Leu Lys Tyr Ile Cys Arg Phe Leu Asp Glu Val Gln Ser Tyr
        115                 120                 125

Ser Gly Val Asn Lys Met Ser Val Gln Asn Leu Ala Thr Val Phe Gly
    130                 135                 140

Pro Asn Ile Leu Arg Pro Lys Val Glu Asp Pro Leu Thr Ile Met Glu
145                 150                 155                 160

Gly Thr Val Val Val Gln Gln Leu Met Ser Val Met Ile Ser Lys His
                165                 170                 175

Asp
```

METHODS FOR THE MODULATION OF ANGIOGENESIS

CROSS REFERENCE TO RELATED APPLICATION

The present application is a 35 U.S.C. §371 National Phase Entry Application of International Application No. PCT/U.S.2009/047935 filed Jun. 19, 2009, which designates the U.S., and which claims the benefit of priority under 35 U.S.C. §119(e) to U.S. Provisional application 61/147,850 filed Jan. 28, 2009 and 61/074,164 filed Jun. 20, 2008, the contents of which are incorporated herein by reference in their entirety.

GOVERNMENT SUPPORT

This invention was made with Governmental support under CA55833 and PO1 CA45548, awarded by the National Institute of Health (NIH). The Government has certain rights in the invention.

BACKGROUND OF THE INVENTION

Angiogenesis is the formation, development and growth of new blood vessels. The normal regulation of angiogenesis is governed by a fine balance between factors that induce the formation of blood vessels and those that halt or inhibit the process. When this balance is upset, it generally results in pathological angiogenesis. Under normal physiological conditions, angiogenesis occur in very specific, restricted situations and is highly regulated through a system of angiogenic stimulators and inhibitors. For example, angiogenesis is normally observed in wound healing, fetal and embryonic development, and formation of the corpus luteum, endometrium and placenta.

In addition, angiogenesis is regulated by external factors. Physical forces applied to extracellular matrix (ECM) can influence the direction of capillary endothelial (CE) cell migration and oriented sprouting that drive angiogenesis. For example, local thinning of the basement membrane precedes initiation of capillary sprout formation, and cells in this region physically extend into surrounding ECM, leading to outward migration and growth of the capillary endothelial cells towards the growth stimulus. Similar changes in capillary cell shape and function, including distortion-related migration and growth, can be produced by changing ECM elasticity, adhesivity or topography, or altering cell-generated traction forces in vitro, as well as by applying mechanical stresses in vitro or in vivo. The growth and development of all living tissues are influenced by physical forces, and deregulation of this form of mechanoregulation can lead to various diseases and debilitating conditions. This is particularly evident in the cardiovascular system where blood pressure, wall strain and fluid shear stress elicit biochemical signals in endothelial cells that are required for normal tissue homeostasis, and when these physical factors are altered, they produce changes in cell function and vascular wall remodeling that can contribute to life threatening diseases, such as hypertension and atherosclerosis. Mechanical forces also play an important role in the microvasculature. For example, micromechanical stresses (e.g., cyclical changes in wall strain in angiogenic atherosclerotic plaques, static stretch in healing wounds or cancer parenchyma) can be potent inducers of capillary ingrowth as chemical factors. Moreover, physical forces actually dominate and govern the local capillary response (i.e., whether CE cells will grow, differentiate, die or move in a specific direction) when stimulated by saturating amounts of soluble angiogenic factors. Thus, understanding the molecular mechanism by which CE cells migrate and grow, causing capillary sprouts to elongate and differentiate into functional vascular networks to form when exposed to mechanical stress could lead to identification of novel targets for therapy in angiogenic diseases, such as cancer, arthritis and diabetic retinopathy.

SUMMARY OF THE INVENTION

The present invention relates to methods and compositions for inhibiting and promoting angiogenesis driven by endothelial cell (EC) migration, growth and associated capillary sprout elongation and vascular network formation, and uses thereof for the purposes of treating angiogenesis-related disorders and diseases, particularly when diseases or disorders are directly related to aberrant angiogenesis, including increased or decreased angiogenesis.

The invention generally relates to compositions and methods for modulating the migration, growth and/or differentiation of microvascular endothelial cells that underlie the angiogenic process. The methods described herein are based upon the discovery of a mechanosensitive signalling pathway that controls the expression of the gene encoding VEGFR2 by modulating antagonistic activities of two opposing transcription factors, TFII-I and GATA2. While not wishing to be bound by theory, the inventors have discovered that TFII-I and GATA2 compete for binding to the VEGFR2 promoter and share sensitivity to p190RhoGAP, which responds to signals elicited by growth factors, ECM adhesion, and mechanical forces.

The invention generally relates to altering angiogenesis in vivo by modulating the levels of p190RhoGAP, TFII-I, or GATA-2. In particular, the inventors herein have discovered that inhibition of the expression of p190RhoGAP or TFII-I, for example using siRNAs directed to p190RhoGAP and/or TFII-I respectively, enhances VEGFR expression and increases angiogenesis in vivo. In addition, the inventors further demonstrate that over-expression of GATA-2 increases angiogenesis in vivo, while the inhibition of GATA-2, for example using siRNA directed to GATA-2 decreases angiogenesis in vivo. Furthermore, the inventors also demonstrate that over-expression or activation of TFII-I has been shown to inhibit the expression of VEGFR and decrease angiogenesis in vivo. Methods for the treatment of macular degeneration and for inhibiting/promoting capillary endothelial (CE) cell migration by modulating the levels of p190RhoGAP, TFII-I, or GATA-2 are also contemplated.

Accordingly, one aspect of the present invention relates to a method for promoting microvascular endothelial cell migration, differentiation, capillary blood vessel growth and/or angiogenesis by administering an pro-angiogenic agent, whereby a pro-angiogenic agent is selected from at least one of an inhibitor of p190RhoGAP, an inhibitor of TFII-I or an activator of GATA-2.

Accordingly, one aspect of the present invention relates to a method for inhibiting microvascular endothelial cell migration, differentiation, capillary blood vessel growth and/or angiogenesis by administering an anti-angiogenic agent, whereby an anti-angiogenic agent is selected from at least one of an activator of p190RhoGAP, an activator of TFII-I or an inhibitor of GATA-2.

Accordingly, embodiments of the present invention relate to methods and compositions to promote or increase endothelial cell migration, capillary sprout formation and formation of microvascular networks, the method comprising contacting an endothelial cell with a pro-angiogenesis agent, for example a pro-angiogenic agent is selected from at least one or any combination of an inhibitor of p190RhoGAP, an inhibitor of TFII-I, or an activator of GATA-2.

Embodiments of the invention also provide methods for promoting or increasing angiogenesis in a mammal in need thereof, the method comprising administering a therapeutically effective amount of a pro-angiogenic agent, for example, a pro-angiogenesis agent, for example a pro-angiogenic agent is selected from at least one or any combination of an inhibitor of p190RhoGAP, an inhibitor of TFII-I, or an activator of GATA-2 and a pharmaceutically acceptable carrier.

Embodiments of the invention also provide methods for treating an angiogenesis-related disease characterized by a decrease or loss in angiogenesis in a mammal in need thereof, the method comprising administering a therapeutically effective amount of a pro-angiogenesis agent, for example a pro-angiogenic agent is selected from at least one or any combination of an inhibitor of p190RhoGAP, an inhibitor of TFII-I, or an activator of GATA-2 and a pharmaceutically acceptable carrier.

In one embodiment, provided herein is a method of promoting microvascular endothelial cell migration, differentiation, capillary blood vessel growth and/or angiogenesis, the method comprising contacting a cell with an inhibitor of TFII-I expression or activity. Inhibition of expression or activity can be achieved, for example, via siRNA, an antibody, or a small molecule inhibitor of TFII-I.

In another embodiment, provided herein is a method of promoting microvascular endothelial cell migration, differentiation, capillary blood vessel growth and/or angiogenesis, the method comprising contacting a cell with an inhibitor of p190RhoGAP expression or activity. Inhibition of expression or activity can be achieved, for example, via siRNA, an antibody, or a small molecule inhibitor of p190RhoGAP.

Other embodiments of the present invention relate to methods and compositions to inhibit endothelial cell migration, the method comprising contacting an endothelial cell with an anti-angiogenic agent, whereby an anti-angiogenic agent is selected from at least one or any combination of an activator of p190RhoGAP, an activator of TFII-I or an inhibitor of GATA-2

Embodiments of the invention also provide methods for inhibiting angiogenesis in a mammal in need thereof, the method comprising administering a therapeutically effective amount of a anti-angiogenic agent, for example, an anti-angiogenic agent is selected from at least one or any combination of an activator of p190RhoGAP, an activator of TFII-I or an inhibitor of GATA-2 and a pharmaceutically acceptable carrier.

Embodiments of the invention also provide methods for treating an angiogenesis-related disease characterized by uncontrolled or increased angiogenesis in a mammal in need thereof, the method comprising administering a therapeutically effective amount of a anti-angiogenic agent, for example, an anti-angiogenic agent is selected from at least one or any combination of an activator of p190RhoGAP, an activator of TFII-I or an inhibitor of GATA-2 and a pharmaceutically acceptable carrier.

In another embodiment, provided herein is a method of inhibiting microvascular endothelial cell migration, differentiation, capillary blood vessel growth and/or angiogenesis, the method comprising contacting a cell with an inhibitor of GATA2 expression or activity. Inhibition of expression or activity can be achieved, for example, via siRNA, an antibody, or a small molecule inhibitor of GATA2.

In another embodiment, there is provided a method of modulating angiogenesis, the method comprising contacting a microvascular endothelial cell with a modulator of one or more of p190RhoGAP, TFII-I, and GATA2. The use of a plurality of such modulators is specifically contemplated.

One aspect of the present invention relates to the use of anti-angiogenic agents for inhibiting angiogenesis through modulation (i.e. inhibition) of microvascular endothelial cell migration, and/or microvascular endothelial cell differentiation and/or capillary blood vessel growth.

One aspect of the present invention relates to the use of pro-angiogenic agents for promoting angiogenesis through modulation (i.e. increase) of microvascular endothelial cell migration, and/or microvascular endothelial cell differentiation and/or capillary blood vessel growth.

One aspect of the present invention relates to the use of an anti-angiogenic agent for inhibiting angiogenesis through modulation (i.e. inhibiting) microvascular endothelial cell migration or differentiation or growth in a mammal, wherein the anti-angiogenic agent is selected from at least one from the group consisting of: a p190RhoGAP activator, a TFII-I activator, a GATA-2 inhibitor.

One aspect of the present invention relates to the use of an siRNA directed specifically against a GATA-2 gene for inhibiting angiogenesis through modulation (i.e. inhibiting) microvascular endothelial cell migration or differentiation or growth. In another embodiment, the present invention relates to the use of an antibody directed specifically against a GATA-2 for inhibiting angiogenesis through modulation (i.e. inhibiting) microvascular endothelial cell migration or microvascular endothelial cell differentiation or microvascular endothelial cell growth, wherein the GATA-2 function is blocked by the antibody. In some embodiments, a siRNA directed specifically against a GATA-2 gene is useful for the manufacture of a medicament for inhibiting angiogenesis by modulating (i.e. inhibiting) microvascular endothelial cell migration, or differentiation or growth in a mammal in need thereof. In some embodiments, an antibody directed specifically against a GATA-2 is useful for inhibiting angiogenesis by modulating (i.e. inhibiting) microvascular endothelial cell migration, differentiation or growth in a mammal in need thereof, wherein the GATA-2 function is blocked by the antibody. In some embodiments, an antibody directed specifically against a GATA-2 for the manufacture of a medicament for inhibiting angiogenesis or microvascular endothelial cell migration or differentiation or growth in a mammal in need thereof, wherein the GATA-2 is blocked by the antibody.

Another aspect of the present invention relates to a pharmaceutical composition comprising a therapeutically effective amount of at least one anti-angiogenic agent selected from the group consisting of: a p190RhoGAP activator, a TFII-I activator, a GATA-2 inhibitor, and a pharmaceutically acceptable carrier for inhibiting angiogenesis through modulation (i.e. inhibition) of microvascular endothelial cell migration, or differentiation or growth in a mammal in need thereof. In some embodiments of all aspects, a pharmaceutical composition is useful for the manufacture of a medicament for inhibiting angiogenesis in a mammal in need thereof.

In all aspects of the invention, a pharmaceutical composition comprising an anti-angiogenic agent is useful for treating a mammal is afflicted with an angiogenesis-related disease or disorder characterized by increased angiogenesis. Examples of angiogenesis-related disease characterized by increased angiogenesis is selected from the group consisting of cancer, macular degeneration; diabetic retinopathy; rheumatoid arthritis; Alzheimer's disease; obesity, psoriasis, atherosclerosis, vascular malformations, angiomata, and endometriosis.

In all aspects of the invention, a pharmaceutical composition comprising an anti-angiogenic agent further comprises at least one additional anti-angiogenic therapy, for example, but not limited to chemotherapy or radiation therapy.

In another aspect, the present invention relates to a method for inhibiting angiogenesis through modulation (i.e. inhibiting) microvascular endothelial cell migration, differentiation or growth in a mammal in need thereof, the method comprising administering a therapeutically effective amount of at least one anti-angiogenic agent selected from the group consisting of: a p190RhoGAP activator, a TFII-I activator, a GATA-2 inhibitor, and a pharmaceutically acceptable carrier.

Another aspect relates to a method of treating an angiogenesis-related disease characterized by increased angiogenesis in a mammal in need thereof, the method comprising administering a therapeutically effective amount an anti-angiogenic agent selected from the group consisting of: p190RhoGAP activator, a TFII-I activator, a GATA-2 inhibitor, and a pharmaceutically acceptable carrier. In some embodiments, the method further comprises administering an anti-angiogenic therapy in conjunction with the anti-angiogenic agent, for example, but not limited to chemotherapy and/or radiation therapy.

In one aspect, the present invention relates to a method of inhibiting angiogenesis by modulating (i.e. inhibiting) microvascular endothelial cell migration and/or differentiation and/or growth comprising contacting said cell with an inhibitor of GATA2 expression or activity.

Another aspect of the present invention relates to the use of an siRNA directed specifically against a GATA-2 gene for inhibiting angiogenesis or microvascular endothelial cell migration, differentiation or growth in a mammal in need thereof, or for example, in the manufacture of a medicament for inhibiting angiogenesis or microvascular endothelial cell migration, differentiation or growth in a mammal in need thereof. In another embodiment relates to the use of an antibody directed specifically against a GATA-2 polypeptide for inhibiting angiogenesis or microvascular endothelial cell migration, differentiation or growth in a mammal in need thereof, wherein the p190RhoGAP function is blocked by the antibody.

In all aspects related to methods, uses and compositions related to an anti-angiogenic agents, a GATA-2 inhibitor is selected from the group consisting of an antibody, an RNA interference molecule, a small molecule, a peptide and an aptamer. In some embodiments, a GATA-2 inhibitor is an RNA interference molecule that inhibits GATA-2 expression in the cell. In some embodiments, a GATA-2 inhibitor is an antibody directed specifically against a GATA-2 polypeptide, wherein the GATA-2 function is blocked by the antibody.

In all aspects related to methods, uses and compositions related to an anti-angiogenic agents, a p190RhoGAP activator is selected from the group consisting of an antibody, a small molecule, a peptide, polypeptide, or nucleic acid.

In all aspects related to methods, uses and compositions related to an anti-angiogenic agents, a TFII-I activator is selected from the group consisting of antibody, a small molecule, a peptide, polypeptide, or nucleic acid.

Another aspect of the present invention relates to the use of a pro-angiogenic agent for promoting angiogenesis through modulation (i.e. increase) in microvascular endothelial cell migration, and/or differentiation and/or growth in a mammal, wherein the pro-angiogenic agent is selected from at least one from the group consisting of: a p190RhoGAP inhibitor, a TFII-I inhibitor, a GATA-2 activator.

In some embodiments, the present invention relates to the use of an siRNA directed specifically against a p190RhoGAP gene for promoting endothelial cell migration. In some embodiments, the present invention relates to the use of an antibody directed specifically against a p190RhoGAP for promoting endothelial cell migration, wherein the p190RhoGAP function is blocked by the antibody.

In some embodiments, the present invention relates to the use of an siRNA directed specifically against a TFII-I gene for promoting endothelial cell migration. In some embodiments, the present invention relates to the use of an antibody directed specifically against a TFII-I for promoting endothelial cell migration, wherein the TFII-I function is blocked by the antibody.

Another aspect of the present invention relates to a pharmaceutical composition comprising a therapeutically effective amount of at least one pro-angiogenic agent selected from the group consisting of: a p190RhoGAP inhibitor; a TFII-I inhibitor, a GATA-2 activator, and a pharmaceutically acceptable carrier for promoting angiogenesis or microvascular endothelial cell migration, differentiation or growth in a mammal in need thereof.

In some embodiments, a pharmaceutical composition comprising a pro-angiogenic agent is useful for the manufacture of a medicament for promoting angiogenesis or microvascular endothelial cell migration, differentiation or growth in a mammal in need thereof.

Another aspect of the present invention relates to the use of an siRNA directed specifically against a p190RhoGAP gene for promoting angiogenesis or microvascular endothelial cell migration, differentiation or growth in a mammal in need thereof. In some embodiments, a siRNA directed specifically against a p190RhoGAP gene is useful for the manufacture of a medicament for promoting angiogenesis or microvascular endothelial cell migration, differentiation or growth in a mammal in need thereof.

In some embodiments, an antibody directed specifically against a p190RhoGAP is useful for promoting angiogenesis by modulating (i.e. increasing) microvascular endothelial cell migration, differentiation or growth in a mammal in need thereof, wherein the p190RhoGAP function is blocked by the antibody. In some embodiments, an antibody directed specifically against a p190RhoGAP polypeptide is useful in a manufacture of a medicament for promoting angiogenesis by modulating (i.e. increasing) microvascular endothelial cell migration, or differentiation or growth in a mammal in need thereof, wherein the p190RhoGAP function is blocked by the antibody.

In another aspect, a siRNA directed specifically against a TFII-I gene is useful for promoting angiogenesis by modulating (i.e. increasing) microvascular endothelial cell migration, differentiation or growth in a mammal in need thereof, or alternatively, is useful in the manufacture of a medicament for promoting angiogenesis or microvascular endothelial cell migration, differentiation or growth in a mammal in need thereof.

In some embodiments, an antibody directed specifically against a TFII-I polypeptide is useful for promoting angiogenesis through modulation (i.e. increase) in microvascular endothelial cell migration and/or differentiation and/or growth in a mammal in need thereof, wherein the TFII-I function is blocked by the antibody, and in some embodiments, is also useful in the manufacture of a medicament for promoting angiogenesis or microvascular endothelial cell migration, differentiation or growth in a mammal in need thereof, wherein the TFII-I is blocked by the antibody.

In some embodiments, a pharmaceutical composition comprising a pro-angiogenic agent is administered to, or is useful to treat a mammal afflicted with an angiogenesis-related disease or disorder characterized by decreased angiogenesis. Examples of angiogenesis-related diseases characterized by decreased angiogenesis are well known in the art, and include, for example ischemic limb disease, coronary artery disease, myocardial infarction, brain ischemia, tissue transplantation therapy and stem cell implantation.

In some embodiments, such a pharmaceutical composition comprising a pro-angiogenic agent is useful to promote angiogenesis or microvascular endothelial cell migration, differentiation or growth in a mammal, wherein the mammal is in need of neovascularization of tissue engineering contructs, organ transplantation, tissue repair, regenerative medicine and wound healing.

Another aspect of the present invention relates to a method for inhibiting angiogenesis through modulation (i.e. inhibiting) microvascular endothelial cell migration and/or differentiation and/or growth, the method comprising contacting an endothelial cell with at least one anti-angiogenic agent selected from the group consisting of: a p190RhoGAP activator, a TFII-I activator, a GATA-2 inhibitor.

Another aspect of the present invention relates to a method for promoting angiogenesis through modulation (i.e. increasing) microvascular endothelial cell migration and/or differentiation and/or growth, the method comprising contacting an endothelial cell with at least one pro-angiogenic agent selected from the group consisting of: a p190RhoGAP inhibitor, a TFII-I inhibitor, a GATA-2 activator.

In another aspect, the present invention provides a method for promoting angiogenesis through modulation (i.e. increasing) or microvascular endothelial cell migration and/or differentiation and/or growth in a mammal in need thereof, the method comprising administering a therapeutically effective amount of at least one pro-angiogenic agent selected from the group consisting of: a p190RhoGAP inhibitor, a TFII-I inhibitor, a GATA-2 activator and a pharmaceutically acceptable carrier.

Another aspect of the present invention provides a method of treating an angiogenesis-related disease characterized by decreased angiogenesis in a mammal in need thereof, the method comprising administering a therapeutically effective amount pro-angiogenic agent selected from the group consisting of: a p190RhoGAP inhibitor, a TFII-I inhibitor, a GATA-2 activator and a pharmaceutically acceptable carrier. In some embodiments, a mammal in need of treatment with an a pro-angiogenic agent is a mammal where it is desirable to increase the neovascularization of a tissue engineering construct or a organ transplant or for tissue repair or any type of regenerative medicine or wound healing.

Another aspect of the present invention relates to a method of promoting angiogenesis or microvascular endothelial cell migration, differentiation or growth comprising contacting a microvascular endothelial cell with an inhibitor of TFII-I expression or activity. Another aspect of the present invention relates to a method of promoting angiogenesis or microvascular endothelial cell migration, differentiation or growth comprising contacting said cell with an inhibitor of p190RhoGAP expression or activity.

In all aspects related to methods, uses and compositions related to a pro-angiogenic agent, a mammal to be treated with such anti-angiogenic agent can be afflicted with an angiogenesis-related disease or disorder characterized by a decrease in angiogenesis. Examples of such angiogenesis-related diseases characterized by decrease in angiogenesis are well known in the art, and include for example but are not limited to ischemic limb disease, coronary artery disease, myocardial infarction, brain ischemia, tissue transplantation therapy and stem cell implantation.

Another aspect of the present invention relates to a method for promoting angiogenesis or microvascular endothelial cell migration, differentiation or growth, the method comprising contacting an endothelial cell with an siRNA directed specifically against a p190RhoGAP gene or a TFII-I gene.

In another aspect, the present invention relates to a method for promoting angiogenesis or microvascular endothelial cell migration, differentiation or growth, the method comprising contacting an endothelial cell with an antibody directed specifically against a p190RhoGAP polypeptide, wherein the p190RhoGAP function is blocked by the antibody.

In another embodiment, the present invention provides a method for promoting angiogenesis or microvascular endothelial cell migration, differentiation or growth, the method comprising contacting an endothelial cell with an antibody directed specifically against a TFII-I polypeptide, wherein the TFII-I function is blocked by the antibody.

In all aspects related to methods, uses and compositions related to a pro-angiogenic agents, a p190RhoGAP inhibitor can be selected from the group consisting of an antibody, an RNA interference molecule, a small molecule, a peptide and an aptamer. In some embodiments, a p190RhoGAP inhibitor is an RNA interference molecule that inhibits p190RhoGAP expression in the cell. In another embodiment, a p190RhoGAP inhibitor is an siRNA directed specifically against a p190RhoGAP gene.

In all aspects related to methods, uses and compositions related to a pro-angiogenic agents, a TFII-I inhibitor can be selected from the group consisting of an antibody, an RNA interference molecule, a small molecule, a peptide and an aptamer. In some embodiments, a TFII-I inhibitor is selected from the group consisting of an antibody, an RNA interference molecule, a small molecule, a peptide and an aptamer. In some embodiments, a TFII-I inhibitor is an RNA interference molecule that inhibits TFII-I expression in the cell, such as a siRNA molecule directed specifically against a TFII-I gene.

In all aspects related to methods, uses and compositions related to a pro-angiogenic agents, a GATA-2 activator is selected from the group consisting of antibody, a small molecule, a peptide, polypeptide, or nucleic acid.

Another aspect of the present invention relates to a method of modulating angiogenesis or microvascular endothelial cell migration and/or differentiation and/or growth, the method comprising contacting a microvascular endothelial cell with an agent which inhibits or activates one or more of p190RhoGAP, TFII-I, and GATA-2. In some embodiments modulating is an increase in angiogenesis or an increase in microvascular endothelial cell migration, or an increase in differentiation or an increase in microvascular growth, and wherein the endothelial cell is contacted with at least one agent which inhibits p190RhoGAP or inhibits TFII-I or activates GATA-2. In alternative embodiments, modulating is a decrease in angiogenesis or microvascular endothelial cell migration, differentiation or growth, and wherein the endothelial cell is contacted with at least one agent which activates p190RhoGAP or activates TFII-I or inhibits GATA-2.

Another embodiments relates to the use of an antibody directed specifically against a GATA-2 polypeptide for the manufacture of a medicament for inhibiting angiogenesis or microvascular endothelial cell migration, differentiation or growth in a mammal in need thereof, wherein the p190RhoGAP function is blocked by the antibody.

In all aspects of the present invention, an microvascular endothelial cell is a mammalian endothelial cell. In some embodiments, a mammalian endothelial cell is a human endothelial cell.

In all aspects of the invention, a mammal can be a human.

BRIEF DESCRIPTION OF THE FIGURES

FIG. 16A shows the mRNA levels of TFII-I, Gata2, p190RhoGAP, and Vegfr2 in mouse retinal tissues in which TFII-I, Gata2, or p190RhoGAP were knocked down by in vivo delivery of respective siRNAs (normalized to mRNA levels in retina injected with control siRNA; n=7, mean±SEM; *, p<0.01 using unpaired student's t-test).

FIG. 16B shows the mRNA levels of TFII-I and GATA2 in retinal tissues in which TFII-I or GATA2 were overexpressed by in vivo delivery of each DNA (normalized to mRNA levels of observed in the retina when control DNA vector was injected; n=7, mean±SEM; *, p<0.01).

FIG. 16C shows the Vegf mRNA levels in retina transfected with siRNA for TFII-I, Gata2, or p190RhoGAP (data are normalized to retina transfected with control siRNA; n=7, mean±SEM; **, p<0.05).

FIG. 16D-F are graphs showing the results of quantifying the total percentage of the peripheral region of retina that contained blood vessels in the whole mount retina of a control mouse eye versus eyes transfected with TFII-I, Gata2, or p190RhoGAP siRNAs (bar=0.8 mm). (n=7, mean±SEM; *, p<0.01).

DETAILED DESCRIPTION

Figures 1A, 1B, 1C, 1D, 1E, 1F:
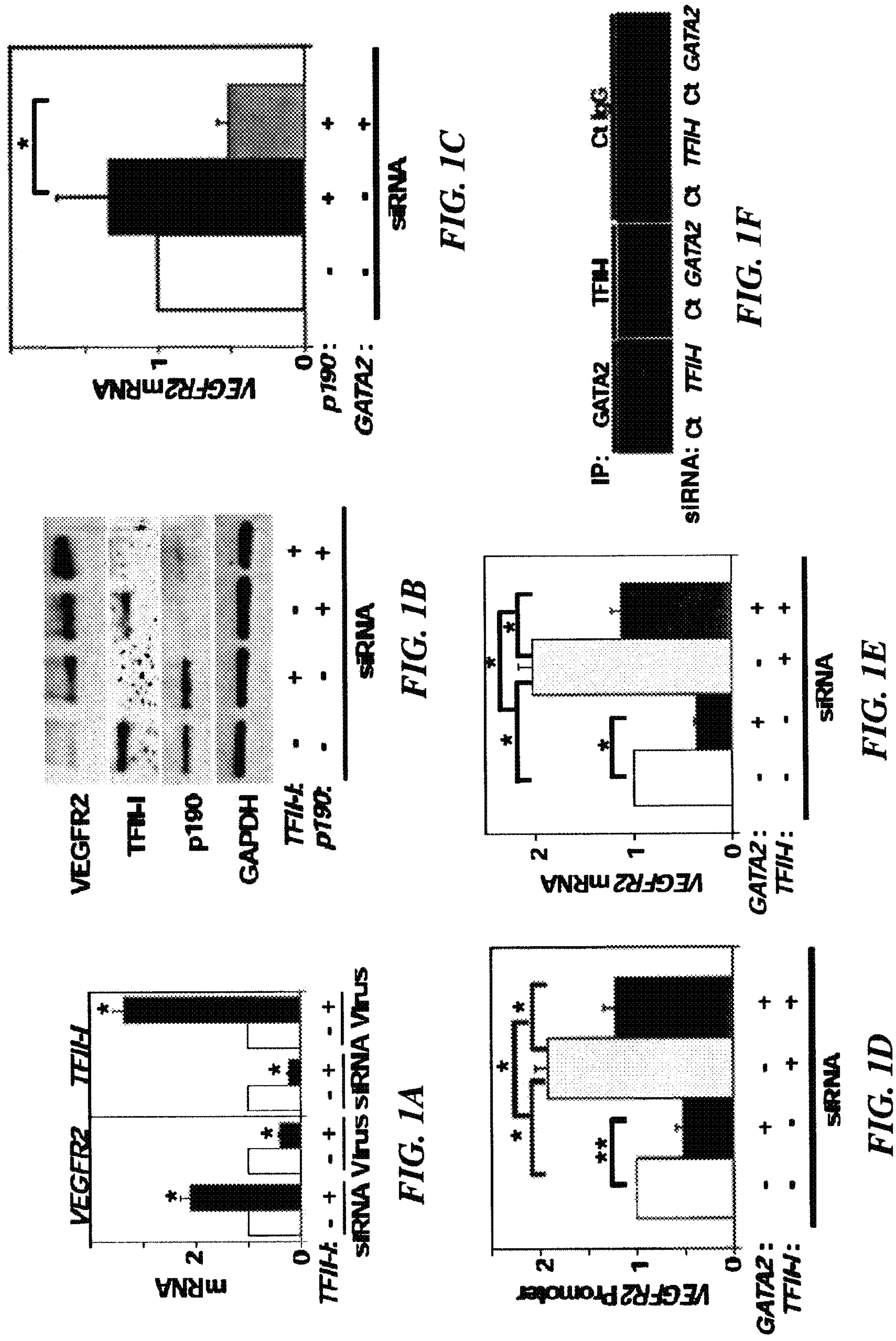
FIG. 1A is a histogram showing the VEGFR2 and TFII-I mRNA levels in cells treated with TFII-I siRNA or lentiviral vectors (virus) relative to control cells (*P<0.05; unpaired Student's t-test is used throughout). All error bars are s.e.m.
FIG. 1B are representative immunoblots showing VEGFR2, TFII-I, p190RhoGAP (p190) and GAPDH protein levels in cells treated with TFII-I or p190RhoGAP siRNAs, or both.
FIG. 1C is a histogram showing the VEGFR2 mRNA levels in cells transfected with p190RhoGAP siRNA alone or with GATA2 siRNA (*P<0.01). All error bars are s.e.m.
FIG. 1D is a histogram showing the VEGFR2 promoter activities in cells transfected with GATA2 or TFII-I siRNA alone or in combination (*P<0.01, **P<0.05). All error bars are s.e.m.
FIG. 1E is a histogram showing the VEGFR mRNA levels in cells transfected with GATA2 or TFII-I siRNA alone or in combination (*P, 0.01, **P<0.05). All error bars are s.e.m.
FIG. 1F shows the ChIP analysis of the VEGFR2 promoter coimmunoprecipitating (IP) with GATA2 or TFII-I antibodies in cells transfected with TFII-I or GATA2 siRNA (n=3). Ct, control.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (3rd ed.), Cold Spring Harbor Laboratory Press, Cold Spring Harbor, N.Y., USA (2000); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI); (John E. Coligan, et. al., ed. John Wiley and Sons, Inc.), Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); Animal Cell Culture Methods (Methods in Cell Biology, Vol. 57, Jennie P. Mather and David Barnes editors, Academic Press, 1st edition, 1998); Methods in Molecular biology, Vol. 180, Transgenesis Techniques by Alan R. Clark editor, second edition, 2002, Humana Press; and Methods in Meolcular Biology, Vo. 203, 2003, Transgenic Mouse, editored by Marten H. Hofker and Jan van Deursen, which are all herein incorporated by reference in their entireties.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention relates to methods of regulating endothelial cell migration and angiogenesis, and uses thereof for the purpose of treating angiogenesis related diseases and disorders, particularly when the diseases or disorders is directly related aberrant angiogenesis.

Embodiments of the present invention are based, at least in part, on the discovery that p190RhoGAP interacts with two antagonistic transcription factors, TFII-I and GATA-2, thereby one can regulate angiogenesis by activating or inhibiting a combination of p190RhoGAP, TFII-I and GATA-2. Without wishing to be bound to theory, the inventors have discovered that protein p190RhoGAP sequesters TFII-I and GATA-2 in the cytoplasm and thereby regulates the expression of the VEGF receptor in capillary endothelial cells. The inventors have also demonstrated that modulation (i.e. decreasing/reducing or increasing) the levels of p190RhoGAP, TFII-I, or GATA-2, it is possible to regulate VEGFR expression and subsequently alter angiogenesis. Briefly, the inventors have demonstrated: (1) Inhibition of TFII-I and/or p190RhoGAP by siRNA results in an increase in angiogenesis in vivo. (2) inhibition of GATA-2 by siRNA results in decrease in angiogenesis in vivo; (3) increase in TFII-I activity by overexpression results in a decrease in angiogenesis in vivo; and (4) increase in GATA-2 activity alone, by overexpression results in an increase in angiogenesis in vivo, which is inhibited by in combination with increase in TFII-I activity (i.e. GATA-2 and TFII-I).

Thus, described herein are methods for promoting or increasing microvascular endothelial cell migration, differentiation, capillary blood vessel growth and/or angiogenesis by administering an pro-angiogenic agent, whereby a pro-angiogenic agent is selected from at least one of an inhibitor of p190RhoGAP, an inhibitor of TFII-I or an activator of GATA-2.

Thus, described herein are methods for inhibiting microvascular endothelial cell migration, differentiation, capillary blood vessel growth and/or angiogenesis by administering an anti-angiogenic agent, whereby an anti-angiogenic agent is selected from at least one of an activator of p190RhoGAP, an activator of TFII-I or an inhibitor of GATA-2.

One aspect of the invention provides a method and compositions for altering angiogenesis by modulating the levels of p190RhoGAP, TFII-I, or GATA-2, by siRNA or over-expression.

One embodiment of this aspect and all other aspects the present invention relates to a method to increase or promote angiogenesis by inhibiting p190RhoGAP, and/or inhibiting TFII-I and/or activating GATA-2. One embodiment of the present invention relates to a method to decrease angiogenesis by activating p190RhoGAP, and/or activating TFII-I and/or inhibiting GATA-2.

Another aspect of the present invention provides a method and compositions for inhibiting/promoting capillary endothelial cell migration and differentiation by modulating the levels of p190RhoGAP, TFII-I, or GATA-2, by siRNA or over-expression.

One embodiment of this aspect and all other aspects the present invention relates to a method to increase or promote endothelial cell migration by inhibiting p190RhoGAP, and/or inhibiting TFII-I and/or activating GATA-2. One embodiment of this aspect and all other aspects of the present invention relates to a method to decrease endothelial cell migration by activating p190RhoGAP, and/or activating TFII-I and/or inhibiting GATA-2.

Another aspect of the present invention provides a method and compositions for the treatment of macular degeneration/tumor/cancer by inhibiting angiogenesis through over expressing p190RhoGAP and/or TFII-I, or inhibition of GATA-2 expression by siRNA directed to GATA-2.

One embodiment of this aspect and all other aspects the present invention relates to a method to treat disorders where it is desirable to decrease angiogenesis by activating p190RhoGAP, and/or activating TFII-I and/or inhibiting GATA-2.

Accordingly, embodiments of the present invention relate to methods and compositions to promote or increase endothelial cell migration, the method comprising contacting an endothelial cell with a pro-angiogenesis agent, for example a pro-angiogenic agent is selected from at least one or any combination of an inhibitor of p190RhoGAP, an inhibitor of TFII-I, or an activator of GATA-2.

Embodiments of the invention also provide methods for promoting or increasing angiogenesis in a mammal in need thereof, the method comprising administering a therapeutically effective amount of a pro-angiogenic agent, for example, a pro-angiogenesis agent, for example a pro-angiogenic agent is selected from at least one or any combination of an inhibitor of p190RhoGAP, an inhibitor of TFII-I, or an activator of GATA-2 and a pharmaceutically acceptable carrier.

Embodiments of the invention also provide methods for treating an angiogenesis-related disease characterized by a decrease or loss in angiogenesis in a mammal in need thereof, the method comprising administering a therapeutically effective amount of a pro-angiogenesis agent, for example a pro-angiogenic agent is selected from at least one or any combination of an inhibitor of p190RhoGAP, an inhibitor of TFII-I, or an activator of GATA-2 and a pharmaceutically acceptable carrier.

Other embodiments of the present invention relate to methods and compositions to inhibit endothelial cell migration, the method comprising contacting an endothelial cell with an anti-angiogenic agent, whereby an anti-angiogenic agent is selected from at least one or any combination of an activator of p190RhoGAP, an activator of TFII-I or an inhibitor of GATA-2

Embodiments of the invention also provide methods for inhibiting angiogenesis in a mammal in need thereof, the method comprising administering a therapeutically effective amount of a anti-angiogenic agent, for example, an anti-angiogenic agent is selected from at least one or any combination of an activator of p190RhoGAP, an activator of TFII-I or an inhibitor of GATA-2 and a pharmaceutically acceptable carrier.

Embodiments of the invention also provide methods for treating an angiogenesis-related disease characterized by uncontrolled or increased angiogenesis in a mammal in need thereof, the method comprising administering a therapeutically effective amount of a anti-angiogenic agent, for example, an anti-angiogenic agent is selected from at least one or any combination of an activator of p190RhoGAP, an activator of TFII-I or an inhibitor of GATA-2 and a pharmaceutically acceptable carrier.

Definitions

As used herein, the term "pro-angiogenic agent" refers to any agent which is an inhibitor of p190RhoGAP (i.e. any agent which decreases or inhibits the expression or function of p190RhoGAP protein), or an inhibitor of TFII-I (i.e. any agent which decreases or inhibits the expression or function of the TFII-I protein), or an activator or GATA-2 (i.e. any agent which increases the expression or function of GATA-2 protein). For example, a pro-angiogenic agent which is an inhibitor of p190RhoGAP or an inhibitor of TFII-I (e.g. any agent which decreases or inhibits the expression or function of a p190RhoGAP or TFII-I protein) can be selected from the group consisting of, but not limited to an antibody, an RNA interference (RNAi) molecule, a small molecule, a peptide and aptamer. In another example, a pro-angiogenic agent which is an activator of GATA-2 (e.g. any agent which increases the expression and/or function of a GATA-2 protein) can be selected from the group consisting of, but not limited to an antibody, a small molecule, a peptide, a polypeptide, nucleic acid, such as RNA or DNA. The effect of a pro-angiogenic agent can be assessed by measuring endothelial cell growth and migration in vitro. Endothelial cell growth can be determined, for example, by measuring cell proliferation using an MTS assay commercially available from a variety of companies including RnD Systems, and Promega, among others. Endothelial cell migration can be assessed, for example, by measuring the migration of cells through a porous membrane using a commercially available kit such as BD BioCoat Angiogenesis System or through a Boyden chamber apparatus.

The pro-angiogenic activity of pro-angiogenic agent, such as an inhibitor of p190RhoGAP, an inhibitor of TFII-I or an activator of GATA-2, can be measured in angiogenesis assay as described herein or known in the art, for example by assessment in vivo by an increase in capillary density or neovascular infiltration using a Matrigel plug assay as described by e.g., Kragh M, et al., (2003) (Kragh M, Hjarnaa P J, Bramm E, Kristjansen P E, Rygaard J, and Binderup L. Int J. Oncol. (2003) 22(2):305-11, which is herein incorporated by reference in its entirety) in a mammal treated with a pro-angiogenic agent, compared to capillary density or neovascular infiltration observed in the absence of a pro-angiogenic agent. An "increase in capillary density" means an increase of cell density of at least 5% in the presence of a pro-angiogenic agent relative to the absence of a pro-angiogenic agent, preferably at least 10% at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more, relative to absence of such pro-angiogenic agent.

As used herein, the term "anti-angiogenic agent" refers to any agent which is an activator of p190RhoGAP (e.g. any agent which increases the expression or function of p190RhoGAP protein), or an activator of TFII-I (e.g. any agent which increases the function or expression of the TFII-I protein), or an inhibitor of GATA-2 (e.g. any agent which decreases or inhibits the function or expression of GATA-2 protein). For example, an anti-apoptotic pro-angiogenic agent which is an activator of p190RhoGAP or activator of TFII-I (e.g. any agent which increases the expression and/or function of a p190RhoGAP protein or a TFII-I protein) can be selected from the group consisting of, but not limited to an antibody, a small molecule, a peptide, a polypeptide, nucleic acid, such as RNA or DNA. In another example, an anti-angiogenic agent which is an inhibitor of GATA-2 (e.g. any agent which decreases or inhibits the expression or function of a GATA-2 protein) can be selected from the group consisting of, but not limited to an antibody, an RNA interference (RNAi) molecule, a small molecule, a peptide and aptamer.

The anti-angiogenic activity of an anti-angiogenic agent, such as an activator of p190RhoGAP, an activator of TFII-I or an inhibitor of GATA-2 can also be assessed in vivo by a decrease in capillary density or neovascular infiltration using a Matrigel plug assay as described by e.g., Kragh M, et al., (2003) (Kragh M, Hjarnaa P J, Bramm E, Kristjansen P E, Rygaard J, and Binderup L. Int J. Oncol. (2003) 22(2):305-11, which is herein incorporated by reference in its entirety) in a mammal treated with an anti-angiogenic agent, compared to capillary density or neovascular infiltration observed in the absence of an anti-angiogenic agent. A "decrease in capillary density" means a decrease of at least 5% in the presence of anti-angiogenic agent as compared to untreated subjects; preferably a decrease in capillary density is at least 10%, at least 20%, at least 30%, at least 40%, at least 50%, at least 60%, at least 70%, at least 80%, at least 90%, at least 95%, at least 99% lower, or even 100% (i.e., absent) in the presence of a an anti-angiogenic agent as compared to that measured in the absence of administration of an anti-angiogenic agent.

As used herein, the term "p190RhoGAP polypeptide" or to a conservative substitution variant or fragment thereof that retains p190RhoGAP activity as that term is defined herein. p190RhoGAP is also known in the art as aliases; GRF-1 (glucocorticoid receptor repression factor 1); P190A; P190-A; KIAA1722; MGC10745; GRLF1 (glucocorticoid receptor DNA binding factor 1). The human p190RhoGAP corresponds to Genbank Accession No. NM_004491, (or M73077, Gene ID: 2909) and human p190RhoGAP refers to a polypeptide of SEQ ID NO. 01 (Genbank Accession No. NM_004491). The human p190RhoGAP polypeptide is encoded by the genomic nucleic acid sequence SEQ ID NO: 2, and the mRNA nucleic acid sequence of SEQ ID NO: 3. It should be understood that the carbohydrate moieties of p190RhoGAP can be involved in p190RhoGAP anti-angiogenic activity, including, e.g., N-linked keratin sulfate chains. By "retaining p190RhoGAP activity" is meant that a polypeptide retains at least 50% of the p190RhoGAP activity of a polypeptide of SEQ ID NO. 1. Also encompassed by the term "p190RhoGAP polypeptide" are mammalian homologs of human p190RhoGAP and conservative substitution variants or fragments thereof that retain p190RhoGAP activity. In one aspect, such homologs or conservative variants thereof inhibit human endothelial cell growth and/or migration as measured, for example, as described herein.

As used herein, the term "TFII-I polypeptide" or to a conservative substitution variant or fragment thereof that retains TFII-I activity as that term is defined herein. TFII-I is also known in the art as aliases; BAP-135, SPIN, BTKAP1, DIWS, IB291 and GTF2I (General Transcription factor II, i). The human TFII-I corresponds to Genbank Accession No. NM_032999, (or U77948, and Gene ID: 2969) and human TFII-I refers to a polypeptide of SEQ ID NO. 04 (Genbank Accession No. NM_032999). The human TFII-I polypeptide is encoded by the genomic nucleic acid sequence SEQ ID NO: 6, and the mRNA nucleic acid sequence of SEQ ID NO: 5. It should be understood that the carbohydrate moieties of TFII-I can be involved in TFII-I anti-angiogenic activity, including, e.g., N-linked keratin sulfate chains. By "retaining TFII-I activity" is meant that a polypeptide retains at least 50% of the TFII-I activity of a polypeptide of SEQ ID NO. 4. Also encompassed by the term "TFII-I polypeptide" are mammalian homologs of human TFII-I and conservative substitution variants or fragments thereof that retain TFII-I activity. In one aspect, such homologs or conservative variants thereof inhibit human endothelial cell growth and/or migration as measured, for example, as described herein.

As used herein, the term "GATA-2 polypeptide" or to a conservative substitution variant or fragment thereof that retains GATA-2 activity as that term is defined herein. GATA-2 is also known in the art as aliases; GATA binding protein 2 (GATA-2), also known in the art by the aliases GATA2, GATA-binding protein 2 and NFE1B). The human GATA-2 corresponds to Genbank Accession No. NM_032638, (or AF169253, and Gene ID: 2624) and human GATA-2 refers to a polypeptide of SEQ ID NO. 07 (Genbank Accession No. NM_0326389). The human GATA-2 polypeptide is encoded by the genomic nucleic acid sequence SEQ ID NO: 9, and the mRNA nucleic acid sequence of SEQ ID NO: 8. It should be understood that the carbohydrate moieties of GATA-2 can be involved in GATA-2 pro-angiogenic activity, including, e.g., N-linked keratin sulfate chains. By "retaining GATA-2 activity" is meant that a polypeptide retains at least 50% of the GATA-2 activity of a polypeptide of SEQ ID NO. 7. Also encompassed by the term "GATA-2 polypeptide" are mammalian homologs of human GATA-2 and conservative substitution variants or fragments thereof that retain GATA-2 activity. In one aspect, such homologs or conservative variants thereof stimulate human endothelial cell growth and/or migration as measured, for example, as described herein.

The term "agent" as used herein refers to a chemical entity or biological product, or combination of chemical entities or biological products. The chemical entity or biological product is preferably, but not necessarily a low molecular weight compound, but can also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. The term "agent" refers to any entity selected from a group comprising; chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, an "inhibitor of p190RhoGAP" or "p190RhoGAP inhibitor" are used interchangeably and refers to any molecule or agent which decreases or inhibits the expression of p190RhoGAP or inhibits the consequences of activated p190RhoGAP, i.e. inhibits the downstream signalling of p190RhoGAP, or inhibits the binding of p190RhoGAP to sequester GATA-2 or TFII-I in a CE cell. For example, a p190RhoGAP inhibitor can be an siRNA or dsRNA that inhibits the expression of p190RhoGAP, a p190RhoGAP small molecule inhibitor, a p190RhoGAP antagonist, a p190RhoGAP inhibiting antibody.

As used herein, the term "inhibiting p190RhoGAP activity" refers to a decrease in the activity of p190RhoGAP by at least 10%, at least 20%, at least 30%, at least 40%, at least 50%, at least 60%, at least 70%, at least 80%, at least 90%, at least 95%, at least 99%, or even 100% (i.e., no activity) in the presence of a p190RhoGAP activity inhibitor compared to the activity of p190RhoGAP in the absence of an inhibitor.

As used herein, the terms an "activator of p190RhoGAP" or a "p190RhoGAP activator" are used interchangeably and refer to any molecule or agent which increases the expression of p190RhoGAP or functions to increase p190RhoGAP activity, i.e. any agent which increases the downstream signalling of p190RhoGAP via binding and sequestering of GATA-2 or TFII-I in a CE cell. For example, a p190RhoGAP activator can be a nucleic acid agent that increases the expression of p190RhoGAP, a p190RhoGAP small molecule activator, a p190RhoGAP agonist, a p190RhoGAP antibody that constitutive activates p190RhoGAP or any agent which inhibits the repression of p190RhoGAP.

As used herein, the terms "increasing p190RhoGAP activity" or "promoting f p190RhoGAP activity" refers to an increase in the anti-angiogenic activity of p190RhoGAP by at least 10% at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of an activator agent of p190RhoGAP, relative to the level of activity of p190RhoGAP activity in the absence of such a p190RhoGAP activator agent.

As used herein, an "inhibitor of TFII-I" or "TFII-I inhibitor" are used interchangeably and refers to any molecule or agent which decreases or inhibits the expression of TFII-I or functions to inhibit TFII-I activity, i.e. inhibits the downstream signalling of TFII-I such a increases cell infiltration, increased vascular density, increased capillary vessel formation and increase Vegfr2 expression in a CE cell. For example, a TFII-I inhibitor can be an siRNA or dsRNA that inhibits the expression of TFII-I, a TFII-I small molecule inhibitor, a TFII-I antagonist, a TFII-I inhibiting antibody.

As used herein, the term "inhibiting TFII-I activity" refers to a decrease in the activity of TFII-I by at least 10%, at least 20%, at least 30%, at least 40%, at least 50%, at least 60%, at least 70%, at least 80%, at least 90%, at least 95%, at least 99%, or even 100% (i.e., no activity) in the presence of a TFII-I activity inhibitor compared to the activity of TFII-I in the absence of an inhibitor.

As used herein, the terms an "activator of TFII-I" or "TFII-I activator" are used interchangeably and refer to any molecule or agent which increases the expression of TFII-I or functions to increase TFII-I activity, i.e. increases the downstream signalling of TFII-I such a decreases cell infiltration, decreases vascular density, decreases capillary vessel formation and decreases Vegfr2 expression in a CE cell. For example, a TFII-I activator can be a nucleic acid agent that increases the expression of TFII-I, a TFII-I small molecule activator, a TFII-I agonist, a TFII-I antibody that constitutive activates TFII-I or any agent which inhibits the repression of TFII-I.

As used herein, the terms "increasing TFII-I activity" or "promoting TFII-I activity" refers to an increase in the anti-angiogenic activity of TFII-I by at least 10% at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of an activator agent of TFII-I, relative to the level of activity of TFII-I activity in the absence of such a TFII-I activator agent.

As used herein, an "inhibitor of GATA-2" or "GATA-2 inhibitor" are used interchangeably and refers to any molecule or agent which decreases or inhibits the expression of GATA-2 or functions to inhibit GATA-2 activity, i.e. inhibits the downstream signalling of GATA-2 such as decreases cell infiltration, decreases vascular density, decreases capillary vessel formation and decreases Vegfr2 expression in a CE cell. For example, a GATA-2 inhibitor can be an siRNA or dsRNA that inhibits the expression of GATA-2, a GATA-2 small molecule inhibitor, a GATA-2 antagonist, a GATA-2 inhibiting antibody.

As used herein, the term “inhibiting GATA-2 activity” refers to a decrease in the activity of GATA-2 by at least 10%, at least 20%, at least 30%, at least 40%, at least 50%, at least 60%, at least 70%, at least 80%, at least 90%, at least 95%, at least 99%, or even 100% (i.e., no activity) in the presence of a GATA-2 activity inhibitor as compared to the activity of GATA-2 in the absence of an inhibitor.

As used herein, the terms an “activator of GATA-2” or “GATA-2 activator” are used interchangeably and refer to any molecule or agent which increases the expression of GATA-2 or increases the consequences of activated GATA-2, i.e. increases the downstream signalling of GATA-2 such a increases cell infiltration, increases vascular density, increases capillary vessel formation and increases Vegfr2 expression in a CE cell. For example, a GATA-2 activator can be a nucleic acid agent that increases the expression of GATA-2, a GATA-2 small molecule activator, a GATA-2 agonist, a GATA-2 antibody that constitutive activates GATA-2 or any agent which inhibits the repression of GATA-2.

As used herein, the terms “increasing GATA-2 activity” or “promoting GATA-2 activity” refers to an increase in the anti-angiogenic activity of GATA-2 by at least 10% at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of an activator agent of GATA-2, relative to the level of activity of GATA-2 activity in the absence of such a GATA-2 activator agent.

As used herein, the terms “inhibiting endothelial cell migration” refer to the reduction in cell migration and/or capillary tube formation in the presence of an anti-angiogenic agent, for example an anti-angiogenic agent is selected from at least one or any combination of an activator of p190RhoGAP, an activator of TFII-I or an inhibitor of GATA-2. Assays for in vitro cell migration and capillary tube formation are well known to one skilled in the art, e.g. in Lingen M W, 2003, Methods Mol. Med. 78:337-47 and McGonigle and Shifrin, 2008, Curr. Prot. Pharmacology, Unit 12.12, and any angiogenesis assays described herein.

As used herein, the term “inhibiting angiogenesis” means the reduction or prevention of growth of new blood vessels. Inhibition include slowing the rate of growth. The growth rate can be reduced by about 20%, about 30%, about 40%, about 50%, about 60%, about 70%, about 80%, about 90%, about 100%, about 125%, about 150% or more compared to a control, untreated condition. Inhibition also means no further growth of new blood vessels from the time of start of treatment administration. The term “inhibiting angiogenesis” also refers to a decrease in a measurable marker of angiogenesis by at least about 10%, at least about 20%, at least about 30%, at least about 40%, at least about 50%, at least about 60%, at least about 70%, at least about 80%, at least about 90%, at least about 95%, at least about 99%, or even 100% (i.e., absent) in the presence of an anti-angiogenic agent, such as for example, an activator of p190RhoGAP, an activator of TFII-I or an inhibitor of GATA-2 as compared to the level of the measurable marker in the absence of an anti-angiogenic agent. Some non-limiting examples of measurable markers of angiogenesis include capillary density, endothelial cell proliferation, endothelial cell migration, and vessel ingrowth. Angiogenesis can be detected by methods known in the art.

As used herein, the terms “increasing angiogenesis” or “promoting angiogenesis” refer to an increase in at least one measurable marker of angiogenesis by at least 10%, at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more, in the presence of a pro-angiogenic agent relative to that marker in the absence of such agent.

The term “angiogenesis” is broadly defined as the creation or spouting of new blood vessels from pre-existing blood vessels and is characterized by endothelial cell proliferation and migration triggered by pro-angiogenic factors. Angiogenesis can be a good and necessary process, for example, in wound healing, or it can be an aberrant and undesired process with detrimental consequences, such as the growth of solid tumors and metastasis, and hemangiomas. Aberrant angiogenesis can lead to certain pathological conditions such as death, blindness, and disfigurement. Angiogeneis and capillary elongation of about 1-2 mm requires both endothelial cell growth (including endothelial cell proliferation) and endothelial cell migration.

As used herein, the term “inhibiting endothelial cell proliferation” refers to a decrease in the proliferation of endothelial cells of at least 10%, at least 20%, at least 30%, at least 40%, at least 50%, at least 60%, at least 70%, at least 80%, at least 90%, at least 95%, at least 99%, or even 100% (i.e., no growth) in the presence of an anti-angiogenic agent as compared to the level of proliferation in the absence of an anti-angiogenic agent.

As used herein, the term “promoting endothelial cell proliferation” refers to an increase in the proliferation of endothelial cells of at least 10%, preferably the increase is at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of a pro-angiogenic agent, as that term is used herein as compared to in the absence of a pro-angiogenic agent.

As used herein, the term “inhibition endothelial cell differentiation” refers to an increase in the number of differentiated endothelial cells in a given population of endothelial cells of at least 10% in the presence of an anti-angiogenic agent, preferably the decrease is at least 20%, at least 30%, at least 40%, at least 50%, at least 60%, at least 70%, at least 80%, at least 90%, at least 95%, at least 99% decrease in the number of differentiated endothelial cells, or even 100% (i.e., no proliferation) of differentiated cells in a population of differentiated cells in the presence of an anti-angiogenic agent as compared to in the absence of an anti-angiogenic agent.

As used herein, the term “promoting endothelial cell differentiation” refers to an increase in the number of differentiated endothelial cells in a given population of endothelial cells of at least 10%, preferably the increase is at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of a pro-angiogenic agent, as that term is used herein as compared to in the absence of a pro-angiogenic agent.

As used herein, the term “migration” as used herein in reference to endothelial cell migration refers to all mechanisms and ways capillary blood vessels can grow or elongate or extend over increasing distances and surface areas.

As used herein, the term “capillary blood vessel growth” as used herein refers to an in increase in the original length of a capillary blood vessel, for example an increase is at least about 10%, or at least about 15%, or at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more the length of the capillary blood vessel as compared to the original length. An inhibition of capillary blood vessel growth would be a reduction or complete attenuation of the rate of the growth of a capillary blood vessel (i.e. the blood vessel does not increase in length or does not elongtate or increases in length at a slower rate), or a retraction of a capillary blood vessel (i.e. the length of the blood vessel decreases) as compared to its original length. Promotion of capillary blood vessel growth would be an increase in the rate of the growth of a capillary blood vessel (i.e. the blood vessel elongates or increases in length or increases the rate at which the length increases), as compared to its original length.

As used herein, the term "inhibition of migration" refers to a decrease in the migration of endothelial cells through a porous membrane (e.g., using a commercially available migration assay kit such as BD BioCoat Angiogenesis System) of at least 10% in the presence of an anti-angiogenic agent, preferably the decrease is at least 20%, at least 30%, at least 40%, at least 50%, at least 60%, at least 70%, at least 80%, at least 90%, at least 95%, at least 99% decrease in the migration of endothelial cells through a porous membrane, or even 100% (i.e., no migration) in the presence of an anti-angiogenic agent as compared to in the absence of an anti-angiogenic agent.

As used herein, the term "promoting migration" refers to an increase in the migration of endothelial cells through a porous membrane of at least 10%, preferably the increase is at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of a pro-angiogenic agent, as that term is used herein as compared to in the absence of a pro-angiogenic agent.

As used herein, the term an "angiogenic disease or disorder" and an "angiogenesis-related disease" which are used in conjunction with the phrase "characterized by uncontrolled or increased angiogenesis", refers to any pathological state or disease or disorder that is the direct result of aberrant blood vessel proliferation (e.g. diabetic retinopathy and hemangiomas) or undesired or pathological blood vessel proliferation (e.g. in the case cancer and tumor growth). The term also refer to diseases or disorders whose pathological progression is dependent on a good blood supply and thus blood vessel proliferation. Examples include but are not limited to abnormal vascular proliferation, ascites formation, psoriasis, age-related macular degeneration, thyroid hyperplasia, preeclampsia, rheumatoid arthritis and osteo-arthritis, Alzheimer's disease, obesity, pleural effusion, atherosclerosis, endometriosis, diabetic/other retinopathies, ocular neovascularization.

As used herein, the term an "angiogenesis-related disease" which used in conjunction with the phrase "characterized by a decrease in angiogenesis", refers to any pathological state or disease or disorder that is the direct result of a loss of blood vessels or a reduction or inhibition of blood vessel proliferation. The term also refer to diseases or disorders whose pathological progression is due to a reduced blood supply or to disorders where it is desirable to increase the blood supply to a particular organ or tissue. Examples include, but are not limited to, ischemic diseases or ischemic injury, ischemia, transplantation therapy (such as, for example post-organ transplant therapy for transplantation of heart, lung, heart/lung, kidney, liver, and post-cell transplantation in cell based therapies such as stem cell therapies), stroke, and the like.

As used herein, the term "pro-angiogenic factors" refers to factors that directly or indirectly promote new blood vessels formation. These factors can be expressed and secreted by normal and tumor cells. In one embodiment, the pro-angiogenic factors include, but are not limited to EGF, E-cadherin, VEGF, angiogenin, angiopoietin-1, fibroblast growth factors: acidic (aFGF) and basic (bFGF), fibrinogen, fibronectin, heparanase, hepatocyte growth factor (HGF), insulin-like growth factor-1 (IGF-1), IGF, BP-3, PDGF, VEGF-A VEGF-C, pigment epithelium-derived factor (PEDF), vitronection, leptin, trefoil peptides (TFFs), CYR61 (CCN1) and NOV (CCN3), leptin, midkine, placental growth factor platelet-derived endothelial cell growth factor (PD-ECGF), platelet-derived growth factor-BB (PDGF-BB), pleiotrophin (PTN), progranulin, proliferin, transforming growth factor-alpha (TGF-alpha), transforming growth factor-beta (TGF-beta), tumor necrosis factor-alpha (TNF-alpha), c-Myc, granulocyte colony-stimulating factor (G-CSF), stromal derived factor 1 (SDF-1), scatter factor (SF), osteopontin, stem cell factor (SCF), matrix metalloproteinases (MMPs), thrombospondin-1 (TSP-1), and inflammatory cytokines and chemokines that are inducers of angiogenesis and increased vascularity, eg. CCL2 (MCP-1), interleukin-8 (IL-8) and CCL5 (RANTES). The pro-angiogenic factors can be used in conjunction with any and all combinations of pro-angiogenic agents (i.e. a p190RhoGAP inhibitor, and/or a TFII-I inhibitor and/or a GATA-2 activator) as described herein.

As used herein, the term "ischemia" refers to inadequate or reduced blood supply (i.e. circulation) to a local area, for example due to a blockage of blood vessels to the area. Ischemic diseases include stroke, ischemic heart disease and the like.

As used herein, the term "ischemic injury" refers to conditions directly associated with reduced blood flow to tissue, for example due to a clot or obstruction of blood vessels which supply blood to the subject tissue and which result, inter alia, in lowered oxygen transport to such tissue, impaired tissue performance, tissue dysfunction and/or necrosis and can contribute to the pathogenesis of heart failure. Alternatively, where blood flow or organ perfusion can be quantitatively adequate, the oxygen carrying capacity of the blood or organ perfusion medium can be reduced, e.g., in hypoxic environment, such that oxygen supply to the tissue is lowered, and impaired tissue performance, tissue dysfunction, and/or tissue necrosis ensues. "Ischemia/reperfusion injury" refers to a subset of ischemic injury in which injury involves a period of reduced blood flow, followed by at least partial restoration of the blood flow. Ischemia/reperfusion injury involves an inflammatory response and oxidative damage accompanied by apoptosis that occur when blood flow has been restored to a tissue subjected to an interruption in blood flow. As used herein, the term "ischemic limb disease" refers to any disease resulting from lack of blood flow to a superficial limb or extremity (e.g., an arm, leg, hand, foot, toe, finger etc.). Ischemic limb disease results from complications due to diabetes or atherosclerosis, among others.

As used herein, the term "ischemic heart disease" refers to a condition in which the blood supply to the heart is decreased or reduced.

As used herein, the term "therapeutically effective amount" or "effective amount" are used interchangeably and refer to the amount of an agent that is effective, at dosages and for periods of time necessary to achieve the desired therapeutic result, e.g., for an increase in angiogenesis for a pro-angiogenic agent, or a decrease or prevention of angiogenesis for an anti-angiogenic agent. By way of example only, an effective amount of an anti-angiogenic agent for treatment of an angiogenesis-related disease characterized by uncontrolled or increased angiogeneis will cause a reduction or even completely halt any new blood vessel formation. An effective amount for treating or ameliorating such an angiogenesis-related disease (i.e. one characterized by uncontrolled or increased angiogeneis) is an amount sufficient to result in a reduction or complete removal of the symptoms of the disorder, disease, or medical condition. By way of example only, an effective amount of a pro-angiogenic agent for treatment of an angiogenesis-related disease characterized by a decrease in angiogeneis will cause an increase in new blood vessel formation or an increase in angiogeneis. An effective amount for treating or ameliorating such an angiogenesis-related disease (i.e. one characterized by a decrease in angiogeneis) is an amount sufficient to result in a reduction or complete removal of the symptoms of the disorder, disease, or medical condition. The effective amount of a given therapeutic agent (i.e. pro-angiogenic agent or anti-angiogenic agent) will vary with factors such as the nature of the agent, the route of administration, the size and species of the animal to receive the therapeutic agent, and the purpose of the administration. A therapeutically effective amount of the agents, factors, or inhibitors described herein, or functional derivatives thereof, can vary according to factors such as disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, an anti-angiogenic agent is determined to be "therapeutically effective" in the methods described herein if (a) measurable symptom(s) of angiogenesis or an angiogenesis-related disease, (e.g., capillary density, tumor growth, rate of vessel formation) are decreased by at least 10% compared to the measurement prior to treatment onset, (b) the progression of the disease is halted (e.g., patients do not worsen, new vessels do not form, or the tumor does not continue to grow, or (c) symptoms are reduced or even ameliorated, for example, by measuring a reduction in tumor size or a reduction in vessel infiltration in the eye or elsewhere. Efficacy of treatment can be judged by an ordinarily skilled practitioner. Where promotion of angiogenesis is desired, e.g., in promotion of wound healing, a pro-angiogenic agent is determined to be "therapeutically effective" in the methods described herein if angiogenesis or one or more markers of angiogenesis or wound healing are increased by at least 10% relative to angiogenesis or the marker measured in the absence of that agent. Efficacy can be assessed in animal models of angiogenesis, cancer and tumor, for example treatment of a rodent with an experimental cancer, and any treatment or administration of an anti-angiogenic agent in a composition or formulation that leads to a decrease of at least one symptom of the cancer, for example a reduction in the size of the tumor or a cessation or slowing of the rate of growth of the tumor indicates effective treatment. Alternatively, pro-angiogenesis efficacy of a pro-angiogenic agent can be assessed in an animal model of reduced angiogenesis, such as e.g., hindlimb ischemia, wherein a treatment is considered efficacious if there is a increase in new vessel formation of the hindlimb compared to untreated animals. As yet another alternative, a corneal pocket assay, aortic ring assay or CAM assay can be used to predict treatment efficacy for a pro-angiogenic agent and/or anti-angiogenic agent.

The term "variant" as used herein refers to a polypeptide or nucleic acid that is "substantially similar" to a wild-type polypeptide or polynucleic acid. A molecule is said to be "substantially similar" to another molecule if both molecules have substantially similar structures (i.e., they are at least 50% similar in amino acid sequence as determined by BLASTp alignment set at default parameters) and are substantially similar in at least one relevant function (e.g., effect on cell migration). A variant differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Some substitutions can be classified as "conservative," in which case an amino acid residue contained in a polypeptide is replaced with another naturally occurring amino acid of similar character either in relation to polarity, side chain functionality or size. Substitutions encompassed by variants as described herein can also be "non-conservative," in which an amino acid residue which is present in a peptide is substituted with an amino acid having different properties (e.g., substituting a charged or hydrophobic amino acid with an uncharged or hydrophilic amino acid), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide). Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, including but not limited to insertion of ornithine which does not normally occur in human proteins.

The term "derivative" as used herein refers to peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half life, etc. The moieties can alternatively decrease the toxicity of the molecule, or eliminate or attenuate an undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" refers to a polypeptide which possess a biological activity that is substantially similar to a biological activity of the entity or molecule of which it is a derivative or variant. By "substantially similar" in this context is meant that at least 50% of the relevant or desired biological activity of a corresponding wild-type peptide is retained. In the instance of promotion of angiogenesis, for example, an activity retained would be promotion of endothelial cell migration; preferably the variant retains at least 60%, at least 70%, at least 80%, at least 90%, at least 95%, at least 100% or even higher (i.e., the variant or derivative has greater activity than the wild-type), e.g., at least 110%, at least 120%, or more compared to a measurable activity (i.e., promotion or inhibition of endothelial cell migration) of the wild-type polypeptide.

The term "protein binding agent" is used interchangeably herein with "protein binding molecule" or "protein binding moiety" and refers to any entity which has specific affinity for a protein. The term "protein-binding molecule" also includes antibody-based binding moieties and antibodies and includes immunoglobulin molecules and immunologically active determinants of immunoglobulin molecules, e.g., molecules that contain an antigen binding site which specifically binds (immunoreacts with) to the Psap proteins. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled. In some embodiments, a "protein-binding agent" is a co-factor or binding protein that interacts with the appendicitis biomarker protein to be measured, for example a co-factor or binding protein or ligand to the appendicitis biomarker protein.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of a appendicitis biomarker protein present in a urine samples correlate to the intensity of the signal emitted from the detectably labeled antibody.

The term "specific affinity" or "specifically binds" or "specific binding" are used interchangeably herein refers to an entity such as a protein-binding molecule or antibody that recognizes and binds a desired polypeptide (e.g. a specific appendicitis biomarker protein) but that does not substantially recognize and bind other molecules in the sample, i.e. a urine sample. In some embodiments, the term "specifically binds" refers to binding with a $K_d$ of 10 micromolar or less, preferably 1 micromolar or less, more preferably 100 nM or less, 10 nM or less, or 1 nM or less.

The term "antibody" is meant to be an immunoglobulin protein that is capable of binding an antigen. Antibody as used herein is meant to include antibody fragments, e.g. $F(ab')_2$, Fab', Fab, capable of binding the antigen or antigenic fragment of interest.

The term "humanized antibody" is used herein to describe complete antibody molecules, i.e. composed of two complete light chains and two complete heavy chains, as well as antibodies consisting only of antibody fragments, e.g. Fab, Fab', $F(ab')_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human subject.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species. In some embodiments, a variable region is derived from a non-human mammalian species and the constant region is derived from a human species. Specifically, the chimeric antibody is preferably produced from a 9 nucleotide sequence from a non-human mammal encoding a variable region and a nucleotide sequence from a human encoding a constant region of an antibody.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

As used herein the term "comprising" or "comprises" is used in reference to compositions, methods, and respective component(s) thereof, that are essential to the invention, yet open to the inclusion of unspecified elements, whether essential or not. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages will mean±1%.

Pro-Angiogenic Agents:

In one embodiment, a method of promoting microvascular endothelial cell migration or angiogenesis requires contacting a microvascular endothelial cell (EC) with at least one pro-angiogenic agent. Another embodiment provides a method of promoting angiogenesis by contacting a microvascular endothelial cell with a pro-angiogenic agent. As defined herein, a pro-angiogenic agent can be at least one of an inhibitor of p190RhoGAP (i.e. any agent which decreases or inhibits the expression or function of p190RhoGAP protein), or an inhibitor of TFII-I (i.e. any agent which decreases or inhibits the expression or function of the TFII-I protein), or an activator of GATA-2

In one embodiment, the p190RhoGAP inhibitor or TFII-I inhibitor is selected from the group consisting of an antibody, an RNA interference molecule, a small molecule, a peptide and an aptamer. In one embodiment, a GATA-2 activator is selected from, but is not limited to an antibody, a small molecule, a peptide, a polypeptide, nucleic acid, such as RNA or DNA As used herein, the term "aptamer" refer to relatively short RNA or DNA oligonucleotides, which binds to, for example, p190RhoGAP, and preferably blocks/prevents/inhibits p190RhoGAP from sequestering TFII-I. Methods of determining p190RhoGAP activation are known in the art (see U.S. Patent Application 2008/0119430, which is incorporated herein by reference in its entirety). "Aptamer" are isolated in vitro using, for example, the selection procedure known as SELEX (systematic evolution of ligands by exponential enrichment) (Tuerk & Gold, 1990; Ellington & Szostak, 1990, U.S. Pat. Nos. 5,475,096 and 5,270,163, which are incorporated herein by reference in their entirety). Because the selection procedure is driven by binding of ligands, aptamers bind their ligands with high affinity and fold into secondary structures which are optimized for ligand binding (Herman & Patel, 2000, incorporated herein by reference in its entirety). In this respect aptamers resemble antibodies by selectively binding corresponding ligand from complex chemical or biological mixtures. Methods to design and synthesize aptamers and aptamer binding sequences are known to those of skill in the art.

In one embodiment, a pro-angiogenic agent, such as a p190RhoGAP inhibitor and/or a TFII-I inhibitor and/or GATA-2 activator increases vegfr2 expression in a cell. In some embodiments, a pro-angiogenic agent, such as a p190RhoGAP inhibitor and/or a TFII-I inhibitor and/or GATA-2 activator increases vascular density. The detection, monitoring and measurement of vascular density can be performed using a variety of angiogenesis assays, including as described herein, an in vivo retinal vessel assay where vessel density is determined by densitometry and immunohistochemical analysis. Other models of angiogenesis are well known to one skilled in the art and can be used, and are described herein in the section entitled "Pro-angiogenic and anti-angiogenic agent assay methods".

Public access software programs and methods of predicting and selecting antisense oligonucleotides and siRNA are known in the art and are also found on the world wide web sites of GENSCRIPT™, AMBION®, DHARMACON™, OLIGOENGINE™, Wadsworth Bioinformatics Center, Whitehead Institute at the Massachusetts Institute of Technology and are also described in U.S. Pat. No. 6,060,248. After selecting the antisense oligonucleotides and siRNA sequences, these molecules can be produced biologically using an expression vector carrying the polynucleotides that encode the siRNA or antisense RNA. General molecular biological methods known in the art can be used to clone these sequences into the expression vectors. Examples of such are described herein.

In one embodiment, a pro-angiogenic agent which is a p190RhoGAP inhibitor specifically inhibits the expression of p190RhoGAP in the cell. In one embodiment, the inhibitor is an RNA interference molecule specific to the p190RhoGAP gene such as an siRNA, shRNA, or dsRNA. The human p190RhoGAP gene is NM_004491 (SEQ. ID. No. 2) (GENBANK™).

In other embodiments, the siRNA p190RhoGAP molecules are:

5'-GGAUUGUGUGGAAUGUAAG-3' (SEQ. ID. No. 12)

5'-ACCGAGAGAGGAAACACAAUA-3' (SEQ. ID. No. 13)

In alternative embodiments, siRNA p190RhoGAP molecules are:

5'-GTAGTCGTGCCACCAGTAG-3', (SEQ ID NO: 45)

5'-AGACTTGGCATACTCGCTG-3'; (SEQ ID NO: 46)

5'-GUAGUCGUGCCACCAGUAG-3; (SEQ ID NO: 47)

5'-AGACUUGGCAUACUCGCUG-3'; (SEQ ID NO: 48)

In other embodiments, a commercially available RNAi molecule which inhibits p190RhoGAP can be used. In alternative embodiments, shRNA p190RhoGAP molecules are:

(SEQ ID NO: 49)
5'-GATCCCCGTAGTCGTGCCACCAGTAGTTCAAGAGACTACTGGTG
GCACGACTACTTTTTGGAAA-3';

(SEQ ID NO: 50)
5'-GATCCCCAGACTTGGCATACTCGCTGTTCAAGAGCAGCGAGTAT
GCCAAGTCTTTTTGGAAA-3'

Isoforms of the p190RhoGAP gene have been identified. The pro-angiogenic agents which are siRNA or shRNA molecules which target p190RhoGAP can be targeted to any one or more of these p190RhoGAP isoforms. Specifically, any one or more of isoform I, II or III can be targeted. The nucleotide and amino acid sequence of isoform I is represented by SEQ ID Numbers: 51 and 52 respectively. Isoform II is the molecule identified as BNO69 in PCT/AU02/01282 and its nucleotide and amino acid sequences are represented herein by SEQ ID Numbers: 53 and 54 respectively. The nucleotide and amino acid sequence of isoform III is represented by SEQ ID Numbers: 55 and 56 respectively. The p190RhoGAP isoforms share a common region of sequence identity, the nucleotide and amino acid sequence of which is represented by SEQ ID Numbers: 57 and 58 respectively. This region of identity includes a GAP domain, the nucleotide and amino acid sequence of which is represented by SEQ ID NO: 59 and 60 respectively. In some embodiments, a pro-angiogenic agent which is a siRNA or shRNA molecules of p190RhoGAP can target the common region shared by all isoforms of p190RhoGA, including the GAP domain, or can bind specifically to one isoform alone.

In a further aspect of the present invention, there is provided an isolated nucleic acid molecule comprising the sequence set forth in one of SEQ ID Numbers: 51, 55, 57 or 59.

In one embodiment, a pro-angiogenic agent which is a TFII-I inhibitor specifically inhibits the expression of TFII-I in the cell. In one embodiment, the inhibitor is an RNA interference molecule specific to the TFII-I gene such as an siRNA, shRNA, or dsRNA. The human TFII-I gene is NM_032999 (SEQ. ID. No. 6) (GENBANK™).

In other embodiments, a commercially available RNAi molecule which inhibits TFII-I can be used. In other embodiments, the siRNA TFII-I molecules are:

```
5'-AGUAUCAGUGGUUGAGAAG-3'    (SEQ. ID. No. 10)

5'-CAAUGAUCUCUAUGUGGA-3'     (SEQ. ID. No. 15)
```

In one embodiment, a pro-angiogenic agent which is a GATA-2 activator which specifically increases the expression of GATA-2 in a cell. In one embodiment, a GATA-2 activator is a nucleic acid molecule of SEQ ID NO: 8, or in alternative embodiments, is a nucleic acid molecule of SEQ ID NO: 9. In another embodiment, the GATA-2 activator is a peptide. In some embodiments, a GATA-2 activator is a peptide comprising at least 50 amino acids of SEQ ID NO: 7.

As used herein, the term “peptide” refer to a polymer of up to 20 amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. “Peptide” further refer to amino acids joined to each other by peptide bonds or modified peptide bonds, i.e., peptide isosteres, and can contain modified amino acids other than the 20 gene-encoded amino acids.

A reduction or decrease in the expression of p190RhoGAP, TFII-I or an increase in the expression of GATA-2 in a cell can be determined by any methods known in the art, e.g. measurement of the messenger RNA by RT-PCR or by Western blots analysis for the protein as described herein.

For the avoidance of doubt, a decrease in expression will be at least 5% relative to in the absence of a p190RhoGAP inhibitor or a TFII-I inhibitor respectively, preferably at least 10%, 20%, 30%, 40%, 50%, 60%, 70%, 80%, 90%, or more, up to and including at least 100% or more. In the case of an increase, for example, of a GATA-2, is at least 2×, 3×, 4×, 5×, . . . 10× or more) as compared to in the absence of a GATA-2 activator. All the percentages in between 5-100% as well as fractions of integer number of folds increase are also included.

In one embodiment, a pro-angiogenic agent, such as a p190RhoGAP inhibitor, a TFII-I inhibitor or a GATA-2 activator increases the expression of vegfr2 in the cell. An increase in the level of vegfr2 expression can be determined by any methods known in the art, e.g. by Western blots analysis for vegfr2 protein, using an antibody specific for anti-VEGFR2 as described herein.

In one embodiment, a pro-angiogenic agent is a p190RhoGAP inhibitory antibody or a TFII-I inhibitory antibody or a GATA-2 activating antibody. In another embodiment, a pro-angiogenic agent is a p190RhoGAP inhibitory antibody. In another embodiment, a pro-angiogenic agent is a TFII-I inhibitory antibody. In another embodiment, a pro-angiogenic agent is a GATA-2 activating antibody.

In one embodiment, an pro-angiogenic agent is an antibody is specific for p190RhoGAP. In one embodiment, an pro-angiogenic agent is an antibody is specific for inhibiting TFII-I. In one embodiment, an pro-angiogenic agent is an antibody which activates GATA-2. Commercially antibodies to p190RhoGAP, TFII-I or GATA-2 are available from MILIPORE®, INVITROGEN™, SIGMA ALDRICH® and R&D Systems to name a few. Alternatively, antibodies to p190RhoGAP, TFII-I or GATA-2 can be made by methods well know to one skilled in the art. The antibodies to p190RhoGAP or TFII-I for use as pro-angiogenic agents can be assayed for the inhibitory function to p190RhoGAP or TFII-I respectively by measuring an increase in the expression of Vegfr2 in the presence and absence of a inhibitor antibody or an increase in vascular density as described herein. Alternatively, a antibodies to p190RhoGAP or TFII-I for use as anti-angiogenic agents can be assayed for their increase in the activation of p190RhoGAP or TFII-I respectively by measuring a decrease in the expression of Vegfr2 in the presence and absence of an activating anti-p190RhoGAP or anti-TFII-I antibody or a decrease in vascular density as described herein. Similarly, antibodies for use as pro-angiogenic agents which activate GATA-2 can be assayed for activation of GATA-2 function by measuring an increase in the expression of Vegfr2 in the presence and absence of a inhibitor antibody or an increase in vascular density as described herein. Alternatively, an inhibitor antibody of GATA-2 for use as an anti-angiogenic agent can be assayed for a decrease in vegfr2 expression or a decrease in vascular density as described herein.

Anti-angiogenic Agents.

In one embodiment, a method of inhibiting microvascular endothelial cell (EC) migration or angiogeneisis involves contacting a microvascular endothelial cell with at least one anti-angiogenic agent. Another embodiment provides a method of inhibiting angiogenesis by contacting a microvascular endothelial cell with a pro-angiogenic agent. As defined herein, an anti-angiogenic agent can be at least one of an activator of p190RhoGAP (e.g. any agent which increases the expression or function of p190RhoGAP protein), or an activator of TFII-I (e.g. any agent which increases the function or expression of the TFII-I protein), or an inhibitor of GATA-2 (e.g. any agent which decreases or inhibits the function or expression of GATA-2 protein). For example, an anti-apoptotic pro-angiogenic agent which is an activator of p190RhoGAP or activator of TFII-I (e.g. any agent which increases the expression and/or function of a p190RhoGAP protein or a TFII-I protein) can be selected from the group consisting of, but not limited to an antibody, a small molecule, a peptide, a polypeptide, nucleic acid, such as RNA or DNA. In another example, an anti-angiogenic agent which is an inhibitor of GATA-2 (e.g. any agent which decreases or inhibits the expression or function of a GATA-2 protein) can be selected from the group consisting of, but not limited to an antibody, an RNA interference (RNAi) molecule, a small molecule, a peptide and aptamer.

In one embodiment, an anti-angiogenic agent is a GATA-2 inhibitor which specifically inhibits the expression of GATA-2 in the cell. In one embodiment, the inhibitor is an RNA interference molecule specific to the GATA-2 gene such as an siRNA, shRNA, or dsRNA. The human GATA-2 gene is NM_032638 (SEQ. ID. No. 9) (GENBANK™).

In other embodiments, a commercially available RNAi molecule which inhibits GATA-2 can be used. In other embodiments, an anti-angiogenic agent is a siRNA GATA-2 molecule are:

```
5'-GAACCGGAAGAUGUCCAAC-3'       (SEQ. ID. No. 11)

5'-GAAUCGGAAGAUGUCCAGCAA-3'     (SEQ. ID. No. 14)
```

In one embodiment, an anti-angiogenic agent which is a p190RhoGAP activator which specifically increases the expression of p190RhoGAP in a cell. In one embodiment, a p190RhoGAP activator is a nucleic acid molecule of SEQ ID NO: 2, or in alternative embodiments, is a nucleic acid molecule of SEQ ID NO: 3. In another embodiment, the p190RhoGAP activator is a peptide. In some embodiments, a p190RhoGAP activator is a peptide comprising at least 50 amino acids of SEQ ID NO: 1.

In one embodiment, an anti-angiogenic agent which is a TFII-I activator which specifically increases the expression of TFII-I in a cell. In one embodiment, a TFII-I activator is a nucleic acid molecule of SEQ ID NO: 5, or in alternative embodiments, is a nucleic acid molecule of SEQ ID NO: 6. In another embodiment, the TFII-I activator is a peptide. In some embodiments, a TFII-I activator is a peptide comprising at least 50 amino acids of SEQ ID NO: 4.

An increase in the expression of p190RhoGAP or TFII-I or a decrease in the expression of GATA-2 in a cell can be determined by any methods known in the art, e.g. measurement of the messenger RNA by RT-PCR or by Western blots analysis for the protein as described herein.

For the avoidance of doubt, a decrease in expression will be at least 5% relative to in the absence of a GATA-2 inhibitor respectively, preferably at least 10%, 20%, 30%, 40%, 50%, 60%, 70%, 80%, 90%, or more, up to and including at least 100% or more. In the case of an increase, for example, of a p190RhoGAP activator or a TFII-I activator, is at least 2×, 3×, 4×, 5×, . . . 10× or more) as compared to in the absence of a p190RhoGAP activator or a TFII-I activator, respectively. All the percentages in between 5-100% as well as fractions of integer number of folds increase are also included.

In one embodiment, an anti-angiogenic agent, such as a p190RhoGAP activator, a TFII-I activator or a GATA-2 inhibitor decreases the expression of vegfr2 in the cell. A decrease in the level of vegfr2 expression can be determined by any methods known in the art, e.g. by Western blots analysis for vegfr2 protein, using an antibody specific for anti-VEGFR2 as described herein.

In one embodiment, an anti-angiogenic agent is a p190RhoGAP activating antibody or a TFII-I activating antibody or a GATA-2 inhibiting antibody. In another embodiment, an anti-angiogenic agent is a p190RhoGAP activating antibody. In another embodiment, an anti-angiogenic agent is a TFII-I activating antibody. In another embodiment, an anti-angiogenic agent is a GATA-2 inhibiting antibody.

In one embodiment, an anti-angiogenic agent is an antibody is specific for activating p190RhoGAP. In one embodiment, an anti-angiogenic agent is an antibody is specific for activating TFII-I. In one embodiment, an anti-angiogenic agent is an antibody which inhibits GATA-2. Commercially antibodies to p190RhoGAP, TFII-I or GATA-2 are available from MILIPORE®, INVITROGEN™, SIGMA ALDRICH® and R&D Systems to name a few. Alternatively, and as discussed above, antibodies to p190RhoGAP, TFII-I or GATA-2 can be made by methods well know to one skilled in the art. The antibodies to p190RhoGAP or TFII-I for use as pro-angiogenic agents can be assayed for the inhibitory function to p190RhoGAP or TFII-I respectively by measuring an increase in the expression of Vegfr2 in the presence and absence of a inhibitor antibody or an increase in vascular density as described herein. Alternatively, antibodies to p190RhoGAP or TFII-I for use as anti-angiogenic agents can be assayed for their increase in the activation of p190RhoGAP or TFII-I respectively by measuring a decrease in the expression of Vegfr2 in the presence and absence of an activating anti-p190RhoGAP or anti-TFII-I antibody or a decrease in vascular density as described herein. Similarly, antibodies for use as pro-angiogenic agents which activate GATA-2 can be assayed for activation of GATA-2 function by measuring an increase in the expression of Vegfr2 in the presence and absence of a inhibitor antibody or an increase in vascular density as described herein. Alternatively, an inhibitor antibody of GATA-2 for use as an anti-angiogenic agent can be assayed for a decrease in vegfr2 expression or a decrease in vascular density as described herein.

General Inhibitors as Pro-angiogenic Agents or Anti-angiogenic Agents: Inhibiting Gene or Protein Function In some embodiments, a pro-angiogenic agent can be a inhibitor of p190RhoGAP function, or an inhibitor of TFII-I function and/or an activator of GATA-2 function. In one embodiment, the p190RhoGAP inhibitor or TFII-I inhibitor is selected from the group consisting of an antibody, an RNA interference molecule, a small molecule, a peptide and an aptamer.

In some embodiments, an anti-angiogenic agent can be a p190RhoGAP activator, or a TFII-I activator or a GATA-2 inhibitor. In one embodiment, a GATA-2 inhibitor can be selected from the group consisting of an antibody, an RNA interference molecule, a small molecule, a peptide and an aptamer.

Essentially any agent that inhibits p190RhoGAP activity, as that term is defined herein, can be used as an pro-angiogenic agent with the methods described herein. It is preferred, however, that a pro-angiogenic agent inhibitor of p190RhoGAP activity is specific, or substantially specific, for p190RhoGAP activity inhibition. Further, it is noted that p190RhoGAP activity can be inhibited by agents that specifically inhibit the expression of the p190RhoGAP as well as by agents that specifically either bind to, or cleave, the p190RhoGAP molecule. Some non-limiting examples of pro-angiogenic agents which inhibit p190RhoGAP function include antibodies, small molecules, RNA interference molecules, aptamers, ligands, peptides, nucleic acids, or a combination thereof. In addition, expression of a dominant negative mutant of a p190RhoGAP polypeptide can also be used to inhibit p190RhoGAP activity. Competitive mutants and/or competitive peptides of a p190RhoGAP polypeptide are also contemplated for use herein for inhibiting p190RhoGAP activity. Inhibitors of p190RhoGAP can be screened for efficacy by measuring p190RhoGAP pro-angiogenic activity in the presence and absence of a p190RhoGAP inhibitor. To avoid doubt, an agent that inhibits p190RhoGAP activity will, at a minimum, increase the pro-angiogenic activity of p190RhoGAP, or alternatively increase blood vessel or vascular density as that term is used herein.

Essentially any agent that inhibits TFII-I activity, as that term is defined herein, can be used as an pro-angiogenic agent with the methods described herein. It is preferred, however, that a pro-angiogenic agent inhibitor of TFII-I activity is specific, or substantially specific, for TFII-I activity inhibition. Further, it is noted that TFII-I activity can be inhibited by agents that specifically inhibit the expression of the TFII-I as well as by agents that specifically either bind to, or cleave, the TFII-I molecule. Some non-limiting examples of pro-angiogenic agents which inhibit TFII-I function include antibodies, small molecules, RNA interference molecules, aptamers, ligands, peptides, nucleic acids, or a combination thereof. In addition, expression of a dominant negative mutant of a TFII-I polypeptide can also be used to inhibit TFII-I activity. Competitive mutants and/or competitive peptides of a TFII-I polypeptide are also contemplated for use herein for inhibiting TFII-I activity. Inhibitors of TFII-I can be screened for efficacy by measuring TFII-I pro-angiogenic activity in the presence and absence of a TFII-I inhibitor. To avoid doubt, an agent that inhibits TFII-I activity will, at a minimum, increase the pro-angiogenic activity of TFII-I, or alternatively increase blood vessel or vascular density as that term is used herein.

Essentially any agent that inhibits GATA-2 activity, as that term is defined herein, can be used as an anti-angiogenic agent with the methods described herein. It is preferred, however, that an anti-angiogenic agent inhibitor of GATA-2 activity is specific, or substantially specific, for GATA-2 activity inhibition. Further, it is noted that GATA-2 activity can be inhibited by agents that specifically inhibit the expression of the GATA-2 as well as by agents that specifically either bind to, or cleave, the GATA-2 molecule. Some non-limiting examples of anti-angiogenic agents which inhibit GATA-2 function include antibodies, small molecules, RNA interference molecules, aptamers, ligands, peptides, nucleic acids, or a combination thereof. In addition, expression of a dominant negative mutant of a GATA-2 polypeptide can also be used to inhibit GATA-2 activity. Competitive mutants and/or competitive peptides of a GATA-2 polypeptide are also contemplated for use herein for inhibiting GATA-2 activity. Inhibitors of GATA-2 can be screened for efficacy by measuring GATA-2 anti-angiogenic activity in the presence and absence of a GATA-2 inhibitor. To avoid doubt, an agent that inhibits GATA-2 activity will, at a minimum, decrease angiogenesis or blood vessel density, as that term is used herein.

Small Molecule Inhibitors

As used herein, the term "small molecule" refers to a chemical agent including, but not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Small molecules inhibitors of p190RhoGAP, TFII-I (as pro-angiogenic agents) and GATA-2 (as anti-angiogenic agents) can be identified from within a small molecule library, which can be obtained from commercial sources such as AMRI (Albany, N.Y.), AsisChem. Inc. (Cambridge, Mass.), TimTec (Newark, Del.), among others, or from libraries as known in the art.

Aptamers

Aptamers are relatively short RNA or DNA oligonucleotides, which bind ligands and are isolated in vitro using, for example, the selection procedure known as SELEX (systematic evolution of ligands by exponential enrichment) (Tuerk & Gold, 1990; Ellington & Szostak, 1990, U.S. Pat. Nos. 5,475,096 and 5,270,163, which are incorporated herein by reference in their entirety). Because the selection procedure is driven by binding of ligands, aptamers bind their ligands with high affinity and fold into secondary structures which are optimized for ligand binding (Herman & Patel, 2000, incorporated herein by reference in its entirety). In this respect aptamers resemble antibodies by selectively binding corresponding ligand from complex chemical or biological mixtures.

The aptamer oligonucleotide of such an embodiment can be any useful aptamer now known or later developed. Methods to design and synthesize aptamers and aptamer binding sequences are known to those of skill in the art.

It is contemplated herein that aptamers directed at binding p190RhoGAP, TFII-I (as pro-angiogenic agents) and GATA-2 (as anti-angiogenic agents) and inhibiting their activity can be used in the methods described herein.

Antibodies

Antibodies can be used as pro-angiogenic agents (i.e. to inhibit function of p190RhoGAP and/or TFII-I) or as anti-angiogenic agents (i.e. to inhibit GATA-2) by e.g., recognition of an epitope such that a bound antibody inhibits p190RhoGAP or TFII-I or GATA-2 activity, respectively. Production of antibodies useful for the methods described herein are known to those of skill in the art, and described in more detail below.

The production of non-human monoclonal antibodies, e.g., murine or rat, can be accomplished by, for example, immunizing the animal with a desired target peptide or polypeptide and preparing hybridomas of spleen cells from the immunized animals, according to well established methods (e.g., See Harlow & Lane, Antibodies, A Laboratory Manual (CSHP NY, 1988, which is herein incorporated by reference in its entirety). Immunogen can be obtained from a natural source, by peptide synthesis or by recombinant expression. Humanized forms of mouse antibodies (e.g., as produced by a hybridoma) can be generated by cloning and linking the CDR regions of the murine antibodies to human constant regions by recombinant DNA techniques. See Queen et al., Proc. Natl. Acad. Sci. USA 86, 10029-10033 (1989) and WO 90/07861 (incorporated by reference herein in their entirety). Human antibodies can be obtained using phage-display methods. See, e.g., Dower et al., WO 91/17271; McCafferty et al., WO 92/01047, which are incorporated herein by reference in their entirety. In these methods, libraries of phage are produced in which members display different antibodies on their outer surfaces. Antibodies are usually displayed as Fv or Fab fragments. Phage displaying antibodies with a desired specificity are selected by binding to a p190RhoGAP polypeptide or a TFII-I polypeptide or a GATA-2 polypeptide or fragments thereof. Increased affinity can be selected by successive rounds of affinity enrichment by binding to the same fragment. Human antibodies against p190RhoGAP, TFII-I, and GATA-2 can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991) (each of which is incorporated by reference in its entirety). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using the respective polypeptide (i.e., p190RhoGAP, TFII-I and GATA-2 polypeptides) as an affinity reagent. Human or humanized antibodies can be designed to have IgG, IgD, IgA and IgE constant region, and any isotype, including IgG1, IgG2, IgG3 and IgG4. Antibodies can be expressed as tetramers containing two light and two heavy chains, as separate heavy chains, light chains, as Fab, Fab'F(ab')2, and Fv, or as single chain antibodies in which heavy and light chain variable domains are linked through a spacer.

Anti-p190RhoGAP, anti-TFII-I antibodies and anti-GATA-2 antibodies can be obtained from commercial sources such as e.g., Santa Cruz Biotechnology Inc. (Santa Cruz, Calif.), Sigma, Millipore (Billerica, Mass.), Novus Biologicals (Littleton, Colo.), AbNova Corporation (Walnut, Calif.), and AbCam (Cambridge, Mass.), and Transduction Laboratories, among others. A mouse polyclonal antibody against human p190RhoGAP and TFII-I can be obtained from Transduction laboratories (Lexington, Ky.) as disclosed in the examples. A polyclonal antibody against human GATA-2 can be obtained from Abcam (Cambridge, Mass.) as disclosed in the examples.

Peptide or Dominant Negative Polypeptides.

In some embodiments, dominant negative polypeptides, i.e. molecules that non-functionally mimic the peptide, can serve as inhibitor agents. For example, a pro-angiogenic agent can be a dominant negative p190RhoGAP polypeptide or a dominant negative TFII-I polypeptide. An anti-angiogenic agent can be a dominant negative GATA-2 polypeptide. For example, a mutant (or mutein) of p190RhoGAP polypeptide, in which the putative GAP activity of p190RhoGAP is eliminated can be a pro-angiogenic agent, specifically a mutant in which Arg82 of SEQ ID NO: 54 is replaced, more specifically in which Arg82 is replaced by Ala (hence an R82A mutation) can be a pro-angiogenic agent.

RNA Interference

In one embodiment, RNAi interference molecules can be used as pro-angiogenic agents (i.e. to inhibit expression of p190RhoGAP and/or TFII-I) or as anti-angiogenic agents (i.e. to inhibit the expression of GATA-2).

RNA interference-inducing molecules include but are not limited to siRNA, dsRNA, stRNA, shRNA, micro RNAi (mRNAi), antisense oligonucleotides etc. and modified versions thereof, where the RNA interference molecule silences the gene expression of either p190RhoGAP or TFII-I (as an pro-angiogenic agent) or GATA-2 (i.e. for an anti-angiogenic agent). An anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like.

RNA interference (RNAi) is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

As used herein, "Short interfering RNA" (siRNA), is used interchangeably herein with "small interfering RNA" and refers to an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. the p190RhoGAP (genomic sequence is SEQ. ID. No. 2; GENBANK™ Accession No. NM_004491 (SEQ. ID. No. 3)); the TFII-I (genomic sequence is SEQ. ID. No. 6; GENBANK™ Accession No. NM_032999 (SEQ. ID. No. 5)); the GATA-2 (genomic sequence is SEQ ID NO: 9, GENBANK™ Accession No. NM_032638). An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

Commercial pre-designed RNA interference molecules to p190RhoGAP, TFII-I or GATA-2 are also available, e.g. from INVITROGEN™ Inc. (STEALTH™ Select RNAi, p190RhoGAP, catalog# IOH5439; HSS104485; HSS104486; HSS104487; TFII-I; catalog# IOH62625; IOH5665; IOH62975, HSS142343; HSS142344: GATA-2, Catalogue # MSS204584; MSS204585; MSS204586) and from DHARMACON™ (SMARTvector Lentiviral shRNA—Human p190RhoGAP catalog #L-004158-00; LQ-004158-00; LU-004158-00). Human p190RhoGAP, TFII-I or GATA-2 siRNA, shRNA and lentiviral particle gene silencers are available from Santa Cruz Biotechnology, Inc.

These sense and anti-sense strand oligonucleotide can be chemically synthesized, annealed and formulated for use, e.g anti-angiogenic agents which are RNAi based agents can be formulated for direct intravitreal injection into an eye affected with macular degeneration or diabetic retinopathy. Alternatively, the anti-sense strand can be designed into short hairpin RNA (shRNA) for plasmid- or vector-based approaches for supplying siRNAs to cells to produce stable p190RhoGAP, TFII-I or GATA-2 gene silencing. Examples of vectors for shRNA are #AM5779: —pSilencer™ 4.1-CMV neo; #AM5777: —pSilencer™ 4.1-CMV hygro; #AM5775: —pSilencer™ 4.1-CMV puro; #AM7209: —pSilencer™ 2.0-U6; #AM7210: —pSilencer™ 3.0-H1; #AM5768: —pSilencer™ 3.1-H1 puro; #AM5762: —pSilencer™ 2.1-U6 puro; #AM5770: —pSilencer™ 3.1-H1 neo;

#AM5764: —pSilencer™ 2.1-U6 neo; #AM5766: —pSilencer™ 3.1-H1 hygro; #AM5760: —pSilencer™ 2.1-U6 hygro; #AM7207: —pSilencer™ 1.0-U6 (circular) from AMBION®.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

siRNA and miRNA molecules having various “tails” covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

siRNAs useful for the methods described herein include siRNA molecules of about 15 to about 40 or about 15 to about 28 nucleotides in length, which are homologous to the p190RhoGAP gene or TFII-I gene (for pro-angiogenic agents) or GATA-2 gene (for an anti-angiogenic agent). Preferably, a targeting siRNA molecule to a p190RhoGAP gene or TFII-I gene (for pro-angiogenic agents) or GATA-2 gene (for an anti-angiogenic agent) have a length of about 19 to about 25 nucleotides. More preferably, the targeting siRNA molecules have a length of about 19, 20, 21, or 22 nucleotides. The targeting siRNA molecules can also comprise a 3' hydroxyl group. The targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of a pro-angiogenic agent or anti-angiogenic RNAi targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the targeting RNA molecule is double stranded—one strand has a 3' overhang and the other strand can be blunt-ended or have an overhang. In the embodiment in which the targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Oligonucleotide Modifications

Unmodified oligonucleotides can be less than optimal in some applications, e.g., unmodified oligonucleotides can be prone to degradation by e.g., cellular nucleases. Nucleases can hydrolyze nucleic acid phosphodiester bonds. However, chemical modifications to one or more of the subunits of oligonucleotide can confer improved properties, and, e.g., can render oligonucleotides more stable to nucleases.

Modified nucleic acids and nucleotide surrogates can include one or more of: (i) alteration, e.g., replacement, of one or both of the non-linking phosphate oxygens and/or of one or more of the linking phosphate oxygens in the phosphodiester backbone linkage. (ii) alteration, e.g., replacement, of a constituent of the ribose sugar, e.g., of the 2' hydroxyl on the ribose sugar; (iii) wholesale replacement of the phosphate moiety with “dephospho” linkers; (iv) modification or replacement of a naturally occurring base with a non-natural base; (v) replacement or modification of the ribose-phosphate backbone; (vi) modification of the 3' end or 5' end of the oligonucleotide, e.g., removal, modification or replacement of a terminal phosphate group or conjugation of a moiety, e.g., a fluorescently labeled moiety, to either the 3' or 5' end of oligonucleotide; and (vii) modification of the sugar (e.g., six membered rings).

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications can be incorporated in a single oligonucleotide or even at a single nucleoside within an oligonucleotide.

In some cases the modification will occur at all of the subject positions in the oligonucleotide but in many, and in fact in most cases it will not. By way of example, a modification can only occur at a 3' or 5' terminal position, can only occur in the internal region, can only occur in a terminal regions, e.g. at a position on a terminal nucleotide or in the last 2, 3, 4, 5, or 10 nucleotides of an oligonucleotide. A modification can occur in a double strand region, a single strand region, or in both. A modification can occur only in the double strand region of an oligonucleotide or can only occur in a single strand region of an oligonucleotide. E.g., a phosphorothioate modification at a non-bridging oxygen position can only occur at one or both termini, can only occur in a terminal regions, e.g., at a position on a terminal nucleotide or in the last 2, 3, 4, 5, or 10 nucleotides of a strand, or can occur in double strand and single strand regions, particularly at termini. The 5' end or ends can be phosphorylated.

A modification described herein can be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific Modifications to Oligonucleotide

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following: S, Se, $BR_3$ (R is hydrogen, alkyl, aryl), C (i.e. an alkyl group, an aryl group, etc. . . . ), H, $NR_2$ (R is hydrogen, alkyl, aryl), or OR (R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non-phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine and peptide nucleic acid (PNA) nucleoside surrogates. A preferred surrogate is a PNA surrogate.

Sugar Modifications

An oligonucleotide can include modification of all or some of the sugar groups of the nucleic acid. E.g., the 2' hydroxyl group (OH) can be modified or replaced with a number of different “oxy” or “deoxy” substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of “oxy”-2' hydroxyl group modifications include alkoxy or aryloxy (OR, e.g., R═H, alkyl, cycloalkyl, aryl, aralkyl, heteroaryl or sugar); polyethyleneglycols (PEG), $O(CH_2CH_2O)_nCH_2CH_2OR$; “locked” nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

“Deoxy” modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; thioalkyl; and alkyl, cycloalkyl, aryl, alkenyl and alkynyl, which can be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include “abasic” sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Preferred substitutents are 2'-O-Me (2'-O-methyl), 2'-O-MOE (2'-O-methoxyethyl), 2'-F, 2'-O-[2-(methylamino)-2-oxoethyl](2'-O-NMA), 2'-S-methyl, 2'-O—CH2-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP) and 2'-O-dimethylaminoethyloxyethyl (2'-O-DMAEOE).

Terminal Modifications

The 3-prime (3') and 5-prime (5') ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. Suitable modifications include: 5'-monophosphate ($(HO)_2(O)P$—O-5'); 5'-diphosphate ($(HO)_2(O)P$—O—P(HO)(O)—O-5'); 5'-triphosphate ($(HO)_2(O)P$—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; $(HO)_2(S)P$—O-5'); 5'-monodithiophosphate (phosphorodithioate; (HO)(HS)(S)P—O-5'), 5'-phosphorothiolate ($(HO)_2(O)P$—S-5'); any additional combination of oxygen/sulfur replaced monophosphate, diphosphate and triphosphates (e.g. 5'-alpha-thiotriphosphate, 5'-beta-thiotriphosphate, 5'-gamma-thiotriphosphate, etc.), 5'-phosphoramidates ($(HO)_2(O)P$—NH-5', $(HO)(NH_2)(O)P$—O-5'), 5'-alkylphosphonates (R=alkyl=methyl, ethyl, isopropyl, propyl, etc., e.g. RP(OH)(O)—O-5'-, $(OH)_2(O)P$-5'-$CH_2$—), 5'-alkyletherphosphonates (R=alkylether=methoxymethyl ($MeOCH_2$—), ethoxymethyl, etc., e.g. RP(OH)(O)—O-5'-). Other embodiments include replacement of oxygen/sulfur with $BH_3$, $BH_3$— and/or Se.

Terminal modifications can also be useful for monitoring distribution, and in such cases the preferred groups to be added include fluorophores, e.g., fluorscein or an ALEXA® dye, e.g., ALEXA® 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and “universal bases” can be employed. Examples include 2-(halo)adenine, 2-(alkyl)adenine, 2-(propyl)adenine, 2(amino)adenine, 2-(aminoalkyll)adenine, 2 (aminopropyl)adenine, 2(methylthio) $N^6$(isopentenyl)adenine, 6(alkyl)adenine, 6(methyl)adenine, 7(deaza)

adenine, 8(alkenyl)adenine, 8-(alkyl)adenine, 8(alkynyl) adenine, 8(amino)adenine, 8-(halo)adenine, 8-(hydroxyl) adenine, 8(thioalkyl)adenine, 8-(thiol)adenine, $N^6$-(isopentyl)adenine, $N^6$(methyl)adenine, $N^6$, $N^6$(dimethyl) adenine, 2-(alkyl)guanine, 2(propyl)guanine, 6-(alkyl) guanine, 6(methyl)guanine, 7(alkyl)guanine, 7(methyl) guanine, 7(deaza)guanine, 8 (alkyl)guanine, 8-(alkenyl) guanine, 8(alkynyl)guanine, 8-(amino)guanine, 8(halo) guanine, 8-(hydroxyl)guanine, 8(thioalkyl)guanine, 8-(thiol) guanine, N(methyl)guanine, 2-(thio)cytosine, 3(deaza)5(aza) cytosine, 3-(alkyl)cytosine, 3(methyl)cytosine, 5-(alkyl) cytosine, 5-(alkynyl)cytosine, 5(halo)cytosine, 5(methyl) cytosine, 5(propynyl)cytosine, 5(propynyl)cytosine, 5(trifluoromethyl)cytosine, 6-(azo)cytosine, N4(acetyl)cytosine, 3(3 amino-3 carboxypropyl)uracil, 2-(thio)uracil, 5(methyl)2(thio)uracil, 5(methylaminomethyl)-2(thio) uracil, 4-(thio)uracil, 5(methyl)4(thio)uracil, 5(methylaminomethyl)-4(thio)uracil, 5(methyl) 2,4(dithio)uracil, 5(methylaminomethyl)-2,4(dithio)uracil, 5(2-aminopropyl) uracil, 5-(alkyl)uracil, 5-(alkynyl)uracil, 5-(allylamino) uracil, 5(aminoallyl)uracil, 5(aminoalkyl)uracil, 5(guanidiniumalkyl)uracil, 5(1,3-diazole-1-alkyl)uracil, 5-(cyanoalkyl)uracil, 5-(dialkylaminoalkyl)uracil, 5(dimethylaminoalkyl)uracil, 5-(halo)uracil, 5-(methoxy)uracil, uracil-5oxyacetic acid, 5(methoxycarbonylmethyl)-2-(thio) uracil, 5(methoxycarbonyl-methyl)uracil, 5(propynyl)uracil, 5(propynyl)uracil, 5(trifluoromethyl)uracil, 6(azo)uracil, dihydrouracil, N3(methyl)uracil, 5-uracil (i.e., pseudouracil), 2(thio)pseudouracil, 4(thio)pseudouracil-2,4-(dithio) pseudouracil, 5-(alkyl)pseudouracil, 5-(methyl)pseudouracil, 5-(alkyl)-2-(thio)pseudouracil, 5-(methyl)-2-(thio) pseudouracil, 5-(alkyl)-4(thio)pseudouracil, 5-(methyl)-4 (thio)pseudouracil, 5-(alkyl)-2,4(dithio)pseudouracil, 5-(methyl)-2,4(dithio)pseudouracil, 1 substituted pseudouracil, 1 substituted 2(thio)-pseudouracil, 1 substituted 4(thio) pseudouracil, 1 substituted 2,4-(dithio)pseudouracil, 1(aminocarbonylethylenyl)-pseudouracil, 1(aminocarbonylethylenyl)-2(thio)-pseudouracil, 1(aminocarbonylethylenyl)-4(thio)pseudouracil, 1(aminocarbonylethylenyl)-2,4-(dithio)pseudouracil, 1(aminoalkylaminocarbonylethylenyl)-pseudouracil, 1(aminoalkylaminocarbonylethylenyl)-2(thio)-pseudouracil, 1(aminoalkylaminocarbonylethylenyl)-4(thio)pseudouracil, 1(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo)thymine, 2-pyridinone, 5 nitroindole, 3 nitropyrrole, 6-(aza)pyrimidine, 2(amino)purine, 2,6-(diamino)purine, 5 substituted pyrimidines, $N^2$-substituted purines, $N^6$-substituted purines, $O^6$-substituted purines, substituted 1,2,4-triazoles, or any O-alkylated or N-alkylated derivatives thereof;

Further purines and pyrimidines include those disclosed in U.S. Pat. No. 3,687,808, hereby incorporated by reference, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino).

Placement Within an Oligonucleotide

Some modifications can preferably be included on an oligonucleotide at a particular location, e.g., at an internal position of a strand, or on the 5' or 3' end of an oligonucleotide. A preferred location of a modification on an oligonucleotide, can confer preferred properties on the agent. For example, preferred locations of particular modifications can confer optimum gene silencing properties, or increased resistance to endonuclease or exonuclease activity.

One or more nucleotides of an oligonucleotide can have a 2'-5' linkage. One or more nucleotides of an oligonucleotide can have inverted linkages, e.g. 3'-3',5'-5',2'-2' or 2'-3' linkages.

An oligonucleotide can comprise at least one 5'-pyrimidine-purine-3' (5'-PyPu-3') dinucleotide wherein the pyrimidine is modified with a modification chosen independently from a group consisting of 2'-O-Me (2'-O-methyl), 2'-O-MOE (2'-O-methoxyethyl), 2'-F, 2'-O-[2-(methylamino)-2-oxoethyl](2'-O-NMA), 2'-S-methyl, 2'-O—$CH_2$-(4'-C) (LNA) and 2'-O—$CH_2CH_2$-(4'-C) (ENA).

In one embodiment, the 5'-most pyrimidines in all occurrences of sequence motif 5'-pyrimidine-purine-3' (5'-PyPu-3') dinucleotide in the oligonucleotide are modified with a modification chosen from a group consisting of 2"-O-Me (2'-O-methyl), 2'-O-MOE (2'-β-methoxyethyl), 2'-F, 2'-O-[2-(methylamino)-2-oxoethyl] (2'-O-NMA), 2'-S-methyl, 2'-O—$CH_2$-(4'-C) (LNA) and 2'-O—$CH_2CH_2$-(4'-C) (ENA).

A double-stranded oligonucleotide can include at least one 5'-uridine-adenine-3' (5'-UA-3')dinucleotide wherein the uridine is a 2'-modified nucleotide, or a 5'-uridine-guanine-3' (5'-UG-3')dinucleotide, wherein the 5'-uridine is a 2'-modified nucleotide, or a terminal 5'-cytidine-adenine-3' (5'-CA-3')dinucleotide, wherein the 5'-cytidine is a 2'-modified nucleotide, or a terminal 5'-uridine-uridine-3' (5'-UU-3')dinucleotide, wherein the 5'-uridine is a 2'-modified nucleotide, or a terminal 5'-cytidine-cytidine-3' (5'-CC-3')dinucleotide, wherein the 5'-cytidine is a 2'-modified nucleotide, or a terminal 5'-cytidine-uridine-3' (5'-CU-3')dinucleotide, wherein the 5'-cytidine is a 2'-modified nucleotide, or a terminal 5'-uridine-cytidine-3' (5'-UC-3')dinucleotide, wherein the 5'-uridine is a 2'-modified nucleotide. Double-stranded oligonucleotides including these modifications are particularly stabilized against endonuclease activity.

General References

The oligoribonucleotides and oligoribonucleotides used in accordance with this invention can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide—s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., Helv. Chim. Acta, 1995, 78, 486-504; Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. J. Org. Chem. 2001, 66, 2789-2801. Preparation of sulfur bridged nucleotides is described in Sproat et al. Nucleosides Nucleotides 1988, 7,651 and Crosstick et al. Tetrahedron Lett. 1989, 30, 4693.

Sugar Group References

Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Hely. Chim. Acta 1996, 79, 1930-1938), "LNA" (Wengel, J. Acc. Chem. Res. 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. Nucleic Acids Res. 1988, 16, 4583. Carbonate replacements are described in Tittensor, J. R. J. Chem. Soc. C 1971, 1933. Carboxymethyl replacements are described in Edge, M. D. et al. J. Chem. Soc. Perkin Trans. 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083 which is incorporated herein in its entirety by reference.

Terminal Modification References

Terminal modifications are described in Manoharan, M. et al. Antisense and Nucleic Acid Drug Development 12, 103-128 (2002) and references therein.

Nuclebases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications Oligonucleotide Production The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other oligonucleotides, such as the phosphorothioates, phosphorodithioates and alkylated derivatives. The double-stranded oligonucleotide compounds of the invention can be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process.

Teachings regarding the synthesis of particular modified oligonucleotides can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having □-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

In Vivo Delivery of Pro-angiogenic or Anti-angiogenic RNA Interference (RNAi) Molecules In general, any method of delivering a nucleic acid molecule can be adapted for use with an RNAi interference molecule (see e.g., Akhtar S, and Julian R L. (1992) Trends Cell. Biol. 2(5):139-144; WO94/02595, which are incorporated herein by reference in their entirety). However, there are three factors that are important to consider in order to successfully deliver an RNAi molecule in vivo: (a) biological stability of the RNAi molecule, (2) preventing non-specific effects, and (3) accumulation of the RNAi molecule in the target tissue. The non-specific effects of an RNAi molecule can be minimized by local administration by e.g., direct injection into a tissue including, for example, a tumor or topically administering the molecule.

Local administration of an RNAi molecule to a treatment site limits the exposure of the e.g., siRNA to systemic tissues and permits a lower dose of the RNAi molecule to be administered. Several studies have shown successful knockdown of gene products when an RNAi molecule is administered locally. For example, intraocular delivery of a VEGF siRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of an siRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55).

For administering an RNAi molecule systemically for the treatment of a disease, the RNAi molecule can be either be modified or alternatively delivered using a drug delivery system; both methods act to prevent the rapid degradation of the RNAi molecule by endo- and exo-nucleases in vivo. Modification of the RNAi molecule or the pharmaceutical carrier can also permit targeting of the RNAi molecule to the target tissue and avoid undesirable off-target effects.

RNA interference molecules can be modified by chemical conjugation to lipophilic groups such as cholesterol to enhance cellular uptake and prevent degradation. For example, an siRNA directed against ApoB conjugated to a lipophilic cholesterol moiety was injected systemically into mice and resulted in knockdown of apoB mRNA in both the liver and jejunum (Soutschek, J., et al (2004) Nature 432:173-178). Conjugation of an RNAi molecule to an aptamer has been shown to inhibit tumor growth and mediate tumor regression in a mouse model of prostate cancer (McNamara, J O., et al (2006) Nat. Biotechnol. 24:1005-1015).

In an alternative embodiment, the RNAi molecules can be delivered using drug delivery systems such as e.g., a nanoparticle, a dendrimer, a polymer, liposomes, or a cationic delivery system. Positively charged cationic delivery systems facilitate binding of an RNA interference molecule (negatively charged) and also enhance interactions at the negatively charged cell membrane to permit efficient uptake of an siRNA by the cell. Cationic lipids, dendrimers, or polymers can either be bound to an RNA interference molecule, or induced to form a vesicle or micelle (see e.g., Kim S H., et al (2008) Journal of Controlled Release 129(2):107-116) that encases an RNAi molecule. The formation of vesicles or micelles further prevents degradation of the RNAi molecule when administered systemically. Methods for making and administering cationic-RNAi complexes are well within the abilities of one skilled in the art (see e.g., Sorensen, D R., et al (2003) J. Mol. Biol. 327:761-766; Verma, U N., et al (2003) Clin. Cancer Res. 9:1291-1300; Arnold, A S et al (2007) J. Hypertens. 25:197-205, which are incorporated herein by reference in their entirety).

Some non-limiting examples of drug delivery systems useful for systemic administration of RNAi include DOTAP (Sorensen, D R., et al (2003), supra; Verma, U N., et al (2003), supra), Oligofectamine, “solid nucleic acid lipid particles” (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an RNAi molecule forms a complex with cyclodextrin for systemic administration. Methods for administration and pharmaceutical compositions of RNAi molecules and cyclodextrins can be found in U.S. Pat. No. 7,427,605, which is herein incorporated by reference in its entirety. Specific methods for administering an RNAi molecule for the inhibition of angiogenesis can be found in e.g., U.S. Patent Application No. 20080152654, which is herein incorporated by reference in its entirety.

In some embodiments, the siRNA, dsRNA, or shRNA vector which is an pro-angiogenic agent (i.e. directed against p190RhoGAP or TFII-I) or which is an anti-angiogenic agent (i.e. directed against GATA-2) can be administered systemically, such as intravenously, e.g. via central venous catheter (CVC or central venous line or central venous access catheter) placed into a large vein in the neck (internal jugular vein), chest (subclavian vein) or groin (femoral vein). Methods of systemic delivery of siRNA, dsRNA, or shRNA vector are well known in the art, e.g. as described herein and in Gao and Huang, 2008, (Mol. Pharmaceutics, Web publication December 30) and review by Rossi, 2006, Gene Therapy, 13:583-584. The siRNA, dsRNA, or shRNA vector can be formulated in various ways, e.g. conjugation of a cholesterol moiety to one of the strands of the siRNA duplex for systemic delivery to the liver and jejunum (Soutschek J. et. al. 2004, Nature, 432:173-178), complexing of siRNAs to protamine fused with an antibody fragment for receptor-mediated targeting of siRNAs (Song E, et al. 2005, Nat. Biotechnol., 23: 709-717) and the use of a lipid bilayer system by Morrissey et al. 2005 (Nat. Biotechnol., 23: 1002-1007). The lipid bilayer system produces biopolymers that are in the 120 nanometer diameter size range, and are labeled as SNALPs, for Stable-Nucleic-Acid-Lipid-Particles. The lipid combination protects the siRNAs from serum nucleases and allows cellular endosomal uptake and subsequent cytoplasmic release of the siRNAs (see WO/2006/007712). These references are incorporated by reference in their entirety.

General Activators as Pro-angiogenic Agents or Anti-angiogenic Agents: Increasing Gene or Protein Function As discussed herein, a pro-angiogenic agent can be a inhibitor of p190RhoGAP function, or an inhibitor of TFII-I function and/or an activator of GATA-2 function. In one embodiment, a GATA-2 activator is selected from, but is not limited to an antibody, a small molecule, a peptide, a polypeptide, nucleic acid, such as RNA or DNA which enhances the function of GATA-2 gene or protein function.

In some embodiments, an anti-angiogenic agent can be a p190RhoGAP activator, or a TFII-I activator or a GATA-2 inhibitor. In one embodiment, a p190RhoGAP activator, and/or a TFII-I activator is selected from, but is not limited to an antibody, a small molecule, a peptide, a polypeptide, nucleic acid, such as RNA or DNA which enhances the function of p190RhoGAP gene or protein function or TFII-I gene or protein function.

Enhancing, stimulating or re-activating a gene's or protein's function can be achieved in a variety of ways. In one aspect of the invention administration of an isolated nucleic acid molecule, as described above, to a subject can be initiated. Typically, a p190RhoGAP and/or TFII-I nucleic acid molecule can be administered as an anti-angiogenic agent to a subject to treat or prevent an angiogenesis-related disorder characterized by uncontrolled or enhanced angiogenesis. Similarly, a GATA-2 nucleic acid molecule can be administered as a pro-angiogenic agent to a subject to treat or prevent an angiogenesis-related disorder characterized by a decrease or loss in angiogenesis. In a further aspect, there is provided the use of a pro-angiogenic isolated nucleic acid molecule (i.e. GATA-2 nucleic acid), as described above, in the preparation of a medicament for the treatment of an angiogenesis-related disorder characterized by a decrease or loss in angiogenesis. In a further aspect, there is provided the use of an anti-angiogenic isolated nucleic acid agent (i.e. p190RhoGAP and/or TFII-I nucleic acid) in the preparation of a medicament for the treatment of an angiogenesis-related disorder characterized by a uncontrolled or enhanced angiogenesis.

Typically, a vector capable of expressing a polypeptide of the invention, or a fragment or derivative thereof, can be administered to a subject to treat or prevent a disorder including, but not limited to, those described above. Transducing retroviral vectors are often used for somatic cell gene therapy because of their high efficiency of infection and stable integration and expression. A nucleic acid molecule of the invention, or portions thereof, can be cloned into a retroviral vector and expression can be driven from its endogenous promoter or from the retroviral long terminal repeat or from a promoter specific for the target cell type of interest. Other viral vectors can be used and include, as is known in the art, adenoviruses, adeno-associated viruses, vaccinia viruses, papovaviruses, lentiviruses and retroviruses of avian, murine and human origin.

Gene therapy can be carried out according to established methods (See for example Friedman, 1991; Culver, 1996). A vector containing a nucleic acid molecule of the invention linked to expression control elements and capable of replicating inside the cells is prepared. Alternatively the vector can be replication deficient and can require helper cells for replication and use in gene therapy.

Gene transfer using non-viral methods of infection in vitro can also be used. These methods include direct injection of DNA, uptake of naked DNA in the presence of calcium phosphate, electroporation, protoplast fusion or liposome delivery. Gene transfer can also be achieved by delivery as a part of a human artificial chromosome or receptor-mediated gene transfer. This involves linking the DNA to a targeting molecule that will bind to specific cell-surface receptors to induce endocytosis and transfer of the DNA into mammalian cells. One such technique uses poly-L-lysine to link asialoglycoprotein to DNA. An adenovirus is also added to the complex to disrupt the lysosomes and thus allow the DNA to avoid degradation and move to the nucleus. Infusion of these particles intravenously has resulted in gene transfer into hepatocytes.

In a further aspect, a suitable pro-angiogenic agent can also include peptides, phosphopeptides or small organic or inorganic compounds that can mimic the function of a GATA-2 polypeptide of the invention, or can include an antibody specific for a GATA-2 polypeptide that is able to enhance or increase the function or activity of a GATA-2 polypeptide.

In a further aspect, a suitable anti-angiogenic agents can also include peptides, phosphopeptides or small organic or inorganic compounds that can mimic the function of a p190RhoGAP polypeptide and/or TFII-I polypeptide of the invention, or can include an antibody specific for a p190RhoGAP polypeptide and/or TFII-I polypeptide that is able to enhance or increase the function or activity of a p190RhoGAP polypeptide and/or TFII-I polypeptide, respectively.

Peptides, phosphopeptides or small organic or inorganic compounds suitable for therapeutic applications can be identified using nucleic acids and polypeptides of p190RhoGAP, TFII-I or GATA-2 using drug screening applications, which are commonly known by one of ordinary skill in the art, and can be assessed for their pro-angiogenic or anti-angiogenic activity using the angiogenesis assays as described herein.

In further embodiments, any pro-angiogenic agent, such as complementary sequences, siRNA molecules, shRNA molecules and inhibitory antibodies to p190RhoGAP and/or TFII-I, can be used in combination with any pro-angiogenic agent selected from nucleic acid molecules, polypeptides, activating antibodies, or vectors to GATA-2 can be administered in combination with other appropriate pharmaceutical or therapeutic agents, or treatment methods. In further embodiments, any anti-angiogenic agent, such as complementary sequences, siRNA molecules, shRNA molecules and inhibitory antibodies to GATA-2, can be used in combination with any anti-angiogenic agent selected from nucleic acid molecules, polypeptides, activating antibodies, or vectors to p190RhoGAP and/or TFII-I can be administered in combination with other appropriate pharmaceutical or therapeutic agents, or treatment methods.

Selection of the appropriate agents and treatment methods can be made by those skilled in the art, according to conventional pharmaceutical principles. The combination of therapeutic agents and treatment methods can act synergistically to effect the treatment or prevention of the various disorders described above. Using this approach, therapeutic efficacy with lower dosages of each agent can be possible, thus reducing the potential for adverse side effects. Any of the therapeutic methods described herein can be applied to any subject, including, for example, mammals such as dogs, cats, cows, horses, rabbits, monkeys, and most preferably, humans.

Polypeptides and Peptides

In some embodiments, a pro-angiogenic agent is a GATA-2 polypeptide or a functional portion thereof to promote angiogenesis, and can be administered to an individual in need thereof. In one approach, a soluble GATA-2 polypeptide, produced, for example, in cultured cells bearing a recombinant GATA-2 expression vector can be administered to the individual. In one embodiment, GATA-2 can be overexpressed in an individual by gene therapy methodologies commonly known by one of ordinary skill in the art.

In some embodiments, an anti-angiogenic agent is a p190RhoGAP polypeptide or a functional portion thereof and/or a TFII-I polypeptide or a portion functional thereof to inhibit angiogenesis, which can be administered to an individual in need thereof. In one approach, a soluble p190RhoGAP polypeptide and/or TFII-I polypeptide, produced, for example, in cultured cells bearing a recombinant p190RhoGAP and/or TFII-I expression vectors, respectively, can be administered to the individual. In one embodiment, p190RhoGAP and/or TFII-I can be overexpressed in an individual by gene therapy methodologies commonly known by one of ordinary skill in the art.

In a further aspect of the present invention, an anti-angiogenic agent is an isolated polypeptide of p190RhoGAP comprising the sequence set forth in one of SEQ ID Numbers: 52, 56, 58 or 60. In some embodiments, an anti-angiogenic agent is an isolated polypeptide of p190RhoGAP, or fragment thereof, comprising the sequence set forth in one of SEQ ID Numbers: 52, 56, 58 or 60. In some embodiments, an anti-angiogenic agent is an isolated polypeptide of p190RhoGAP having at least 70%, preferably 85%, and more preferably 95%, identity to any one of SEQ ID Numbers: 52, 56, 58 or 60. Sequence identity is typically calculated using the BLAST algorithm, described in Altschul et al (1997) with the BLOSUM62 default matrix.

An pro-angiogenic polypeptide agent (i.e. GATA-2 polypeptide or a functional portion thereof) or an anti-angiogenic polypeptide agent (i.e. a p190RhoGAP polypeptide or a functional portion thereof and/or a TFII-I polypeptide or a portion functional thereof) will generally be administered intravenously. This approach rapidly delivers the protein throughout the system and maximizes the chance that the protein is intact when delivered. Alternatively, other routes of therapeutic protein administration are contemplated, such as by inhalation. Technologies for the administration of agents, including protein agents, as aerosols are well known and continue to advance. Alternatively, the polypeptide agent can be formulated for topical delivery, including, for example, preparation in liposomes. Further contemplated are, for example, transdermal administration, and rectal or vaginal administration. Further options for the delivery of polypeptides as an pro-angiogenic agent or an anti-angiogenic agent for use in the methods as described herein are discussed in the section "Formulation and Administration" herein below.

Generation of Recombinant GATA-2 Protein as a Pro-angiogenic Agent or Recombinant p190RhoGAP Protein and/or TFII-I Protein as Anti-angiogenic Agents Vectors for transduction of a GATA-2 or p190RhoGAP or TFII-1-encoding sequence are well known in the art. While overexpression using a strong non-specific promoter, such as a CMV promoter, can be used, it can be helpful to include a tissue- or cell-type-specific promoter on the expression construct—for example, the use of a skeletal muscle-specific promoter or other cell-type-specific promoter can be advantageous, depending upon what cell type is used as a host. Further, treatment can include the administration of viral vectors that drive the expression of pro-angiogenic polypeptides (i.e. GATA-2 polypeptides) or anti-angiogenic polypeptides (e.g. p190RhoGAP or TFII-I polypeptides) in infected host cells. Viral vectors are well known to those skilled in the art and discussed in more detail herein.

These vectors are readily adapted for use in the methods of the present invention. By the appropriate manipulation using recombinant DNA/molecular biology techniques to insert an operatively linked nucleic acid sequence encoding the gene to be expressed (e.g. GATA-2 nucleic acid sequence of SEQ ID NO: 8; or p190RhoGAP nucleic acid sequence of SEQ ID NO: 3; or TFII-I nucleic acid sequence of SEQ ID NO: 5) into the selected expression/delivery vector, many equivalent vectors for the practice of the methods described herein can be generated. It will be appreciated by those of skill in the art that cloned genes readily can be manipulated to alter the amino acid sequence of a protein.

Examples of expression vectors and host cells are the pET vectors (NOVAGEN®), pGEX vectors (GE Life Sciences), and pMAL vectors (New England labs. Inc.) for protein expression in *E. coli* host cell such as BL21, BL21(DE3) and AD494(DE3)pLysS, Rosetta(DE3), and Origami(DE3) ((NOVAGEN®); the strong CMV promoter-based pcDNA3.1 (INVITROGEN™ Inc.) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (CLONTECH®), pAd/CMV/V5-DEST, pAd-DEST vector (INVITROGEN™ Inc.) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN™ Inc.) for lentivirus-mediated gene transfer and expression in mammalian cells; adenovirus-associated virus expression vectors such as pAAV-MCS, pAAV-IRES-hrGFP, and pAAV-RC vector (STRATAGENE®) for adeno-associated virus-mediated gene transfer and expression in mammalian cells; BACpak6 baculovirus (CLONTECH®) and pFastBac™ HT (INVITROGEN™ Inc.) for the expression in *Spodopera frugiperda* 9 (Sf9) and Sf11 insect cell lines; pMT/BiP/V5-His (INVITROGEN™ Inc.) for the expression in *Drosophila* Schneider S2 cells; *Pichia* expression vectors pPICZα, pPICZ, pFLDα and pFLD (INVITROGEN™ Inc.) for expression in *Pichia pastoris* and vectors pMETα and pMET for expression in *P. methanolica*; pYES2/GS and pYD1 (INVITROGEN™ Inc.) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol. Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduced the vector in the algae. Upon its entry into chloroplasts, the foreign DNA is released from the gene gun particles and integrates into the chloroplast genome through homologous recombination.

In one embodiment, the expression vector is a viral vector, such as a lentivirus, adenovirus, or adeno-associated virus. A simplified system for generating recombinant adenoviruses is presented by He T C. et. al. Proc. Natl. Acad. Sci. USA, 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli* BJ5183 cells with an adenoviral backbone plasmid, e.g. pAdEasy-1 of STRATAGENE®'s ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenovirus are generated within the HEK 293 cells.

In one embodiment, the preferred viral vector is a lentiviral vector and there are many examples of use of lentiviral vectors for gene therapy for inherited disorders of haematopoietic cells and various types of cancer, and these references are hereby incorporated by reference (Klein, C. and Baum, C. (2004), Hematol. J., 5:103-111; Zufferey, R et. al. (1997), Nat. Biotechnol., 15:871-875; Morizono, K. et. al. (2005), Nat. Med., 11:346-352; Di Domenico, C. et. al. (2005). Hum. Gene Ther., 16:81-90). The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with VIRAPOWER™ Lentiviral Expression systems from INVITROGEN™ Inc.

In one embodiment, the expression viral vector can be a recombinant adeno-associated virus (rAAV) vector. Using rAAV vectors, genes can be delivered into a wide range of host cells including many different human and non-human cell lines or tissues. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying the chimeric DNA coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

The cloned gene for an pro-angiogenic agent (i.e. the GATA-2 gene) or an anti-angiogenic agent (e.g. p190RhoGAP gene and/or TFII-I gene) can be manipulated by a variety of well known techniques for in vitro mutagenesis, among others, to produce variants of the naturally occurring human protein, herein referred to as muteins or variants or mutants of GATA-2, p190RhoGAP or TFII-I, respectively, which can be used in accordance with the methods and compositions described herein. The variation in primary structure of muteins of GATA-2, p190RhoGAP or TFII-I, useful in the invention, for instance, can include deletions, additions and substitutions. The substitutions can be conservative or non-conservative. The differences between the natural protein and the mutein generally conserve desired properties, mitigate or eliminate undesired properties and add desired or new properties. For example, in some embodiments, a pro-angiogenic agent can be a GATA-2 polypeptide of at least 50 amino acids of SEQ ID NO: 7, or a functional mutein or variant thereof. In some embodiments, an anti-angiogenic agent can be a p190RhoGAP polypeptide of at least 50 amino acids of SEQ ID NO: 1, or a functional mutein or variant thereof. For example, in some embodiments, an anti-angiogenic agent can be a TFII-I polypeptide of at least 50 amino acids of SEQ ID NO: 4, or a functional mutein or variant thereof.

In some embodiments, the expressed GATA-2 polypeptide (as a pro-angiogenic agent) or expressed p190RhoGAP and/or TFII-I polypeptides (both as anti-angiogenic agents) can also be a fusion polypeptide, fused, for example, to a polypeptide that targets the product to a desired location, or, for example, a tag that facilitates its purification, if so desired.

Fusion to a polypeptide sequence that increases the stability of an expressed polypeptide, i.e. an expressed GATA-2 polypeptide (as a pro-angiogenic agent) or expressed p190RhoGAP and/or TFII-I polypeptide (i.e. as anti-angiogenic agents) is also contemplated. For example, fusion to a serum protein, e.g., serum albumin, can increase the circulating half-life of a GATA-2, p190RhoGAP or TFII-I polypeptide. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use. In another aspect, biodegradable or absorbable polymers can provide extended, often localized, release of polypeptide agents. Such synthetic bioabsorbable, biocompatible polymers, which can release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(ester-amides). Suitable bioabsorbable polymers to be used in manufacturing of drug delivery materials and implants are discussed e.g. in U.S. Pat. Nos. 4,968,317 and 5,618,563, which are incorporated herein in their entirety by reference and among others, and in “Biomedical Polymers” edited by S. W. Shalaby, Carl Hanser Verlag, Munich, Vienna, New York, 1994 and in many references cited in the above publications. The particular bioabsorbable polymer that should be selected will depend upon the particular patient that is being treated.

Antibodies:

In some embodiment, pro-angiogenic agents, and anti-angiogenic agents which are antibodies, or antibody fragments can be generated by any methods known in the art, for example, immunizing a mammal with a p190RhoGAP protein or a TFII-I protein or a GATA-2 protein. Large quantities of such proteins can be made using standard molecular recombinant protein expression methods. Protein coding nucleic acid sequences of p190RhoGAP or TFII-I or GATA-2 protein or fragments thereof can be amplified by polymerase chain reaction (PCR) and cloned into protein expression vectors. The resultant expression vectors can be then be transfected into corresponding host for protein expression.

Generating Antibodies to p190RhoGAP, TFII-I and GATA-2 Proteins

As discussed previously, an pro-angiogenic agent or an anti-angiogenic agent can be an antibody. For example, a pro-angiogenic agent which is an antibody can be selected from an antibody which inhibits p190RhoGAP function, and/or an antibody which inhibits TFII-I function and/or an antibody which activates GATA-2 function. Alternatively, an anti-angiogenic agent which is an antibody can be selected from an antibody which activates p190RhoGAP function, and/or an antibody which activates TFII-I function and/or an antibody which inhibits GATA-2 function.

As used herein, the term “antibody” refers to immunoglobulin molecules and immunologically active portions of immunoglobulin molecules, i.e., molecules that contain an antigen binding site that immunospecifically binds an antigen. The terms also refers to antibodies comprised of two immunoglobulin heavy chains and two immunoglobulin light chains as well as a variety of forms besides antibodies; including, for example, Fv, Fab, and $F(ab)'_2$ as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2nd ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference.).

In one embodiment, a pro-angiogenic agent antibody (i.e. inhibitor antibody of p190RhoGAP or inhibitor antibody of TFII-I or activating antibody of GATA-2) is a polyclonal antibody or a monoclonal antibody. In one embodiment, a pro-angiogenic agent antibody (i.e. inhibitor antibody of p190RhoGAP or inhibitor antibody of TFII-I or activating antibody of GATA-2) is a humanized antibody or a chimeric antibody. In yet another embodiment, a pro-angiogenic agent antibody (i.e. inhibitor antibody of p190RhoGAP or inhibitor antibody of TFII-I or activating antibody of GATA-2) includes, but are not limited to multispecific, human, single chain antibodies, Fab fragments, $F(ab)'_2$ fragments, fragments produced by a Fab expression library, domain-deleted antibodies (including, e.g., CH2 domain-deleted antibodies), anti-idiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

In one embodiment, an anti-angiogenic agent antibody (i.e. activating antibody of p190RhoGAP or activating antibody of TFII-I or inhibiting antibody of GATA-2) is a polyclonal antibody or a monoclonal antibody. In one embodiment, an anti-angiogenic agent antibody (i.e. activating antibody of p190RhoGAP or activating antibody of TFII-I or inhibiting antibody of GATA-2) is a humanized antibody or a chimeric antibody. In yet another embodiment, an anti-angiogenic agent antibody (i.e. activating antibody of p190RhoGAP or activating antibody of TFII-I or inhibiting antibody of GATA-2) includes, but are not limited to multispecific, human, single chain antibodies, Fab fragments, $F(ab)'_2$ fragments, fragments produced by a Fab expression library, domain-deleted antibodies (including, e.g., CH2 domain-deleted antibodies), anti-idiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Encompassed in the methods disclosed herein are pro-angiogenic agent antibodies (i.e. inhibitor antibodies of p190RhoGAP or inhibitor antibodies of TFII-I or activating antibodies of GATA-2) or anti-angiogenic agent antibodies (i.e. activating antibodies of p190RhoGAP or activating antibodies of TFII-I or inhibiting antibodies of GATA-2) that are, but are not limited to, engineered forms of antibodies and antibody fragments such as diabodies, triabodies, tetrabodies, and higher multimers of scFvs, single-domain antibodies, as well as minibodies, such as two scFv fragments joined by two constant (C) domains. See, e.g., Hudson, P. J. and Couriau, C., Nature Med. 9: 129-134 (2003); U.S. Publication No. 20030148409; U.S. Pat. No. 5,837,242.

In one embodiment, pro-angiogenic agent antibodies (i.e. inhibitor antibodies of p190RhoGAP or inhibitor antibodies of TFII-I or activating antibodies of GATA-2) or anti-angiogenic agent antibodies (i.e. activating antibodies of p190RhoGAP or activating antibodies of TFII-I or inhibiting antibodies of GATA-2) can be obtained from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al. which is incorporated herein by reference in its entirety.

In a preferred embodiment for use in humans, pro-angiogenic agent antibodies (i.e. inhibitor antibodies of p190RhoGAP or inhibitor antibodies of TFII-I or activating antibodies of GATA-2) or anti-angiogenic agent antibodies (i.e. activating antibodies of p190RhoGAP or activating antibodies of TFII-I or inhibiting antibodies of GATA-2) are human or humanized antigen-binding antibody fragments of the present invention and include, but are not limited to, Fab, Fab and $F(ab)'_2$, Fd, single-chain Fvs (scFv), single-domain antibodies, triabodies, tetrabodies, minibodies, domain-deleted antibodies, single-chain antibodies, disulfide-linked Fvs (sdFv) and fragments comprising either a variable light chain (VL) or variable heavy chain VH region. Antigen-binding antibody fragments, including single-chain antibodies, can comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains.

Preferred pro-angiogenic agent antibodies (i.e. inhibitor antibodies of p190RhoGAP or inhibitor antibodies of TFII-I or activating antibodies of GATA-2) or anti-angiogenic agent antibodies (i.e. activating antibodies of p190RhoGAP or activating antibodies of TFII-I or inhibiting antibodies of GATA-2) for use in the therapeutic methods of the invention are those containing a deletion of the CH2 domain.

As used herein, the term "humanized" immunoglobulin or "humanized" antibody refers to an immunoglobulin comprising a human framework, at least one complementarity determining regions (CDR) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. For example, a humanized immunoglobulin would not encompass a chimeric mouse variable region/human constant region antibody.

As used herein, the term "framework region" refers to those portions of antibody light and heavy chain variable regions that are relatively conserved (i.e., other than the CDRs) among different immunoglobulins in a single species, as defined by Kabat, et al., op. cit. As used herein, a "human framework region" is a framework region that is substantially identical (about 85% or more) to the framework region of a naturally occurring human antibody.

As used herein, the term "chimeric" antibody refers to an antibody whose heavy and light chains have been constructed, typically by genetic engineering, from immunoglobulin gene segments belonging to different species. For example, the variable (V) segments of the genes from a mouse monoclonal antibody can be joined to human constant (C) segments, such as gamma1 and/or gamma4. A typical therapeutic or diagnostic chimeric antibody is thus a hybrid protein comprising at least one V region (e.g., VH or VL) or the entire antigen-binding domain (i.e., VH and VL) from a mouse antibody and at least one C (effector) region (e.g., CH(CH1, CH2, CH3, or CH4) or CL or the entire C domain (i.e., CH and CL) from a human antibody, although other mammalian species can be used. In some embodiments, especially for use in the therapeutic methods of the pro-angiogenic agent antibodies (i.e. inhibitor antibodies of p190RhoGAP or inhibitor antibodies of TFII-I or activating antibodies of GATA-2) or anti-angiogenic agent antibodies (i.e. activating antibodies of p190RhoGAP or activating antibodies of TFII-I or inhibiting antibodies of GATA-2) should contain no CH2 domain.

In one embodiment, a pro-angiogenic agent chimeric antibody (i.e. inhibitor chimeric antibody of p190RhoGAP or inhibitor chimeric antibody of TFII-I or activating chimeric antibody of GATA-2) or an anti-angiogenic agent chimeric antibody (i.e. activating chimeric antibody of p190RhoGAP or activating chimeric antibody of TFII-I or inhibiting chimeric antibody of GATA-2) can contain at least the p190RhoGAP or TFII-I or GATA-2 antigen binding Fab or $F(ab)'_2$ region, respectively, while a humanized antibody can contain at least the p190RhoGAP or TFII-I or GATA-2 antigen binding Fv region, respectively fused to a human Fc region.

The terms "antigen" is well understood in the art and refer to the portion of a macromolecule which is specifically recognized by a component of the immune system, e.g., an antibody or a T-cell antigen receptor. The term antigen includes any protein determinant capable of specific binding to an immunoglobulin. Antigenic determinants usually consist of chemically active surface groupings of molecules such as amino acids or sugar side chains and usually have specific three dimensional structural characteristics, as well as specific charge characteristics.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (Skerra et al., Science 242:1038-1041 (1988)).

Recombinant expression of an antibody disclosed herein, or fragment, derivative or analog thereof, (e.g., a heavy or light chain of an antibody of the invention or a single chain antibody of the invention), including a recombinant protein derived from the antibody antigen-binding region, requires construction of an expression vector containing a polynucleotide that encodes the antibody. Once a polynucleotide encoding an antibody molecule or a heavy or light chain of an antibody or portion thereof (preferably containing the heavy or light chain variable domain) of the invention has been obtained, the vector for the production of the antibody molecule can be produced by recombinant DNA technology using techniques well known in the art. Thus, methods for preparing a protein by expressing a polynucleotide containing an antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors can include the nucleotide sequence encoding the constant region of the antibody molecule (see, e.g., PCT publication WO 86/05807; PCT publication WO 89/01036; and U.S. Pat. No. 5,122,464, which are incorporated herein in their entirety by reference) and the variable domain of the antibody can be cloned into such a vector for expression of the entire heavy or light chain. Methods for generating multivalent and bispecific antibody fragments are described by Tomlinson I. and Holliger P. (2000) Methods Enzymol, 326, 461-479 and the engineering of antibody fragments and the rise of single-domain antibodies is described by Holliger P. (2005) Nat. Biotechnol. September; 23(9):1126-36, and are both hereby incorporated by reference.

Gene Therapy

In gene therapy, a vector comprising a nucleic acid encoding a pro-angiogenic agent (i.e. encoding GATA-2) or an anti-angiogenic agent (i.e. encoding p190RhoGAP and/or TFII-I) or a fusion, or truncated nucleic acid thereof includes but is not limited to adenovirus, retrovirus, lentivirus, adeno associated virus, envelope protein pseudotype virus (chimeric virus), and virosomes (e.g. liposomes combined with an inactivated HIV or influenza virus).

In addition, an anti-angiogenic agent the present invention provides isolated nucleic acid molecules of p190RhoGAP comprising the sequence set forth in one of SEQ ID Numbers: 51, 55, 57 or 59, or fragments thereof. Such diseases include, but are not restricted to, cancer; inflammatory disorders including arthritis; corneal, retinal or choroidal neovascularization including macular degeneration and diabetic retinopathy; psoriasis; cardiovascular diseases. Useful fragments of p190RhoGAP nucleic acid SEQ ID Numbers: 51, 55, 57 or 59 can include those which are unique and which do not overlap any previously identified genes, unique fragments which do overlap with a known sequence, and fragments which span alternative splice junctions etc.

In some embodiments, an anti-angiogenic agent is an isolated nucleic acid molecule that is at least 70% identical to any one of SEQ ID Numbers: 51, 55, 57 or 59 and which encodes a polypeptide that plays a role in an angiogenic process. Such variants will have preferably at least about 85%, and most preferably at least about 95% sequence identity to these sequences. Sequence identity is typically calculated using the BLAST algorithm, described in Altschul et al (1997) with the BLOSUM62 default matrix. The invention also encompasses an isolated nucleic acid molecule which hybridizes under stringent conditions with any one of SEQ ID Numbers: 51, 55, 57 or 59 and which plays a role in an angiogenic process.

A simplified system for generating recombinant adenoviruses is presented by He T C. et. al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli*. BJ5183 cells with an adenoviral backbone plasmid, e.g. pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenovirus are generated within the HEK 293 cells.

Recombinant lentivirus has the advantage of delivery and expression of a nucleic acid encoding a pro-angiogenic agent (i.e. encoding GATA-2) or an anti-angiogenic agent (i.e. encoding p190RhoGAP and/or TFII-I) or a fusion, or truncated nucleic acid thereof in either dividing and non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

A preferred embodiment is the use of AAV viral vectors comprising a nucleic acid encoding a pro-angiogenic agent (i.e. encoding GATA-2) or an anti-angiogenic agent (i.e. encoding p190RhoGAP and/or TFII-I) or a fusion, or truncated nucleic acid thereof and/or its variant forms. Recombinant adeno-associated virus (rAAV) vectors are applicable to a wide range of host cells including many different human and non-human cell lines or tissues. Because AAV is non-pathogenic and does not ellicit an immune response, a multitude of pre-clinical studies have reported excellent safety profiles. rAAVs are capable of transducing a broad range of cell types and transduction is not dependent on active host cell division. High titers, $>10^8$ viral particle/ml, are easily obtained in the supernatant and $10^{11}$-$10^{12}$ viral particle/ml with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying the coding nucleic acid, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Uses

Treatment of Angiogenesis-related Diseases Characterized by Inhibited or Decreased Angiogenesis In one embodiment, a pro-angiogenic agent as described herein is useful in the treatment of an angiogenesis-related disease characterized by inhibited or decreased angiogenesis, for example, where an angiogenesis-related disease characterized by inhibited or decreased angiogenesis can selected from the group consisting of, but not limited to; ischemic limb disease, coronary artery disease, myocardial infarction, brain ischemia and other ischemic diseases, as well as other therapies where it is desirable to enhance or promote vascular expansion, for example tissue transplantation, stem cell implantation and other therapeutic stratagies where increased angiogeneis is desired.

One aspect of the present invention provides a method for increasing angiogenesis in a tissue associated with a disease process or condition characterized by reduced or inhibited angiogeneis or blood vessel growth, and thereby affect events in the tissue which depend upon angiogenesis. Generally, the method comprises administering to a subject, or to the tissue of a subject associated with, or suffering from a disease process or condition, an angiogenesis-increasing amount of a composition comprising at least one pro-angiogenic agent as described herein (i.e. at least one of; a p190RhoGAP inhibitor, and/or a TFII-I inhibitor and/or a GATA-2 activator).

Any of a variety of tissues, or organs comprised of organized tissues, can support angiogenesis in disease conditions including heart, skin, muscle, gut, connective tissue, brain tissue, nerve cells, joints, bones and the like tissue in which blood vessels can invade upon angiogenic stimuli.

In one aspect of the invention, at least one pro-angiogenic agent as described herein (i.e. at least one of; a p190RhoGAP inhibitor, and/or a TFII-I inhibitor and/or a GATA-2 activator) is used to treat cardiac disorders.

In one preferred embodiment, the cardiac disorder is associated with myocardial tissue that has a decreased blood supply, including, but not limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, myocardial infarction, and the like.

In one preferred embodiment the cardiac disorder is cardiac hypertrophy. As used herein, the term "cardiac hypertrophy" refers to the process in which adult cardiac myocytes respond to stress through hypertrophic growth.

In one preferred embodiment, the cardiac disorder is heart failure that can be due to a variety of causes, including but not limited to, congestive heart failure, heart failure with diastolic dysfunction, heart failure with systolic dysfunction, heart failure associated with cardiac hypertrophy, and heart failure that develops as a result of chemically induced cardiomyopathy, congenital cardiomyopathy, and cardiomyopathy associated with ischemic heart disease or myocardial infarction.

Any diseases or condition that would benefit from the potentiation of angiogenesis can be treated by methods of the present invention. For example, stimulation of angiogenesis can aid in the enhancement of collateral circulation where there has been vascular occlusion or stenosis (e.g. to develop a "biopass" around an obstruction of an artery, vein, or of a capillary system). Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like.

Other conditions or diseases that can be prevented using the methods of the invention include, but are not necessarily limited to, heart attack (myocardial infarction) or other vascular death, stroke, death or loss of limbs associated with decreased blood flow, and the like. In addition, the methods of the invention can be used to accelerate healing of wounds or ulcers; to improve the vascularization of skin grafts or reattached limbs so as to preserve their function and viability; to improve the healing of surgical anastomoses (e.g., as in reconnecting portions of the bowel after gastrointestinal surgery); and to improve the growth of skin or hair.

In one preferred embodiment, at least one pro-angiogenic agent as described herein (i.e. at least one of; a p190RhoGAP inhibitor, and/or a TFII-I inhibitor and/or a GATA-2 activator) are used in methods and compostions to treat vascular complications of diabetes.

In one embodiment, at least one pro-angiogenic agent as described herein (i.e. at least one of; a p190RhoGAP inhibitor, and/or a TFII-I inhibitor and/or a GATA-2 activator) are used in method and compostions to treat cardiac disorders associated with diabetes, such as hypertrophic cardiac myopathy.

Also encompassed in some embodiments of the invention is the use of the pro-angiogenic agents as described herein (i.e. p190RhoGAP inhibitors, TFII-I inhibitors and GATA-2 activators) in methods and compostions for the promotion of angiogeneis or promotion of neovascularization in tissue engineering constructs, tissue repair, regenerative medicine, and wound healing. Tissue engineering is the use of a combination of cells, engineering and material methods, and suitable biochemical and physiochemical factors to improve or replace biological functions. Tissue engineering aims at developing functional cell, tissue, and organ substitutes to repair, replace or enhance biological function that has been lost due to congenital abnormalities, injury, disease, or aging, or repair fascia in hernias. The tissue that is engineered is used to repair or replace portions of or whole tissues (i.e., bone, cartilage, blood vessels, heart valves, bladder, diaphragm, etc.). Often, the tissues involved require certain mechanical and structural properties for proper function. Tissue engineering also encompass the efforts to perform specific biochemical functions using cells within an artificially-created support system (e.g. an artificial pancreas, or a bioartificial liver). The term regenerative medicine is often used synonymously with tissue engineering, although those involved in regenerative medicine place more emphasis on the use of stem cells to produce tissues and on promoting repair in situ. Tissue regeneration aims to restore and repair tissue function via the interplay of living cells, an extracellular matrix and cell communicators.

In some embodiments, the pro-angiogenic agents as described herein (i.e. p190RhoGAP inhibitors, TFII-I inhibitors and GATA-2 activators) are useful in methods and compostions to promote in vivo therapeutic neovascularization, for example for tissue repair and healing of chronic wound in humans. The human body has a great capacity to heal itself when damaged. However, sometimes, the body's innate healing function becomes impaired or reduced due to metabolic diseases such as diabetes, poor blood circulation, blocked or damaged blood vessels. Accordingly, in some embodiments, the pro-angiogenic agents as described herein can be used to artificially increase blood vessels and blood vessel growth in the damaged area, by de novo formation of blood vessels and also stimulates new blood vessels formation from existing ones. The new blood vessels bring oxygen, nutrients and growth factors to stimulate the body's own natural healing process by activating the body's inherent ability to repair and regenerate. In vivo therapeutic neovascularization helps speed up healing and helps injuries that will not heal or repair on their own. In vivo therapeutic neovascularization can be used to heal broken bones, severe burns, chronic wounds, heart damage, nerve damage, damaged tissue of the heart, muscles, skin, adipose tissue, brain, liver, lungs, intestines, limbs, and kidneys to name a few.

In one embodiment, the methods and compostions comprising a pro-angiogenic agent as described herein (i.e. a p190RhoGAP inhibitor, and/or a TFII-I inhibitor and/or a GATA-2 activator) can help cardiac tissue to repair itself weeks after a heart attack. In some embodiments, a composition comprising at least one pro-angiogenic agent as described herein (i.e. at least one of; a p190RhoGAP inhibitor and/or a TFII-I inhibitor and/or a GATA-2 activator) can be administered to a subject after a heart attack (or myocardial infarction) or a subject at risk of having a myocardial infarction.

In addition, in some embodiments methods and compostions comprising a pro-angiogenic agents as described herein (i.e. at least one of; a p190RhoGAP inhibitor, and/or a TFII-I inhibitor and/or a GATA-2 activator) can be used to promote viability of transplanted cells into a subject. For example, embryonic stem cells have been shown to regenerate damaged heart muscle, when transplanted within a 3-dimensional scaffold into the infracted heart. Embryonic stem cells have a higher rate of successful treatment in restoring heart muscle when transplanted within a 3-dimensional matrix into damaged hearts in an animal model of severe infarction. In addition to the stem cell transplantation, a composition comprising at least one pro-angiogenic agent as described herein (i.e. at least one of; a p190RhoGAP inhibitor, and/or a TFII-I inhibitor and/or a GATA-2 activator) can be administered concurrent with, post or prior the implantation of the stem cells or cells in a cell-based therapy to the infracted heart tissue. In some embodiments, cells for transplantation (i.e. embryonic stem cells, induced pluripotent stem cells (iPS) or other types of cells, such as tissue-derived (parenchymal) cells can be used with a composition comprising at least one pro-angiogenic agent as described herein (i.e. at least one of; a p190RhoGAP inhibitor, and/or a TFII-I inhibitor and/or a GATA-2 activator) are seeded on a suitable biocompatible scaffold or matrix prior to implantation to the tissue repair location. Methods of constructing cardiac related structures are described in U.S. Pat. Nos. 5,880,090, 5,899,937, 6,695,879, 6,666,886, 7,214,371, and US Pat. Publication No. 20040044403 and they are hereby incorporated by reference.

In another embodiment, method and compostions comprising at least one pro-angiogenic agent as described herein (i.e. at least one of; a p190RhoGAP inhibitor, and/or a TFII-I inhibitor and/or a GATA-2 activator) can be administered to a subject concurrent with, or prior to, or post-transplantation of an organ, such as a lung transplant, cardiac transplant, heart-lung transplant and other organ transplantations.

In one embodiment, methods and compositions comprising at least one pro-angiogenic agent as described herein (i.e. at least one of; a p190RhoGAP inhibitor, and/or a TFII-I inhibitor and/or a GATA-2 activator) are useful to promote angiogeneis or neovascularization in a subject can optionally include growth, differentiation, and/or other pro-angiogenesis factors that are known in the art to stimulated cell proliferation, differentiation, and angiogenesis the cells at the site where the composition is delivered. Examples of such pro-angiogenic factors which can be used in combination with a pro-angiogenic agent as described herein (i.e. at least one of; a p190RhoGAP inhibitor, and/or a TFII-I inhibitor and/or a GATA-2 activator) include, but are not limited to Angiopoietin-1 (Ang-1), bFGF, EGF, Fibrinogen, Fibronectin, Heparanase, HGF, IGF-1, IGF BP-3, PDGF, VEGF-A, VEGF-C and vitronection. Other pro-angiogenic factors are disclosed herein, and include, but are not limited to E-cadherin, angiogenin, fibroblast growth factors: acidic (aFGF) and basic (bFGF), heparanase, hepatocyte growth factor (HGF), insulin-like growth factor-1 (IGF-1), IGF BP-3, PDGF, VEGF-A VEGF-C, pigment epithelium-derived factor (PEDF), vitronection, leptin, trefoil peptides (TFFs), CYR61 (CCN1) and NOV (CCN3), leptin, midkine, placental growth factor platelet-derived endothelial cell growth factor (PD-ECGF), platelet-derived growth factor-BB (PDGF-BB), pleiotrophin (PTN), progranulin, proliferin, transforming growth factor-alpha (TGF-alpha), transforming growth factor-beta (TGF-beta), tumor necrosis factor-alpha (TNF-alpha), c-Myc, granulocyte colony-stimulating factor (G-CSF), stromal derived factor 1 (SDF-1), scatter factor (SF), osteopontin, stem cell factor (SCF), matrix metalloproteinases (MMPs), thrombospondin-1 (TSP-1), and inflammatory cytokines and chemokines that are inducers of angiogenesis and increased vascularity, eg. CCL2 (MCP-1), interleukin-8 (IL-8) and CCL5 (RANTES). The pro-angiogenic factors can be used in conjunction with any and all combinations of a pro-angiogenic agent (i.e. a p190RhoGAP inhibitor, and/or a TFII-I inhibitor and/or a GATA-2 activator) as described herein, for example, pro-angiogenic factors can be administered within the same composition as, or administered to a subject substantially at the same time (i.e. shortly before or shortly after) the administration of, a composition comprising at least one pro-angiogenic agent.

In one embodiment, a composition comprising at least one pro-angiogenic agent as described herein (i.e. at least one of; a p190RhoGAP inhibitor, and/or a TFII-I inhibitor and/or a GATA-2 activator) is directly implanted to the site needing repair, for example, the part of the heart that has suffered a myocardial infarction (Dinender K. Singla, et. al., Am J Physiol Heart Circ Physiol 293: H1308-H1314, 2007). A composition comprising at least one pro-angiogenic agent as described herein (i.e. at least one of; a p190RhoGAP inhibitor, and/or a TFII-I inhibitor and/or a GATA-2 activator) can be injected into the tissue repair site together with at least one pro-angiogenic factor, or other growth, differentiation, and angiogenesis factors that are known in the art to stimulate cell growth, differentiation, and angiogenesis in the appropriate cell type of the recipient tissue. As discussed previously, suitable growth factors include but are not limited to transforming growth factor-beta (TGFβ), vascular endothelial growth factor (VEGF), platelet derived growth factor (PDGF), angiopoietins, epidermal growth factor (EGF), bone morphogenic protein (BMP) and basic fibroblast growth factor (bFGF). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In another embodiment, a composition comprising at least one pro-angiogenic agent as described herein (i.e. at least one of; a p190RhoGAP inhibitor, and/or a TFII-I inhibitor and/or a GATA-2 activator) can be implanted in a tissue in need of vascularization or angiogeneis by direct injection of the composition. Direct injection is useful for the repair of ischemic tissue, for example, cardiac muscles, blood vessels, kidney, liver, bones, ischemic limb disease, brain (in the case of stroke), the pancreas and connective and support tissues such as ligaments, muscles, tendons and those tissues, such as the collagen-containing tissues which encapsulate organs, to name a few. Ischemia in a tissue can be determined by methods known to one skilled in the art, such as SPECT and diffusion/perfusion MRI, ankle-brachial index (ABI), Doppler ultrasound, segmental pressures and waveforms, duplex ultrasound, and transcutaneous oxygen pressure. Methods of direct implantation of stem cells for tissue repair are described in Shake J G et, al. 2002 (Ann Thorac Surg. 73:1919-25), Yoshinori Miyaharal, et. al., 2006 (Nature Medicine 12, 459-465), Atta Behfar, et. al., 2005 (Ann. N.Y. Acad. Sci. 1049: 189-198), Luciano C. Amado, et. al., 2005, (PNAS, 102: 11474-9), Khalil P N, et. al., 2007, (Gastroenterology. 132:944-54), Lee R H, et. al., 2006 (Proc Natl Acad Sci USA.; 103:17438-43), and Chamberlain J., et. al., 2007, (Hepatology. 2007 Aug. 17, in press), S. P. Bruder, et. al., 1998, (J. Bone and Joint Surgery 80:985-96), Pignataro G., et. al., J. Cereb Blood Flow Metab. 2007 May; 27(5):919-27 and are hereby incorporated by reference.

In yet another embodiment, the composition comprising at least one pro-angiogenic agent as described herein (i.e. at least one of; a p190RhoGAP inhibitor, and/or a TFII-I inhibitor and/or a GATA-2 activator) can be "seeded" into an artificial structure or matrix capable of supporting three-dimensional tissue formation. These structures, typically called scaffolds or matracies, are often critical, both ex vivo as well as in vivo, for cell viability and correct cell morphology and/or phenotype of transplanted cells in cell-based therapies, in order for the transplanted cells to recapitulating the in vivo milieu and allowing transplanted cells to influence their own microenvironments. Scaffold-guided tissue engineering involves seeding highly porous biodegradable scaffolds with cells and/or growth factors, followed by culturing the tissue engineering constructs in vitro for a time period. Subsequently the scaffolds are implanted into a host to induce and direct the growth of new tissue. The goal is for the cells to attach to the scaffold, then replicate, differentiate, and organize into normal healthy tissue as the scaffold degrades. This method has been used to create various tissue analogs including skin, cartilage, bone, liver, nerve, vessels, to name a few examples. Thus, one embodiment of the present invention encompasses the use of at least one pro-angiogenic agent as described herein (i.e. at least one of; a p190RhoGAP inhibitor, and/or a TFII-I inhibitor and/or a GATA-2 activator) in contact with a scaffold and/or cell coated scaffold to promote the neovascularization of the tissue engineering construct after implantation or transplantation into a host subject.

Treatment of Angiogenesis-related Diseases Characterized by Uncontrolled or Enhanced Angiogenesis In one embodiment, an anti-angiogenic agent as described herein is useful in the treatment of an angiogenesis-related disease characterized by uncontrolled or enhanced angiogenesis, for example, where an angiogenesis-related disease characterized by uncontrolled or enhanced angiogenesis can selected from the group consisting of: cancer, macular degeneration; diabetic retinopathy; rheumatoid arthritis; Alzheimer's disease; obesity, psoriasis, atherosclerosis, vascular malformations, angiomata, and endometriosis.

In one embodiment, an anti-angiogenic agent is used in the treatment of angiogenesis-related disease characterized by uncontrolled or enhanced angiogenesis related to the eyes, e.g. macular degeneration or diabetic retinopathy, comprises directly injecting an siRNA, dsRNA, or shRNA vector directed against p190RhoGAP or the TFII-I gene into the vitreous cavity of the affected eye. In one embodiment, a mixture of several different siRNAs is injected directly into the vitreous cavity. In another embodiment, the siRNA can be combined with other anti-angiogenic therapy, such as anti-VEGF therapy, and injected directly into the vitreous cavity. In another embodiment, the siRNA can be combined with other p190RhoGAP or TFII-I inhibitors, e.g. an anti-p190RhoGAP antibody, or a anti-TFII-I antibody or an activator of GATA-2 as described herein, and injected directly into the vitreous cavity.

In one embodiment, an anti-angiogenic agent is used for the treatment of an angiogenesis-related disease characterized by uncontrolled or enhanced angiogenesis related to the eyes, e.g. macular degeneration or diabetic retinopathy, where an anti-angiogenic agent (i.e. activator of p190RhoGAP or activator of TFII-I inhibitor of GATA-2) is directly injected specifically into the vitreous cavity of the eye. In one embodiment, an anti-angiogenic agent can be combined with other anti-angiogenic therapy, such as anti-VEGF therapy, and injected directly into the vitreous cavity. In another embodiment, the anti-angiogenic agent can be an inhibitory antibody to GATA-2 or an activating antibody to p190RhoGAP or activating antibody to TFII-I which be combined with other anti-angiogenic agents, such as siRNA to GATA-2 as described herein, and injected directly into the vitreous cavity.

In some embodiments, where the pro-angiogenic agent or the anti-angiogenic agent is an antibody, an antibody can be administered intravenously, e.g. via central venous catheter (CVC or central venous line or central venous access catheter) placed into a large vein in the neck (internal jugular vein), chest (subclavian vein) or groin (femoral vein). Systemic delivery of antibodies can be performed according to any methods known in the art, e.g. as described in Loberg et. al. 2007, Cancer Research 67:9417 and WO/2000/050008). These references are incorporated by reference in their entirety. The antibody or variants or fragments thereof can be formulated for systemic delivery such as in liposomes.

In one embodiments, an anti-angiogenic agent can be used in a method for the treatment of angiogenesis-related diseases characterized by uncontrolled or enhanced angiogenesis having localized aberrant angiogenesis, e.g. solid non-metastatic tumor, arthritis, and endometriosis, the method comprising directly injecting an anti-angiogenic agent, such as a siRNA, dsRNA, or shRNA vector directed against GATA-2 gene to the location or tissue with aberrant angiogenesis. In one embodiment, a mixture of several different siRNAs to GATA-2 can be used, directly injected into the bodily site having localized aberrant angiogenesis. In another embodiment, an anti-angiogenic agent which is a siRNA is combined with other anti-angiogenic therapy, such as anti-VEGF therapy, and injected directly into the bodily site. In another embodiment, an anti-angiogenic agent which is a siRNA can be combined with other anti-angiogenic agents, e.g. small molecule inhibitors of GATA-2 and/or activators of p190RhoGAP and/or activators of TFII-I which can be injected directly into the bodily site.

In another embodiment, an anti-angiogenic agent can be combined with other anti-angiogenic therapy, such as anti-VEGF therapy, and injected directly into the bodily site having localized aberrant angiogenesis.

In other embodiments, the treatment of an angiogenesis-related disease or disorder characterized by enhanced or uncontrolled angiogenesis with an anti-angiogenic agent comprises systemic administration of an anti-angiogenic agent (e.g. such as an siRNA, dsRNA, shRNA vector directed against a GATA-2 gene and/or an inhibitory antibody specifically against GATA-2 and/or activator of p190RhoGAP and/or an activator of TFII-I function) into the mammal in need thereof. Such a mammal can have been diagnosed with an angiogenesis-related disease or disorder characterized by uncontrolled or enhanced angiogenesis by a skilled physician.

In one embodiment, the methods described herein of use of an anti-angiogenic agent for the treatment of an angiogenesis-related disease can be administered in conjunction with other anti-angiogenesis factor/drugs and treatment regime for the afflicted mammals, such as chemotherapy and radiation therapy.

Mammals include but are not limited to human, cat, dog, horse, monkey, cow, sheep, goats and other ungulates. In one embodiment, the mammal is a human.

An angiogenesis-related disease or disorder characterized by uncontrolled or enhanced angiogenesis can be selected, for example, from a group consisting of cancer, ascites formation, psoriasis, age-related macular degeneration, thyroid hyperplasia, preeclampsia, rheumatoid arthritis and osteoarthritis, Alzheimer's disease, obesity, psoriasis, atherosclerosis, vascular malformations, angiomata, pleural effusion, atherosclerosis, endometriosis, diabetic/other retinopathies, neovascular glaucoma, age-related macular degeneration, hemangiomas, corneal neovascularization, sickle cell anemia, sarcoidosis, syphilis, pseudoxanthoma elasticum, Paget's disease, vein occlusion, artery occlusion, carotid obstructive disease, chronic uveitis/vitritis, *Mycobacteria* infections, Lyme disease, systemic lupus erythematosis, retinopathy of prematurity, vascular malformations, angiomata, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, histoplasmosis, trauma and post-laser complications. In one embodiment, the age-related macular degeneration is wet macular degeneration. Other eye-associated diseases that can involve inappropriate angiogenesis include, but are not limited to, diseases associated with rubeosis (neovascularization of the angle) and diseases caused by the abnormal proliferation of fibrovascular or fibrous tissue, including all forms of prolific vitreoretinopathy.

In one embodiment, an angiogenesis-related disease or disorder characterized by uncontrolled or enhanced angiogenesis is cancer, where the rapidly dividing neoplastic cancer cells require an efficient blood supply to sustain the continued growth of the tumor. As used herein, "cancer" refers to any of various malignant neoplasms characterized by the proliferation of anaplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Administration of a pharmaceutically effective amount of an anti-angiogenic agent or a pharmaceutical composition comprising an anti-angiogenic agent and a pharmaceutically acceptable carrier can inhibit angiogenesis. By inhibiting angiogenesis at the primary tumor site and secondary tumor site, embodiments of the invention serve to prevent and limit the progression of the disease.

It is emphasized that any solid tumor that requires an efficient blood supply to keep growing is a candidate target. For example, candidates for the treatment methods described herein include carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include, for example, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In one embodiment, the methods of anti-angiogenic agents as disclosed herein can be used in preventing blinding blood vessel growth associated with diabetic eye diseases, namely diabetic retinopathy. The methods described herein can antagonize the effects of VEGF, a substance naturally produced in the body that promotes blood vessel formation. Released by the retina (light-sensitive tissue in back of the eye) when normal blood vessels are damaged by tiny blood clots due to diabetes, VEGF turns on its receptor, igniting a chain reaction that culminates in new blood vessel growth. However, the backup blood vessels are faulty; they leak, bleed and encourage scar tissue that detaches the retina, resulting in severe loss of vision. Such growth is the hallmark of diabetic retinopathy, the leading cause of blindness among young people in developed countries.

In yet another embodiment, anti-angiogenic agents as disclosed herein can be used in the treatment of age-related macular degeneration, as it is known that VEGF also contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula. Administration of an anti-angiogenic agent, such as a p190RhoGAP activator, and/or a TFII-I activator and/or a GATA-2 inhibitor, can serve to inhibit unwanted neovascularization in the choroid layer of the eye.

In one embodiment, the angiogenesis-related disease or disorder characterized by uncontrolled or enhanced angiogenesis is rheumatoid arthritis. Rheumatoid arthritis (RA) is characterized by synovial tissue swelling, leukocyte ingress and angiogenesis, or new blood vessel growth. The disease is thought to occur as an immunological response to an as yet unidentified antigen. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognised as a key event in the formation and maintenance of the pannus in RA (Paleolog, E. M., 2002, Arthritis Res. 4 (Suppl 3):S81-S90). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis, leukocyte ingress could not occur (Koch, A. E., 2000, Ann. Rheum. Dis.; 59(Suppl 1):i65-i71). Disruption of the formation of new blood vessels would not only prevent delivery of nutrients to the inflammatory site, it could also reduce joint swelling due to the additional activity of VEGF, a potent pro-angiogenic factor in RA, as a vascular permeability factor. Anti-VEGF hexapeptide RRKRRR (dRK6) (SEQ. ID. NO. 42) can suppress and mitigate the arthritis severity (Seung-Ah Yoo, et. al., J. Immunol. 2005, 174:5846-55). Inhibition of angiogenesis by a pharmaceutically effective amount of anti-angiogenic agent can also suppress and mitigate the arthritis severity.

In one embodiment, the angiogenesis-related disease or disorder characterized by uncontrolled or enhanced angiogenesis is Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with anti-angiogenic effects, seem to prevent Alzheimer's disease and/or influence the outcome of AD patients. Therefore, it has been speculated that angiogenesis in the brain vasculature can play an important role in AD. In Alzheimer's disease, the brain endothelium secretes the precursor substrate for the beta-amyloid plaque and a neurotoxic peptide that selectively kills cortical neurons. Moreover amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies based on VEGF inhibition can interfere with endothelial cell activation in AD (Schultheis s C., el. al., 2006, Angiogenesis. 9(2):59-65; Grammas P., et. al., 1999, Am. J. Path., 154(2):337-42) and can be used for preventing and/or treating AD. In the same way, the anti-angiogenic properties of a pharmaceutically effective amount of an anti-angiogenic agent (i.e. p190RhoGAP activator, and/or TFII-I activator and/or GATA-2 inhibitor) can be useful preventing and/or treating AD.

In one embodiment, the pathological angiogenic disease or disorder is obesity. Adipogenesis in obesity requires close interplay between differentiating adipocytes, stromal cells, and blood vessels. There are close spatial and temporal interrelationships between blood vessel formation and adipogenesis, and the sprouting of new blood vessels from preexisting vasculature is coupled to adipocyte differentiation. Adipogenic/angiogenic cell clusters can morphologically and immunohistochemically be distinguished from crown-like structures frequently seen in the late stages of adipose tissue obesity. Administration of anti-VEGF antibodies inhibited not only angiogenesis but also the formation of adipogenic/angiogenic cell clusters, indicating that the coupling of adipogenesis and angiogenesis is essential for differentiation of adipocytes in obesity. (Satoshi Nishimura et. al., 2007, Diabetes 56:1517-1526). It has been shown that the angiogenesis inhibitor, TNP-470 was able to prevent diet-induced and genetic obesity in mice (Ebba Bråkenhielm et. al., Circulation Research, 2004; 94:1579). TNP-470 reduced vascularity in the adipose tissue, thereby inhibiting the rate of growth of the adipose tissue and obesity development. Accordingly, treatment of obesity by the method and compositions comprising anti-angiogenic agents as disclosed herein is also encompassed.

In one embodiment, the angiogenesis-related disease or disorder characterized by uncontrolled or enhanced angiogenesis is endometriosis. Excessive endometrial angiogenesis is proposed as an important mechanism in the pathogenesis of endometriosis (Healy, D L., et. al., 1998, Human Reproduction Update, 4:736-740). The endometrium of patients with endometriosis shows enhanced endothelial cell proliferation. Moreover there is an elevated expression of the cell adhesion molecule integrin vβ3 in blood vessels in the endometrium of women with endometriosis when compared with normal women. U.S. Pat. No. 6,121,230 described the use of anti-VEGF agents in the treatment of endometriosis and this patent is incorporated hereby reference. Encompassed in the methods disclosed herein is the treatment of endometriosis with an anti-angiogenic agent, such as a p190RhoGAP activator, and/or a TFII-I activator and/or a GATA-2 inhibitor. Encompassed in the methods disclosed herein is the treatment of obesity with anti-angiogenic therapy, including the use of a pharmaceutically effective amount of an anti-angiogenic agent, such as a p190RhoGAP activator, and/or a TFII-I activator and/or a GATA-2 inhibitor.

Diseases associated with chronic inflammation are accompanied by an increase in angiogenesis and can be treated using an anti-angiogenic agent, such as a p190RhoGAP activator, and/or a TFII-I activator and/or a GATA-2 inhibitor, in the compositions and methods of the present invention. Diseases with symptoms of chronic inflammation include obesity, inflammatory bowel diseases such as Crohn's disease and ulcerative colitis, psoriasis, sarcoidosis, atherosclerosis including plaque rupture, Sjogrens disease, acne rosacea, syphilis, chemical burns, bacterial ulcers, fungal ulcers, Behcet's syndrome, Stevens-Johnson's disease, *Mycobacteria* infections, Herpes simplex infections, Herpes zoster infections, protozoan infections, Mooren's ulcer, leprosy, Wegener's sarcoidosis, pemphigoid, lupus, systemic lupus erythematosis, polyarteritis, lyme's disease, Bartonelosis, tuberculosis, histoplasmosis and toxoplasmosis. Angiogenesis is a key element that these chronic inflammatory diseases have in common. The chronic inflammation depends on continuous formation of capillary sprouts to maintain an influx of inflammatory cells. The influx and presence of the inflammatory cells sometimes produce granulomas to help maintain the chronic inflammatory state. Inhibition of angiogenesis by the compositions and methods comprising anti-angiogenic agents as disclosed herein is also encompassed for the prevention of the formation of the granulomas and to alleviate the disease.

The inflammatory bowel diseases also show extraintestinal manifestations such as skin lesions. Such lesions are characterized by inflammation and angiogenesis and can occur at many sites other than the gastrointestinal tract. In some embodiments, an anti-angiogenic agent, such as a p190RhoGAP activator, and/or a TFII-I activator and/or a GATA-2 inhibitor, can be used in the compositions and methods of the present invention for treating these lesions by preventing the angiogenesis, thus, reducing the influx of inflammatory cells and the lesion formation. Accordingly, treatment of inflammatory lesions and skin lesions by the method and compositions comprising anti-angiogenic agents as disclosed herein is also encompassed.

Sarcoidosis is another chronic inflammatory disease that is characterized as a multisystem granulomatous disorder. The granulomas of this disease can form anywhere in the body, and, thus, the symptoms depend on the site of the granulomas and whether the disease active. The granulomas are created by the angiogenic capillary sprouts providing a constant supply of inflammatory cells. Accordingly, treatment of sarcoidosis by the method and compositions comprising anti-angiogenic agents as disclosed herein is also encompassed.

Combination Therapy of an Anti-angiogenic Agent with Other Anti-angiogenic Factors/Drugs for the Treatment of Angiogenesis-related Disorder Characterized by Uncontrolled or Increased Angiogeneis In one embodiment, the therapeutically effective amount of an anti-angiogenic agent (i.e. p190RhoGAP activator, and/or TFII-I activator and/or GATA-2 inhibitor) can be administered in conjunction with one or more additional anti-angiogenic factors, drugs or therapeutics. For example, other potent angiogenesis inhibitors such as angiostatin, endostatin and cleaved antithrombin III can be incorporated into the composition.

There are three main types of anti-angiogenic drugs that are currently approved by the United States Food and Drug Administration (FDA) for the treatment of cancer and tumors: (1) Drugs that stop new blood vessels from sprouting (true angiogenesis inhibitors); (2) Drugs that attack a tumor's established blood supply (vascular targeting agents); and (3) Drugs that attack both the cancer cells as well as the blood vessel cells (the double-barreled approach).

In one embodiment, an anti-angiogenic agent as described herein can be used in combination with an anti-angiogenic therapy, such as but is not limited to the administration of monoclonal antibody therapies directed against specific pro-angiogenic growth factors and/or their receptors. Examples of these are: bevacizumab (AVASTIN®), cetuximab (ERBITUX®), panitumumab (VECTIBIX™), and trastuzumab (HERCEPTIN®).

In another embodiment, In one embodiment, an anti-angiogenic agent as described herein can be used in combination with an anti-angiogenic therapy, where the anti-angiogenic therapies include but are not limited to administration of small molecule tyrosine kinase inhibitors (TKIs) of multiple pro-angiogenic growth factor receptors. The three TKIs that are currently approved as anti-cancer therapies are erlotinib (TARCEVA®), sorafenib (NEXAVAR®), and sunitinib (SUTENT®).

In another embodiment, an anti-angiogenic agent as described herein can be used in combination with an anti-angiogenic therapy, where the anti-angiogenic therapies include but are not limited to administration of inhibitors of mTOR (mammalian target of rapamycin) such as temsirolimus (TORICEL™), bortezomib (VELCADE®), thalidomide (THALOMID®) and Doxycyclin.

Many of the current anti-angiogenesis factors or drugs attack the VEGF pathway. Bevacizumab (AVASTIN®) was the first drug that targeted new blood vessels to be approved for use against cancer. It is a monoclonal antibody that binds to VEGF, thereby blocking VEGF from reaching the VEGF receptor (VEGFR). Other drugs, such as sunitinib (SUTENT®) and sorafenib (NEXAVAR®), are small molecules that attach to the VEGF receptor itself, preventing it from being turned on. Such drugs are collectively termed VEGF inhibitors.

As the VEGF protein interacts with the VEGFRs, inhibition of either the ligand VEGF, e.g. by reducing the amount that is available to interact with the receptor; or inhibition of the receptor's intrinsic tyrosine kinase activity, blocks the function of this pathway. This pathway controls endothelial cell growth, as well as permeability, and these functions are mediated through the VEGFRs.

"VEGF inhibitors" include any compound or agent that produces a direct or indirect effect on the signaling pathways that promote growth, proliferation and survival of a cell by inhibiting the function of the VEGF protein, including inhibiting the function of VEGF receptor proteins. These include any organic or inorganic molecule, including, but not limited to modified and unmodified nucleic acids such as antisense nucleic acids, RNAi agents such as siRNA or shRNA, peptides, peptidomimetics, receptors, ligands, and antibodies that inhibit the VEGF signaling pathway. The siRNAs are targeted at components of the VEGF pathways and can inhibit the VEGF pathway. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (Æ terna Zentaris Inc; Quebec City, Calif.), ZM323881 (CALBIOCHEM® CA, USA), pegaptanib (MACUGEN) (Eyetech Pharmaceuticals), an anti-VEGF aptamer and combinations thereof.

VEGF inhibitors are also disclosed in U.S. Pat. Nos. 6,534,524 and 6,235,764. Additional VEGF inhibitors are described, for example, in WO 99/24440; WO 95/21613; WO 98/50356; WO 99/10349; WO 97/22596; WO 97/32856; WO 98/54093; WO 98/02438; WO 99/16755; WO 99/61422; WO 99/62890; WO 98/02437; WO 01/02369; WO 01/95353; WO 02/44158; WO 03/106462A1; U.S. Pat. Publ. No. 20060094032; U.S. Pat. Nos. 6,534,524; 5,834,504; 5,883,113; 5,886,020; 5,792,783; 6,653,308; U.S. Provisional Application No. 60/491,771; and 60/460,695. These references are incorporated herein in their entirety.

In one embodiment, the pharmaceutically effective amount of an anti-angiogenic agent (i.e. a p190RhoGAP activator, and/or TFII-I activator and/or GATA-2 inhibitor) can be administered in conjunction with VEGF inhibitors.

In another embodiment, other anti-angiogenic factors which can be administered with an anti-angiogenic agent as that term is defined herein (i.e. a p190RhoGAP activator, and/or TFII-I activator and/or GATA-2 inhibitor) include but are not limited to alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C—X—C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronection (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-b), vasculostatin, and vasostatin (calreticulin fragment), pamidronate-thalidomide, TNP470, the bisphosphonate family such as amino-bisphosphonate zoledronic acid. bombesin/gastrin-releasing peptide (GRP) antagonists such as RC-3095 and RC-3940-II (Bajol A M, et. al., British Journal of Cancer (2004) 90, 245-252), and anti-VEGF peptide RRKRRR (dRK6) (SEQ. ID. NO. 42) (Seung-Ah Yoo, J. Immuno, 2005, 174: 5846-5855).

Pro-angiogenic Agent and Anti-angiogenesis Agent Assay Methods

The effectiveness of any given pro-angiogenic agent (i.e. a p190RhoGAP inhibitor, and/or a TFII-I inhibitor and/or a GATA-2 activator) or anti-angiogenic agent (i.e. an p190RhoGAP activator, and/or TFII-I activator and/or GATA-2 inhibitor) can be evaluated in vitro or in vivo or both, as described, e.g., in the examples provided herein in the Examples and below.

For the avoidance of doubt, one can also use other assays commonly accepted in the field. For example, one can use the "CAM" assay. The chick chorioallantoic membrane (CAM) assay is frequently used to evaluate the effects of angiogenesis regulating factors because it is relatively easy and provides relatively rapid results. A pro-angiogenic agent (i.e. a p190RhoGAP inhibitor, and/or a TFII-I inhibitor and/or a GATA-2 activator) useful in the methods described herein will increase the number of microvasculars in the modified CAM assay described by Iruela-Arispe et al., 1999, Circulation 100: 1423-1431, relative to controls with no pro-angiogenic agent added (i.e. negative control). An anti-angiogenic agent (i.e. an p190RhoGAP activator, and/or TFII-I activator and/or GATA-2 inhibitor) useful in the methods described herein will decrease the number of microvasculars in the modified CAM assay described by Iruela-Arispe et al., 1999, Circulation 100: 1423-1431 (incorporated herein by reference in its entirety), relative to controls with no anti-angiogenic agent added (i.e. negative control). The method is based on the vertical growth of new capillary vessels into a collagen gel pellet placed on the CAM. In the assay as described by Iruela-Arispe et al., the collagen gel is supplemented with $VEGF_{165}$ (250 ng/gel) in the presence or absence of at least one pro-angiogenic agent or at least one anti-angiogenic agent. The extent of the vessel growth (i.e. pro-angiogenic effect) or vessel decrease (i.e. anti-angiogenic effect) is measured using FITC-dextran (50 μg/mL) (SIGMA ALDRICH®) injected into the circulation of the CAM. The degree of fluorescence intensity parallels variations in capillary density; the linearity of this correlation can be observed with a range of capillaries between 5 and 540. Morphometric analyses are performed, for example, by acquisition of images with a CCD camera. Images are then analyzed by importing into an analysis package, e.g., NHImage version 1.59, and measurements of fluorescence intensity are obtained as positive pixels. Each data point is compared with its own positive and negative controls present in the same CAM and interpreted as a percentage of inhibition, considering the positive control to be 100% ($VEGF_{165}$ alone) and the negative control (vehicle alone) 0%. Statistical evaluation of the data is performed to check whether groups differ significantly from random, e.g., by analysis of contingency with Yates' correction.

Additional angiogenesis assays are known in the art and can be used to evaluate a pro-angiogenic agent (i.e. a p190RhoGAP inhibitor, and/or a TFII-I inhibitor and/or a GATA-2 activator) or anti-angiogenic agent (i.e. an p190RhoGAP activator, and/or TFII-I activator and/or GATA-2 inhibitor) for use in the methods described herein. These include, for example, the corneal micropocket assay, hamster cheek pouch assay, the MATRIGEL™ assay and modifications thereof, and co-culture assays. Donovan et al. describe a comparison of three different in vitro assays developed to evaluate angiogenesis regulators in a human background (Donovan et al., 2001, Angiogenesis 4: 113-121, incorporated herein by reference). Briefly, the assays examined include: 1) a basic MATRIGEL™ assay in which low passage human endothelial cells (Human umbilical vein endothelial cells, HUVEC) are plated in wells coated with MATRIGEL™ (Becton Dickinson, Cedex, France) with or without angiogenesis regulator(s); 2) a similar MATRIGEL™ assay using "growth factor reduced" or GFR MATRIGEL™; and 3) a co-culture assay in which primary human fibroblasts and HUVEC are co-cultured with or without additional angiogenesis regulator(s)—the fibroblasts produce extracellular matrix and other factors that support HUVEC differentiation and tubule formation. In the Donovan et al. paper the co-culture assay provided microvascular networks that most closely resembled microvascular networks in vivo. Other CE cells, such as the bovine CE cells described herein, can be used instead of HUVEC. In addition, the basic MATRIGEL™ assay and the GFR MATRIGEL™ assay can also be used by one of skill in the art to evaluate whether a given pro-angiogenic agent (i.e. a p190RhoGAP inhibitor, and/or a TFII-I inhibitor and/or a GATA-2 activator) or anti-angiogenic agent (i.e. an p190RhoGAP activator, and/or TFII-I activator and/or GATA-2 inhibitor) inhibits vessel growth as necessary for the methods described herein. Finally, an in vitro angiogenesis assay kit is marketed by CHEMICON®. The Fibrin Gel in vitro Angiogenesis Assay Kit is CHEMICON® Catalog No. ECM630.

A pro-angiogenic agent (i.e. a p190RhoGAP inhibitor, and/or a TFII-I inhibitor and/or a GATA-2 activator) as described herein is considered useful in a method for promoting angiogenesis and for the treatment (including prophylaxis treatment) of a angiogenesis-related disease or disorder characterized by inhibited or reduced angiogenesis or reduced blood vessel growth as described herein if it reduces angiogenesis in any one of these assays by 10% or more relative to a control assay performed the absence of any anti-angiogenic agent.

An anti-angiogenic agent (i.e. an p190RhoGAP activator, and/or TFII-I activator and/or GATA-2 inhibitor) as described herein preferably reduces angiogenesis in one or more of these assays by at least 20%, at least 30%, at least 40%, at least 50%, at least 60%, at least 70%, at least 80%, at least 90% or more, up to and including 100% inhibition.

An anti-angiogenic agent (i.e. an p190RhoGAP activator, and/or TFII-I activator and/or GATA-2 inhibitor) as described herein is considered useful in a method for the inhibition of angiogenesis and for the treatment of an angiogenesis-related disease or disorder characterized by uncontrolled or enhanced angiogenesis as described herein if it reduces angiogenesis in any one of these assays by 10% or more relative to a control assay performed the absence of any anti-angiogenic agent. An anti-angiogenic agent as described herein preferably reduces angiogenesis in one or more of these assays by at least 20%, at least 30%, at least 40%, at least 50%, at least 60%, at least 70%, at least 80%, at least 90% or more, up to and including 100% inhibition.

Alternatively, angiogenesis inhibition can be measured functionally downstream, as a reduction or cessation of tumor growth or tumor size. For example, if there is zero growth of tumor mass, or at least 5% reduction in the size of the tumor mass, there is angiogenesis inhibition by the methods as described herein.

Formulation and Administration

In one embodiment, a pro-angiogenic agent (i.e. a p190RhoGAP inhibitor, and/or a TFII-I inhibitor and/or a GATA-2 activator) or anti-angiogenic agent (i.e. an p190RhoGAP activator, and/or TFII-I activator and/or GATA-2 inhibitor) is delivered in a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

As used herein, the terms "administering," refers to the placement of pro-angiogenic agent (i.e. a p190RhoGAP inhibitor, and/or a TFII-I inhibitor and/or a GATA-2 activator) or anti-angiogenic agent (i.e. an p190RhoGAP activator, and/or TFII-I activator and/or GATA-2 inhibitor) that can promote or inhibit angiogenesis, respectively into a subject by a method or route which results in at least partial localization of the pro-angiogenic agent or anti-angiogenic agent at a desired site. The pro-angiogenic agent (i.e. a p190RhoGAP inhibitor, and/or a TFII-I inhibitor and/or a GATA-2 activator) or anti-angiogenic agent (i.e. an p190RhoGAP activator, and/or TFII-I activator and/or GATA-2 inhibitor) can be administered by any appropriate route which results in an effective treatment in the subject.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

The term "consisting of" refers to methods, and respective components thereof as described herein, which are exclusive of any element not recited in that description of the embodiment.

Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Specifically contemplated pharmaceutical compositions are active RNAi ingredients in a preparation for delivery as described herein above, or in references cited and incorporated herein in that section. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Routes of administration include, but are not limited to, direct injection, intradermal, intravitreal, intramuscular, intraperitoneal, intravenous, subcutaneous, intranasal, epidural, and oral routes. The agent can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local.

The precise dose and formulation to be employed depends upon the potency of the inhibitor, and include amounts large enough to produce the desired effect, e.g., a reduction in invasion of new blood vessels in the eye or elsewhere. The dosage should not be so large as to cause unacceptable adverse side effects. Generally, the dosage will vary with the type of pro-angiogenic agent or anti-angiogenic agent used (e.g., an antibody or fragment, small molecule, siRNA, etc.), as well as the combination of pro-angiogenic agents (i.e. any and all possible combinations of a p190RhoGAP inhibitor, and/or a TFII-I inhibitor and/or a GATA-2 activator) or combination of anti-angiogenic agents administered (i.e. any and all combinations of an p190RhoGAP activator, and/or TFII-I activator and/or GATA-2 inhibitor), as well as the age, condition, and sex of the patient are also considered. Dosage and formulation of the pro-angiogenic agent or anti-angiogenic agent will also depend on the route of administration, and the seriousness of the disease or disorder, and should be decided according to the judgment of the practitioner and each patient's circumstances. Effective doses can be extrapolated from dose-response curves derived from in vitro or animal model test systems.

The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight. Alternatively, the dose range will be titrated to maintain serum levels between 5 μg/mL and 30 μg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

As exemplary, for the treatment of solid tumors that are accessible by catheters or needles, an anti-angiogenic agent (i.e. an p190RhoGAP activator, and/or TFII-I activator and/or GATA-2 inhibitor) and a pharmaceutically acceptable carrier can be formulated for direct application by injection into the solid tumor and/or adjacent to the tumor site, e.g. melanoma and hemangiomas. A pro-angiogenic agent or anti-angiogenic agent can also be formulated for a transdermal delivery, e.g. a skin patch.

For cancers or tumors not so easily accessible, an anti-angiogenic agent (i.e. a p190RhoGAP activator, and/or TFII-I activator and/or GATA-2 inhibitor) can be administered to one of the main blood vessel that drains the cancer site, e.g. into the portal vein for liver cancer. For the treatment of macular degeneration or retinopathy, the anti-angiogenic agent can be formulated for direct injection into the vitreous cavity of the affected eye.

In one embodiment, where the pro-angiogenic agent (i.e. a p190RhoGAP inhibitor, and/or a TFII-I inhibitor) or anti-angiogenic agent (i.e. GATA-2 inhibitor) is an RNA interference molecule such as an siRNA. Such siRNA is delivered by delivering a vector encoding small hairpin RNA (shRNA) in a pharmaceutically acceptable carrier to the cells in an organ of an individual. The shRNA is converted by the cells after transcription into siRNA capable of targeting p190RhoGAP, TFII-I or GATA-2 respectively. In one embodiment, the vector can be a regulatable vector, such as tetracycline inducible vector. Such vectors with inducible promoters are well known in the art and are also easily found in the commercial sector, e.g. pSingle-tTS-shRNA vector from CLONTECH®.

In one embodiment, the treatment of angiogenesis-related diseases characterized by uncontrolled or increased angiogenesis in the eyes, e.g. macular degeneration or diabetic retinopathy, comprises directly injecting an siRNA, dsRNA, or shRNA vector directed against a GATA-2 gene into the vitreous cavity of the affected eye, and optionally in combination with other anti-angiogenic agents such as activators of p190RhoGAP and/pr activators of TFII-I.

In other embodiments, the treatment of angiogenesis-related diseases characterized by uncontrolled or increased angiogenesis having localized aberrant angiogenesis, e.g. solid non-metastatic tumor, arthritis, and endometriosis, comprises directly injecting an siRNA, dsRNA, or shRNA vector directed against a GATA-2 gene to the location of tissue with aberrant angiogenesis, and optionally in combination with other anti-angiogenic agents such as activators of p190RhoGAP and/pr activators of TFII-I.

In one embodiment, the RNA interfering molecules used in the methods described herein are taken up actively by cells in vivo following intravenous injection, e.g., hydrodynamic injection, without the use of a vector, illustrating efficient in vivo delivery of the RNA interfering molecules, e.g., the siRNAs used in the methods of the invention.

Other strategies for delivery of the RNA interfering molecules, e.g., the siRNAs or shRNAs used as pro-angiogenic agents (i.e. a p190RhoGAP inhibitor, and/or a TFII-I inhibitor) or an anti-angiogenic agent (i.e. GATA-2 inhibitor) according to the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

In some embodiments, vectors comprising RNA interfering molecules, e.g., the siRNAs, dsRNA or shRNAs used as pro-angiogenic agents (i.e. RNAi molecules directed against p190RhoGAP gene, and/or the TFII-I gene) or an anti-angiogenic agent (i.e. RNAi molecules directed against GATA-2 gene) can be administered intravenously, e.g. via central venous catheter (CVC or central venous line or central venous access catheter) placed into a large vein in the neck (internal jugular vein), chest (subclavian vein) or groin (femoral vein). Methods of systemic delivery of siRNA, dsRNA, or shRNA vector are well known in the art, e.g. as described herein and in Gao and Huang, 2008, (Mol. Pharmaceutics, Web publication December 30) and review by Rossil, 2006, Gene Therapy, 13:583-584. The siRNA, dsRNA, or shRNA vector can be formulated in various ways, e.g. conjugation of a cholesterol moiety to one of the strands of the siRNA duplex for systemic delivery to the liver and jejunum (Soutschek J. et. al. 2004, Nature, 432:173-178), complexing of siRNAs to protamine fused with an antibody fragment for receptor-mediated targeting of siRNAs (Song E, et al. 2005, Nat. Biotechnol., 23: 709-717) and the use of a lipid bilayer system by Morrissey et al. 2005 (Nat. Biotechnol., 23: 1002-1007). The lipid bilayer system produces biopolymers that are in the 120 nanometer diameter size range, and are labeled as SNALPs, for Stable-Nucleic-Acid-Lipid-Particles. The lipid combination protects the siRNAs from serum nucleases and allows cellular endosomal uptake and subsequent cytoplasmic release of the siRNAs (see WO/2006/007712). These references are incorporated by reference in their entirety.

In another embodiment, the treatment of angiogenesis-related diseases characterized by uncontrolled or increased angiogenesis in the eye, e.g. macular degeneration or diabetic retinopathy comprises directly injecting an anti angiogenic agent into the vitreous cavity of the eye.

In other embodiments, the treatment of angiogenesis-related diseases characterized by uncontrolled or increased angiogenesis having localized aberrant angiogenesis, e.g. solid non-metastatic tumor, arthritis, and endometriosis, comprises directly injecting an anti-angiogenic agent (i.e. an p190RhoGAP activator, and/or a TFII-I activator or a GATA-2 inhibitor) into the location or tissue with aberrant angiogenesis, wherein the integrin function is blocked by the antibody.

In some embodiments, a pro-angiogenic agent (i.e. an p190RhoGAP inhibitor, and/or a TFII-I inhibitor or a GATA-2 activator) or an anti-angiogenic agent (i.e. an p190RhoGAP activator, and/or a TFII-I activator or a GATA-2 inhibitor) is a an antibody. a small molecule, a peptide or an aptamer. Such a pro-angiogenic agent or anti-angiogenic agent can be targeted to specific organ or tissue by means of a targeting moiety, such as e.g., an antibody or targeted liposome technology. In some embodiments, for example, an anti-angiogenic agent can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The conjugation of an anti-angiogenic agent permits the anti-angiogenic agent attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

For therapeutic applications, a pro-angiogenic antibody agent or an anti-angiogenic antibody agent can be administered to a mammal, preferably a human, in a pharmaceutically acceptable dosage form, including those that can be administered to a human intravenously as a bolus or by continuous infusion over a period of time, by intramuscular, subcutaneous, intra-articular, intrasynovial, intrathecal, oral, topical, or inhalation routes. A pro-angiogenic antibody agent or an anti-angiogenic antibody agent can also suitably administered by intratumoral, peritumoral, intralesional, or perilesional routes, to exert local as well as systemic therapeutic effects.

In some embodiments, a pro-angiogenic antibody agent or an anti-angiogenic antibody agent is administered intravenously, e.g. via central venous catheter (CVC or central venous line or central venous access catheter) placed into a large vein in the neck (internal jugular vein), chest (subclavian vein) or groin (femoral vein).

Such dosage forms encompass pharmaceutically acceptable carriers that are inherently nontoxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. A pro-angiogenic antibody agent or an anti-angiogenic antibody agent will typically be formulated in such vehicles at a concentration of about 0.1 mg/ml to 100 mg/ml.

Depending on the type and severity of the disease, about 0.015 to 15 mg/kg of a pro-angiogenic antibody agent or an anti-angiogenic antibody agent is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens can be useful.

The effectiveness of a pro-angiogenic antibody agent or an anti-angiogenic antibody agent in treating disease can be improved by administering the antibody serially or in combination with another agent that is effective for those purposes, such as another antibody directed against a different epitope or neutralizing a different protein than the first antibody, or one or more conventional therapeutic agents such as, for example, alkylating agents, folic acid antagonists, antimetabolites of nucleic acid metabolism, antibiotics, pyrimidine analogs, 5-fluorouracil, purine nucleosides, amines, amino acids, triazol nucleosides, corticosteroids, calcium, retinoids, lipoxygenase and cyclooxygenase inhibitors, fumaric acid and its salts, analgesics, psychopharmaceuticals, local anesthetics, spasmolytics, and beta-blockers. Such other agents can be present in the composition being administered or can be administered separately. Also, a pro-angiogenic antibody agent or an anti-angiogenic antibody agent can be suitably administered serially or in combination with radiological treatments, whether involving irradiation or administration of radioactive substances.

Efficacy testing can be performed during the course of treatment using the methods described herein. Measurements of the degree of severity of a number of symptoms associated with a particular ailment are noted prior to the start of a treatment and then at later specific time period after the start of the treatment. For example, when treating an autoimmune disease such as rheumatoid arthritis, the severity of joint pain can be scored from a number of 1-10, with a score of 1 representing mild discomfort and a score of 10 represent constant unbearable pain with or without movement; the range of motion of an affected joint can also are be measured as a degree of angle for which that joint can move. The joint pain and range of motion are noted before and after a treatment. The severity of joint pain and range of motion after the treatment are compared to those before the treatment. A decrease in the pain score and/or an increase in the degree of angle of joint movement indicate that the treatment is effective in reducing inflammation in the affected joint, thereby decreasing pain and improving joint movement. Other methods of efficacy testing includes evaluating for visual problems, new blood vessel invasion, rate of vessel growth, angiogenesis, etc.: (1) inhibiting the disease, e.g., arresting, or slowing the pathogenic growth of new blood vessels; or (2) relieving the disease, e.g., causing regression of symptoms, reducing the number of new blood vessels in a tissue exhibiting pathology involving angiogenesis (e.g., the eye); and (3) preventing or reducing the likelihood of the development of a neovascular disease, e.g., an ocular neovascular disease).

The present invention can be defined in any of the following numbered paragraphs:

1. The use of an anti-angiogenic agent for inhibiting angiogenesis through modulation of microvascular endothelial cell migration, or microvascular endothelial cell differentiation or capillary blood vessel growth in a mammal, wherein the anti-angiogenic agent is selected from at least one from the group consisting of: a p190RhoGAP activator, a TFII-I activator, a GATA-2 inhibitor.
2. The use of paragraph 1, wherein the GATA-2 inhibitor is selected from the group consisting of an antibody, an RNA interference molecule, a small molecule, a peptide and an aptamer.
3. The use of paragraph 1, wherein the p190RhoGAP activator is selected from the group consisting of an antibody, a small molecule, a peptide, polypeptide, or nucleic acid.
4. The use of paragraph 1, wherein the TFII-I activator is selected from the group consisting of antibody, a small molecule, a peptide, polypeptide, or nucleic acid.
5. The use of an siRNA directed specifically against a GATA-2 gene for inhibiting endothelial cell migration.
6. The use of an antibody directed specifically against a GATA-2 for inhibiting endothelial cell migration, wherein the GATA-2 function is blocked by the antibody.
7. The use of any of paragraphs 1-6, wherein the endothelial cell is a mammalian endothelial cell.
8. The use of paragraph 7, wherein the mammalian endothelial cell is a human endothelial cell.
9. A pharmaceutical composition comprising a therapeutically effective amount of at least one anti-angiogenic agent selected from the group consisting of: a p190RhoGAP activator, a TFII-I activator, a GATA-2 inhibitor, and a pharmaceutically acceptable carrier for inhibiting angiogenesis through modulation of microvascular endothelial cell migration, or microvascular endothelial cell differentiation or capillary blood vessel growth in a mammal in need thereof.
10. The pharmaceutical composition of paragraph 9 for the manufacture of a medicament for inhibiting angiogenesis in a mammal in need thereof.
11. The pharmaceutical composition of paragraph 9, wherein the GATA-2 inhibitor is selected from the group consisting of an antibody, an RNA interference molecule, a small molecule, a peptide and an aptamer.
12. The pharmaceutical composition of paragraph 9, wherein the p190RhoGAP activator is selected from the group consisting of an antibody, a small molecule, a peptide, polypeptide, or nucleic acid.
13. The pharmaceutical composition of paragraph 9, wherein the TFII-I activator is selected from the group consisting of antibody, a small molecule, a peptide, polypeptide, or nucleic acid.
14. The use of an siRNA directed specifically against a GATA-2 gene for inhibiting angiogenesis through modulation of microvascular endothelial cell migration, or microvascular endothelial cell differentiation or capillary blood vessel growth in a mammal in need thereof.
15. The use of an siRNA directed specifically against a GATA-2 gene for the manufacture of a medicament for inhibiting angiogenesis through modulation of microvascular endothelial cell migration, or microvascular endothelial cell differentiation or capillary blood vessel growth in a mammal in need thereof.
16. The use of an antibody directed specifically against a GATA-2 for inhibiting angiogenesis through modulation of microvascular endothelial cell migration, or microvascular endothelial cell differentiation or capillary blood vessel growth in a mammal in need thereof, wherein the GATA-2 function is blocked by the antibody.
17. The use of an antibody directed specifically against a GATA-2 for the manufacture of a medicament for inhibiting angiogenesis through modulation of microvascular endothelial cell migration, or microvascular endothelial cell differentiation or capillary blood vessel growth in a mammal in need thereof, wherein the GATA-2 is blocked by the antibody.
18. The pharmaceutical composition of paragraph 9, wherein the mammal is afflicted with an angiogenesis-related disease or disorder characterized by increased angiogenesis.

19. The use of any of paragraphs 14-17, wherein the mammal is afflicted with an angiogenesis-related disease or disorder characterized by increased angiogenesis.
20. The use of paragraphs 18 or 19, the angiogenesis-related disease characterized by increased angiogenesis is selected from the group consisting of cancer, macular degeneration; diabetic retinopathy; rheumatoid arthritis; Alzheimer's disease; obesity, psoriasis, atherosclerosis, vascular malformations, angiomata, and endometriosis.
21. The use of any of paragraphs 1, 14-17 and 19, wherein the mammal is a human.
22. The pharmaceutical composition of paragraph 9 for use in the treatment of an angiogenesis-related disease characterized by increased angiogenic in a mammal in need thereof.
23. The pharmaceutical composition of paragraphs 19 or 18, wherein the mammal is a human.
24. The pharmaceutical composition of paragraph 9, further comprising at least one additional anti-angiogenic therapy.
25. The pharmaceutical composition of paragraph 24, wherein the anti-angiogenic therapy is chemotherapy or radiation therapy.
26. The use of a pro-angiogenic agent for promoting angiogenesis through modulation of microvascular endothelial cell migration, or microvascular endothelial cell differentiation or capillary blood vessel growth in a mammal, wherein the pro-angiogenic agent is selected from at least one from the group consisting of: a p190RhoGAP inhibitor, a TFII-I inhibitor, a GATA-2 activator.
27. The use of paragraph 26, wherein the p190RhoGAP inhibitor is selected from the group consisting of an antibody, an RNA interference molecule, a small molecule, a peptide and an aptamer.
28. The use of paragraph 26, wherein the TFII-I inhibitor is selected from the group consisting of an antibody, an RNA interference molecule, a small molecule, a peptide and an aptamer.
29. The use of paragraph 26, wherein the GATA-2 activator is selected from the group consisting of antibody, a small molecule, a peptide, polypeptide, or nucleic acid.
30. The use of an siRNA directed specifically against a p190RhoGAP gene for promoting endothelial cell migration.
31. The use of an siRNA directed specifically against a TFII-I gene for promoting endothelial cell migration.
32. The use of an antibody directed specifically against a p190RhoGAP for promoting endothelial cell migration, wherein the p190RhoGAP function is blocked by the antibody.
33. The use of an antibody directed specifically against a TFII-I for promoting endothelial cell migration, wherein the TFII-I function is blocked by the antibody
34. The use of any of paragraphs 26-33, wherein the endothelial cell is a mammalian endothelial cell.
35. The use of paragraph 34, wherein the mammalian endothelial cell is a human endothelial cell.
36. A pharmaceutical composition comprising a therapeutically effective amount of at least one pro-angiogenic agent selected from the group consisting of: a p190RhoGAP inhibitor; a TFII-I inhibitor, a GATA-2 activator, and a pharmaceutically acceptable carrier for promoting angiogenesis through modulation of microvascular endothelial cell migration, or microvascular endothelial cell differentiation or capillary blood vessel growth in a mammal in need thereof.
37. The pharmaceutical composition of paragraph 36 for the manufacture of a medicament for promoting angiogenesis through modulation of microvascular endothelial cell migration, or microvascular endothelial cell differentiation or capillary blood vessel growth in a mammal in need thereof.
38. The pharmaceutical composition of paragraph 36, wherein the p190RhoGAP inhibitor is selected from the group consisting of an antibody, an RNA interference molecule, a small molecule, a peptide and an aptamer.
39. The pharmaceutical composition of paragraph 36, wherein the TFII-I inhibitor is selected from the group consisting of an antibody, an RNA interference molecule, a small molecule, a peptide and an aptamer.
40. The pharmaceutical composition of paragraph 36, wherein the GATA-2 activator is selected from the group consisting of an antibody, a small molecule, a peptide, polypeptide, or nucleic acid.
41. The use of an siRNA directed specifically against a p190RhoGAP gene for promoting angiogenesis through modulation of microvascular endothelial cell migration, or microvascular endothelial cell differentiation or capillary blood vessel growth in a mammal in need thereof.
42. The use of an siRNA directed specifically against a p190RhoGAP gene for the manufacture of a medicament for promoting angiogenesis through modulation of microvascular endothelial cell migration, or microvascular endothelial cell differentiation or capillary blood vessel growth in a mammal in need thereof.
43. The use of an antibody directed specifically against a p190RhoGAP for promoting angiogenesis through modulation of microvascular endothelial cell migration, or microvascular endothelial cell differentiation or capillary blood vessel growth in a mammal in need thereof, wherein the p190RhoGAP function is blocked by the antibody.
44. The use of an antibody directed specifically against a p190RhoGAP polypeptide for the manufacture of a medicament for promoting angiogenesis through modulation of microvascular endothelial cell migration, or microvascular endothelial cell differentiation or capillary blood vessel growth in a mammal in need thereof, wherein the p190RhoGAP function is blocked by the antibody.
45. The use of an siRNA directed specifically against a TFII-I gene for promoting angiogenesis through modulation of microvascular endothelial cell migration, or microvascular endothelial cell differentiation or capillary blood vessel growth in a mammal in need thereof.
46. The use of an siRNA directed specifically against a TFII-I gene for the manufacture of a medicament for promoting angiogenesis through modulation of microvascular endothelial cell migration, or microvascular endothelial cell differentiation or capillary blood vessel growth in a mammal in need thereof.
47. The use of an antibody directed specifically against a TFII-I polypeptide for promoting angiogenesis through modulation of microvascular endothelial cell migration, or microvascular endothelial cell differentiation or capillary blood vessel growth in a mammal in need thereof, wherein the TFII-I function is blocked by the antibody.
48. The use of an antibody directed specifically against a TFII-I polypeptide for the manufacture of a medicament for promoting angiogenesis through modulation of microvascular endothelial cell migration, or microvascular endothelial cell differentiation or capillary blood vessel growth in a mammal in need thereof, wherein the TFII-I is blocked by the antibody.
49. The pharmaceutical composition of paragraph 36, wherein the mammal is afflicted with an angiogenesis-related disease or disorder characterized by decreased angiogenesis.

50. The use of any of paragraphs 26 and 41-48, wherein the mammal is afflicted with an angiogenesis-related disease or disorder characterized by decreased angiogenesis.
51. The use of paragraphs 49 or 50, the angiogenesis-related disease characterized by decreased angiogenesis is selected from the group consisting of ischemic limb disease, coronary artery disease, myocardial infarction, brain ischemia, tissue transplantation therapy and stem cell implantation.
52. The use of the pharmaceutical composition of paragraph 26 for to promote angiogenesis through modulation of microvascular endothelial cell migration, or microvascular endothelial cell differentiation or capillary blood vessel growth in a mammal, wherein the mammal is in need of neovascularization of tissue engineering contructs, organ transplantation, tissue repair, regenerative medicine and wound healing.
53. The use of any of paragraphs 26-35, 41-48 and 52, wherein the mammal is a human.
54. The pharmaceutical composition of paragraph 36 for use in the treatment of an angiogenesis-related disease characterized by decrease in angiogenesis in a mammal in need thereof.
55. A method for inhibiting angiogenesis through modulation of microvascular endothelial cell migration, or microvascular endothelial cell differentiation or capillary blood vessel growth, the method comprising contacting an endothelial cell with at least one anti-angiogenic agent selected from the group consisting of: a p190RhoGAP activator, a TFII-I activator, a GATA-2 inhibitor.
56. A method for inhibiting angiogenesis through modulation of microvascular endothelial cell migration, or microvascular endothelial cell differentiation or capillary blood vessel growth in a mammal in need thereof, the method comprising administering a therapeutically effective amount of at least one anti-angiogenic agent selected from the group consisting of: a p190RhoGAP activator, a TFII-I activator, a GATA-2 inhibitor, and a pharmaceutically acceptable carrier.
57. A method of treating an angiogenesis-related disease characterized by increased angiogenesis in a mammal in need thereof, the method comprising administering a therapeutically effective amount a anti-angiogenic agent selected from the group consisting of: p190RhoGAP activator, a TFII-I activator, a GATA-2 inhibitor, and a pharmaceutically acceptable carrier.
58. The method of any of paragraphs 55-57, wherein the GATA-2 inhibitor is selected from the group consisting of an antibody, an RNA interference molecule, a small molecule, a peptide and an aptamer.
59. The method of any of paragraphs 55-57, wherein the GATA-2 inhibitor is an RNA interference molecule that inhibits GATA-2 expression in the cell.
60. The method any of paragraphs 55-57, wherein the GATA-2 inhibitor is an siRNA directed specifically against a GATA-2 gene.
61. The method any of paragraphs 55-57, wherein the GATA-2 inhibitor is an antibody directed specifically against a GATA-2 polypeptide, wherein the GATA-2 function is blocked by the antibody.
62. The method of any of paragraphs 55-57, wherein the p190RhoGAP activator is selected from the group consisting of an antibody, a small molecule, a peptide, polypeptide, or nucleic acid.
63. The method of any of paragraphs paragraph 55-57, wherein the TFII-I activator is selected from the group consisting of an antibody, a small molecule, a peptide, polypeptide, or nucleic acid.
64. The method of paragraph 55, wherein the endothelial cell is a mammalian endothelial cell.
65. The method of paragraph 63, wherein the mammalian endothelial cell is a human endothelial cell.
66. The method of any of paragraphs 56-57, wherein the mammal is afflicted with an angiogenesis-related disease or disorder characterized by increase in angiogenesis.
67. The method of paragraph 66, wherein the angiogenesis-related disease characterized by increase in angiogenesis is selected from the group consisting of cancer, macular degeneration; diabetic retinopathy; rheumatoid arthritis; Alzheimer's disease; obesity, psoriasis, atherosclerosis, vascular malformations, angiomata, and endometriosis.
68. The method of any of paragraphs 56-57, wherein the mammal is a human.
69. The method of any of paragraphs 55-57, further comprising administering an anti-angiogenic therapy in conjunction with the anti-angiogenic agent.
70. The method of paragraph 69, wherein an anti-angiogenic therapy is chemotherapy and/or radiation therapy.
71. A method for promoting angiogenesis through modulation of microvascular endothelial cell migration, or microvascular endothelial cell differentiation or capillary blood vessel growth, the method comprising contacting an endothelial cell with at least one pro-angiogenic agent selected from the group consisting of: a p190RhoGAP inhibitor, a TFII-I inhibitor, a GATA-2 activator.
72. A method for promoting angiogenesis through modulation of microvascular endothelial cell migration, or microvascular endothelial cell differentiation or capillary blood vessel growth in a mammal in need thereof, the method comprising administering a therapeutically effective amount of at least one pro-angiogenic agent selected from the group consisting of: a p190RhoGAP inhibitor, a TFII-I inhibitor, a GATA-2 activator and a pharmaceutically acceptable carrier.
73. A method of treating an angiogenesis-related disease characterized by decreased angiogenesis in a mammal in need thereof, the method comprising administering a therapeutically effective amount pro-angiogenic agent selected from the group consisting of: a p190RhoGAP inhibitor, a TFII-I inhibitor, a GATA-2 activator and a pharmaceutically acceptable carrier.
74. The method of any of paragraphs 71-73, wherein the p190RhoGAP inhibitor is selected from the group consisting of an antibody, an RNA interference molecule, a small molecule, a peptide and an aptamer.
75. The method of any of paragraphs 71-73, wherein the p190RhoGAP inhibitor is an RNA interference molecule that inhibits p190RhoGAP expression in the cell.
76. The method any of paragraphs 71-73, wherein the p190RhoGAP inhibitor is an siRNA directed specifically against a p190RhoGAP gene.
77. The method of any of paragraphs 71-73, wherein the TFII-I inhibitor is selected from the group consisting of an antibody, an RNA interference molecule, a small molecule, a peptide and an aptamer.
78. The method of any of paragraphs 71-73, wherein the TFII-I inhibitor is an RNA interference molecule that inhibits TFII-I expression in the cell.
79. The method any of paragraphs 71-73, wherein the TFII-I inhibitor is an siRNA directed specifically against a TFII-I gene.

80. The method of any of paragraphs 71-73, wherein the GATA-2 activator is selected from the group consisting of an antibody, a small molecule, a peptide, polypeptide, or nucleic acid.
81. The method of paragraph 71, wherein the endothelial cell is a mammalian endothelial cell.
82. The method of paragraph 81, wherein the mammalian endothelial cell is a human endothelial cell.
83. The method of paragraph 72, wherein the mammal in need thereof is in need of neovascularization of a tissue engineering construct, organ transplant, tissue repair, regenerative medicine, and wound healing.
84. A method for inhibiting angiogenesis through modulation of microvascular endothelial cell migration, or microvascular endothelial cell differentiation or capillary blood vessel growth, the method comprising contacting an endothelial cell with an siRNA directed specifically against a p190RhoGAP gene or a TFII-I gene.
85. A method for inhibiting angiogenesis through modulation of microvascular endothelial cell migration, or microvascular endothelial cell differentiation or capillary blood vessel growth, the method comprising contacting an endothelial cell with an antibody directed specifically against a p190RhoGAP polypeptide, wherein the p190RhoGAP function is blocked by the antibody.
86. A method for inhibiting angiogenesis through modulation of microvascular endothelial cell migration, or microvascular endothelial cell differentiation or capillary blood vessel growth, the method comprising contacting an endothelial cell with an antibody directed specifically against a TFII-I polypeptide, wherein the TFII-I function is blocked by the antibody.
87. The method of any of paragraphs 72 or 73, wherein the mammal is afflicted with an angiogenesis-related disease or disorder characterized by a decrease in angiogenesis.
88. The method of paragraph 87, wherein the angiogenesis-related disease characterized by decrease in angiogenesis is selected from the group consisting of ischemic limb disease, coronary artery disease, myocardial infarction, brain ischemia, tissue transplantation therapy and stem cell implantation.
89. The method of any of paragraphs 72 and 73, wherein the mammal is a human.
90. A method of promoting angiogenesis through modulation of microvascular endothelial cell migration, or microvascular endothelial cell differentiation or capillary blood vessel growth comprising contacting said cell with an inhibitor of TFII-I expression or activity.
91. A method of promoting angiogenesis through modulation of microvascular endothelial cell migration, or microvascular endothelial cell differentiation or capillary blood vessel growth comprising contacting said cell with an inhibitor of p190RhoGAP expression or activity.
92. A method of inhibiting angiogenesis through modulation of microvascular endothelial cell migration, or microvascular endothelial cell differentiation or capillary blood vessel growth comprising contacting said cell with an inhibitor of GATA2 expression or activity.
93. A method of modulating angiogenesis through modulation of microvascular endothelial cell migration, or microvascular endothelial cell differentiation or capillary blood vessel growth, the method comprising contacting a microvascular endothelial cell with an agent which inhibits or activates one or more of p190RhoGAP, TFII-I, and GATA-2.
94. The method of paragraph 93, wherein modulating is an increase in angiogenesis through modulation of microvascular endothelial cell migration, or microvascular endothelial cell differentiation or capillary blood vessel growth, and wherein the endothelial cell is contacted with at least one agent which inhibits p190RhoGAP or inhibits TFII-I or activates GATA-2.
95. The method of paragraph 93, wherein modulating is a decrease in angiogenesis through modulation of microvascular endothelial cell migration, or microvascular endothelial cell differentiation or capillary blood vessel growth, and wherein the endothelial cell is contacted with at least one agent which activates p190RhoGAP or activates TFII-I or inhibits GATA-2.
96. The use of an siRNA directed specifically against a GATA-2 gene for inhibiting angiogenesis through modulation of microvascular endothelial cell migration, or microvascular endothelial cell differentiation or capillary blood vessel growth in a mammal in need thereof.
97. The use of an siRNA directed specifically against a GATA-2 gene for the manufacture of a medicament for inhibiting angiogenesis through modulation of microvascular endothelial cell migration, or microvascular endothelial cell differentiation or capillary blood vessel growth in a mammal in need thereof.
98. The use of an antibody directed specifically against a GATA-2 polypeptide for inhibiting angiogenesis through modulation of microvascular endothelial cell migration, or microvascular endothelial cell differentiation or capillary blood vessel growth in a mammal in need thereof, wherein the p190RhoGAP function is blocked by the antibody.
99. The use of an antibody directed specifically against a GATA-2 polypeptide for the manufacture of a medicament for inhibiting angiogenesis through modulation of microvascular endothelial cell migration, or microvascular endothelial cell differentiation or capillary blood vessel growth in a mammal in need thereof, wherein the p190RhoGAP function is blocked by the antibody.

EXAMPLES

Angiogenesis is controlled by physical interactions between cells and extracellular matrix as well as soluble angiogenic factors, such as VEGF. However, the mechanism by which mechanical signals integrate with other microenvironmental cues to regulate neovascularization remains unknown. Here, the inventors demonstrate that the Rho inhibitor, p190RhoGAP, controls capillary network formation in vitro and retinal angiogenesis in vivo by modulating the balance of activities between two antagonistic transcription factors—TFII-I and GATA2 that govern gene expression of the VEGF receptor, VEGFR2. Moreover, this novel angiogenesis signaling pathway is sensitive to extracellular matrix elasticity as well as soluble VEGF. This is the first known functional cross-antagonism between transcription factors that controls tissue morphogenesis, and that responds to both mechanical and chemical cues. The inventors herein demonstrate methods to promote or inhibit microvascular endothelial cell migration, endothelial cell differentiation, capillary blood vessel growth and/or angiogenesis by modulation (i.e. inhibiting or activating) p190RhoGAP, TFII-I and GATA-2.

VEGF and its receptor VEGFR2 are of particular importance in angiogenesis because they are essential for normal blood vessel development[12,13], and deregulation of these factors leads to various pathological conditions[1,2,14]. The inventors have investigated the role of VEGF and VEGFR2 in the mechanism by which these mechanical forces regulate capillary development. Analysis of cellular mechanotransduction during angiogenesis has revealed that the small GTPase, Rho, mediates growth control in vitro[10,15], as well as blood vessel development in vivo[9], by modulating the mechanical force balance that governs cell shape. Stress-induced distortion of the capillary cell cytoskeleton regulates Rho activity by controlling its upstream inhibitor, p190RhoGAP[16]. p190RhoGAP was shown to bind to the transcription factor TFII-I and sequester it in the cytoplasm of fibroblasts[17], and TFII-I is a multifunctional transcription factor that regulates VEGFR2 expression in large vessel endothelial cells[18 19]. Although it remains unknown whether it plays a role in angiogenesis, TFII-I deletions are associated with cardiovascular defects[20].

Deregulation of angiogenesis—the growth of blood capillaries—contributes to development of many diseases, including cancer, arthritis and blindness[1,2]. FDA-approved angiogenesis inhibitors solely target the oxygen-sensitive vascular endothelial growth factor, VEGF; however, neovascularization is also controlled by other microenvironmental signals, including mechanical forces conveyed by extracellular matrix (ECM). For example, although capillary development is driven by angiogenic mitogens, cell sensitivity to these soluble cues can be modulated by physical interactions between cells and ECM that alter cell shape and cytoskeletal structure[3-8]. Similar changes in capillary cell shape and function can be produced by changing ECM elasticity, adhesivity or topography, applying mechanical stresses, or altering cell-generated traction forces[3-8]. Mechanical tension also stimulates capillary growth and vascular remodeling in vivo[9], and regional variations of ECM mechanics and cell shape appear mediate how neighboring cells undergo localized differentials of growth and differentiation that drive three-dimensional (3D) tissue pattern formation[10,11]. But the mechanism by which mechanical signals conveyed by ECM converge with those elicited by growth factors to control gene transcription required for angiogenic control remains unknown.

Example 1 p190RhoGAP and TFII-I Regulate VEGFR2

To explore whether p190RhoGAP modulates vascular development by altering gene transcription, the inventors knocked down p190RhoGAP in human microvascular endothelial (HMVE) cells using siRNA. TFII-I protein levels were approximately 1.5 times higher in the nuclear fraction of knockdown cells (FIGS. 7A and 7B), and this was confirmed by fluorescence microscopy (FIG. 7C). As first shown in fibroblasts[17], the inventors discovered that p190RhoGAP co-precipitates with TFII-I (and vice versa) (FIG. 7D), demonstrating that p190RhoGAP can also bind TFII-I and sequester it in the cytoplasm of human capillary cells.

Figure 8B:
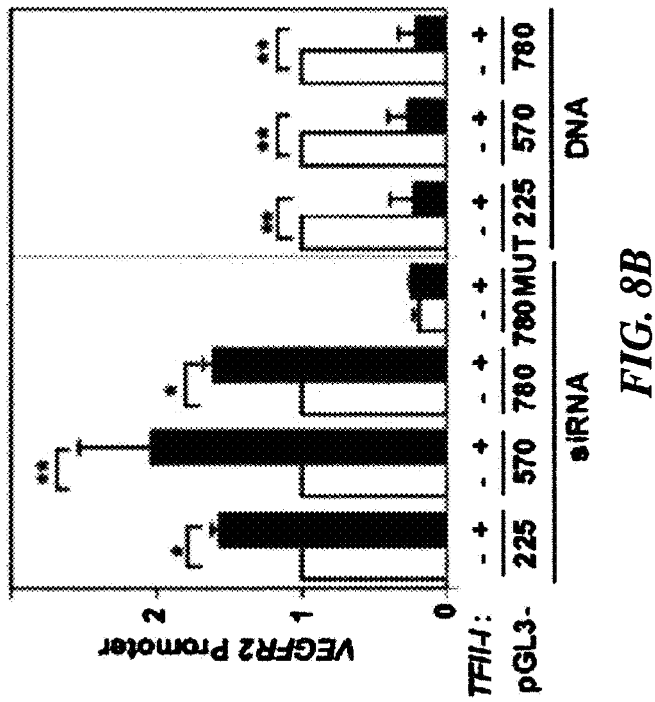
FIG. 8B shows the VEGFR2 promoter activity in cells transfected with TFII-I siRNA or DNA. Activities of VEGFR2 promoters (pGL3-225, -570, -780) and the Inr region mutant (pGL3-780MUT) are presented as ratio of VEGFR2 promoter activity normalized to cells transfected with control siRNA or DNA (*, p<0.05; **, p<0.01). Error Bars represent s.e.m of 3 replica experiments.
Figure 8A:
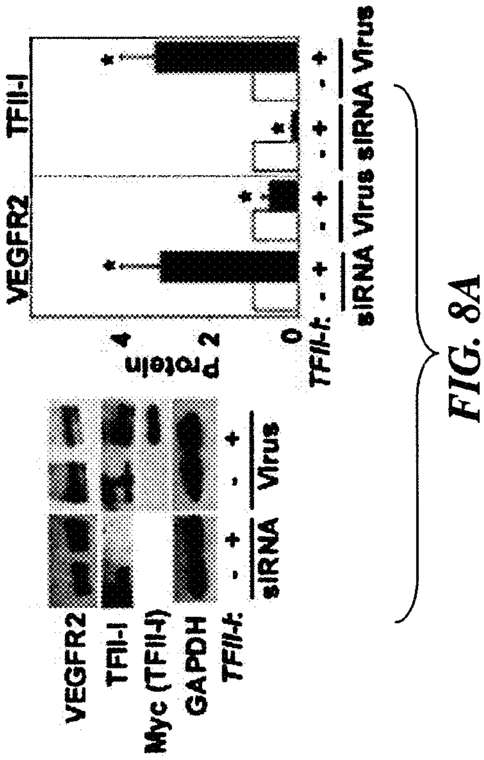
FIG. 8A shows the VEGFR2, TFII-I and GAPDH protein levels in cells treated with TFII-I siRNA or lentiviral vectors (virus) encoding myc-tagged TFII-I. Quantitative results show the ratio of VEGFR2 and TFII-I protein levels relative to GAPDH normalized to those in cells treated with control siRNA or virus(*, p<0.05). Error Bars represent s.e.m of 3 replica experiments.

TFII-I upregulates VEGFR2 protein expression in human aortic endothelial cells by binding to the VEGFR2 promoter[18]. But TFII-I knockdown in the HMVE cells increased (rather than decreased) VEGFR2 mRNA and protein levels by 2- to 3-fold relative to control cells, and overexpressing TFII-I (delta isoform[21]) using lentiviral transduction produced the opposite effect (FIG. 1A, FIG. 8A). This difference may be due to the fact that macrovascular and microvascular endothelial cells undergo distinct morphogenetic programs (produce large tubes versus branching capillaries).

Figure 8F:
FIG. 8F are immunoblots of GATA2 co-immunoprecipitated with anti-p190RhoGAP antibody (left), and p190RhoGAP with anti-HA antibody in cells overexpressing HA-GATA2 (right).
Figures 8C, 8D, 8E:
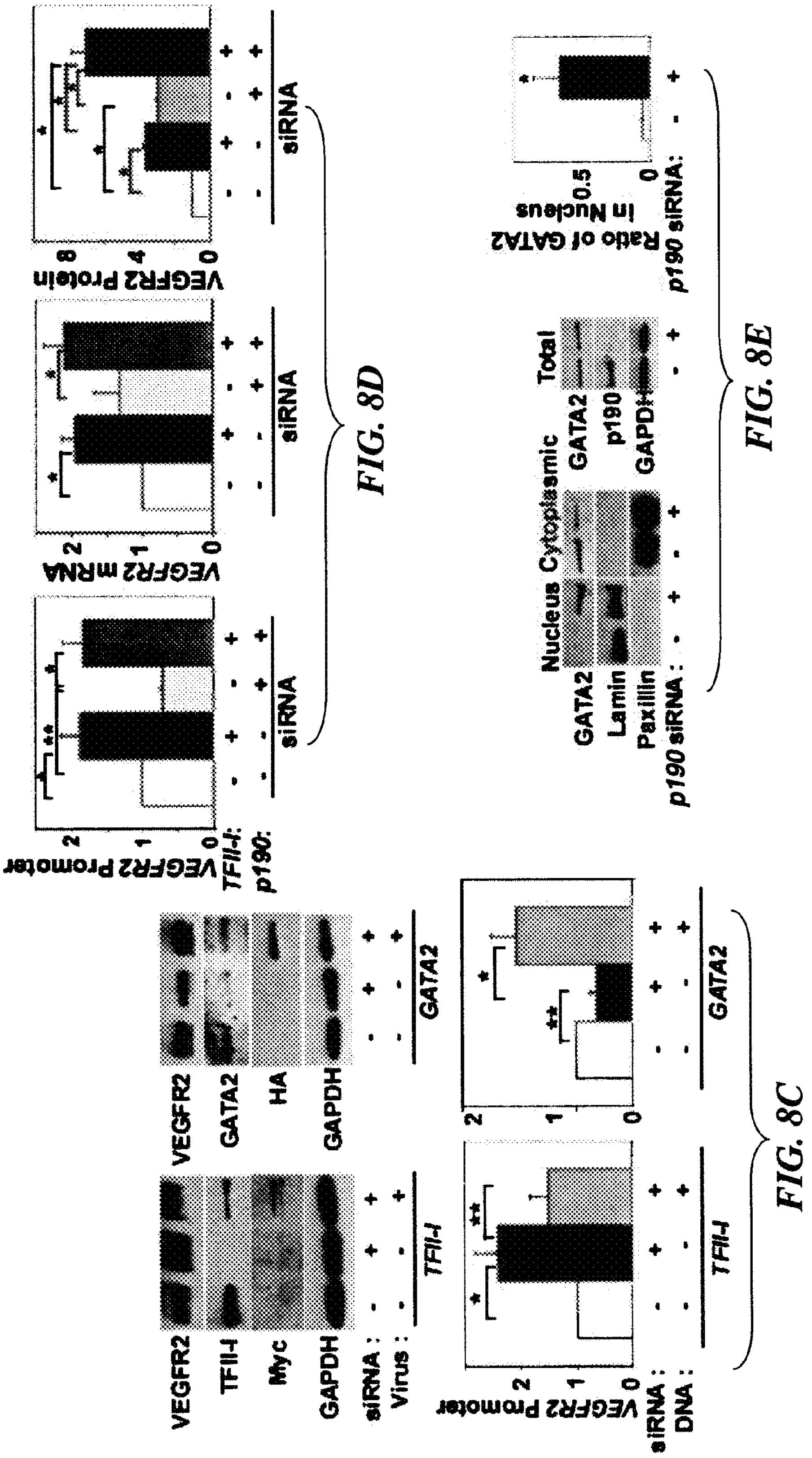
FIG. 8C are immunoblots showing the VEGFR2, TFII-I, GATA2, and GAPDH protein levels in HMVE cells treated with human TFII-I or GATA2 siRNA alone or in combination with virus expressing mouse TFII-I or Gata2 (upper). Histogram shows the VEGFR2 promoter activity (pGL3-780) in HUVE cells transfected with human TFII-I or GATA2 siRNA alone or in combination with DNA encoding mouse TFII-I or Gata2 (lower; normalized to cells expressing control siRNA and DNA vector; *, p<0.01; **, p<0.05). Error Bars represent s.e.m of 3 replica experiments.
FIG. 8D shows the VEGFR2 promoter activity (pGL3-780) and mRNA and protein levels relative to GAPDH in HMVE cells treated with siRNAs for TFII-I or p190RhoGAP, or both in combination; results are normalized to control cells treated with control siRNA (*, $p<0.01$, **, $p<0.05$). Error Bars represent s.e.m of 3 replica experiments.
FIG. 8E are immunoblots showing GATA2 distribution in the nucleus and cytoplasm, and the expression levels of GATA2 and p190RhoGAP in the total cell lysates of control or p190RhoGAP knockdown HMVE cells. Quantitation of results from triplicate studies reveals that the ratio of GATA2 in the nucleus to the total cell lysate increases significantly (*, $p<0.05$) in p190RhoGAP knockdown cells. Error Bars represent s.e.m of 3 replica experiments.

TFII-I binds to the Inr region of the VEGFR2 gene promoter, and smaller portions of this promoter (human VEGFR2: −225 to +268, −570 to +268, and −780 to +268) have similar or greater activity compared to the full length promoter (4 kb)[18,22]. When these various VEGFR2 promoters were characterized using a luciferase assay in human umbilical vein endothelial (HUVE) cells, TFII-I knockdown increased, and overexpression of TFII-I using DNA transfection decreased, VEGFR2 promoter activity by 1.5 to 2-fold and one-fifth normal levels, respectively (FIG. 8B). The promoter-less pGL3 basic reporter showed no promoter activity (not shown). Moreover, mutagenesis of the VEGFR2 Inr (−780+268; 780MUT) decreased promoter activity in both control and TFII-I knockdown cells (FIG. 8B), demonstrating that TFII-I decreases VEGFR2 promoter activity through the Inr region. Importantly, the specificity of these effects of TFII-I knockdown were confirmed by demonstrating that reconstitution of TFII-I can reverse these effects (FIG. 8C).

Example 2

Figure 7A:
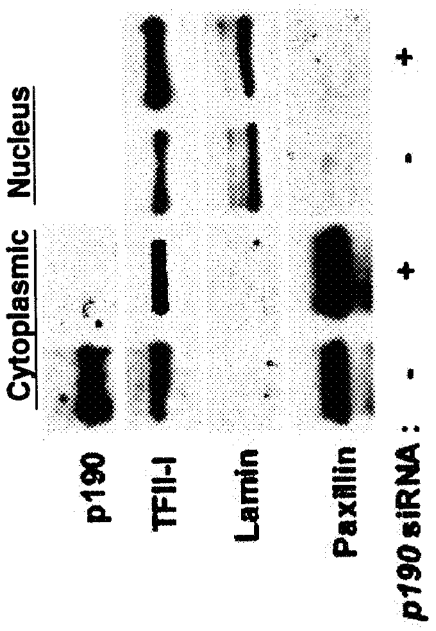
FIG. 7A is an immunoblots showing TFII-I distribution in cytoplasmic versus nuclear fractions in HMVE cells treated with p190RhoGAP siRNA. Lamin and paxillin are nuclear and cytoplasmic markers, respectively.
Figure 7B:
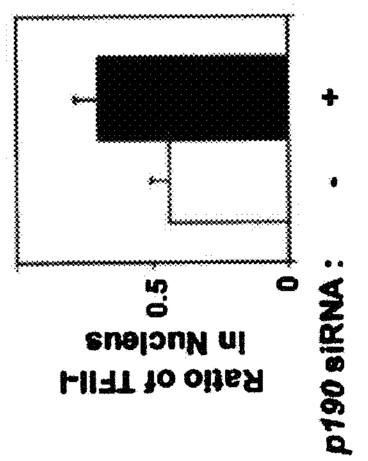
FIG. 7B is a histogram showing the quantitative results of the ratio of TFII-I in the nucleus versus total cell lysate (mean±S.E.M. of 3 or more replica experiments for all graphs).
Figure 7C:
FIG. 7C is a histogram showing the quantitative results of the ratio of TFII-I in the nucleus versus the whole cell in control and p190RhoGAP knockdown cells.
Figure 7D:
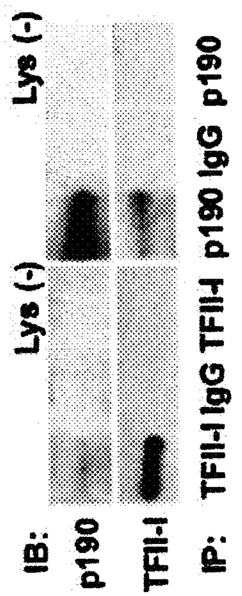
FIG. 7D is an immunoblots of p190RhoGAP co-immunoprecipitated with anti-TFII-I antibody, and vice versa (mouse IgG was used as a control); Lys(−) is the immunoprecipitation control without protein lysate.

The inventors next determined whether p190RhoGAP stimulates VEGFR2 expression by restricting nuclear translocation of TFII-I (FIGS. 7A, 7B, 7C). TFII-Iknockdown increased, and p190RhoGAP knockdown decreased, VEGFR2 promoter activity (−780+268) relative to control cells (FIG. 8D). The double knockdown of p190RhoGAP and TFII-I exhibited the same stimulation as observed in the TFII-I knockdown cells (FIG. 8D). However, p190RhoGAPknockdown did not decrease VEGFR2 mRNA and protein levels; in fact, it increased VEGFR2 protein levels (FIG. 1C, 8D). Moreover, p190RhoGAP and TFII-I double knockdown produced similar or slightly higher levels of VEGFR2 mRNA and protein expression (FIG. 1B, FIG. 8D) compared to either p190RhoGAP or TFII-I knockdown alone. These results raised the intriguing possibility that an antagonist of TFII-I activity might exist that also contributes to p190RhoGAP-dependent control of VEGFR2 expression.

Example 3

GATA2 Upregulates VEGFR2

Figure 9A:
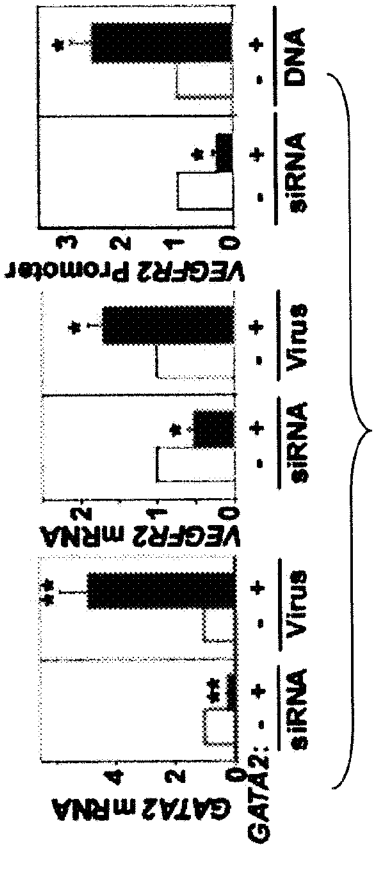
FIG. 9A shows the GATA2 (left) and VEGFR2 (middle) mRNA levels in HMVE cells transfected with siRNA or transduced with lentiviral vector (virus) encoding GATA2 (normalized to the cells expressing control siRNA or DNA; *, $p<0.01$, **, $p<0.05$). VEGFR2 promoter activity (pGL3-780) in HUVE cells transfected with siRNA or DNA encoding GATA2 (right; *, $p<0.01$).
Figure 9B:
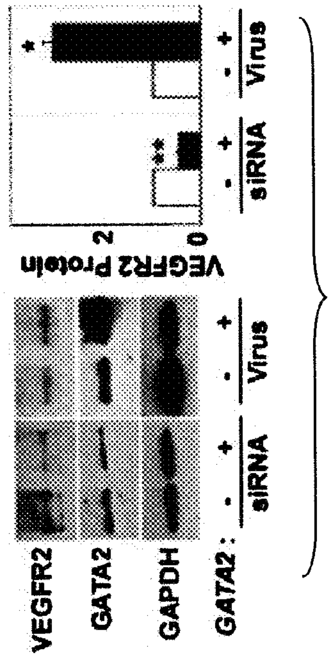
FIG. 9B (left) are the immunoblots showing VEGFR2, GATA2 and GAPDH protein levels in GATA2 knockdown (siRNA) or overexpressing cells (virus). right; The ratio of VEGFR2 protein levels relative to GAPDH in GATA2 knockdown (siRNA) or overexpressing (virus) HMVE cells normalized to the cells expressing control siRNA or DNA vector (*, $p<0.01$, **, $p<0.05$).
Figure 9C:
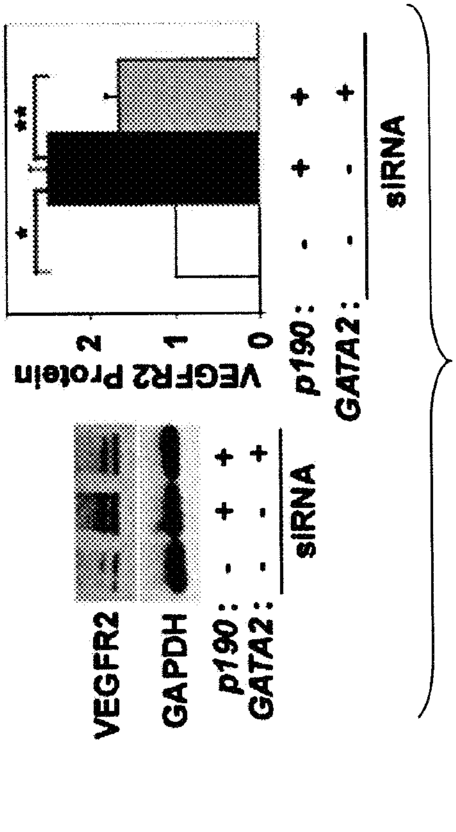
FIG. 9C are the immunoblots showing VEGFR2 and GAPDH protein levels in cells transfected with p190RhoGAP siRNA with or without GATA2 siRNA (left) and quantitative results showing VEGFR2 protein levels relative to GAPDH normalized to the control siRNA transfected cells (right; *, $p<0.01$, **, $p<0.05$).

GATA2 is another transcription factor that binds the VEGFR2 promoter and regulates its activity[23,24]. Because many GATA family members antagonize the effects of other transcription factors at promoter sites[25-28], the inventors explored whether GATA2 mediates p190RhoGAP-dependent control of VEGFR2 expression by opposing TFII-I activity. When p190RhoGAP was knocked down, GATA2 levels in the nucleus increased dramatically (>10-fold) relative to control cells even though total GATA2 levels remained the same, as shown by immunoblotting (FIG. 8E) and fluorescence microscopy (data not shown). p190RhoGAP also co-immunoprecipitated with GATA2 and vice versa (FIG. 8F). Importantly, this increase in nuclear GATA2 was significantly higher than the 1.5-fold increase in nuclear TFII-I produced using p190RhoGAP siRNA (FIG. 7A, 7B, 7C), demonstrating that p190RhoGAP binds and sequesters GATA2 in the cytoplasm more efficiently than TFII-I in capillary cells. GATA2 knockdown using siRNA decreased VEGFR2 promoter activity, as well as levels of mRNA and protein (FIG. 9A, 9B) as previously observed[23], while GATA2 overexpression produced the opposite effects. These effects of GATA2 siRNA on VEGFR2 promoter activity and protein expression were specific as they were reversed by Gata2 reconstitution (FIG. 8C). Interestingly, p190RhoGAP knockdown increased the expression of VEGFR2 mRNA and protein, and double knockdown with GATA2 inhibited these effects (FIG. 1C, FIG. 9C). Thus, GATA2 appears to upregulate VEGFR2 promoter activity and mediate the effects of p190RhoGAP on VEGFR2 gene expression in capillary cells. However, knockdown of p190RhoGAP, which releases more GATA2 than TFII-I and increases VEGFR2 expression, did not increase VEGFR2 promoter activity (FIG. 8D). This can be because cellular TFII-I levels are 5 times higher than GATA2 levels (not shown). The inventors also measured VEGFR2 promoter activity using only a portion of its promoter, and hence, TFII-I and GATA2 also can exert regulatory activities at other promoter sites; alternatively, p190RhoGAP might elicit signals that influence mRNA stability.

Figure 9D:
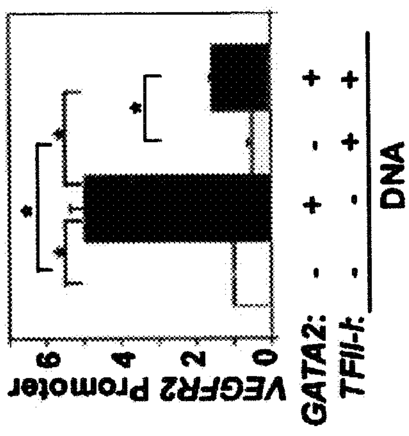
FIG. 9D shows VEGFR2 promoter activity in HUVE cells transfected with DNA encoding GATA2 or TFII-I, alone or in combination (*, $p<0.01$).
Figure 9E:
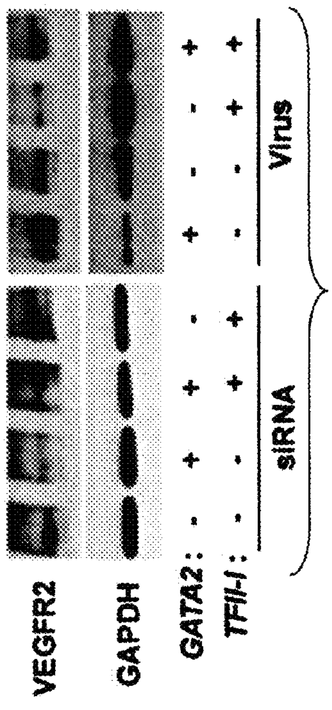
FIG. 9E are the immunoblots showing VEGFR2 and GAPDH protein expression level in HMVE cells transfected with siRNA or transduced with lentiviral vectors encoding GATA2 or TFII-I, alone or in combination.
Figure 9F:
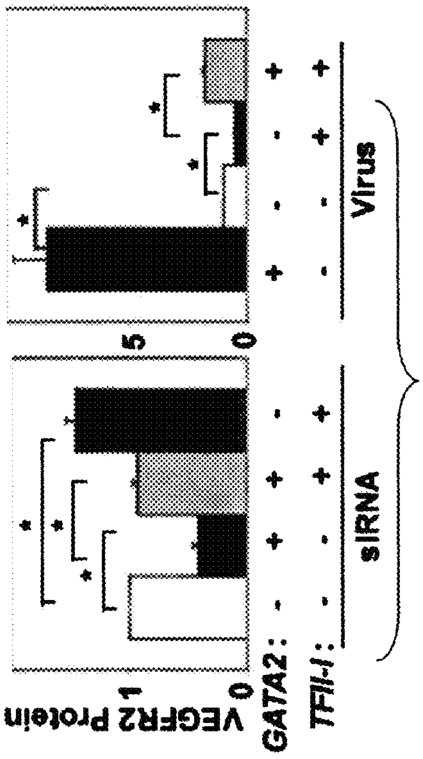
FIG. 9F shows the quantitative results of VEGFR2 and GAPDH protein expression levels in cells of FIG. 9E. The protein levels relative to control GAPDH were normalized to cells treated with control siRNA or virus (*, $p<0.01$). Error Bars represent s.e.m of 3 replica experiments.
Figure 10A:
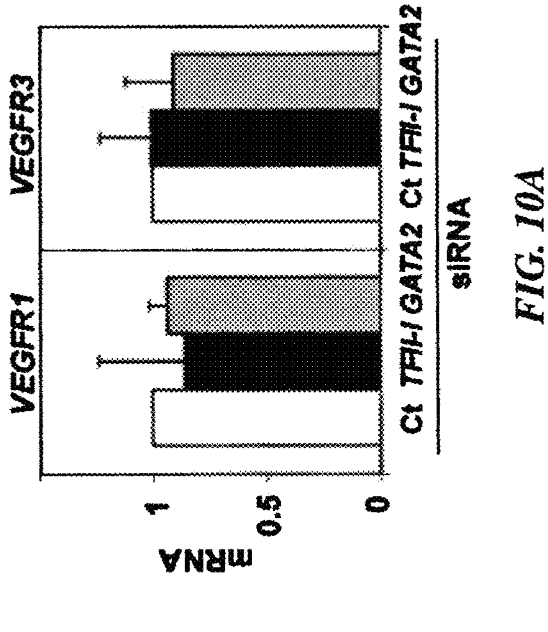
FIG. 10A demonstrates the VEGFR1 and VEGFR3 mRNA levels in HMVE cells transfected with TFII-I or GATA2 siRNA (mRNA levels were normalized to those in cells transfected with control siRNA).
Figure 10B:
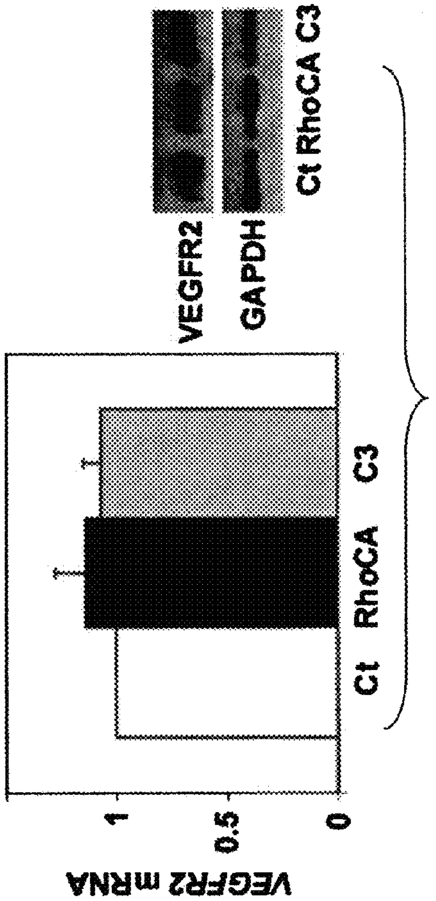
FIG. 10B shows the VEGFR2 mRNA (left) and protein (right) levels in HMVE cells treated with lentivirus expressing constitutively active RhoA or cell permeable Rho inhibitor C3 exoenzyme (2 μg/ml) (mRNA levels were normalized relative to those in cells transfected with control virus).

The inventors next asked whether GATA2 and TFII-I directly antagonize each other. Simultaneous knockdown of TFII-I and GATA2 abrogated each other's effects on VEGFR2 promoter activity (FIG. 1D), mRNA production (FIG. 1D) and protein expression levels (FIG. 9E), and simultaneous overexpression of TFII-I and GATA2 produced similar effects (FIG. 9D, 9E). These effects were specific for VEGFR2 as knockdown of TFII-I or GATA2 did not alter expression of VEGFR1 or VEGFR3 in HMVE cells (FIG. 10A). Importantly, although p190RhoGAP is a Rho inhibitor, altering Rho activity with constitutively active RhoA, membrane-permeable C3 exoenzyme or siRNA directed to another Rho-inhibiting RhoGAP (p73RhoGAP)[29] did not change VEGFR2 mRNA or protein levels (Supplementary 10B, 10C). Thus, p190RhoGAP appears to control VEGFR2 expression solely by its ability to sequester these transcription factors.

Figure 6:
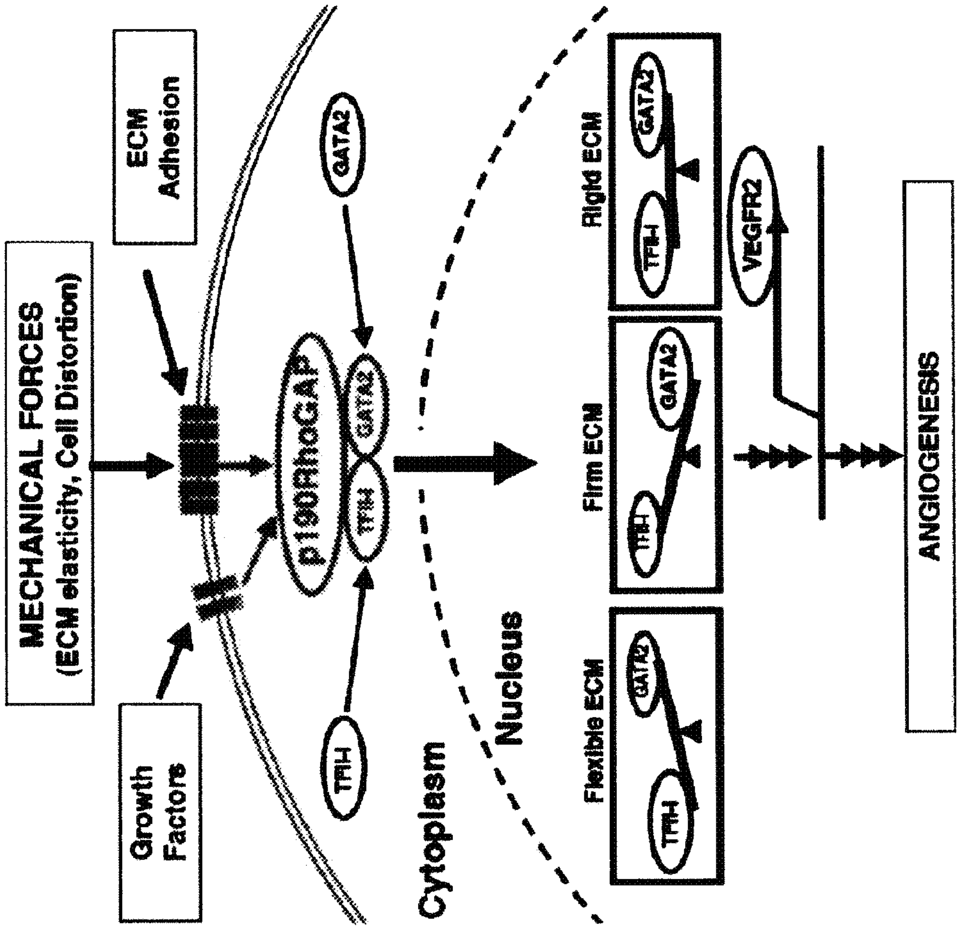
FIG. 6 shows a schematic model for the mechanical control of angiogenesis via transcriptional control of VEGFR2 expression through the transcription factors GATA2 and TFII-I.
Figures 10C, 11A, 11B, 11C, 11D:
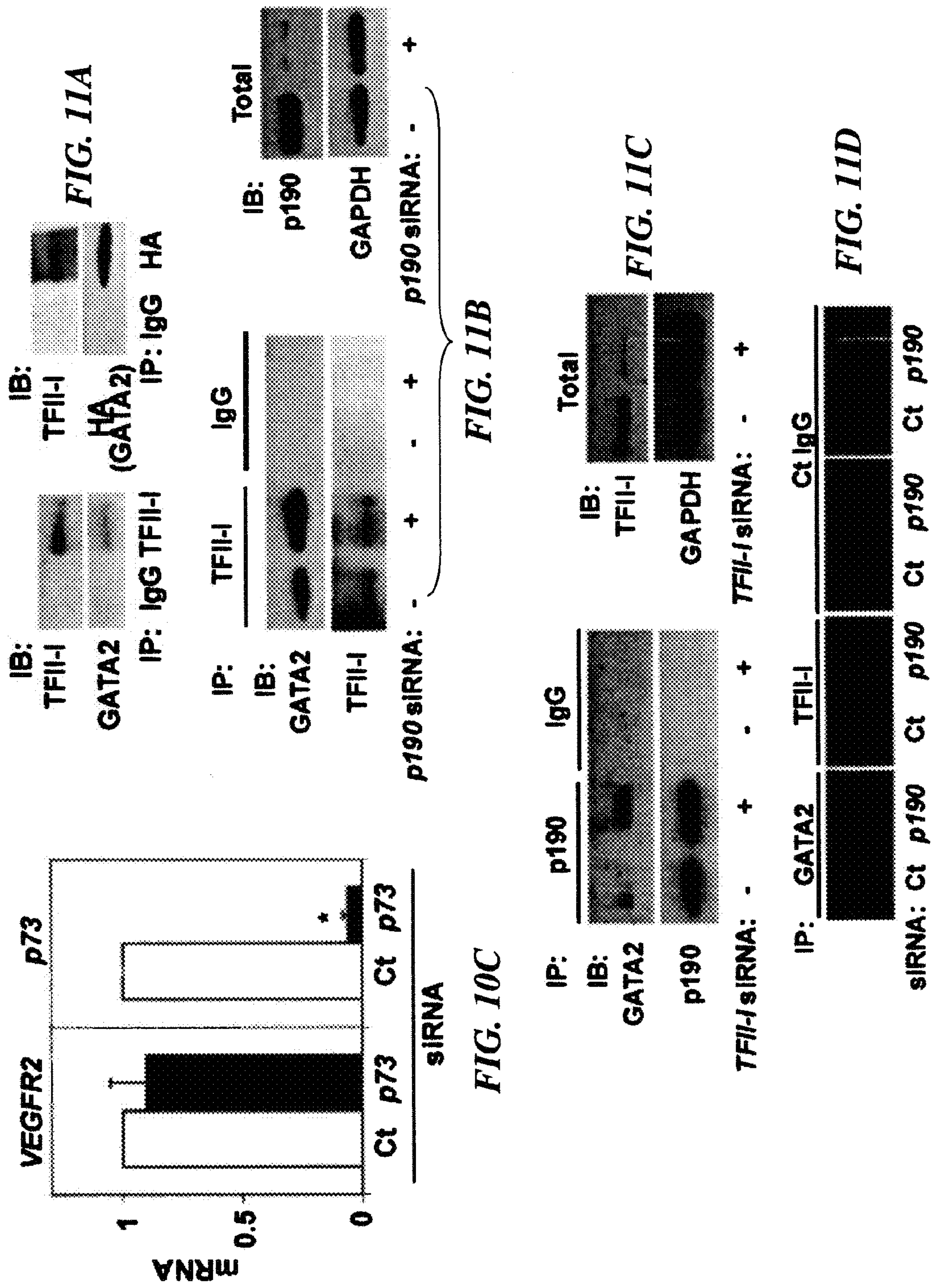
FIG. 10C shows the VEGFR2 and p73RhoGAP mRNA levels in HMVE cells transfected with p73RhoGAP siRNA (normalized to those in cells transfected with control siRNA; *, $p<0.01$). Error Bars represent s.e.m of 3 replica experiments.
FIG. 11A are immunoblots showing GATA2 co-immunoprecipitated with anti-TFII-I antibody, and TFII-I with anti-HA antibody in the same cells overexpressing HA-GATA2.
FIG. 11B are immunoblots of GATA2 coimmunoprecipitated with anti-TFII-I antibody in p190RhoGAP knockdown HMVE cells (mouse IgG was used as a control), and immunoblots of p190RhoGAP in the total cell lysate (upper).
FIG. 11C are immunoblots of GATA2 coimmunoprecipitated with anti-p190RhoGAP antibody in TFII-I knockdown HMVE cells (mouse IgG was used as a control) and immunoblots of TFII-I in total cell lysate (lower).
FIG. 11D are gel pictures showing the PCR products derived from the VEGFR2 promoter region co-immunoprecipitates with antibody against GATA2 or TFII-I in HMVE cells transfected with p190RhoGAP siRNA, as detected using the ChIP assay (control IgG was used as a control).

Analysis of this mechanism of functional cross-antagonism revealed that GATA2 and TFII-I associate with each other, as GATA2 co-immunoprecipitated with TFII-I, and vice versa (FIG. 11A). Furthermore, GATA2 even binds to TFII-I in p190RhoGAP knockdown cells and to p190RhoGAP in TFII-I knockdown cells (FIG. 11B, 11C). These results demonstrate that the various heterodimeric combinations of TFII-I, GATA2, and p190RhoGAP exist in separate pools, and that these heterodimers then associate to form a larger ternary complex (FIG. 6).

Chromatin immunoprecipitation (ChIP) analysis revealed that TFII-I knockdown cells exhibited increased recruitment of GATA2 to the GATA binding site (−150-+150) compared to control cells and vice versa (FIG. 1F), whereas control IgG did not immunoprecipitate these DNAs (FIG. 1F). p190RhoGAP knockdown decreased recruitment of TFII-I, but not GATA2, to this promoter site, which resulted in a relative net increase in GATA2 recruitment to this site (FIG. 11D). TFII-I and GATA2 therefore compete with each other for occupancy of a common region of the VEGFR2 promoter, which is controlled by p190RhoGAP.

Example 4

Mechanical Control of VEGFR2

Figure 2B:
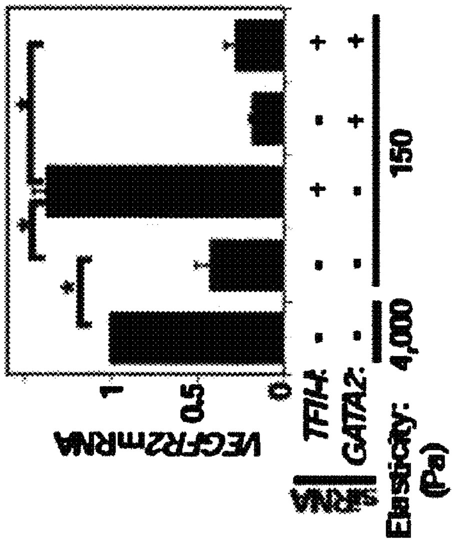
FIG. 2B is a histogram showing the VEGFR2 mRNA levels in HMVE cells on soft gels (150 Pa) transfected with TFII-I or GATA2 siRNA alone or in combination (normalized to cells on the stiffest gels; *P<0.01). Error bars represent s.e.m. of three replica experiments.
Figure 2A:
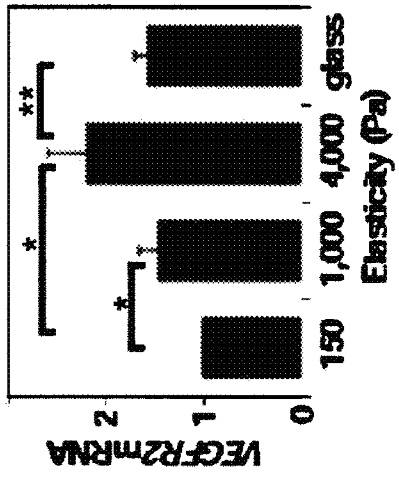
FIG. 2A is a histogram showing the VEGFR2 mRNA levels in HMVE cells cultured on rigid fibronectin-coated glass or the gels of different elasticity (150, 1,000 and 4,000 Pa; normalized to that in cells on the softest gels; *P<0.01, **P<0.05). Error bars represent s.e.m. of three replica experiments.
Figure 12A:
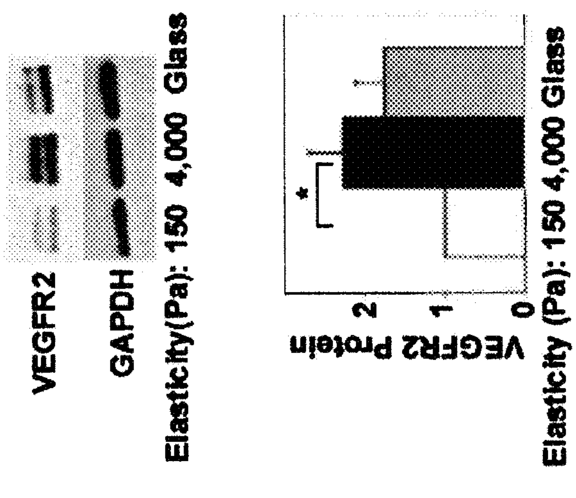
FIG. 12A are immunoblots showing the VEGFR2 and GAPDH protein expression levels in HMVE cells cultured on rigid fibronectin-coated glass or on gels of different elasticity (150 and 4000 Pa); protein levels relative to GAPDH were normalized to those in cells on the softer gels (*, $p<0.01$).
Figure 12B:
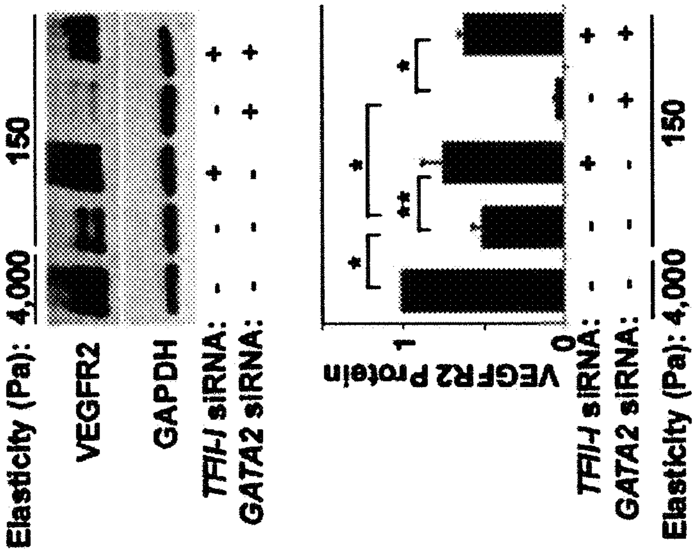
FIG. 12B are immunoblots showing the VEGFR2 and GAPDH protein levels in HMVE cells on soft gels (150 Pa) transfected with TFII-I or GATA2 siRNA alone or in combination. Protein levels relative to control GAPDH were normalized to those in cells on the stiff gels (*, $p<0.01$, **, $p<0.05$). Error Bars represent s.e.m of 3 replica experiments.

Soluble growth factors, integrin binding to ECM and mechanical distortion of the cytoskeleton all regulate p190RhoGAP activity in cells[30]. Cell binding to growth factors and adhesive contact formation with ECM also control VEGFR2 expression[31,32], and soluble mitogens (5% serum plus VEGF, bFGF and PDGF) increase nuclear translocation of TFII-I and GATA2 in HMVE cells (data not shown). The inventors next assessed whether changes in mechanical interactions between cells and ECM regulate this pathway as well. When HMVE cells were cultured in the absence of mitogens on fibronectin-coated polyacrylamide gels with different elasticity (Young's moduli of 150 to 4000 Pa), they appeared round on the soft gels, while they flattened on the stiffer gels, as previously observed[33,34], which is based on differences in their ability to physically resist cell traction forces[8,33,34]. Nuclear GATA2 levels were significantly higher in cells on the stiffer gels, whereas nuclei exhibit similar high levels of TFII-I regardless of ECM stiffness (data not shown), and similar results were obtained in the presence of multiple soluble factors or VEGF alone (data not shown). Moreover, VEGFR2 mRNA and protein levels were higher in cells on the stiffer (4000 Pa) gels (FIG. 12A and data not shown). Interestingly, this relatively stiff, but still compliant, ECM gel appeared to support optimal responsiveness of this signaling pathway as VEGFR2 mRNA and protein levels were significantly lower in cells cultured on rigid glass ECM substrates (FIG. 2A, FIG. 12B). This demonstrates that ECM elasticity can regulate VEGFR2 expression preferentially via GATA2, particularly over the stiffness range analyzed in this study.

Figure 2C:
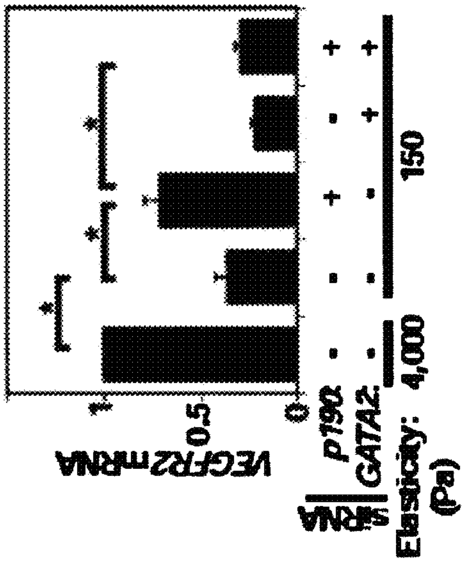
FIG. 2C is a histogram showing the VEGFR2 mRNA levels in HMVE cells on soft gels transfected with p190RhoGAP or GATA2 siRNA alone or in combination (normalized to cells on stiffest gels; *P<0.01). Error bars represent s.e.m. of three replica experiments.
Figure 12C:
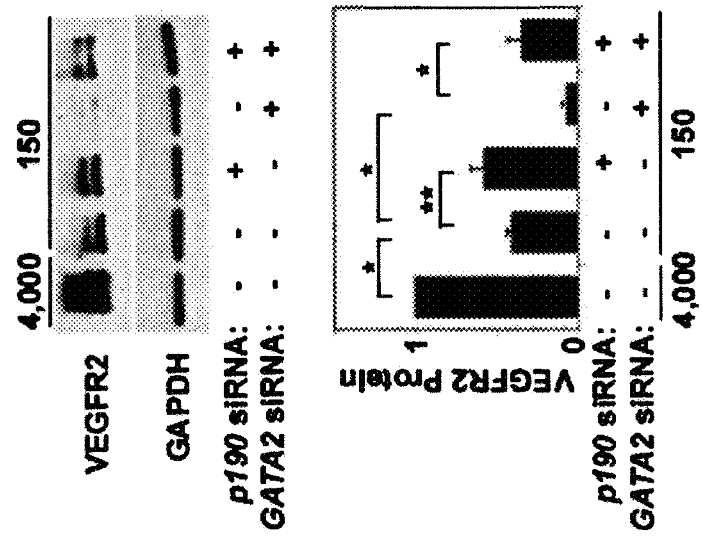
FIG. 12C are immunoblots showing the VEGFR2 and GAPDH protein levels in HMVE cells on soft gels (150 Pa) transfected with p190RhoGAP or GATA2 siRNA alone or in combination. Protein levels relative to control GAPDH were normalized to those in cells on the stiff gels (*, $p<0.01$, **, $p<0.05$). Error Bars represent s.e.m of 3 replica experiments.

Further analysis revealed that TFII-I knockdown restored VEGFR2 expression in cells on soft gels to levels similar to those in cells on stiff gels, and double knockdown with GATA2 (which decreases VEGFR2 expression) abrogated TFII-I's effects (FIG. 2B, FIG. 12B and FIG. 12C). p190RhoGAP knockdown also increased expression of VEGFR2 mRNA and protein, and double knockdown with GATA2 inhibited these effects on soft gels (FIG. 2C, FIGS. 12B and 12C). These data demonstrate that p190RhoGAP and the mutually antagonistic TFII-I and GATA2 transcription factors mediate the effects of ECM elasticity on VEGFR2 expression in these cells, which is preferentially shifted to GATA2 on stiffer gels.

Example 5

Transcriptional Control of Angiogenesis

Figure 3A:
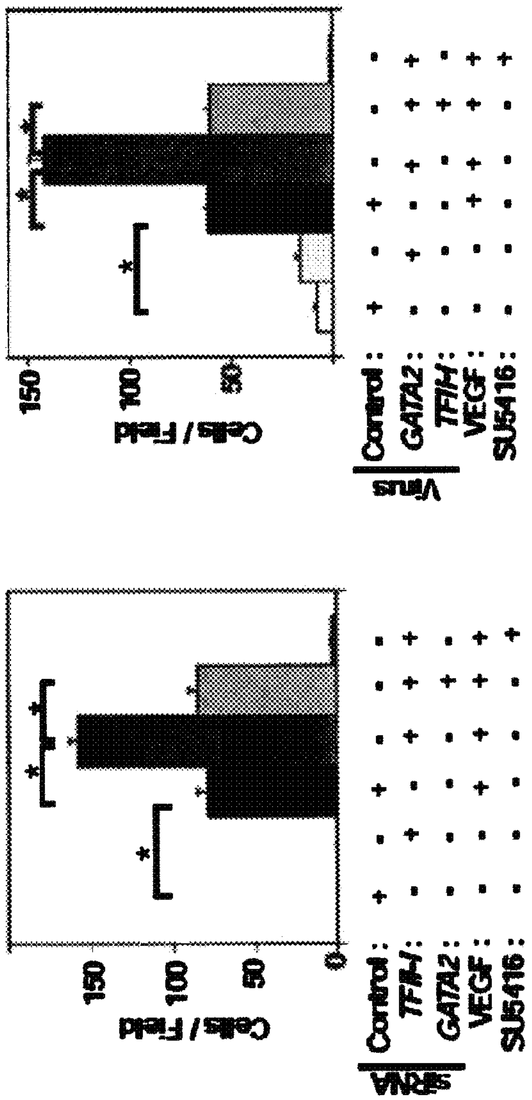
FIG. 3A are histograms showing the motility of HMVE cells transfected with human siRNAs or transduced with lentiviral vectors encoding GATA2 or TFII-I, alone or in combination, as quantified using the transwell migration assay (*P<0.01). Where demonstrated, VEGF (10 ng/ml) was added to the lower chamber and SU5416 was added in both chambers. Error bars represent s.e.m. of three replica experiments.
Figures 13A, 13B, 13C, 13E:
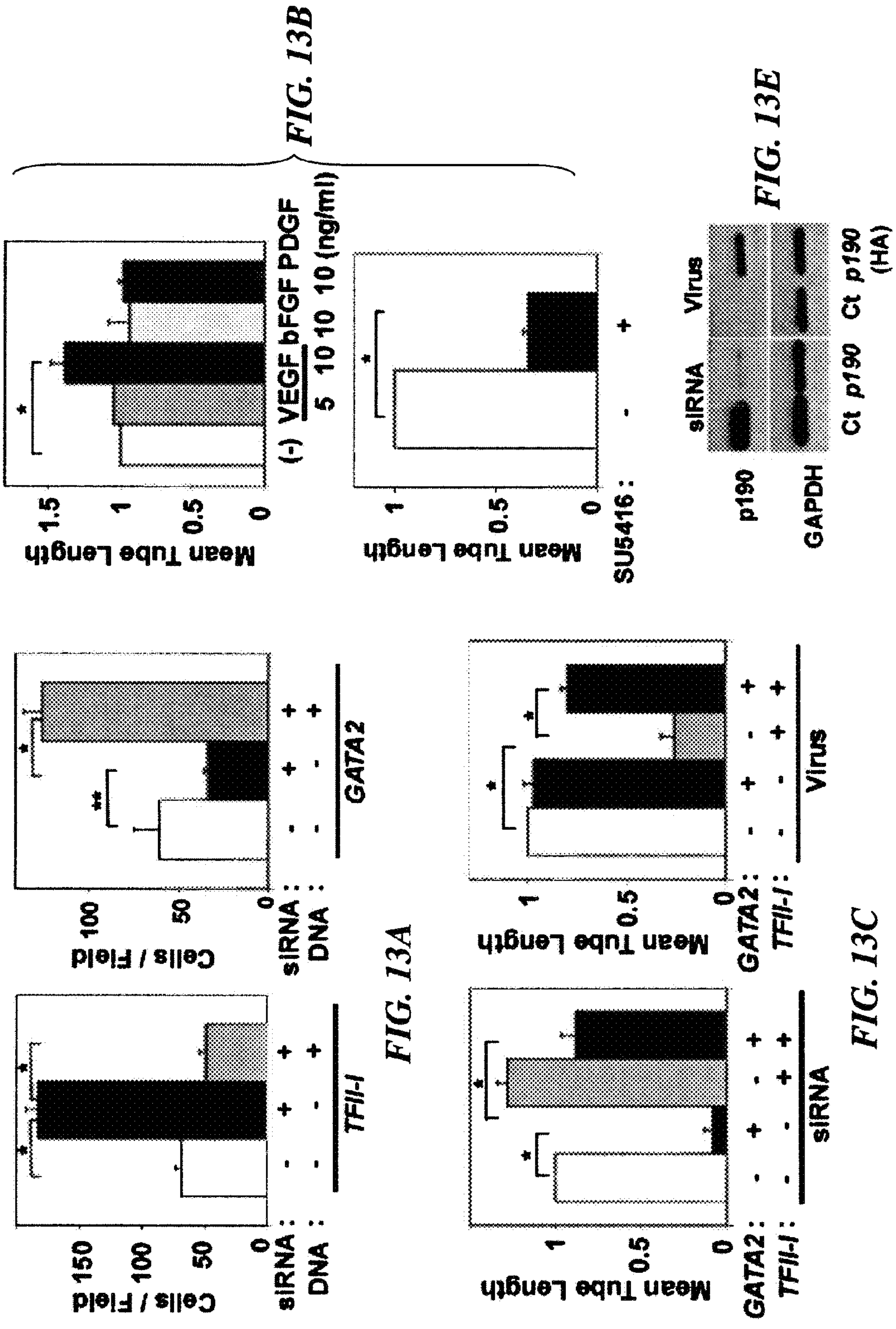
FIG. 13A shows the motility of HUVE cells transfected with human siRNAs alone or in combination with DNA encoding mouse Gata2 or TFII-I was quantitated using the Transwell migration assay (*, $p<0.01$, **, $p<0.05$). Results are migrated cells from three experiments (mean±s.e.m.).
FIG. 13B are graphs showing the mean tube length from ten fields of forming tubes as measured using the MATRIGEL™ angiogenesis assay in combination with various added growth factors (upper) or VEGFR2 kinase inhibitor SU5416 (lower) in HMVE cells (*, $p<0.01$). Results are mean tube length in ten fields from three experiments (mean±s.e.m.)
FIG. 13C are graphs showing the mean tube length from ten fields of forming tubes induced by VEGF (10 ng/ml) in HMVE cells transfected with siRNAs or transduced with lentiviral vectors encoding GATA2 or TFII-I, alone or in combination (*, $p<0.01$). Results are mean tube length in ten fields from three experiments (mean±s.e.m.).
FIG. 13E are immunoblots showing the p190RhoGAP and GAPDH protein levels in p190RhoGAP knockdown (siRNA) or overexpressing (virus) cells.

The inventors next examined the functional relevance of this antagonism between GATA2 and TFII-I by analyzing capillary cell migration and differentiation (tube formation) in vitro. When HMVE cells were transfected with TFII-I siRNA and analyzed using the Transwell migration assay, VEGF-stimulated cell motility increased by 2-fold, whereas this induction was prevented by knocking down GATA2 simultaneously with TFII-I (FIG. 3A). The VEGFR2 kinase inhibitor SU5416 totally inhibited the migration of these cells (FIG. 3A), confirming that these effects are mediated by VEGFR2 signaling. Moreover, GATA2 overexpression increased VEGF-induced cell migration by 3-fold, and simultaneous overexpression of GATA2 and TFII-I abolished these effects (FIG. 3A). These effects were specific in that reconstitution of TFII-I or Gata2 reversed the effects of knocking down TFII-I or GATA2, respectively (FIG. 13A). Thus, the inventors herein demonstrate methods to promote microvascular endothelial cell migration, endothelial cell differentiation, capillary blood vessel growth and/or angiogenesis by inhibiting p190RhoGAP and/or TFII-I and activating (e.g. overexpressing) GATA-2.

Figure 3B:
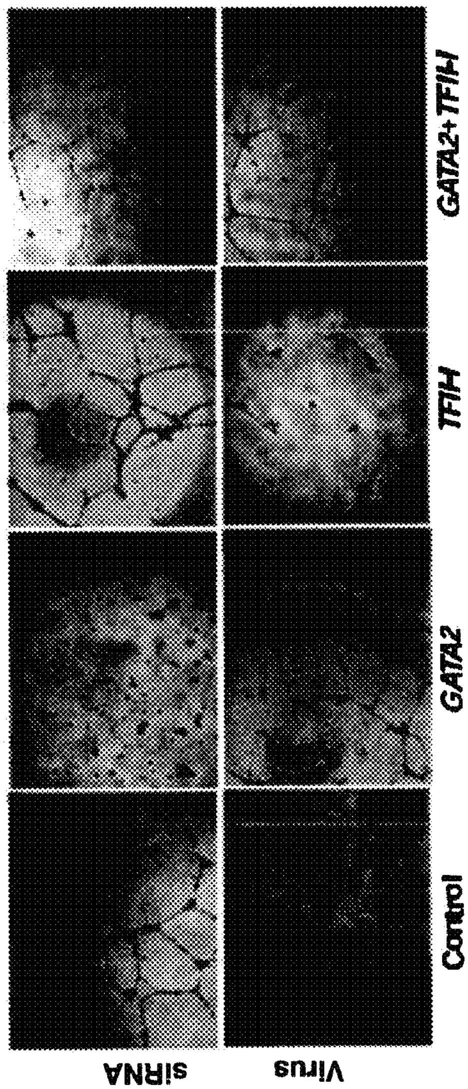
FIG. 3B are micrographs showing in vitro tube formation induced by VEGF (10 ng/ml) in HMVE cells transfected with siRNAs or transduced with lentiviral vectors encoding GATA2 or TFII-I, alone or in combination (scale bar, 500 μm).
Figures 13D, 13F, 14A, 14B, 15A, 15B:
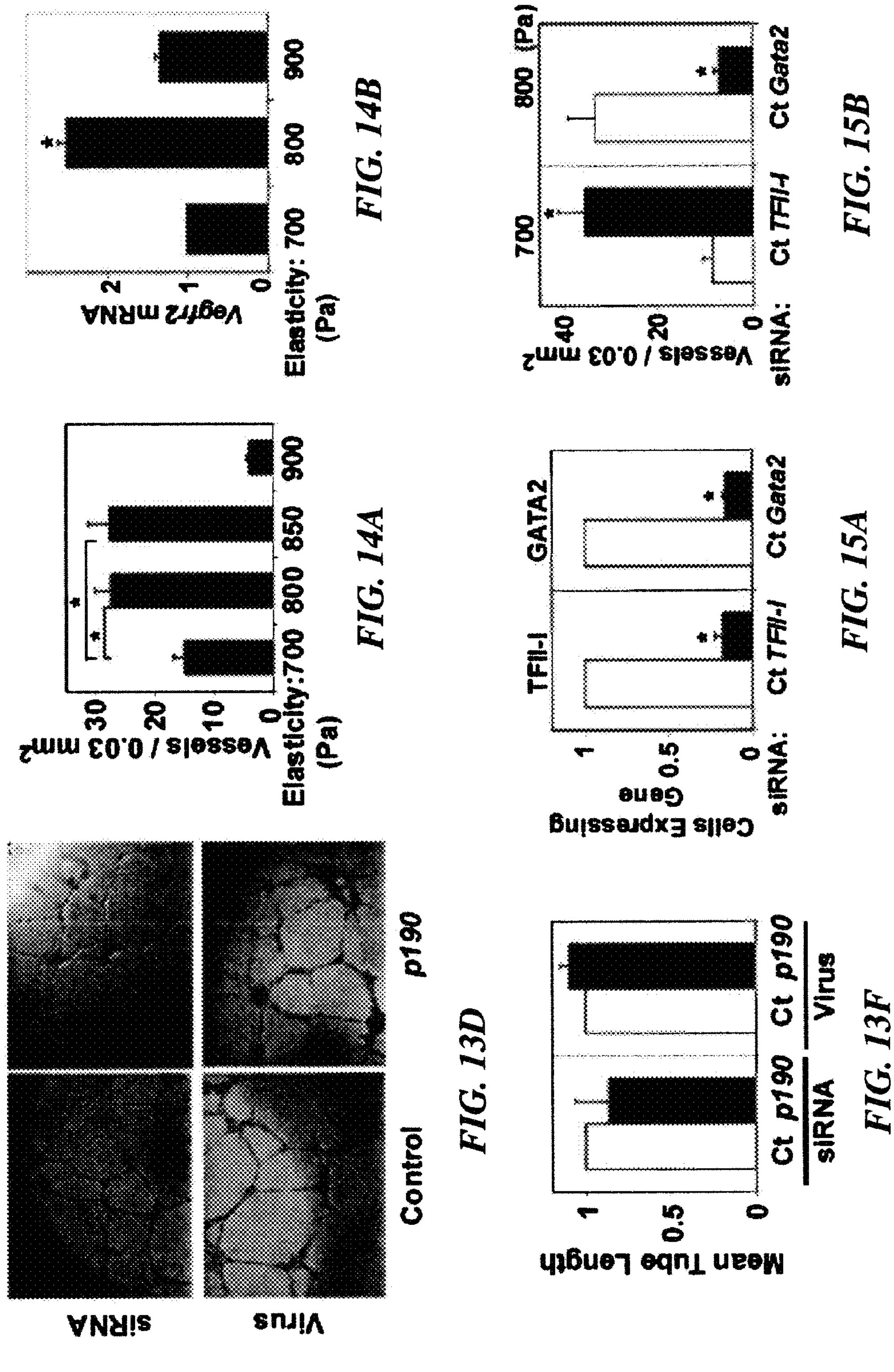
FIG. 13D are micrographs showing in vitro tube formation induced by VEGF (10 ng/ml) in HMVE cells transfected with siRNAs or transduced with lentiviral vectors encoding p190RhoGAP (left).
FIG. 13F are histograms of the quantitative results showing the mean tube length in ten fields from three experiments. Results are mean tube length in ten fields from three experiments (mean±s.e.m.).
FIG. 14A is a graph showing the number of ConA-positive blood vessels per high power field (0.03 $mm^2$) (n=6, mean±SEM; *, $p<0.01$) observed in fluorescence confocal sections through MATRIGEL™ plugs with different elasticity implanted in the mouse for 7 days that were stained with fluorescent-ConA to visual capillary blood vessels.
FIG. 14B is a graph showing the Vegfr2 mRNA levels in cells infiltrating MATRIGEL™ plugs with different elasticity (normalized to those in cells in the softest gels; n=6, mean±SEM; *, $p<0.01$).
FIG. 15A is a graph showing the relative gene expression levels of TFII-I and GATA2 in gels of mouse implanted for 7 days with MATRIGEL™ gel plugs treated with TFII-I or GATA2 siRNA, normalized to values obtained in in vivo implanted MATRIGEL™ gels plugs treated with control siRNA. (n=6; mean±SEM; *, p<0.01)
FIG. 15B is a graph showing the number of ConA-positive blood vessels in the gels of mouse implanted for 7 days with MATRIGEL™ gel plugs treated with TFII-I or GATA2 siRNA, normalized to values obtained in in vivo implanted MATRIGEL™ gels plugs treated with control siRNA. (n=6; mean±SEM; *, p<0.01).

The inventors then assessed capillary tube formation by HMVE cells cultured within the ECM gel, Matrigel, which supports angiogenesis in part because of its flexibility. Tube formation was stimulated by VEGF in a dose-dependent manner, whereas bFGF and PDGF were ineffective, and the effects of VEGF were inhibited by SU5416 (FIG. 13B). GATA2 knockdown and TFII-I overexpression suppressed VEGF-stimulated capillary development, and once again either knocking down or overexpressing both transcription factors simultaneously negated these effects (FIG. 3B, FIG. 13C). TFII-I knockdown or GATA2 overexpression alone did not produce significant effects on tube formation, apparently because it was already optimally stimulated under these conditions (FIG. 3B); knockdown or overexpression of p190RhoGAP also did not alter tube formation (FIG. 13D, 13E, 13F). Thus, functional antagonism between GATA2 and TFII-I at the level of VEGFR2 transcription translates into biologically relevant changes in capillary cell behavior that are required for formation of 3D capillary networks. Thus, the inventors herein demonstrate methods to inhibit microvascular endothelial cell migration, endothelial cell differentiation, capillary blood vessel growth and/or angiogenesis by activating (i.e. overexpressing) p190RhoGAP and/or TFII-I and inhibiting GATA-2.

Example 6

Control of Angiogenesis In Vivo

Figure 4A:
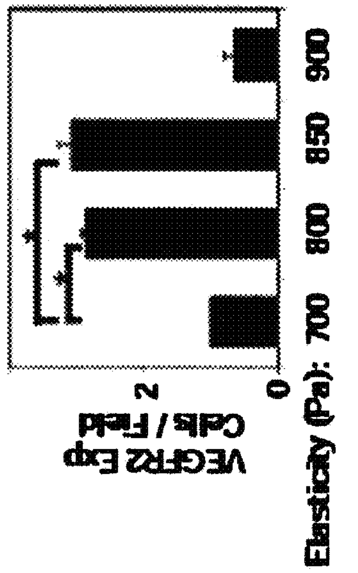
FIG. 4A is a histogram showing the cell infiltration and VEGFR2 expression (exp) in MATRIGEL™ with different elasticity implanted in mice for 7 days without TfII-I or Gata2 siRNAs. The number of VEGFR2-positive blood vessels was normalized to that in the 700 Pa gels and to that in gels treated with control siRNA in d (n=6). Data are mean±s.e.m., *P<0.01.

The inventors next assessed whether ECM mechanics governs vessel formation in vivo using a modified Matrigel implant assay. Maximal levels of cell infiltration, capillary blood vessel formation, and VEGFR2 expression were observed in Matrigel with intermediate stiffness (800 Pa) compared to cells in more or less rigid gels (900 or 700 Pa, respectively) (FIGS. 4D, 14A and 14B, and data not shown). VEGFR2, GATA2, and TFII-I all localized within cells lining CD31-positive staining microvasculars (data not shown). The finding that the optimal ECM stiffness required for angiogenesis in vivo (800 Pa) was different than that observed in vitro (4000 Pa) is likely due to different requirements by cells when cultured on 2D ECM versus within a 3D ECM gel; it also can relate to how the Matrigel is remodeled over time in vivo.

Figure 4B:
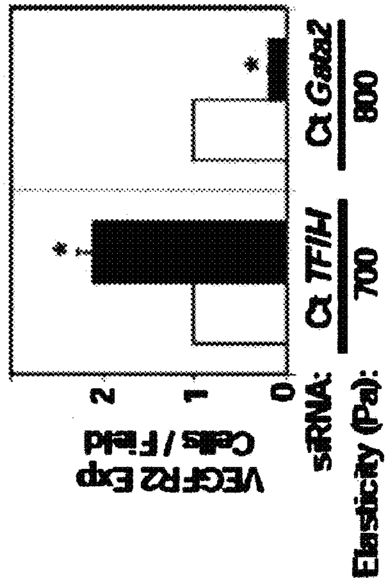
FIG. 4B is a histogram showing the cell infiltration and VEGFR2 expression (exp) in MATRIGEL™ with different elasticity implanted in mice for 7 days with TfII-I or Gata2 siRNAs. The number of VEGFR2-positive blood vessels was normalized to that in the 700 Pa gels and to that in gels treated with control siRNA in d (n=6). Data are mean±s.e.m., *P<0.01.
Figure 15D:
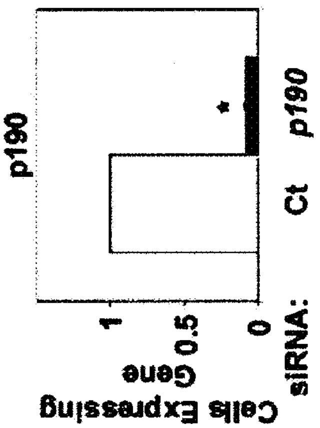
FIG. 15D is a graph showing the number of ConA-positive blood vessels in the gels of mouse implanted for 7 days with MATRIGEL™ gel plugs treated with p190RhoGAP siRNA, normalized to values obtained in in vivo implanted MATRIGEL™ gels plugs treated with control siRNA. (n=6; mean±SEM; *, p<0.01).
Figure 15C:
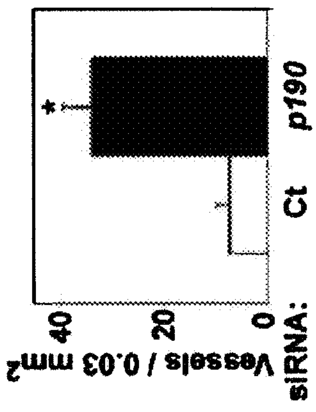
FIG. 15C is a graph showing the relative gene expression levels of p190RhoGAP in gels of mouse implanted for 7 days with MATRIGEL™ gel plugs treated with p190RhoGAP siRNA, normalized to values obtained in in vivo implanted MATRIGEL™ gels plugs treated with control siRNA. (n=6; mean±SEM; *, p<0.01)

The inventors next performed siRNA-mediated gene knockdown in the in vivo Matrigel assay. Interestingly, TFII-I knockdown increased cell infiltration, capillary vessel formation and VEGFR2 expression by cells in the soft gels so that it mimicked the behavior of cells on the intermediate stiffness gel, whereas Gata2 knockdown produced the opposite effects (FIG. 4B, 15A, 15B and data not shown), and p190RhoGAP knockdown also increased the level of vessel formation in the soft gels (FIG. 15C, 15D). These results demonstrate that TFII-I, GATA2, and p190RhoGAP mediate the signaling effects of ECM mechanics on vessel formation in vivo.

Figure 5A:
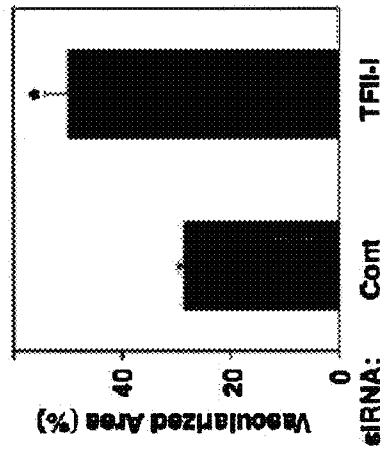
FIG. 5A is a graph showing the quantification of the total percentage of the peripheral region of retina that contained blood vessels, wherein the retinal tissues' expression of TFII-I was knocked down by in vivo delivery of respective siRNAs (n=7; *, p<0.01).
Figure 5B:
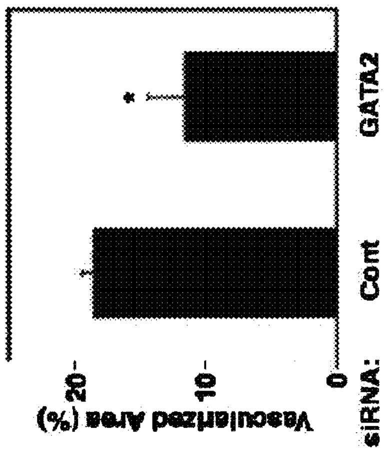
FIG. 5B is a graph showing the quantification of the total percentage of the peripheral region of retina that contained blood vessels, wherein the retinal tissues' expression of GATA2 was knocked down by in vivo delivery of respective siRNAs (n=7; *, p<0.01).
Figure 5C:
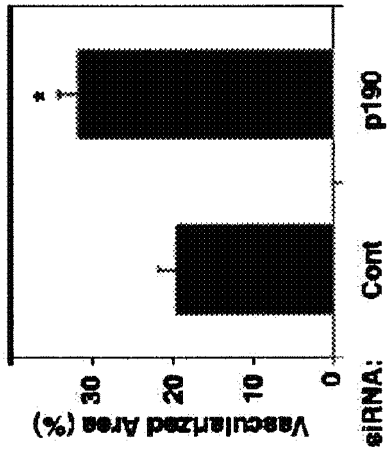
FIG. 5C is a graph showing the quantification of the total percentage of the peripheral region of retina that contained blood vessels, wherein the retinal tissues' expression of p190RhoGAP was knocked down by in vivo delivery of respective siRNAs (n=7; *, p<0.01).
Figure 16B:
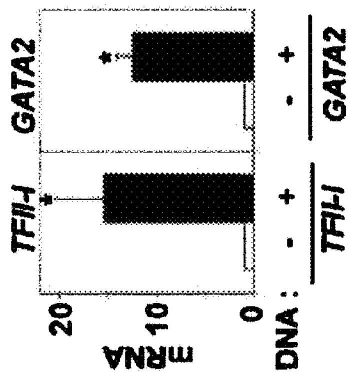
FIG. 16A-F. TFII-I, GATA2, and p190RhoGAP control microvascular formation in vivo within the P16 mouse retina.
Figure 16C:
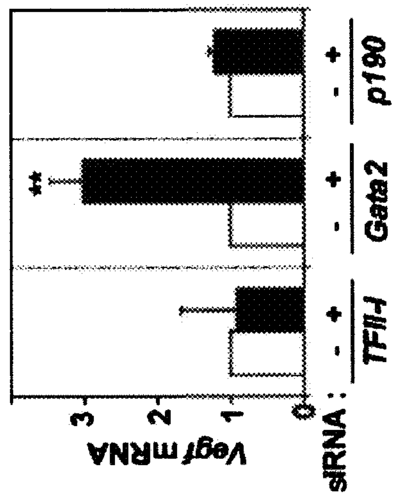
Figure 16A:
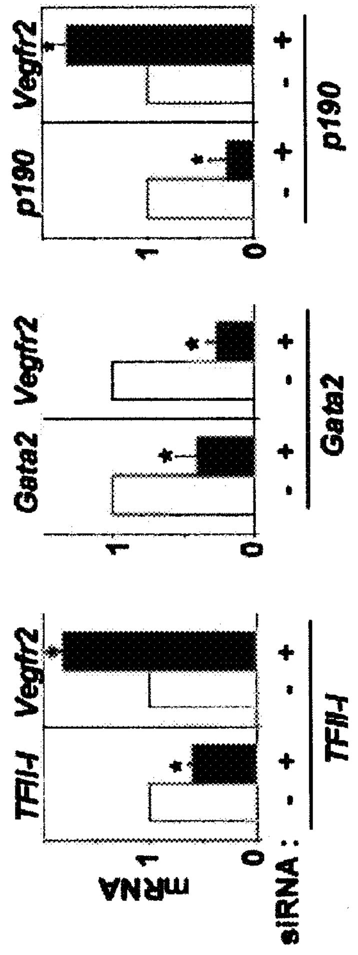
Figure 16F:
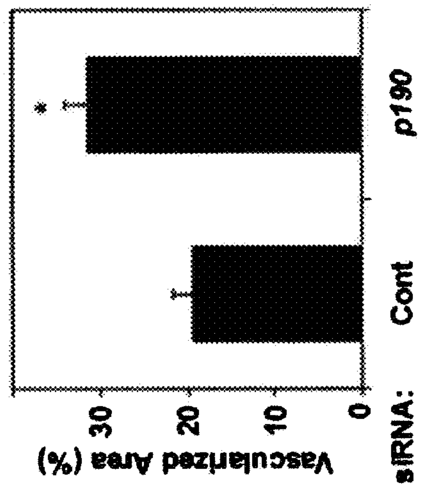
Figure 16E:
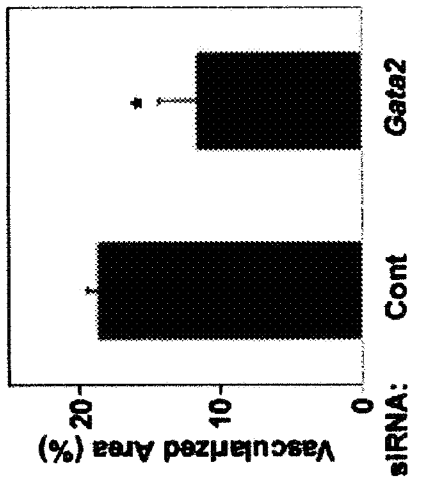
Figure 16D:
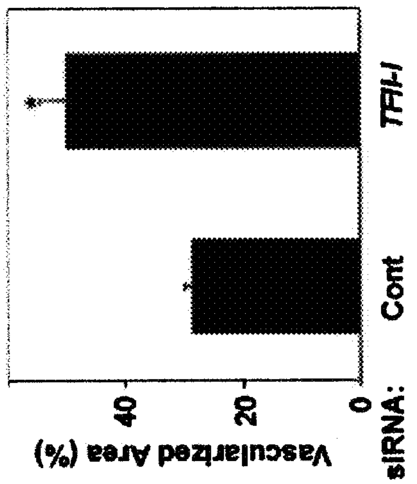
Figure 17C:
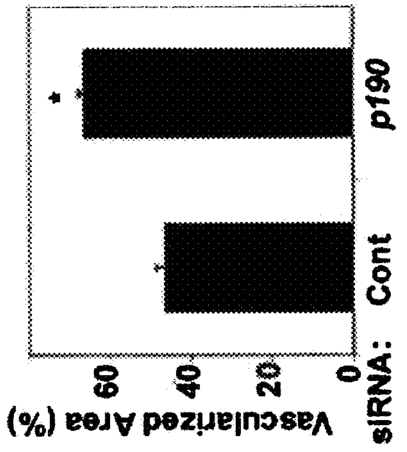
FIG. 17A-C are graphs showing the total percentage of the peripheral region of retina that contained blood vessels in normal P7 mouse retina transfected with siRNA for TFII-I, Gata2, or p190RhoGAP, or a control siRNA. Data are normalized to retina transfected with control siRNA (n=7, mean±SEM; *, p<0.01).
Figure 17B:
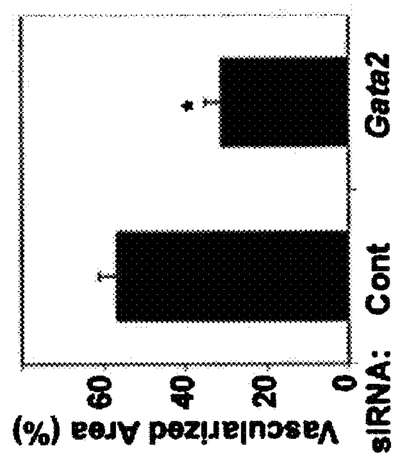
Figure 17A:
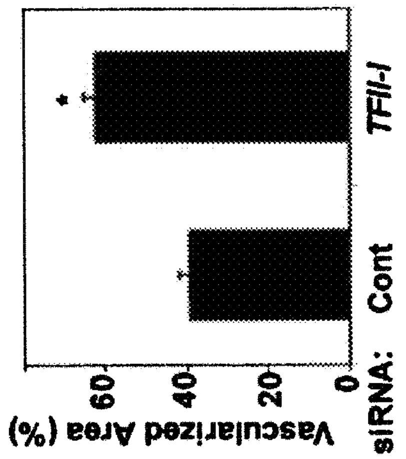

To unequivocally confirm the functional and clinical relevance of regulatory interactions between TFII-I, GATA2, and p190RhoGAP, the inventors modulated their expression in the neonatal mouse retina because angiogenesis in this growing organ is tightly regulated by VEGF and its receptors[14,35,36]. TFII-I, GATA2, and VEGFR2 localized to the three layers of the retina where blood vessels are located in postnatal day 15 mice (data not shown). Consistent with in vitro data, knocking down TFII-I using intravitreal injection of siRNA to p14 mice resulted in increased Vegfr2 expression and the appearance of highly tortuous dilated vessels and a significant increase in vascular density in the retina, whereas Gata2 knockdown suppressed Vegfr2 expression, disrupted capillary network formation and decreased vascular density (FIG. 5A, FIG. 16A). Knockdown of p190RhoGAP also increased Vegfr2 expression and vessel density, but it resulted in a slightly different capillary growth pattern, perhaps in part because of its known effects on vascular permeability[37] (FIG. 5A and FIG. 16A). Similar effects were observed in earlier (P5) retina that contain rapidly growing microvasculars (FIG. 17). Furthermore, overexpression of TFII-I and GATA2 produced opposite effects on vascular density in P14 retina, and simultaneous overexpression of both factors abolished these effects, confirming our in vitro findings (FIG. 5B and FIG. 16B). Knockdown of p190RhoGAP or TFII-I did not significantly change Vegf expression levels in the retina, whereas Gata2 knockdown increased (rather than decreased) its expression (FIG. 16C). The decrease of Vegfr2 expression appears to be sufficient to abrogate this Vegf response in Gata2 knockdown retina, and thereby inhibit angiogenesis. Hence, the inventors have demonstrated that p190RhoGAP controls Vegfr2 expression and vascular development by modulating the balance between TFII-I and GATA2 activities such that TFII-I activity dominates (and Vegfr2 expression is suppressed) in retina. As angiogenesis and capillary elongation of about 1-2 mm in length requires capillary blood vessel growth and endothelial cell migration, the inventors have demonstrated methods to promote or increase endothelial cell migration, differentiation, capillary blood vessel growth and/or angiogenesis in an animal in vivo.

Transcription factors change their activities in a spatiotemporal manner during development, and thereby specify cell fate[38,39]. Here the inventors demonstrate that p190RhoGAP, which has been shown to be regulated by growth factors, ECM binding and cytoskeletal distortion also controls VEGFR2 expression, as well as angiogenesis in vitro and in vivo, by altering the balance between two mutually antagonistic transcription factors: TFII-I and GATA2 (FIG. 6). Moreover, the inventors demonstrate that p190RhoGAP and this downstream transcriptional control mechanism are controlled by mechanical signals conveyed by variations in ECM elasticity. This mechanism is analogous to other developmental mechanisms used by hematopoietic cells and mammary epithelium[38-40] [28]; however, this is the first demonstration that transcriptional cross-antagonism can govern histodifferentiation and tissue morphogenesis, and be sensitive to mechanical as well as chemical cues.

The inventors herein have demonstrated that an appropriate level of ECM stiffness can be required for optimal VEGFR2 expression and vascular development in vitro and in vivo. In fact, the fates of different cell types are exquisitely sensitive to distinct ECM elasticity values that often match those exhibited by their host tissues[41]. Abrupt local changes in ECM mechanics also accompany the switch between active growth and quiescent differentiation of functional capillary networks in living tissues[42]. Cell rounding suppressed p190RhoGAP activity within 1 to 2 hours by altering its binding to the cytoskeletal protein, filamin[16]. A similar cytoskeleton-based effect could mediate the effect of ECM elasticity on p190RhoGAP activity at later times, and thereby control the TFII-I:GATA2 balance and VEGFR2 transcription. Since VEGFR2 is expressed in neurons as well as in endothelial cells in retina, some of the effects of gene knockdown the inventors observed can not be specific to capillary cells. But even these alterations might be relevant for control of vascular development because neuron-vessel interactions are indispensable for normal microvasculature function and patterning[43].

In summary, the inventors have discovered a previously unknown mechano sensitive signaling pathway that controls VEGFR2 promoter activity and expression, and which represents a point of convergence for all three classes of microenvironmental signals that regulate capillary morphogenesis. Development of specific modifiers of this pathway could therefore lead to novel therapeutic approaches for various angiogenesis-dependent diseases, including proliferative retinopathy, arthritis, and cancer in the future.

Methods

Expression of TFII-I, GATA2, and VEGFR2 were evaluated by qRT-PCR and immunoblotting. A luciferase reporter assay was used to measure VEGFR2 promoter activity. To test the effects of TFII-I and GATA2 on VEGFR2 expression and angiogenesis in vitro, siRNA-mediated knockdown or lentiviral transduction was performed in HMVE cells. in vitro analysis of angiogenesis was carried out using Transwell migration and Matrigel tube formation assays, and similar results were obtained using both native and growth factor-reduced forms of Matrigel. A subcutaneous Matrigel angiogenesis assay was used to analyze the effects of ECM mechanics on capillary formation in vivo. Retinal vessel formation was also studied in newborn C57BL/6 mice, and gene expression was manipulated in whole living retina by intravitreal injection of siRNA or DNA into the eye at P5 or P14.

Materials. Anti-GATA2 polyclonal antibody was from Abcam (Cambridge, Mass.); anti-HA monoclonal antibody from Covance (Princeton, N.J.); monoclonal antibodies against TFII-I, p190RhoGAP, PECAM (CD31), and paxillin from Transduction laboratory (Lexington, Ky.); anti-GAPDH antibody from Chemicon (Temecula, Calif.); anti-lamin monoclonal antibody from Upstate (Lake Placid, N.Y.); anti-VEGFR2 antibody from Cell Signaling (Danvers, Mass.); and anti-myc antibody from Santa Cruz (Santa Cruz, Calif.). Protein G-sepharose was from Amersham-Pharmacia (Uppsala, Sweden) and SU5416 was from Calbiochem (SanDiego, Calif.). VEGF-A was from NIH; bFGF and PDGF were from Roche (Basel, Switzerland) and Biovision (Mountain View, Calif.) respectively. Cell permeable Rho inhibitor (C3 exoenzyme) was from Cytoskeleton (Denver, Colo.). HMVE and HUVE cells (Cambrex, Walkersville, Md.) were cultured in EBM2 medium containing 5% FBS and growth factors (VEGF, bFGF, and PDGF) for all experiments[16] except the nuclear translocation assays in which the inventors used EBM2 with 0.3% serum. Cells were plated on plastic dishes for molecular biochemical assays, and on fibronectin-coated glass coverslips for cell staining, except for experiments using flexible substrates.

Plasmid construction and gene knockdown. pGL3-VEGFR2-225 (−225+268), −570 (−570+268), −780 (−780+268) were constructed using the reverse transcription (RT)-PCR with genomic DNA from HUVE cells, and subcloned into pGL3 vector (Promega) at the SacI/XhoI sites. For pGL3-VEGFR2−780Inr-MUT, the Inr (CACT to GTGC) was point mutated using the QuickChange mutagenesis kit (Stratagene, La Jolla, Calif.). For lentivirus construction, human myc-TFII-I (delta isoform), HA-GATA2, and HA p190RhoGAP were constructed by PCR using template plasmids from Open Bio systems (Huntsville, Ala.) and H. Sabe (OBI, Osaka, Japan). For retrovirus construction, mouse myc-TFII-I (gamma isoform) and HA-Gata2 were constructed using template plasmids from Open Biosystems and T. Nakano (Osaka University, Osaka, Japan), respectively. To generate delta isoform of mouse TFII-I, 256-274 and 294-314aa were deleted from the gamma isoform. Construction of constitutively active RhoA and generation of viral vectors were previously described[37]. For gene knockdown, siRNA transfection was performed as described[16]. siRNA sequences are shown in Table 1.

TABLE 1 siRNA sequences for human p190RhoGAP, human TFII-I and GATA-2

| | |
|---|---|
| Human TFII-I | 5'AGUAUCAGUGGUUGAGAAG3' (SEQ. ID. No. 10) |
| Human GATA2 | 5'GAACCGGAAGAUGUCCAAC3' (SEQ. ID. No. 11) |
| Human/Mouse p190RhoGAP | 5'GGAUUGUGUGGAAUGUAAG3' (SEQ. ID. No. 12) |
| Human p73RhoGAP | 5'ACCGAGAGAGGAAACACAAUA3' (SEQ. ID. No. 13) |
| Mouse GATA2 | 5'GAAUCGGAAGAUGUCCAGCAA3' (SEQ. ID. No. 14) |
| Mouse TFII-I | 5'CAAUGAUCUCUAUGUGGA3' (SEQ. ID. No. 15) |

Biochemical Methods. For luciferase reporter assays, HUVE cells were transfected using Superfect (QIAGEN) and assayed using Dual-Luciferase reporter assay kit (Promega). Luciferase activity was measured in duplicate using a luminometer (TD20/20, Turner Designs). Cytoplasmic and nuclear cell extracts were prepared with a Nuclear Extraction Kit (Chemicon).

Molecular biological methods. Quantitative RT-PCR was performed with the Quantitect SYBR Green RT-PCR kit (QIAGEN) using ABI7300 real-time PCR system (Applied Biosystems, Foster City, Calif.); __2 microglobulin or cyclophilin controlled for cDNA content. The primers used are shown in Table 2. For ChIP assay, DNA from HMVE cells transfected with control or TFII-I siRNA was immunoprecipitated with the GATA2 antibody or control immunoglobulin (Jackson Immuno Research), or vice versa, according to the manufacturer instructions (Active Motif). GATA2- and TFII-1-binding region was amplified using primers, 5'-GTAAATGGGCTTGGGGAGCTG-3' (SEQ. ID. NO: 43) and 5'-GGCGGCTGCAGGGGCGTCT-3' (SEQ. ID. NO: 44).

TABLE 2 primer sequences for human p190RhoGAP, human TFII-I and GATA-2

| | Forward Reverse | Reverse |
|---|---|---|
| Human VEGFR2 | 5'-CACCACTCAAACGCTGACATGTA-3' (SEQ. ID. No. 16) | 5'-CCAACTGCCAATACCAGTGGA-3' (SEQ. ID. No. 17) |
| Human TFII-I | 5'-AAAGAACTGGCCAAGTCCAAAGCC-3' (SEQ. ID. No. 18) | 5'-AAGCACGTCCTCTTTCAGTTCCGA-3' (SEQ. ID. No. 19) |
| Human GATA2 | 5'-GTCACTGACGGAGAGCATGA-3' (SEQ. ID. No. 20) | 5'-GCCTTCTGAACAGGAACGAG-3' (SEQ. ID. No. 21) |
| Human VEGFR1 | 5'-CTGTCATGCTAATGGTGTCCC-3' (SEQ. ID. No. 22) | 5'-TGCTGCTTCCTGGTCCTAAAATA-3' (SEQ. ID. No. 23) |

TABLE 2-continued primer sequences for human p190RhoGAP, human TFII-I and GATA-2

| | Forward Reverse | Reverse |
|---|---|---|
| Human VEGFR3 | 5'-CTCGGCTCACGCAGAACTT-3' (SEQ. ID. No. 24) | 5'-GCTGCACAGATAGCGTCCC-3' (SEQ. ID. No. 25) |
| Human p73RhoGAP | 5'-GGGCAACAGCAGCAGCAACCACA-3' (SEQ. ID. No. 26) | 5'-TCGCTCGGCATTTCGCATTTTTAT-3' (SEQ. ID. No. 27) |
| Human β2 MICROGLOBULIN | 5'-GAATGGAGAGAGAATTGAAAAAGTGGAGCA-3' (SEQ. ID. No.28) | 5'CAATCCAAATGCGGCATCTTCAAAC-3' (SEQ. ID. No.29) |
| Mouse VEGFR2 | 5'-GCCCTGCCTGTGGTCTCACTAC-3' (SEQ. ID. No. 30) | 5'-CAAAGCATTGCCCATTCGAT-3' (SEQ. ID. No. 31) |
| Mouse TFII-I | 5'-AAAGAGCTGGCCAAGTCCAAGGCT-3' (SEQ. ID. No. 32) | 5'AAGCACGCCCTCTTTCGGTTCCAA-3' (SEQ. ID. No. 33) |
| Mouse GATA2 | 5'-CACGCCACCCAAAGAAGTGT-3' (SEQ. ID. No. 34) | 5'-CCGCCTTCCATCTTCATGCT-3' (SEQ. ID. No. 35) |
| Mouse p190RhoGAP | 5'-GCTCTGCTACCCCGTAGGA-3' (SEQ. ID. No. 36) | 5'GTTGGAGGAAAGCCACACAC-3' (SEQ. ID. No. 37) |
| Mouse VEGF | 5'-GCACTGGACCCTGGCTTTACTGCTGTA-3' (SEQ. ID. No. 38) | 5'GAACTTGATCACTTCATGGGACTTCTGCTC-3' (SEQ. ID. No. 39) |
| Mouse CYCLOPHILIN | 5'-CAGACGCCACTGTCGCTTT-3' (SEQ. ID. No. 40) | 5'-TGTCTTTGGAACTTTGTCTGCAA-3' (SEQ. ID. No. 41) |

Cell analysis methods. Flexible polyacrylamide gel culture substrates were prepared as described[34,44] and coated with fibronectin (1 μg/cm$^2$). Substrate flexibility was controlled by varying the acrylamide (2-4%) and the bis-acrylamide (0.1-0.5%) concentration; the Young's modulus (stiffness) was determined as described[45]. HMVE cells were cultured for 6 hrs on the gels and immunostaining was performed and analyzed using confocal Leica SP2 microscope[15]. For cell migration assay, Transwell membranes (Coster, N.Y.) were coated with 0.5% gelatin, and cells were seeded ($10^5$ cells/100 μl) with 0.3% FBS/EBM2. Cells were stained with Giemsa solution 16 h later, and counted in 10 random fields (×400). For the in vitro angiogenesis assay, HMVE cells ($10^4$ cells/150_1 of EBM-2) were plated on Matrigel™ (BD biosciences), and incubated for 12-16 hrs in the presence of VEGF (10 ng/ml); tube formation was assessed in 10 random fields (4×).

In vivo Matrigel implantation assay. All animal studies were reviewed and approved by the animal care and use committee of Children's Hospital Boston. Matrigel plugs with different elasticity were cast in 4×4 mm (ID×H) polydimethylsiloxane (PDMS) molds and incubated at 37° C. overnight before implanting them subcutaneously on the backs of C57BL/6 mice. The stiffness of the Matrigel was modulated over a narrow range (i.e., without making it rigid) by altering ECM protein cross-linking using a microbial transglutaminase (2.5-20 U/g; Ajinomoto, Japan)[46]. The storage modulus (G') of the gels was measured with an AR-G2 rheometer (TA Instruments) using a standard 20 mm aluminum parallel plate (1 Hz, 1% strain, 37° C.). The Young's modulus for an equivalent polyacrylamide gel was calculated by E=2*G'(1+_) using an average Poisson's Ratio (_) of 0.5. After 7 days, the PDMS molds containing the gel plugs were harvested, fixed, and cryosectioned. H&E staining and immunostaining were performed as described[15 47]. Stacks of optical sections (20 μm thick) were compiled to form 3D images using Velocity 4.4 (Improvision, PerkinElmer). Vessel formation was evaluated by counting the number of vessels that stained positive for fluorescein-conjugated ConA injected into the tail vein or VEGFR2 in 5 different areas (n=6), individual cell nuclei were identified by DAPI staining. Cell recovery solution (BD Biosciences) was used to collect cells from the recovered Matrigel plugs. In some studies, siRNA (7_g) was mixed into the Matrigels and 10_g of additional siRNA was injected into the implanted Matrigel after 3 days (n=6); the same amount of scrambled siRNA was used as a control. Gene knockdown was evaluated by counting the number of cells expressing each gene in the five different regions.

In vivo analysis for retinal vessel formation. For gene knockdown in living retina, siRNA (0.5 μg) for each gene was injected intravitreally into one eye of C57BL/6 mouse at P5 or P14, and the same amount of control siRNA was injected to the other eye. To overexpress genes, the complex of DNA (0.5 μg) for TFII-I and/or GATA2 and jetPEI transfection reagent (Polyplus transfection, CA) was injected to the eye at P14. Vascular network formation in the retina was assessed 2 days after injection using flat-mounted, fluorescein-conjugated isolectin-staining and immunohistochemical analysis (n=7). Retinal RNA was purified and gene expression was quantified using qRT-PCR (n=7). Quantification of vessel density was performed with Adobe Photoshop.

REFERENCES

The references cited herein and throughout the specification and examples are herein incorporated by reference in their entirety.

1. Ferrara, N., Gerber, H. P. & LeCouter, J. The biology of VEGF and its receptors. Nat Med 9, 669-76 (2003).
2. Ferrara, N., Mass, R. D., Campa, C. & Kim, R. Targeting VEGF-A to treat cancer and age-related macular degeneration. Annu Rev Med 58, 491-504 (2007).
3. Ingber, D. E. & Folkman, J. Mechanochemical switching between growth and differentiation during fibroblast growth factor-stimulated angiogenesis in vitro: role of extracellular matrix. J Cell Biol 109, 317-30 (1989).

4. Chen, C. S., Mrksich, M., Huang, S., Whitesides, G. M. & Ingber, D. E. Geometric control of cell life and death. Science 276, 1425-8 (1997).
5. Dike, L. E. et al. Geometric control of switching between growth, apoptosis, and differentiation during angiogenesis using micropatterned substrates. in vitro Cell Dev Biol Anim 35, 441-8 (1999).
6. Parker, K. K. et al. Directional control of lamellipodia extension by constraining cell shape and orienting cell tractional forces. Faseb J 16, 1195-204 (2002).
7. Matthews, B. D., Overby, D. R., Mannix, R. & Ingber, D. E. Cellular adaptation to mechanical stress: role of integrins, Rho, cytoskeletal tension and mechanosensitive ion channels. J Cell Sci 119, 508-18 (2006).
8. Kumar, S. et al. Viscoelastic retraction of single living stress fibers and its impact on cell shape, cytoskeletal organization, and extracellular matrix mechanics. Biophys J 90, 3762-73 (2006).
9. Moore, K. A. et al. Control of basement membrane remodeling and epithelial branching morphogenesis in embryonic lung by Rho and cytoskeletal tension. Dev Dyn 232, 268-81 (2005).
10. Huang, S. & Ingber, D. E. The structural and mechanical complexity of cell-growth control. Nat Cell Biol 1, E131-8 (1999).
11. Folkman, J. & Moscona, A. Role of cell shape in growth control. Nature 273, 345-9 (1978).
12. Folkman, J. & Kalluri, R. Cancer without disease. Nature 427, 787 (2004).
13. Matsumoto, T. & Claesson-Welsh, L. VEGF receptor signal transduction. Sci STKE 2001, RE21 (2001).
14. Wong, C. G., Rich, K. A., Liaw, L. H., Hsu, H. T. & Berns, M. W. Intravitreal VEGF and bFGF produce florid retinal neovascularization and hemorrhage in the rabbit. Curr Eye Res 22, 140-7 (2001).
15. Mammoto, A., Huang, S., Moore, K., Oh, P. & Ingber, D. E. Role of RhoA, mDia, and ROCK in cell shape-dependent control of the Skp2-p27kip1 pathway and the G1/S transition. J Biol Chem 279, 26323-30 (2004).
16. Mammoto, A., Huang, S. & Ingber, D. E. Filamin links cell shape and cytoskeletal structure to Rho regulation by controlling accumulation of p190RhoGAP in lipid rafts. J Cell Sci 120, 456-67 (2007).
17. Jiang, W. et al. An FF domain-dependent protein interaction mediates a signaling pathway for growth factor-induced gene expression. Mol Cell 17, 23-35 (2005).
18. Jackson, T. A., Taylor, H. E., Sharma, D., Desiderio, S. & Danoff, S. K. Vascular endothelial growth factor receptor-2: counter-regulation by the transcription factors, TFII-I and TFII-IRD1. J Biol Chem 280, 29856-63 (2005).
19. Roy, A. L. Biochemistry and biology of the inducible multifunctional transcription factor TFII-I. Gene 274, 1-13 (2001).
20. Francke, U. Williams-Beuren syndrome: genes and mechanisms. Hum Mol Genet. 8, 1947-54 (1999).
21. Roy, A. L. Signal-induced functions of the transcription factor TFII-I. Biochim Biophys Acta 1769, 613-21 (2007).
22. Patterson, C. et al. Cloning and functional analysis of the promoter for KDR/flk-1, a receptor for vascular endothelial growth factor. J Biol Chem 270, 23111-8 (1995).
23. Minami, T., Rosenberg, R. D. & Aird, W. C. Transforming growth factor-beta 1-mediated inhibition of the flk-1/KDR gene is mediated by a 5'-untranslated region palindromic GATA site. J Biol Chem 276, 5395-402 (2001).
24. Minami, T. et al. Interaction between hex and GATA transcription factors in vascular endothelial cells inhibits flk-1/KDR-mediated vascular endothelial growth factor signaling. J Biol Chem 279, 20626-35 (2004).
25. Cantor, A. B. & Orkin, S. H. Hematopoietic development: a balancing act. Curr Opin Genet Dev 11, 513-9 (2001).
26. Grogan, J. L. & Locksley, R. M. T helper cell differentiation: on again, off again. Curr Opin Immunol 14, 366-72 (2002).
27. Pai, S. Y., Truitt, M. L. & Ho, I. C. GATA-3 deficiency abrogates the development and maintenance of T helper type 2 cells. Proc Natl Acad Sci USA 101, 1993-8 (2004).
28. Kouros-Mehr, H., Slorach, E. M., Sternlicht, M. D. & Werb, Z. GATA-3 maintains the differentiation of the luminal cell fate in the mammary gland. Cell 127, 1041-55 (2006).
29. Su, Z. J. et al. A vascular cell-restricted RhoGAP, p73RhoGAP, is a key regulator of angiogenesis. Proc Natl Acad Sci USA 101, 12212-7 (2004).
30. Arthur, W. T., Petch, L. A. & Burridge, K. Integrin engagement suppresses RhoA activity via a c-Src-dependent mechanism. Curr Biol 10, 719-22 (2000).
31. Robinson, C. J. & Stringer, S. E. The splice variants of vascular endothelial growth factor (VEGF) and their receptors. J Cell Sci 114, 853-65 (2001).
32. Sheibani, N. & Frazier, W. A. Down-regulation of platelet endothelial cell adhesion molecule-1 results in thrombospondin-1 expression and concerted regulation of endothelial cell phenotype. Mol Biol Cell 9, 701-13 (1998).
33. Numaguchi, Y. et al. Caldesmon-dependent switching between capillary endothelial cell growth and apoptosis through modulation of cell shape and contractility. Angiogenesis 6, 55-64 (2003).
34. Polte, T. R., Eichler, G. S., Wang, N. & Ingber, D. E. Extracellular matrix controls myosin light chain phosphorylation and cell contractility through modulation of cell shape and cytoskeletal prestress. Am J Physiol Cell Physiol 286, C518-28 (2004).
35. Pierce, E. A., Avery, R. L., Foley, E. D., Aiello, L. P. & Smith, L. E. Vascular endothelial growth factor/vascular permeability factor expression in a mouse model of retinal neovascularization. Proc Natl Acad Sci USA 92, 905-9 (1995).
36. Stalmans, I. et al. Arteriolar and venular patterning in retinas of mice selectively expressing VEGF isoforms. J Clin Invest 109, 327-36 (2002).
37. Mammoto, T. et al. Angiopoietin-1 requires p190RhoGAP to protect against vascular leakage in vivo. J Biol Chem (2007).
38. Singh, H., Medina, K. L. & Pongubala, J. M. Contingent gene regulatory networks and B cell fate specification. Proc Natl Acad Sci USA 102, 4949-53 (2005).
39. Swiers, G., Patient, R. & Loose, M. Genetic regulatory networks programming hematopoietic stem cells and erythroid lineage specification. Dev Biol 294, 525-40 (2006).
40. Gottgens, B. et al. Establishing the transcriptional programme for blood: the SCL stem cell enhancer is regulated by a multiprotein complex containing Ets and GATA factors. Embo J 21, 3039-50 (2002).
41. Engler, A. J., Sen, S., Sweeney, H. L. & Discher, D. E. Matrix elasticity directs stem cell lineage specification. Cell 126, 677-89 (2006).
42. Clark, E. R. & Clark, E. L. Microscopic observations on the growth of blood capillaries in the living mammal. Am. J. Anat. 64, 251-301 (1938).
43. Carmeliet, P. & Tessier-Lavigne, M. Common mechanisms of nerve and blood vessel wiring. Nature 436, 193-200 (2005).

44. Pelham, R. J., Jr. & Wang, Y. Cell locomotion and focal adhesions are regulated by substrate flexibility. Proc Natl Acad Sci USA 94, 13661-5 (1997).

45. Wang, N. et al. Cell prestress. I. Stiffness and prestress are closely associated in adherent contractile cells. Am J Physiol Cell Physiol 282, C606-16 (2002).

46. Yung, C. W. et al. Transglutaminase crosslinked gelatin as a tissue engineering scaffold. J Biomed Mater Res A 83, 1039-46 (2007).

47. Connor, K. M. et al. Increased dietary intake of omega-3-polyunsaturated fatty acids reduces pathological retinal angiogenesis. Nat Med 13, 868-73 (2007).

What is claimed:

1. A method for inhibiting ocular angiogenesis in a mammal in need thereof, the method comprising administering an amount of at least one anti-angiogenic nucleic acid to decrease ocular angiogenesis, the anti-angiogenic nucleic acid selected from the group consisting of: a p190RhoGAP activator, a TFII-I activator, and a GATA-2 inhibitor, wherein the TFII-I activator is a DNA encoding a TFII-I polypeptide.

2. The method of claim 1, wherein the GATA-2 inhibitor is an RNA interference molecule.

3. The method of claim 1, wherein the p190RhoGAP activator is a nucleic acid encoding a p190RhoGAP polypeptide or a derivative thereof.

4. The method of claim 1, wherein the ocular angiogenesis selected from the group consisting of: a pathological blood vessel proliferation in the eye, macular degeneration, diabetic retinopathy, neovascular glaucoma, age-related macular degeneration, corneal neovascularization, ocular histoplasmosis, chronic retinal detachment, trauma and post-laser eye complications, rubeosis, and vascular malformations in the eye.

5. The method of claim 1, wherein the mammal is a human.

6. The method of claim 1, further comprising administering an anti-angiogenic therapy in conjunction with the anti-angiogenic nucleic acid.

7. The method of claim 1, wherein the ocular angiogenesis is retinal angiogenesis.

8. The method of claim 1, wherein the ocular angiogenesis is ocular neovascularization.

* * * * *